United States Patent
Maines et al.

(10) Patent No.: US 10,117,844 B2
(45) Date of Patent: Nov. 6, 2018

(54) DPA-ENRICHED COMPOSITIONS OF OMEGA-3 POLYUNSATURATED FATTY ACIDS IN FREE ACID FORM

(71) Applicants: Omthera Pharmaceuticals, Inc., Princeton, NJ (US); Chrysalis Pharma AG, Sachseln (CH)

(72) Inventors: Timothy J. Maines, Potomac, MD (US); Bernardus N. Machielse, North Potomac, MD (US); Bharat M. Mehta, Mendham, NJ (US); Gerald L. Wisler, Windermere, FL (US); Michael H. Davidson, Highland Park, IL (US); Peter Ralph Wood, Glen View (GB)

(73) Assignees: Omthera Pharmaceuticals, Inc., Princeton, NJ (US); Chrysalis Pharma AG (CH)

( * ) Notice: Subject to any disclaimer, the term of this patent is extended or adjusted under 35 U.S.C. 154(b) by 0 days.

(21) Appl. No.: 14/699,556

(22) Filed: Apr. 29, 2015

(65) Prior Publication Data

US 2015/0320715 A1 Nov. 12, 2015

Related U.S. Application Data

(63) Continuation of application No. 13/734,846, filed on Jan. 4, 2013, now Pat. No. 9,050,308.

(60) Provisional application No. 61/583,796, filed on Jan. 6, 2012, provisional application No. 61/664,047, filed on Jun. 25, 2012, provisional application No. 61/669,940, filed on Jul. 10, 2012, provisional application No. 61/680,622, filed on Aug. 7, 2012, provisional application No. 61/710,517, filed on Oct. 5, 2012, provisional application No. 61/713,388, filed on Oct. 12, 2012.

(51) Int. Cl.
*A61K 31/202* (2006.01)
*A61K 31/366* (2006.01)
*A61K 9/48* (2006.01)
*A61K 45/06* (2006.01)

(52) U.S. Cl.
CPC .......... *A61K 31/202* (2013.01); *A61K 9/4825* (2013.01); *A61K 31/366* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,377,526 A | 3/1983 | Fujita et al. | |
| 5,106,542 A | 4/1992 | Traitler et al. | |
| 5,130,061 A | 7/1992 | Cornieri et al. | |
| 5,243,046 A | 9/1993 | Traitler et al. | |
| 5,502,077 A * | 3/1996 | Breivik | A61K 31/20 514/549 |
| 5,656,667 A | 8/1997 | Breivik | |
| 5,661,180 A | 8/1997 | DeMichele et al. | |
| 5,679,809 A | 10/1997 | Bertoli et al. | |
| 5,698,594 A | 12/1997 | Breivik | |
| 5,792,795 A | 8/1998 | Buser et al. | |
| 5,886,037 A | 3/1999 | Klor et al. | |
| 5,945,318 A | 8/1999 | Breivik et al. | |
| 5,948,818 A | 9/1999 | Buser et al. | |
| 6,284,268 B1 | 9/2001 | Mishra | |
| 6,326,355 B1 | 12/2001 | Abbruzzese et al. | |
| 6,479,544 B1 | 11/2002 | Horrobin | |
| 6,528,699 B1 | 3/2003 | Kulas et al. | |
| 6,664,405 B2 | 12/2003 | Lee | |
| 6,893,658 B1 | 5/2005 | Iida et al. | |
| 7,112,609 B2 | 9/2006 | Hermelin et al. | |
| 7,541,480 B2 | 6/2009 | Bruzzese | |
| 7,642,287 B2 | 1/2010 | Guzman | |
| 7,709,668 B2 | 5/2010 | Catchpole et al. | |
| 7,829,708 B2 | 11/2010 | Roberts et al. | |
| 7,960,370 B2 | 6/2011 | Sachetto et al. | |
| 8,003,813 B2 | 8/2011 | Wanasundara et al. | |
| 8,282,961 B2 | 10/2012 | Sin et al. | |
| 8,383,678 B2 | 2/2013 | Sachetto et al. | |
| 8,613,945 B2 | 12/2013 | Manku et al. | |
| 8,663,662 B2 | 3/2014 | Manku et al. | |
| 9,492,545 B2 | 11/2016 | Machielse et al. | |
| 2002/0025983 A1 | 2/2002 | Horrobin | |
| 2004/0106591 A1 | 6/2004 | Pacioretty et al. | |
| 2004/0236128 A1 | 11/2004 | Rubin | |
| 2006/0088596 A1 | 4/2006 | Labrecque et al. | |
| 2006/0111272 A1 | 5/2006 | Roberts et al. | |
| 2006/0211763 A1 | 9/2006 | Fawzy | |
| 2006/0229461 A1 | 10/2006 | Sung et al. | |
| 2007/0020340 A1 | 1/2007 | Rubin et al. | |
| 2007/0265341 A1 | 11/2007 | Dana et al. | |
| 2007/0269507 A1 | 11/2007 | Sachetto et al. | |
| 2008/0107791 A1 | 5/2008 | Fichtali et al. | |
| 2009/0182049 A1 | 7/2009 | Opheim | |
| 2009/0304784 A1 | 12/2009 | Mane et al. | |
| 2010/0160435 A1 | 6/2010 | Bruzzese | |
| 2011/0034555 A1 | 2/2011 | Osterloh et al. | |
| 2011/0071176 A1 | 3/2011 | Rowe | |
| 2011/0081338 A1 | 4/2011 | Roberts et al. | |
| 2011/0082149 A1 | 4/2011 | Roberts et al. | |

(Continued)

FOREIGN PATENT DOCUMENTS

BR PI8803255 A 2/1990
CN 1410075 A 4/2003

(Continued)

OTHER PUBLICATIONS

1991, "Eudragit® NE Aqueous acrylic polymer dispersion," *Röhm Pharma GMBH Weiterstadt* data sheet (INFO NED-2/e) 1-2.

(Continued)

*Primary Examiner* — John Pak
*Assistant Examiner* — Daniel L Branson
(74) *Attorney, Agent, or Firm* — Dechert LLP; Carl A. Morales

(57) ABSTRACT

DPA-enriched pharmaceutical compositions of polyunsaturated fatty acids in free acid form, therapeutic methods for their use, and processes for refining the compositions from fish oil are presented.

43 Claims, 66 Drawing Sheets

(56) References Cited

U.S. PATENT DOCUMENTS

| | | |
|---|---|---|
| 2011/0097394 A1 | 4/2011 | Sachetto |
| 2012/0121698 A1 | 5/2012 | Manku et al. |
| 2012/0157530 A1 | 6/2012 | Manku et al. |
| 2012/0157531 A1 | 6/2012 | Osterloh et al. |
| 2012/0252850 A1 | 10/2012 | Milne et al. |
| 2012/0321602 A1 | 12/2012 | Rosedale |
| 2013/0095178 A1 | 4/2013 | Manku |
| 2013/0095179 A1 | 4/2013 | Davidson et al. |
| 2013/0209556 A1 | 8/2013 | Maines et al. |
| 2013/0295173 A1 | 11/2013 | Machielse |
| 2014/0017306 A1 | 1/2014 | Manku et al. |
| 2014/0080909 A1 | 3/2014 | Manku et al. |
| 2014/0088194 A1 | 3/2014 | Manku et al. |
| 2014/0094520 A1 | 4/2014 | Bobotas et al. |
| 2014/0100272 A1 | 4/2014 | Bobotas et al. |
| 2014/0100273 A1 | 4/2014 | Bobotas et al. |
| 2014/0100274 A1 | 4/2014 | Bobotas et al. |
| 2014/0100275 A1 | 4/2014 | Bobotas et al. |
| 2014/0100281 A1 | 4/2014 | Bobotas et al. |
| 2014/0107198 A1 | 4/2014 | Bobotas et al. |
| 2014/0107199 A1 | 4/2014 | Fawzy et al. |
| 2014/0107200 A1 | 4/2014 | Fawzy et al. |
| 2014/0107205 A1 | 4/2014 | Bobotas et al. |
| 2014/0107206 A1 | 4/2014 | Fawzy et al. |
| 2014/0154310 A1 | 6/2014 | Osterloh et al. |
| 2014/0155455 A1 | 6/2014 | Osterloh et al. |
| 2014/0194512 A1 | 7/2014 | Fawzy et al. |
| 2014/0249226 A1 | 9/2014 | Bobotas et al. |
| 2014/0316001 A1 | 10/2014 | Driscoll |
| 2014/0348930 A1 | 11/2014 | Sancilio et al. |
| 2015/0297529 A1 | 10/2015 | Spleiss |

FOREIGN PATENT DOCUMENTS

| | | |
|---|---|---|
| CN | 1929824 | 3/2007 |
| CN | 101208083 | 6/2008 |
| CN | 102311868 A | 1/2012 |
| DE | 10214005 A1 | 10/2003 |
| DE | 102006008030 A1 | 8/2007 |
| EP | 0 289 204 | 2/1988 |
| EP | 302481 A2 | 2/1989 |
| EP | 302482 A2 | 2/1989 |
| EP | 0347509 A1 | 12/1989 |
| EP | 0 825 858 | 3/1998 |
| EP | 0843972 A1 | 5/1998 |
| EP | 1106072 A1 | 6/2001 |
| EP | 1 202 950 | 9/2003 |
| EP | 1352648 A1 | 10/2003 |
| EP | 1157692 | 10/2005 |
| EP | 1645617 A1 | 4/2006 |
| EP | 1 755 565 | 2/2007 |
| EP | 2229939 | 9/2010 |
| FR | 2896172 B1 | 10/2008 |
| GB | 2 090 529 | 7/1982 |
| GB | 2 223 943 | 4/1990 |
| GB | 2300807 A | 11/1996 |
| JP | 59-157018 | 9/1984 |
| JP | S59-225115 | 12/1984 |
| JP | S61-126016 | 6/1986 |
| JP | H07-053356 | 2/1995 |
| JP | 2001054396 A | 2/2001 |
| JP | 2008502631 | 1/2008 |
| JP | 2008509154 A | 3/2008 |
| JP | 2008533029 | 8/2008 |
| JP | 2009518381 | 5/2009 |
| JP | 2015503590 | 2/2015 |
| KR | 100684641 B1 | 2/2007 |
| RU | 2127115 C1 | 3/1999 |
| RU | 2332445 C2 | 8/2007 |
| RU | 2388490 C2 | 5/2010 |
| RU | 2009145010 A | 6/2011 |
| WO | WO-1990/004391 | 5/1990 |
| WO | WO-1995/009622 A1 | 4/1995 |
| WO | WO-1995/022901 A1 | 8/1995 |
| WO | WO-1997/039759 A2 | 10/1997 |
| WO | WO-2000/049117 A1 | 8/2000 |
| WO | WO-2001/006983 A2 | 2/2001 |
| WO | WO-2001/015552 A1 | 3/2001 |
| WO | WO-2001/049282 A2 | 7/2001 |
| WO | WO-2002/010322 A1 | 2/2002 |
| WO | WO-2002/102394 A2 | 12/2002 |
| WO | WO-2003/072111 A2 | 9/2003 |
| WO | WO-2003/072784 A1 | 9/2003 |
| WO | WO-2003/082339 A1 | 10/2003 |
| WO | WO-2004/043894 A1 | 5/2004 |
| WO | WO-2004/056370 A1 | 7/2004 |
| WO | WO-2004/098311 A1 | 11/2004 |
| WO | WO-2005/005585 A1 | 1/2005 |
| WO | WO-2005/025334 A1 | 3/2005 |
| WO | WO-2005/060954 A1 | 7/2005 |
| WO | 2005079853 | 9/2005 |
| WO | WO-2005/079853 | 9/2005 |
| WO | 2005123061 | 12/2005 |
| WO | WO-2005/123060 | 12/2005 |
| WO | WO-2005/123061 A1 | 12/2005 |
| WO | WO-2006/004438 A1 | 1/2006 |
| WO | WO-2006/009464 A2 | 1/2006 |
| WO | WO-2006/009465 A2 | 1/2006 |
| WO | WO-2006/017692 A1 | 2/2006 |
| WO | WO-2006/017698 A2 | 2/2006 |
| WO | WO-2006/029385 A2 | 3/2006 |
| WO | WO-2006/069668 A1 | 7/2006 |
| WO | WO-2006/077495 A1 | 7/2006 |
| WO | WO-2006/088418 A1 | 8/2006 |
| WO | 2006096806 | 9/2006 |
| WO | WO-2006/100241 A2 | 9/2006 |
| WO | WO-2006/102896 A2 | 10/2006 |
| WO | WO-2006/117664 A1 | 11/2006 |
| WO | WO-2006/117668 A1 | 11/2006 |
| WO | WO-2007/017240 A2 | 2/2007 |
| WO | WO-2007/019373 A1 | 2/2007 |
| WO | 2007066178 | 6/2007 |
| WO | 2007/075841 | 7/2007 |
| WO | WO-2007/096387 A1 | 8/2007 |
| WO | WO-2007/128801 A1 | 11/2007 |
| WO | WO-2007/130713 A1 | 11/2007 |
| WO | WO-2007/130714 A1 | 11/2007 |
| WO | WO-2008/088808 A1 | 7/2008 |
| WO | WO-2008/103753 A2 | 8/2008 |
| WO | WO-2008/113177 A1 | 9/2008 |
| WO | WO-2008/133573 A1 | 11/2008 |
| WO | 2009/087938 | 12/2008 |
| WO | WO-2009-009040 A2 | 1/2009 |
| WO | WO-2009/014452 A1 | 1/2009 |
| WO | WO-2009/017102 A1 | 2/2009 |
| WO | WO-2009/020406 A1 | 2/2009 |
| WO | WO-2009/028457 A1 | 3/2009 |
| WO | WO-2009/040676 A2 | 4/2009 |
| WO | WO-2009/065395 A2 | 5/2009 |
| WO | WO-2009/139641 A1 | 11/2009 |
| WO | WO-2010/029433 A1 | 3/2010 |
| WO | WO-2010/039030 A1 | 4/2010 |
| WO | WO-2010/049954 A1 | 5/2010 |
| WO | WO-2010/103402 A1 | 9/2010 |
| WO | WO-2010/118761 A1 | 10/2010 |
| WO | WO-2010-119319 A1 | 10/2010 |
| WO | 2010/124387 | 11/2010 |
| WO | WO-2011-048493 | 4/2011 |
| WO | WO-2011/095284 A1 | 8/2011 |
| WO | WO-2011/128626 A1 | 10/2011 |
| WO | WO-2011/133610 A1 | 10/2011 |
| WO | WO-2011/161702 A1 | 12/2011 |
| WO | 2012032415 | 3/2012 |
| WO | WO-2012/038833 A1 | 3/2012 |
| WO | WO-2012/083034 A1 | 6/2012 |
| WO | WO-2012/087153 A1 | 6/2012 |
| WO | WO-2012/095525 A1 | 7/2012 |
| WO | WO-2012/112511 A1 | 8/2012 |
| WO | WO-2012-112517 A1 | 8/2012 |
| WO | WO-2012/112520 A1 | 8/2012 |
| WO | WO-2012/112527 A1 | 8/2012 |
| WO | WO-2012/112531 A1 | 8/2012 |
| WO | WO-2012/112902 A1 | 8/2012 |
| WO | WO-2012/156986 A1 | 11/2012 |

(56) References Cited

FOREIGN PATENT DOCUMENTS

| WO | 2013040507 | 3/2013 |
|---|---|---|
| WO | WO-2013/040507 | 3/2013 |
| WO | 2013059669 | 4/2013 |
| WO | WO-2013059669 | 4/2013 |
| WO | WO-2013/063067 A1 | 5/2013 |
| WO | 2013/103902 | 7/2013 |
| WO | 2013/169797 | 11/2013 |
| WO | WO-2013/192109 A1 | 12/2013 |
| WO | WO-2014/040921 A1 | 3/2014 |
| WO | 2016/137825 | 1/2016 |
| WO | 2016069446 | 5/2016 |
| WO | 2016073335 | 5/2016 |
| WO | 2016130417 | 8/2016 |

OTHER PUBLICATIONS

1994, "Eudragit ® Acrylic Polymers International Availability and Acceptability for their Use in Drug Manufacture," *Rohm* 1-2.
1999, "Adis R&D Profile Purepa®," *Drugs R&D* 3:268-269.
2002, "Third Report of the National Cholesterol Education Program (NCEP) Expert Panel on Detection, Evaluation, and Treatment of High Blood Cholesterol in Adults (Adult Treatment Panel III) Final Report," *National Institutes of Health (National Heart, Lung, and Blood Institute)* (updated 2004) 1-200.
2002, "Third Report of the National Cholesterol Education Program (NCEP) Expert Panel on Detection, Evaluation, and Treatment of High Blood Cholesterol in Adults (Adult Treatment Panel III) Final Report," *National Institutes of Health (National Heart, Lung, and Blood Institute)* (updated 2004) 201-283.
2010, "Australian Public Assessment Report for Omega-3-acid ethyl ester 90," *Therapeutic Goods Administration* 1-134.
2011, "Omega-3-Acid Ethyl Esters," *The United States Pharmacopeial Conventions: Official Monographs* (34):3714-3716.
Anonymous, 2010, "Withdrawal Assessment Report for Ethyl Eicosapent Soft Gelatin Capsules," *European Medicines Agency* 1-22.
Bays et al., 2008, "Prescription omega-3 fatty acids and their lipid effects: physiologic mechanisms of action and clinical implications," *Expert Rev Cardiovasc Ther.* 6(3):391-409.
Bays et al., 2010, Effects of Prescription Omega-3-Acid Ethyl Esters on Non-High-Density Lipoprotein Cholesterol When Coadministered with Escalating Does of Atorvastatin *Mayo Clinic Proceedings* 85(2)122-128.
Beckermann et al., 1990, "Comparative Bioavailability of Eicosapentaenoic Acid and Docasahexaenoic Acid from Triglycerides, Free Fatty Acids and Ethyl Esters in Volunteers," *Arzneimit-telforschung* Abstract 40(6)1.
Belluzzi et al., 1993, "Polyunsaturated fatty acid pattern and fish oil treatment in inflammatory bowel disease," *GUT* 34:1289.
Belluzzi et al., 1994, "Effects of New Fish Oil Derivative on Fatty Acid Phospholipid-Membrane Pattern in a Group of Crohn's Disease Patients," *Digestive Diseases and Sciences* 39(12):2589-2594.
Belluzzi et al., 1995, "New fish oil derivative for preventing clinical relapses in Crohn's disease: A double blind placebo controlled randomized trial," *Gastroenterology* 108(4)Supp 2:A781.
Belluzzi et al., 1996, "Effect of an Enteric-coated Fish-oil Preparation on Relapses in Crohn's Disease," *The New England Journal of Medicine* 334(24):1557-1560.
Belluzzi et al., 2000, "Polyunsaturated fatty acids and inflammatory bowel disease," *The American Journal of Clinical Nutrition* 71(suppl):339S-342S.
Belluzzi et al., 2002, "n-3 Fatty acids for the treatment of inflammatory bowel diseases," *Proceedings of the Nutrition Society* 61:391-395.
Belluzzi et al., 2004, "Polyunsaturated fatty acids (n-3 PUFAs) and inflammatory bowel disease (IBD): pathogenesis and treatment," *European Review for Medical and Pharmacological Sciences* 8:225-229.

Bobotas et al., U.S. Appl. No. 61/660,757, filed Jun. 17, 2012 (64 pages).
Bobotas et al., U.S. Appl. No. 61/734,331, filed Dec. 6, 2012 (71 pages).
Bobotas et al., U.S. Appl. No. 61/780,948, filed Mar. 13, 2013 (76 pages).
Burns et al., 2007, "Effect of Omega-3 Fatty Acid Supplementation on the Arachidonic Acid: Eicosapentaenoic Acid Ratio," *Pharmacotherapy* 27(5):633-638.
Chan et al., 2002, "Factorial Study of the Effects of Atorvastatin and Fish Oil on Dyslipidaemia in Visceral Obesity," *European Journal of Clinical Investigation* 32(6):429-436.
Cohen et al., 2008, "Changes in the Prevalence of Abnormal Lipid Fractions Amount US Adults: Results from the National Health and Nutrition Examination Survey II, III and 1999-2006," *Presented at the American Heart Association (AHA) conference.* Nov. 8-12, 2008, New Orleans, LA.
Conner et al., 1993, "N-3 Fatty Acids from Fish Oil: Effects on Plasma Liporoteins and Hypertriglyceridemic Patients," *Annals new York Academy of Sciences* 683:16-34.
Davidson et al., 2009, "Effects of prescription omega-3-acid ethyl esters on lipoprotein particle concentrations, apolipoproteins AI and CIII, and lipoprotein-associated phospholipase A(2) mass in statin-treated subjects with hypertriglyceridemia," *J Clin Lipidol.* 3(5):332-40.
Davidson et al., 2011, "Bioavailability of a Single 4g Dose Epanova® (Omega-3 Free Fatty Acids) Versus Lovaza® (Omega-3-Acid Ethyl Esters) When Consumed with Low-Fat and High-Fat Meals in Healthy Adults," *Drugs Affecting Lipid Metabolism (DALM) Symposium* Poster 1.
Davidson et al., 2011, "Novel developments in omega-3 fatty acid-based strategies," *Current Opinion in Lipidology* 22:437-444.
Davidson et al., 2011, "Poor Bioavailability of Ester Omega-3's on a Low-fat Diet is Significantly Improved with a Free Fatty Acid Formulation," Presentation, American Heart Association Annual Meeting 2011 (Nov. 2011).
Davidson et al., 2012, "A novel omega-3 free fatty acid formulation has dramatically improved bioavailability during a low-fat diet compared with omega-3-acid ethyl esters: The ECLIPSE (Epanova® compared to Lovaza® in a pharmacokinetic single-dose evaluation) study," *Journal of Clinical Lipidology* 6(6):1-12 (Epub Jan 24, 2012).
Davidson et al., Abstract 18775: "Low Levels of Omega-3s in Hispanics Due to Genetic and Dietary Factors Can be Significantly Improved with a Highly Bioavailable Omega-3 Free fatty Acid Formulation," 2012 AHA Meeting.
Davidson, 2008, "Is LDL-C passed [sic] its prime? The emerging role of non-HDL, LDL-P and ApoB in CHD risk assessment," *Arterioscler Thromb Vasc Biol.* 28(9):1582-1583.
Davidson, M.H. et al., "Addition of omega-3 carboxylic acids to statin therapy in patients with persistent hypertriglyceridemia," Expert Rev. Cardiovasc. Ther. 12(9) 1-10 (2014).
Davidson, M.H. et al., "Novel developments in omega-3 fatty acid-based strategies," Current Opinion in Lipidology 2011, 22: 437-444.
Davidson, M.H., "Omega-3 fatty acids: new insights into the pharmacology and biology of docosahexaenoic acid, docosapentaenoic acid, and eicosapentaenoic acid," Curr. Opin. Lipodol. 2013, 24: 1-8.
De Caterina, 2011, "n-3 Fatty acids in cardiovascular disease," *New England Journal of Medicine* 364:2439-2450.
De Caterina, 2011, "n-3 Fatty acids in cardiovascular disease," *New England Journal of Medicine* Supplementary Appendix 1-19.
Deckelbaum et al., 2006, "n-3 Fatty acids and gene expression," *Am J Clin Nutr* 83(suppl):1520S-1525S.
Donadio et al., 2001, "A Randomized Trial of High-Dose Compared with Low-Dose Omega-3 Fatty Acids in Severe IgA Nephropathy," *J Am Soc Nephrol* 12:791-799.
Durrington et al., 2001, "An Omega-3 Polyunsaturated Fatty Acid Concentrate Administered for One Year Decreased Triglycerides in Simvastatin Treated Patients with Coronary Heart Disease and Persisting Hypertriglyceridaemia," *Heart* 85:544-548.

(56) References Cited

OTHER PUBLICATIONS

Dyerberg et al., 1995, "20. Bioavailability of n-3 fatty Acid Formulations," *Prevention and Treatment in Vascular Disease* Bi & Gi Publishers 217-226.
Eslick et al., 2009, "Benefits of fish oil supplementation in hyperlipidemia: a systematic review and meta-analysis," *Intn'l J. Cardiol.* 136:4-16.
Farzaneh-Far et al., 2010, "Association of Marine Omega-3 Fatty Acid Levels with Telomeric Aging in patients with Coronary Heart Disease," *JAMA* 303(3):250-257.
FDA Draft Guidance on Omega-3-Acid Ethyl Esters (Sep. 2012).
FDA Product Label for LOVAZA® 1-14 (Dec. 2010).
FDA Product Label for Omacor (Nov. 10, 2004).
FDA Product Label for VASCEPA™ 1-12 (Jul. 2012).
Feagan et al., 2008, "Omega-3 Free Fatty Acids for the Maintenance of Remission in Crohn disease: The EPIC Randomized Controlled Trials," *Original Contribution* 299(14):1690-1697.
Fojo et al., 1992, "Hypertriglyceridaemia due to genetic defects in lipoprotein lipase and apolipoprotein C-II," *J. of Int. Med.* 231:669-677.
Gregory et al., 2011, "Elongase Reactions as Control Points in Long- Chain Polyunsaturated Fatty Acid Synthesis," *PLoS One* 6(12) e29662: 1-9.
Grimsgaard et al., 1997, "Highly purified eicosapentaenoic acid and docosahexaenoic acid in humans have similar triacylglycerol-lowering effects but divergent effects on serum fatty acids," *American Journal of Clinical Nutrition* 66:649-659.
Guil-Guerrero et al., 2001, "Purification Process for Cod Liver Oil Polyunsaturated Fatty Acids," *JAOCS* 78(5):477-484.
Hansen, et al., 1998, "Effects of Highly Purified Eicosapentaenoic Acid and Docosahexaenoic Acid on Fatty Acid Absorption, Incorporation into Serum Phospholipids and Postprandial Triglyceridemia," *Lipids* 33(2):131-138.
Harper et al., 2010, "Using Apolipoprotein B to Manage Dyslipidemic Patients: Time for a Change?," *Mayo Clin Proc* 85(5):440-445.
Harris et al., 1990, "Fish Oils in Hypertriglyceridemia: a dose-response study," *American Society for Clinical Nutrition* 51:399-406.
Harris et al., 1997, "Safety and Efficacy of Omacor in Severe Hypertriglyceridemia," *Journal of Cardiovascular Risk* 4:385-391.
Harris et al., 2007, "Comparison of the Effects of Fish and Fish-oil Capsules on the n-3 Fatty Acid content of Blood Cells and Plasma Phospholipids," *American Society for Nutrition* 86:1621-1625.
Harris et al., 2008, "Omega-3 fatty acids and coronary heart disease risk: clinical and mechanistic perspectives," *Atherosclerosis* 197(1):12-24.
Harris et al., 2008, "Role of Omega-3 Fatty Acids in Cardiovascular Disease Prevention," *Lipids Online Slide Library* 1-30.
Harris et al., 2009, "The Omega-3 Index: From Biomarker to Risk Marker to Risk Factor," *Current Atherosclerosis Report* 11:411-417.
Harris et al., 2010, "The Omega-3 Index: Clinical utility for therapeutic intervention," *Curr Cardiol Rep* 12:503-508.
Harris, W.S. et al., "RE: Plasma Phospholipid Fatty Acids and Prostate Cancer Risk in the SELECT Trial," *JNCI Journal of the National Cancer Institute Advance Access* published Mar. 31, 2014, p. 1 of 1.
Hawthorne et al., 1992, "Treatment of ulcerative colitis with fish oil supplementation: a prospective 12 month randomized controlled trial," *GUT* 33:922-928.
Hayes et al., 2001, "Triangular Phase Diagrams to Predict the Fractionation of Free Fatty Acid Mixtures Via Urea Complex Formation," *Separation Science and Technology* 36(1):45-58.
Hayes, 2005, "Purification of Free Fatty Acids via Urea Inclusion Compounds," *Handbook of Functional Lipids* 77-88.
Homma et al., 1991, "Effects of eicosapentaenoic acid on plasma lipoprotein subfractions and activities of lecithin: cholesterol acyltransferase and lipid transfer protein," *Atherosclerosis* 91(1):145-153.

Huang et al., 2012, "Effect of n-3 polyunsaturated fatty acid on gene expression of the critical enzymes involved in homocysteine metabolism," *Nutrition Journal* 11(6): 1-8.
Kastelein et al., Abstract 16374: "Dose Response of a Novel Free-Fatty Acid Formulation of Omega-3 for the Management of Dyslipidemia in Patients with Severe Hypertriglyceridemia—EpanoVa for Lowering Very High TriglycErides (The EVOLVE Trial)," 2012 AHA Meeting.
Kastelein, J.J.P. et al., "Omega-3 free fatty acids for the treatment of severe hypertriglyceridemia: The EpanoVa fOr Lowering Very high TriglyceridEs (EVOLVE) trial," Journal of Clinical Lipidology (2014) 8, 94-106.
Kataoka,Y. et al., "Epanova and hypertriglyceridemia: pharmacological mechanisms and clinical efficacy," Future Cardiol. (2013) 9(2), 177-186.
Kaur et al., 2010, "Short-term docosapentaenoic acid (22:5n-3) supplementation increases tissue docosapentaenoic acid, DHA and EPA concentrations in rats," *British Journal of Nutrition* 103:32-37.
Kaur et al. 2011, "Docosapentaenoic acid (22:5n-3): A review of its biological effects," *Progress in Lipid Research* 50:28-34.
Kelley et al., 2007, "Docosahexaenoic Acid Supplementation Improves Fasting and Postprandial Lipid Profiles in Hypertriglyceridemic Men," *The American Journal of Clinical Nutrition* 86(2):324-333.
Kelley et al., 2009, "DHA supplementation decreases serum C-reactive protein and other markers of inflammation in hypertriglyceridemic men," *J. Nutrition* 139(3):495-501.
Kling et al., 2011, "Omega-3 Free Fatty Acids Demonstrate More Than 4-Fold Greater Bioavailability for EPA and DHA Compared with Omega-3-acid Ethyl Esters in Conjunction with a Low-Fat Diet: The ECLIPSE Study," *Encore presentation from XVII Drugs Affecting Lipid Metabolism Symposium* Mar. 2011.
Laidlaw et al., 2003, "Effects of Supplementation with Fish Oil-Derived n-3 Fatty Acids and Gamma-Linolenic Acid on Circulating Plasma Lipids and Fatty Acid Profiles in Women," *The American Journal of Clinical Nutrition* 77(1):37-42.
Lavie et al., 2009, "Omega-3 Polyunsaturated Fatty Acids and Cardiovascular Diseases," *Journal of the American college of Cardiology* 54(7):585-594.
Lawson et al., 1988, "Absorption of Eicosapentaenoic Acid and Docosahexaenoic Acid from Fish Oil Triacylglycerols or Fish Oil Ethyl Esters Co-Ingested with a High-Fat Meal," *Biochemical and Biophysical Research Communications* 156(2):960-963.
Lawson et al., 1988, "Human Absorption of Fish Oil Fatty Acids as Triacylglycerols, Free Acids, or Ethyl Esters," *Biochemical and Biophysical Research Communications* 156(1):328-335.
Lemaitre et al., 2011, "Genetic loci associated with plasma phospholipid n-3 fatty acids: A meta-analysis of genome-wide association studies from the CHARGE consortium," *PLoS Genetics* 7(7)e1002193:1-12.
Liu et at., 2006, "Concentration of docosahexaenoic acid (DHA) and eicosapentaenoic acid (EPA) of tuna oil by urea complexation: optimization of process parameters," *Journal of Food Engineering* 73:203-209.
Maki et al., 2010, "Baseline lipoprotein lipids and low-density lipoprotein cholesterol response to prescription omega-3 acid ethyl ester added to Simvastatin therapy," *Am. J. Cardiol.* 105(10):1409-1412.
Maki et al., 2011, "Effects of Prescription Omega-3-Acid Ethyl Esters, Coadministered with Atorvastatin, on Circulating Levels of Lipoprotein Particles, Apolipoprotein CIII, and Lipoprotein-Associated Phospholipase $A_2$ Mass in Men and Women with Mixed Dyslipidemia," *Journal of Clinical Lipidology* 5(6):483-492.
Maki, K.C. et al., "A Highly Bioavailable Omega-3 Free Fatty Acid Formulation Improves the Cardiovascular Risk Profile in High-Risk, Statin-Treated Patients With Residual Hypertriglyceridemia (the ESPIRIT Trial)," Clinical Therapeutics vol. 35, No. 9 1400-1411 (2013).
Matsuzaki, et al., 2009, "Incremental Effects of Eicosapentaenoic Acid on Cardiovascular Events in Statin-Treated Patients with Coronary Artery Disease," *Circulation Journal* 73:1283-1290.
Meyer et al., 2007, "Dose-Dependent Effects of Docosahexaenoic Acid Supplementation on Blood Lipids in Statin-Treated Hyperlipidaemic Subjects," *Lipids* 42:109-115.

(56) References Cited

OTHER PUBLICATIONS

Mori et al., 1999, "Docosahexaenoic Acid but not Eicosapentaenoic Acid Lowers Ambulatory Blood Pressure and Heart Rate in Humans," *Hypertention: Journal of the American Heart Association* 34:253-260.
Mori et al., 2000, "Purified eicosapentaenoic and docosahexaenoic acids have differential effects on serum lipids and lipoproteins, LDL particle size, glucose, and insulin in mildly hyperlipidemic men," *American Journal of Clinical Nutrition* 71:1085-1094.
Mori et al., 2006, "The independent effects of eicosapentaenoic acid and docosahexaenoic acid on cardiovascular risk factors in humans," *Curr Opin Clin Nutr Metab Care* 9:95-104.
Mori et al., 2011 "Eicosapentaenoic Acid and Docosahexaenoic Acid: Are They different?," *PUFA* 1-2.
Mozaffarian et al., 2012, "(n-3) Fatty Acids and Cardiovascular Health: Are Effects of EPA and DHA Shared or Complementary?," *American Society for Nutrition* (Suppl):614S-625S.
Nakamura et al., 2012, "Both EPA/AA ratio and absolute AA levels constitute an independent risk factor for coronary atherosclerosis in type 2 diabetic patients," *Endocrine Abstracts* 29 OC19.1.
Neubronner et al., 2011, "Enhanced Increase of Omega-3 Index in Response to Long-Term n-3 Fatty Acid Supplementation from Triacylglycerides Versus Ethyl Esters," European Journal of Clinical Nutrition 65:247-254.
Norris et al., 2012, "Omega-3 fatty acids cause dramatic changes in TLR4 and purinergic eicosanoid signaling," *Proceedings of the National Academy of Sciences of the United States of America* 109(22):8517-8522.
Notarnicola et al., 2011, "Polyunsaturated fatty acids reduce Fatty Acid Synthase and Hydroxy-Methyl-Glutaryl CoA-Reductase gene expression and promote apoptosis in HepG2 cell line," *Lipids in Health and Disease* 10(10)1-7.
Notarnicola et al., 2011, "Synergic effect of Eicosapentaenoic acid and Lovastatin on gene expression of HMGCoA ," *Lipids in Health and Disease* 10(10)1-7.
Nozue et al., 2013, "Effects of Serum n-3 to n-6 Polyunsaturated Fatty Acids Ratios on Coronary Atherosclerosis in Statin-Treated Patients With Coronary Artery Disease," *Am J Cardiol.* 111(1):6-11 (Epub Oct. 2, 2012).
Obajimi et al., 2005, "Differential Effects of Eicosapentaenoic and Docosahexaenoic Acids upon Oxidant-Stimulated Release and Uptake of Arachidonic Acid in Human Lymphoma U937 Cells," *Pharmacological Research* 52:183-191.
Offman, E. et al., "Steady-state bioavailablity of prescription omega-3 on a low-fat diet is significantly improved with a free fatty acid formulation compared with an ethyl ester formulation: the ECLIPSE II study," Vascular Health and Risk Management 2013:9 563-573.
Oliva et al., 2005, "Inherited Apolipoprotein A-V Deficiency in Severe Hypertriglyceridemia," *Arteriosclerosis, Thrombosis, and Vascular Biology* 25:411-417.
Omega-3-acid Ethyl Esters (European Pharmacopeia Sep. 20, 2001) 1668-1670.
Omthera Pharmaceuticals, Inc. & Rx Communications Group, LLC "Omthera Pharmaceuticals Presents Successful Phase 3 Results from EVOLVE and ESPRIT Clinical Studies for Epanova™; Both Trials Meet Primary and Secondary Endpoints," Press Release dated Nov. 5, 2012 1-4.
Omthera Pharmaceuticals, Inc. & Rx Communications Group, LLC, "Omthera Pharmaceuticals Announces Positive Long Term Bioavailability Data Comparing Epanova™ to Lovaza®", Press Release dated Jan. 9, 2012 1-2.
Omthera Pharmaceuticals, Inc. & Rx Communications Group, LLC, "Omthera Pharmaceuticals Announces Positive Top-Line from Phase 3 EVOLVE Study," Press Release dated Apr. 26, 2012 1-2.
Omthera Pharmaceuticals, Inc. & Rx Communications Group, LLC, "Omthera Pharmaceuticals Completes Enrollment of Pivotal Phase III EVOLVE Trial for Epanova™ in Patients with Very High Triglycerides," Press Release dated Nov. 29, 2011.
Omthera Pharmaceuticals, Inc. & Rx Communications Group, LLC, "Omthera Pharmaceuticals Initiates Pivotal Phase III EVOLVE Trial for Epanova™ in Patients with Very High Triglycerides," Press Release dated Mar. 14, 2011.
Omthera Pharmaceuticals, Inc. & Rx Communications Group, LLC, "Omthera Pharmaceuticals, Inc. Announces Initiation of the ECLIPSE Trial: Epanova Compared to Lovaza in a Pharmacokinetic Single-dose Evaluation," Press Release dated Nov. 8, 2010.
Omthera Pharmaceuticals, Inc. and Rx Communications Group, LLC, "Omthera Pharmaceuticals, Inc. Initiates Phase III ESPRIT Trial of Add-on Epanova™ to Statin Therapy in Patients with Hypertriglyceridemia," Press Release dated Aug. 15, 2011.
Omthera Pharmaceuticals, Inc., "Omthera Pharmaceuticals Developing the Best-In-Class Prescription Omega-3 Therapy", JP Morgan Healthcare Conference, San Francisco, CA dated Jan. 13, 2011.
Omthera Pharmaceuticals, Inc., "Omthera Pharmaceuticals Matching An Unmet Medical Need With a Best-In-Class Therapy," JP Morgan Healthcare Conference, San Francisco, CA, dated Jan. 20, 2012.
Otvos et al., 2011 "Clinical Implications of Discordance Between Low-Density Lipoprotein Cholesterol and Particle Number," Journal of Clinical Lipidology 5:105-113.
Ouguerram et al., 2006, "Effect of n-3 Fatty acids on Metabolism of apoB100-containing Lipoprotein in Type 2 Diabetic Subjects," *British Journal of Nutrition* 96:100-106.
PCT International Search Report from PCT/US13/20398 dated Mar. 13, 2013.
Pejic et al., 2006, "Hypertriglyceridemia," *The Journal of the American Board of Family Medicine* 19(3):310-316.
Phillipson et al., 1985, "Reduction of Plasma Lipids, Lipoproteins, and Apoproteins by Dietary Fish Oils in Patients with Hypertriglyceridemia," *The New England Journal of Medicine* 1210-1216.
Portolesi et al., 2007, "Competition between 24:5n-3 and ALA for Δ6 desaturase may limit the accumulation of DHA in HepG2 cell membranes," *Journal of Lipid Research* 48:1592-1598.
Rader et al., Abstract 19030: "Apolipoprotein C-III is Significantly Reduced by Prescription Omega-3 Free Fatty Acids (Epanova) in patients with Severe Hypertriglyceridemia and Changes Correlate with Increases in LDL-C: A Sub-analysis of the EVOLVE trial," 2012 AHA meeting.
Rupp et al., 2004, "Risk Stratification by the 'EPA+DHA Level' and the 'EPA/AA Ratio' Focus on Anti-Inflammatory and Antiarrhythmogenic Effects of Long-Chain Omega-3 Fatty Acids," *Herz* 29:673-685.
Saito et al., 2008, "Effects of EPA on Coronary Artery Disease in Hypercholesterolemic Patients with Multiple Risk Factors: Sub-Analysis of Primary Prevention Cases from the Japan EPA Lipid Intervention Study (JELIS)," Atherosclerosis 200:135-140.
Simopoulos, 2008, "The Importance of the Omega-6/Omega-3 Fatty Acid Ratio in Cardiovascular Disease and Other Chronic Diseases," *Experimental Biology and Medicine* 233:674-688.
Skulas-Ray et al., 2008, "Omega-3 fatty acid concentrates in the treatment of moderate hypertriglyceridemia," *Expert Opin. Pharmacother.* 9(7):1237-48.
Sun et al., 2008, "Blood Concentrations of individual long-chain n-3 fatty acids and risk of nonfatal myocardial infarction," *American Society for Nutrition* 88:216-223.
Trehan, Naresh, 2006, "Cardiovascular Disease Trends in India," *Slide Presentation* 1-24.
Von Schacky C., 2011, "The Omega-3 Index as a risk factor for cardiovascular diseases," *Prostaglandins and other Lipid Mediators* 96(1-4):94-98.
Davidson et al., "Abstract 15894: Poor Bioavailability of Ethyl Ester Omega-3's on a Low-Fat Diet is Dramatically Improved With a Free Fatty Acid Foundation," Circulation, vol. 124, No. Suppl 21 A15894, Nov. 22, 2011 (2 pages).
Kaur et al., "Docosapentaenoic acid (22:5n-3): A review of its biological effects," Progress in Lipid Research, vol. 50, No. 1, Jan. 2011 (pp. 28-34).
Wang, "Apolipoprotein CIII and hypertriglyceridemia," Progress in Physiology, vol. 41, No. 1, Feb. 2010 (7 pages).
Davidson et al. "A novel omega-3 free fatty acid formulation has dramatically improved bioavailability during a low-fat diet compared with omega-3-acid ethyl esters: The ECLIPSE (Epanova®

(56) References Cited

OTHER PUBLICATIONS compared to Lovaza® in a pharmacokinetic single-dose evaluation) study." Journal of Clinical Lipidology 6(6), pp. 573-584 (2012).
Guangdong Agricultural Science 6(6), 153-155 (2009) (partial translation).
U.S. Appl. No. 61/535,192, Methods and Compositions for Treating or Preventing Resistance to Antiplatelet Therapy, Davidson, Michael H. and Wisler, Gerald L., 53 pages, Sep. 15, 2011.
U.S. Appl. No. 61/549,907, Methods and Compositions for Treating or Preventing Resistance to Antiplatelet Therapy, Davidson, Michael H. and Wisler, Gerald L., 54 pages, Oct. 21, 2011.
U.S. National Institutes of Health. Clinical Trial: Epanova® Compared to Lovaza® in a Pharmacokinetic, Single-dose, Evaluation (ECLIPSE). Last updated Jun. 19, 2015. https://clinicaltrials.gov/ct2/show/NCT01208961.
U.S. National Institutes of Health. Clinical Trial: Epanova® for Lowering Very High Triglycerides (EVOLVE). Last updated Jun. 24, 2016. https://clinicaltrials.gov/ct2/show/NCT01242527.
U.S. National Institutes of Health. Clinical Trial: Epanova® Compared to Lovaza® in a Pharmacokinetic, Single-dose, Evaluation (ECLIPSE). Last updated Sep. 2, 2011. https://clinicaltrials.gov/ct2/show/NCT01208961.
U.S. National Institutes of Health. Clinical Trial: Epanova® for Lowering Very High Triglycerides (EVOLVE). Last updated Dec. 19, 2011. https://clinicaltrials.gov/archive/NCT01242527.
European Search Opinion and Supplementary Search Report. European Application No. 13733671.5. dated May 20, 2015. 9 pages.
International Preliminary Report on Patentability. International Patent Application No. PCT/US2013/020398. dated Jul. 8, 2014. 9 pages.
Gotoh et al. Effects of Three Different Highly Purified n-3 Series Highly Unsaturated Fatty Acids on Lipid Metabolism in C57BL/KsJ-db/db Mice. J. Agric. Food Chem. 2009, 57, pp. 11047-11054.
Skulus-Ray et al. Effects of Marine Omega-3 Fatty Acids on Triglyceride-Rich Apolipoprotein Subclasses in People with Moderately Elevated Triglycerides: Novel Methods for Assessing the Antiatherogenic Effects of Triglyceride Lowering. 2009 Joint Conference—Nutrition, Physical Activity and Metabolism and 49th Cardiovascular Disease Epidemiology and Prevention. vol. 119, No. 10, Abstract No. P47, p. E293.
Omthera Pharmaceuticals, Inc. & Rx Communications Group, LLC, "Omthera Pharmaceuticals Reports Favorable Pharmacokinetics Data from ECLIPSE Trial," Press Release dated Jan. 7, 2011.
Omthera Pharmaceuticals, Inc. & Rx Communications Group, LLC, "Omthera Pharmaceuticals Receives Special Protocol Assessment Agreement from the FDA for its Pivotal Phase III EVOLVE Trial of Epanova™ in Patients with Very High Triglycerides," Press Release dated Nov. 22, 2010.

\* cited by examiner

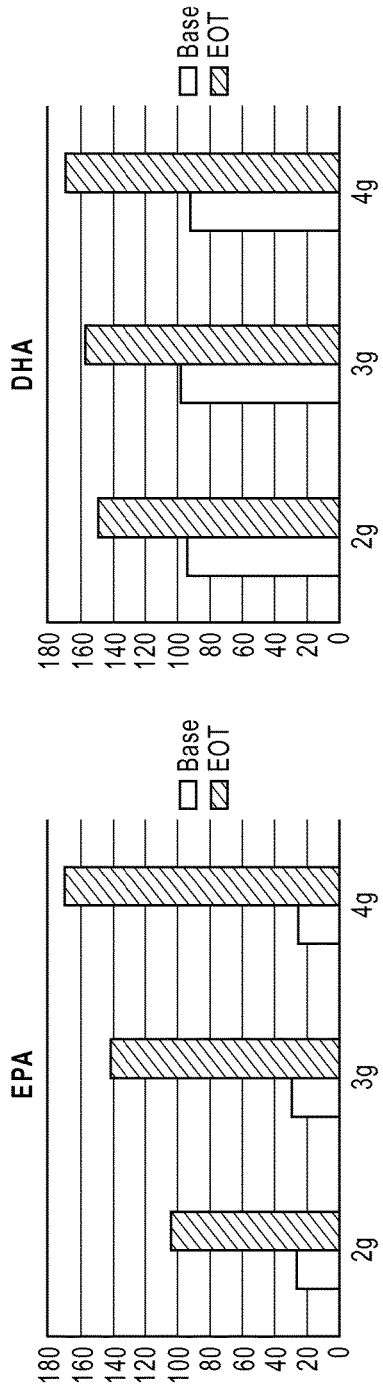
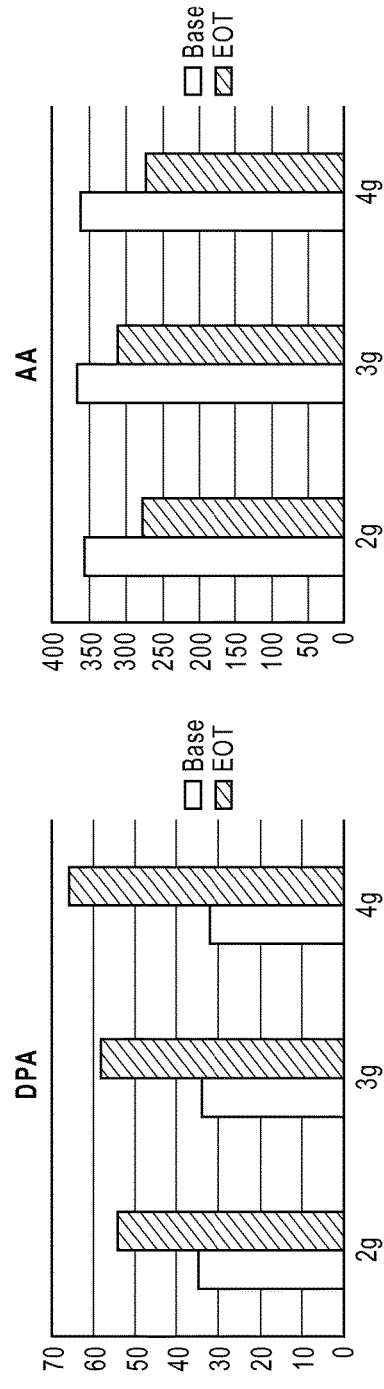
FIG. 21A, FIG. 21B, FIG. 21C, FIG. 21D

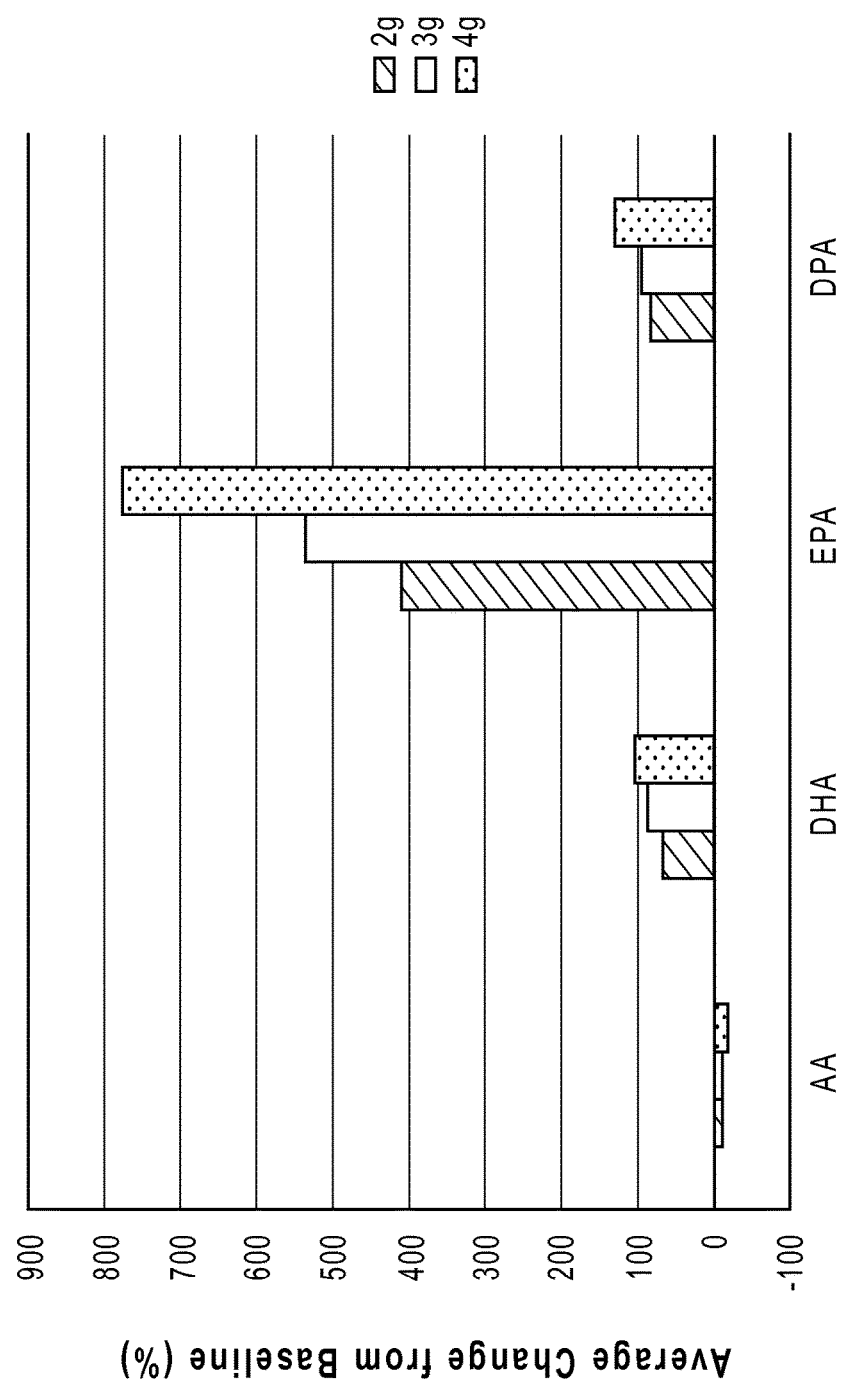

Average Absolute Plasma Levels (mg/dL)

Average Absolute Plasma Levels (mg/dL)

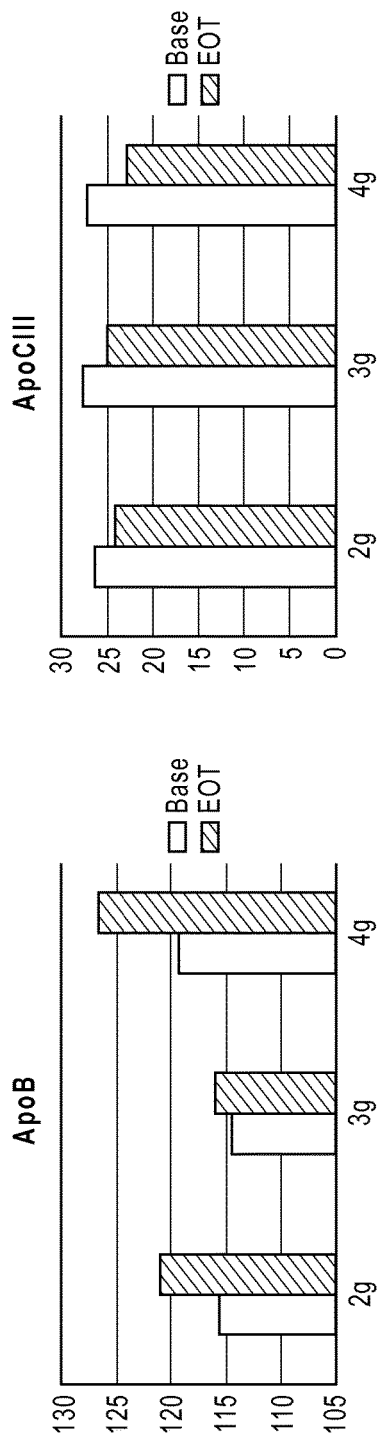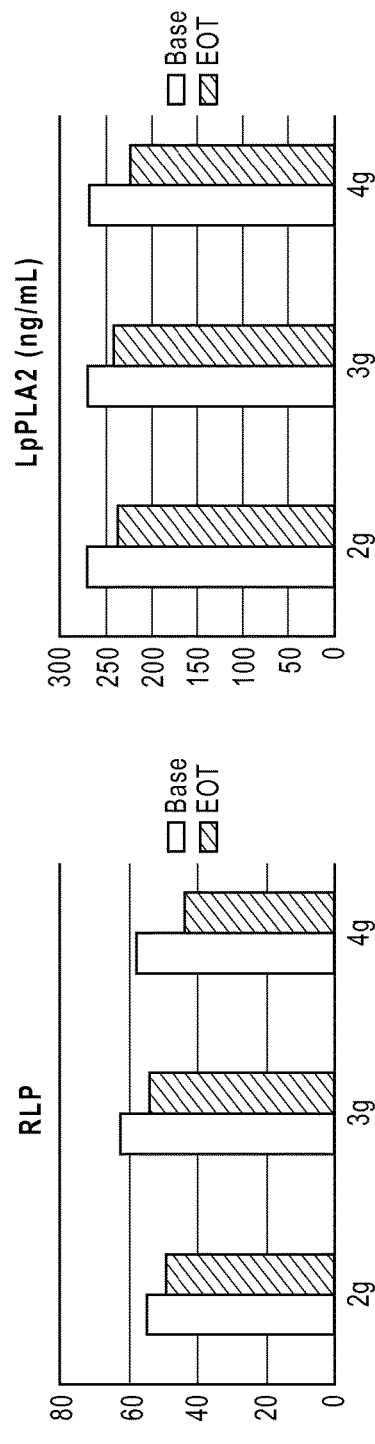

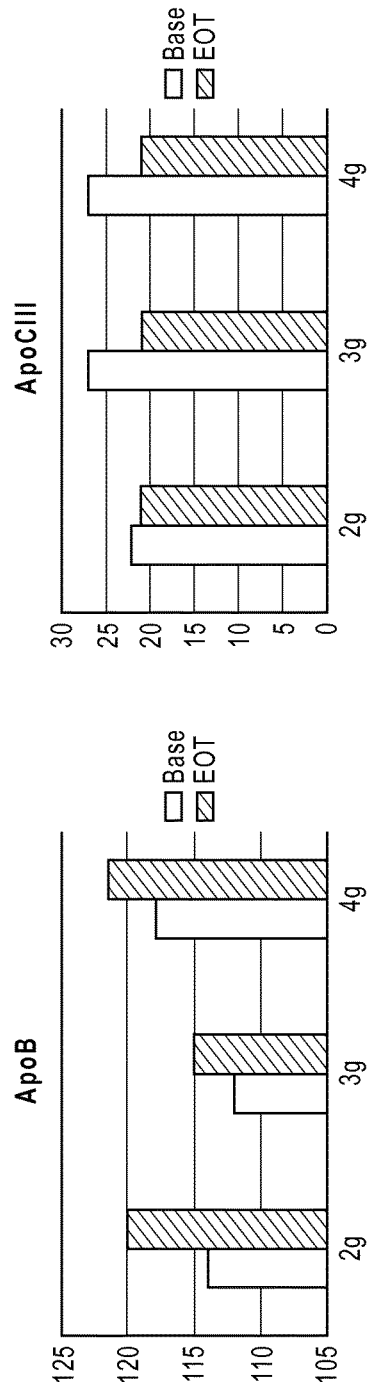
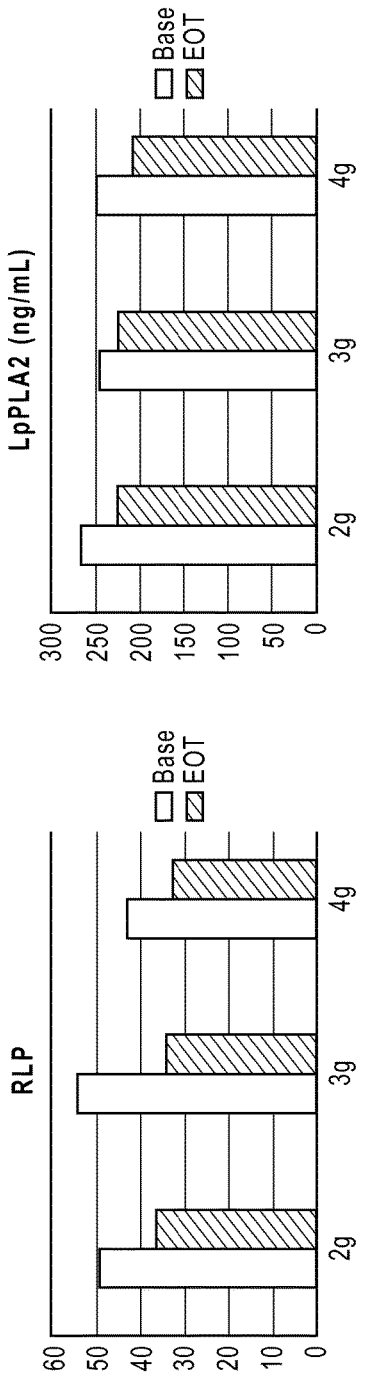

DPA-ENRICHED COMPOSITIONS OF OMEGA-3 POLYUNSATURATED FATTY ACIDS IN FREE ACID FORM

1. CROSS-REFERENCE TO RELATED APPLICATIONS

This application is a continuation of U.S. patent application Ser. No. 13/734,846, filed Jan. 4, 2013 (now U.S. Pat. No. 9,050,308), which claims the benefit under 35 U.S.C. § 119(e) of U.S. Provisional Application Nos. 61/583,796, filed Jan. 6, 2012; 61/664,047, filed Jun. 25, 2012; 61/669,940, filed Jul. 10, 2012; 61/680,622, filed Aug. 7, 2012; 61/710,517, filed Oct. 5, 2012; and 61/713,388, filed Oct. 12, 2012, the contents of all of which are incorporated herein by reference in their entireties.

2. BACKGROUND

Pharmaceutical compositions rich in omega-3 ("ω-3" or "n-3") polyunsaturated fatty acids ("PUFAs") are being developed to treat a variety of clinical indications.

These products, which are derived from natural sources, typically fish oils, are heterogeneous compositions, and comprise various species of omega-3 PUFAs, omega-6 PUFAs, and other minor components, including mono-unsaturated and saturated fatty acids. The observed clinical effects are typically attributed to the composition as a whole, although the most prevalent of the PUFA species present in the mixture, usually EPA and DHA, are believed to contribute a substantial portion of the observed clinical effect. Because they are heterogeneous compositions, the products are defined to include certain obligate polyunsaturated fatty acid species, each within a defined percentage tolerance range. The compositions are further defined to limit certain undesired components, both those originating in the natural source, such as certain environmental contaminants, and those potentially created in the refining process.

The optimal composition likely differs as among intended clinical indications. Even for the first approved clinical indication, however, treatment of severe hypertriglyceridemia (TGs>500 mg/dl), the optimal composition has not yet been defined.

Thus, the first-approved pharmaceutical composition for treatment of severe hypertriglyceridemia comprises the omega-3 PUFA species eicosapentaenoic acid ("EPA") and docosahexaenoic acid ("DHA") in the form of ethyl esters in weight percentages of approximately 46:38 (EPA:DHA), with EPA and DHA together accounting for approximately 84% of all PUFA species in the composition. By contrast, the more recently approved product, Vascepa® (previously known as AMR101), which is approved for the same clinical indication, is >96% pure EPA in the ethyl ester form, with substantially no DHA. The nutraceutical product, OMAX3, sold as a dietary supplement and promoted in part to lower triglyceride levels, comprises EPA and DHA in a weight ratio of about 4.1:1, wherein the EPA and DHA are likewise in the ethyl ester form, the formulation being more than 84% EPA and DHA by weight and more than 90% omega-3 fatty acids by weight.

These wide variations in composition reflect continuing uncertainty as to the optimal composition for this clinical indication.

The uncertainty is due, in part, to competing clinical goals. For example, the omega-3 PUFA species, DHA, is known to be more potent in lowering serum triglycerides than is EPA, but is known to have a greater tendency to increase LDL levels, Mori et al., *Am. J. Clin. Nutr.* 71:1085-94 (2000), Grimsgaard et al., *Am. J. Clin. Nutr.* 66:649-59 (1997); elevation of LDL has been thought to be clinically disfavored in subjects with elevated cardiovascular risk. Although decrease in platelet aggregation and thrombogenesis by omega-3 PUFAs is often clinically desired, the potential increase in bleeding time has prompted some to propose adding a certain amount of the omega-6 PUFA species, arachidonic acid ("AA"), to pharmaceutical compositions that are rich in omega-3 PUFAs. See US pre-grant publication no. 2010/0160435.

The difficulty in defining an optimal composition is also due in part to enzymatic interconversion among certain omega-3 PUFA species, and to competition between omega-3 and omega-6 polyunsaturated fatty acids for shared enzymes in their respective biosynthetic pathways from medium chain dietary PUFAs (see FIG. 1).

A further challenge in designing an optimal composition is variation in bioavailability of orally administered PUFA compositions. Absorption of PUFAs in the form of ethyl esters is known, for example, to depend on the presence of pancreatic lipase, which is released in response to ingested fats. Absorption of PUFA ethyl esters is therefore inefficient, and is subject to substantial variation, both among subjects and in any individual subject, depending on dietary intake of fat. See Lawson et al., "Human absorption of fish oil fatty acids as triacylglycerols, free acids, or ethyl esters," *Biochem Biophys Res Commun.* 152:328-35 (1988); Lawson et al., *Biochem Biophys Res Commun.* 156:960-3 (1988). Absorption is particularly reduced in subjects on low-fat diets, a diet advocated for subjects with elevated serum triglyceride levels or cardiovascular disease.

For any specifically desired PUFA pharmaceutical composition, the refining process is designed to produce a final product having the obligate fatty acid components within pre-defined percentage tolerance ranges and to limit certain undesired components to levels below certain pre-defined tolerance limits, with sufficient yield to make the process commercially feasible and environmentally sustainable. Differences in the desired final composition dictate differences in the refining process.

Various known process steps present trade-offs that make composition-specific adaptation and optimization of the refining process difficult, however. For example, urea inclusion complexation (clathration) in the presence of ethanol is often used to remove saturated and mono-unsaturated long chain fatty acids, increasing the relative proportion of desired long chain omega-3 polyunsaturated fatty acids in the resulting composition. Too little urea reduces long chain omega-3 PUFA enrichment. Excess urea, however, can lead to concentration of unwanted components, and has the potential to lead, at any given temperature and reaction time, to increased production of ethyl carbamate, a carcinogen that is impermissible above certain defined low limits. Existing alternatives to urea complexation, however, present other difficulties.

There is, therefore, a need for improved pharmaceutical compositions rich in omega-3 polyunsaturated fatty acids, especially for treatment of hypertriglyceridemia and mixed dyslipidemias, and for improved processes for refining such compositions from fish oil.

3. SUMMARY

In a first aspect, the present disclosure provides DPA-enriched pharmaceutical compositions of omega-3 polyunsaturated fatty acids in free acid form. Enrichment in DPA content was an unintended and unexpected consequence of the commercial-scale production process. These DPA-enriched pharmaceutical compositions have been demonstrated to have exceptional pharmacological and clinical efficacy in in vitro experiments and in human clinical trials.

Accordingly, in another aspect, methods of treatment are provided. In one series of treatment embodiments, methods of treating severe hypertriglyceridemia (TGs>500 mg/dL) are provided. In another series of treatment embodiments, methods of treating hypertriglyceridemia (200 mg/dL-500 mg/dL) by adjunctive administration of a statin and the pharmaceutical compositions described herein are provided. Further treatment methods include, inter alia, treatments to increase plasma EPA:AA ratios, treatments to decrease ApoCIII levels, and treatments to reduce or prevent resistance to platelet aggregation inhibitors.

Also disclosed herein are methods of making the pharmaceutical compositions at commercial scale, including methods that include a urea complexation step in which compositionally-constrained batches of transesterified intermediate feedstock are subjected to a urea complexation step using urea amounts within ranges determined by a new process algorithm.

4. BRIEF DESCRIPTION OF THE FIGURES

Figure 3A:
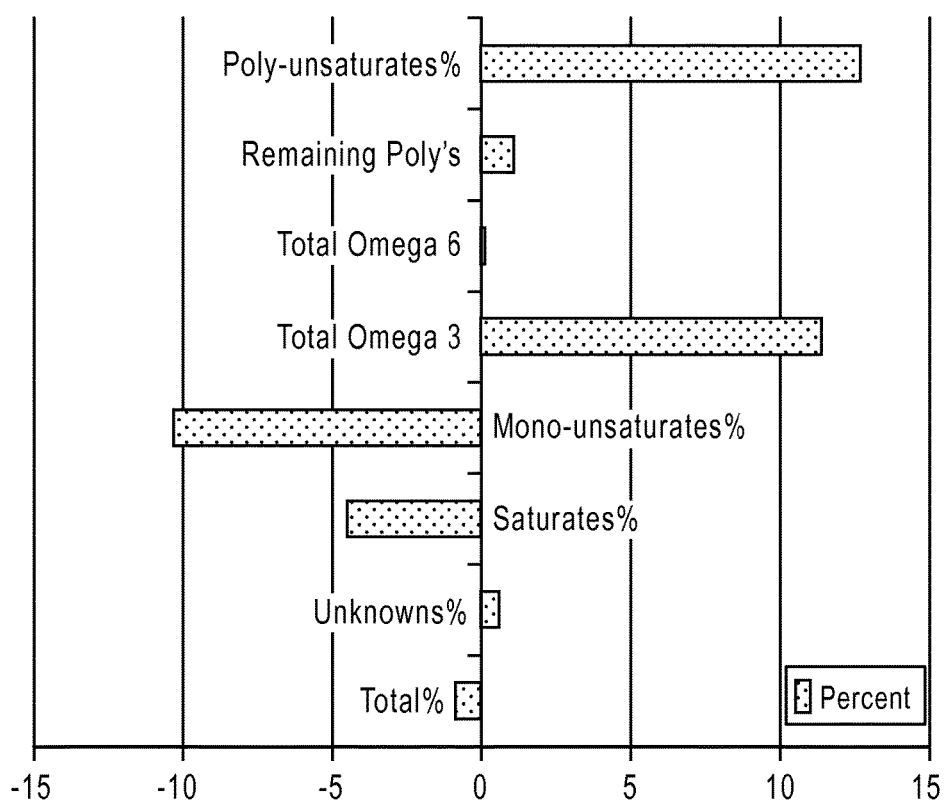

FIG. 3A plots the average relative purification of classes of fatty acids by a urea complexation step in which algorithmically-determined amounts of urea are added to compositionally-defined intermediate feedstock of PUFA ethyl esters.

Figure 3B:
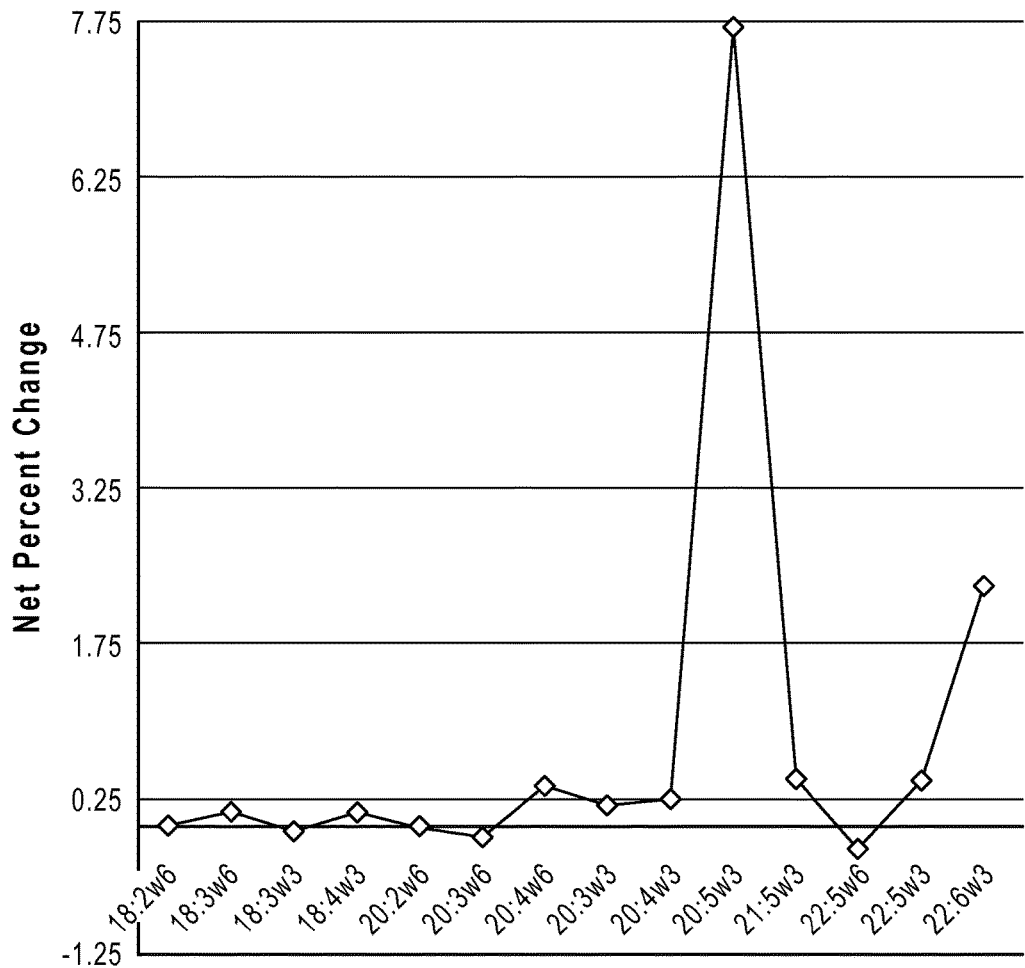

FIG. 3B illustrates the average differential purification of individual species of omega-3 and omega-6 PUFA ethyl esters when algorithmically-determined amounts of urea are added to compositionally-defined intermediate feedstock of PUFA ethyl esters.

Figure 4:
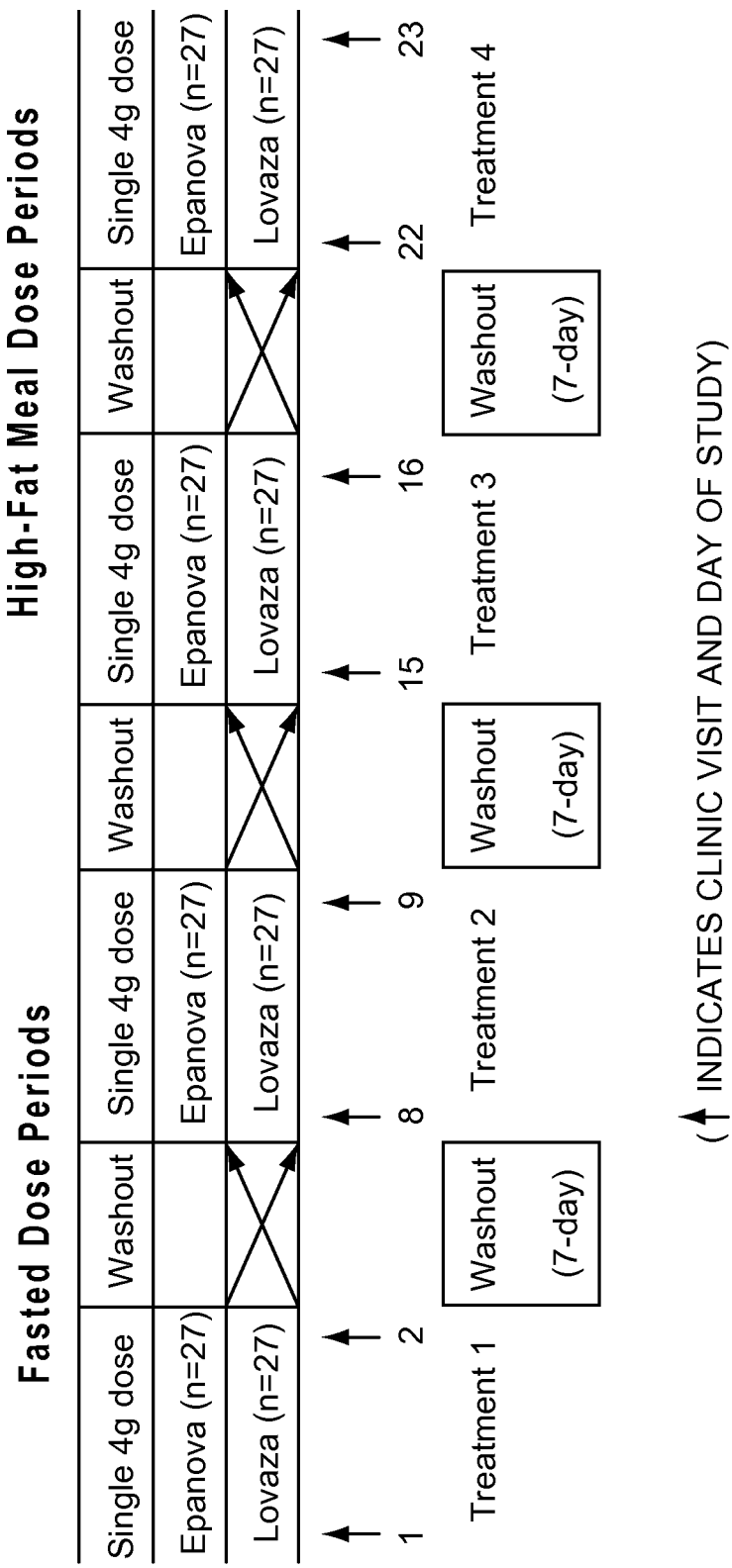

FIG. 4 is a treatment flow diagram illustrating the design of the ECLIPSE clinical study further described in Example 7.

Figure 5:
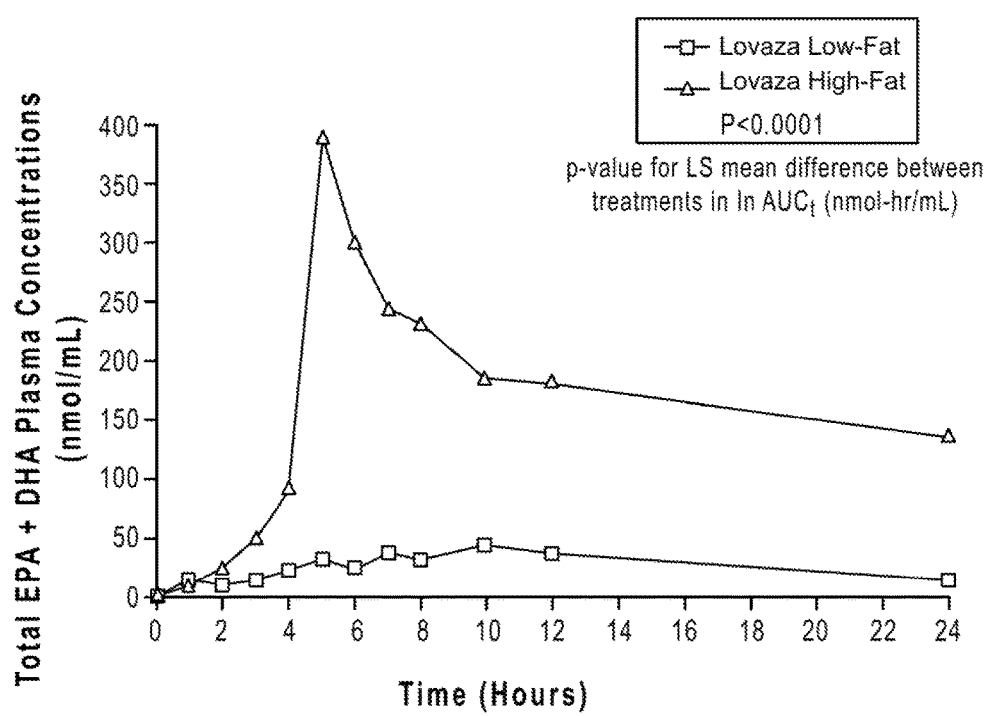

FIG. 5 compares the bioavailability of total EPA+DHA (baseline-adjusted change) following a single dose (4 g) of Lovaza® during the high-fat and low-fat diet periods.

Figure 6:
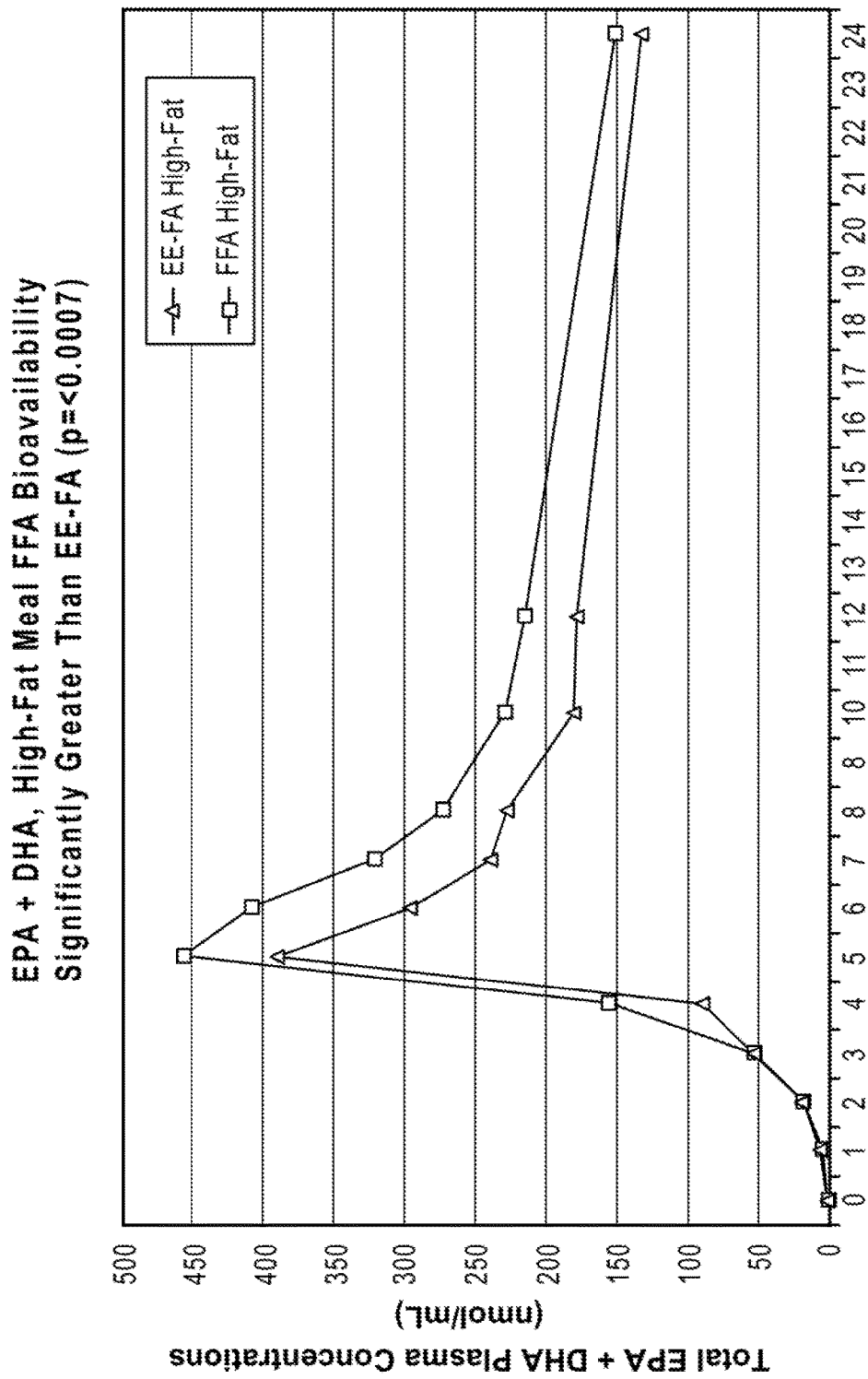

FIG. 6 compares the bioavailability of total EPA+DHA (baseline-adjusted change) following a single dose (4 g) of Lovaza® ("EE-FA") or Epanova®, a DPA-enriched composition of omega-3 PUFAs in free acid form ("FFA"), during the high-fat diet period.

Figure 7:
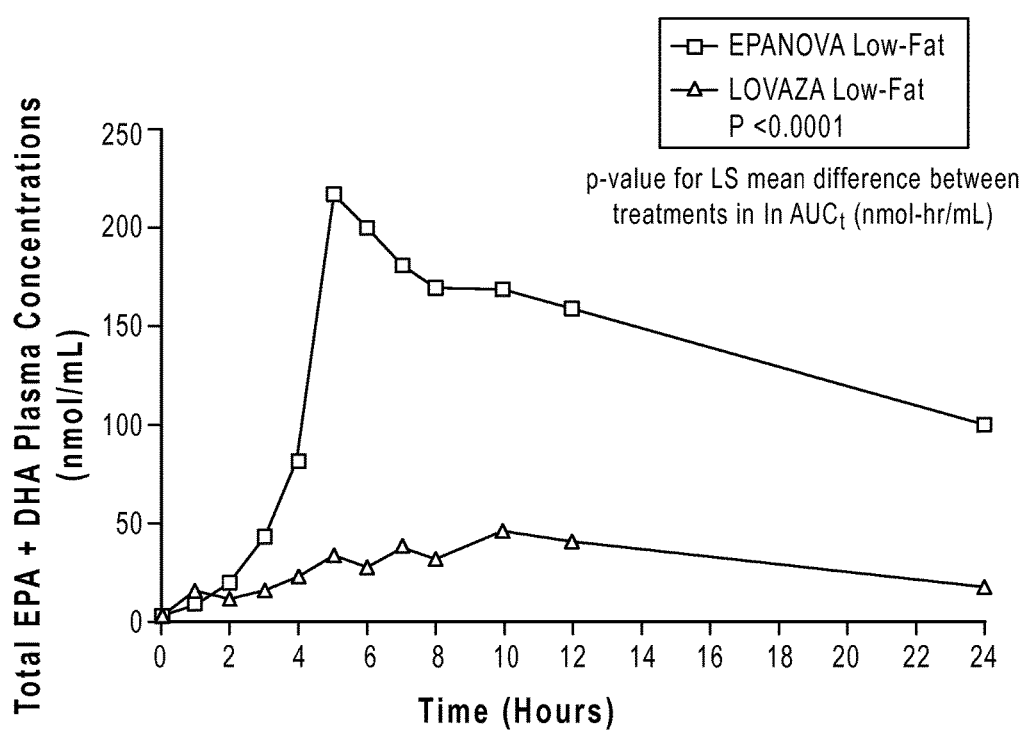

FIG. 7 compares the total plasma EPA+DHA concentrations (baseline-adjusted change) following a single dose (4 g) of Lovaza® or Epanova® during the low-fat diet period.

Figure 8:
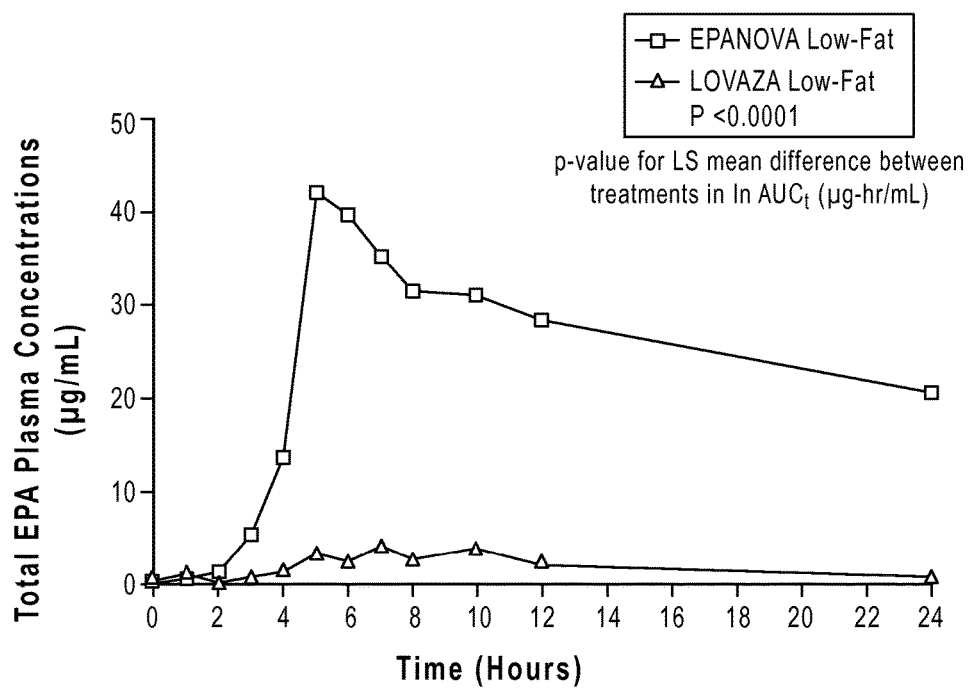

FIG. 8 compares the total plasma EPA concentrations (baseline-adjusted change) following a single dose (4 g) of Lovaza® or Epanova® during the low-fat diet period.

Figure 9:
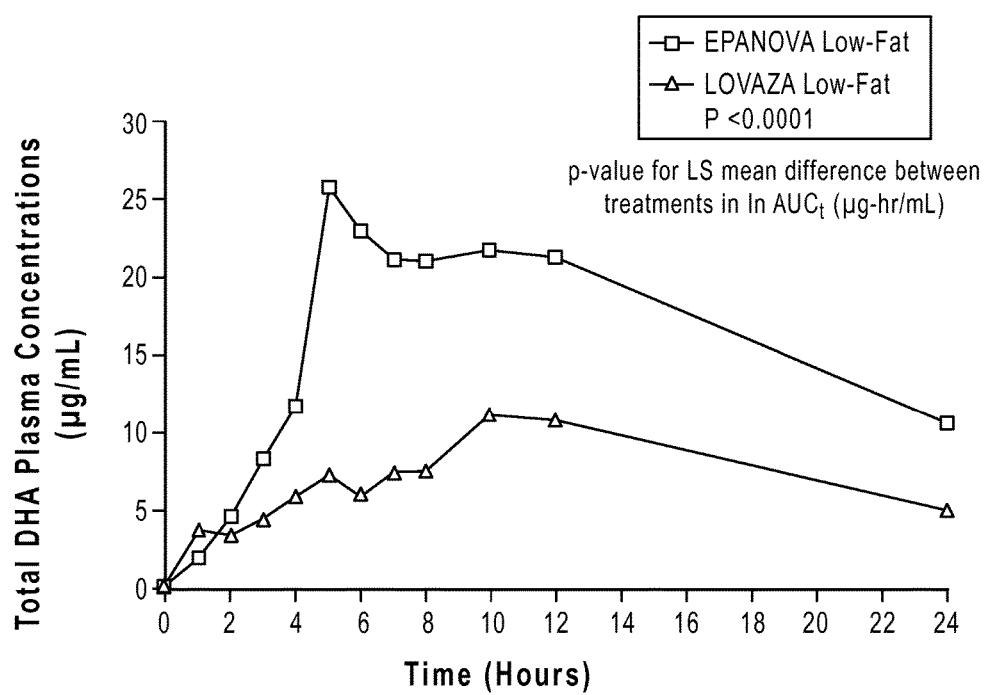

FIG. 9 compares the total plasma DHA concentrations (baseline-adjusted change) following a single dose of (4 g) of Lovaza® or Epanova® during the low-fat diet period.

Figure 10A:
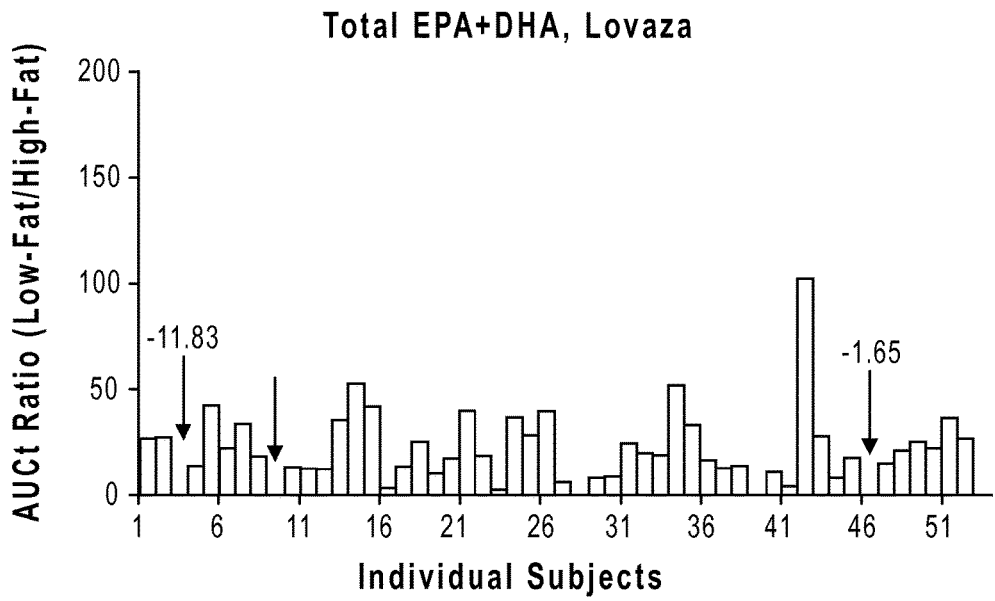
Figure 10B:
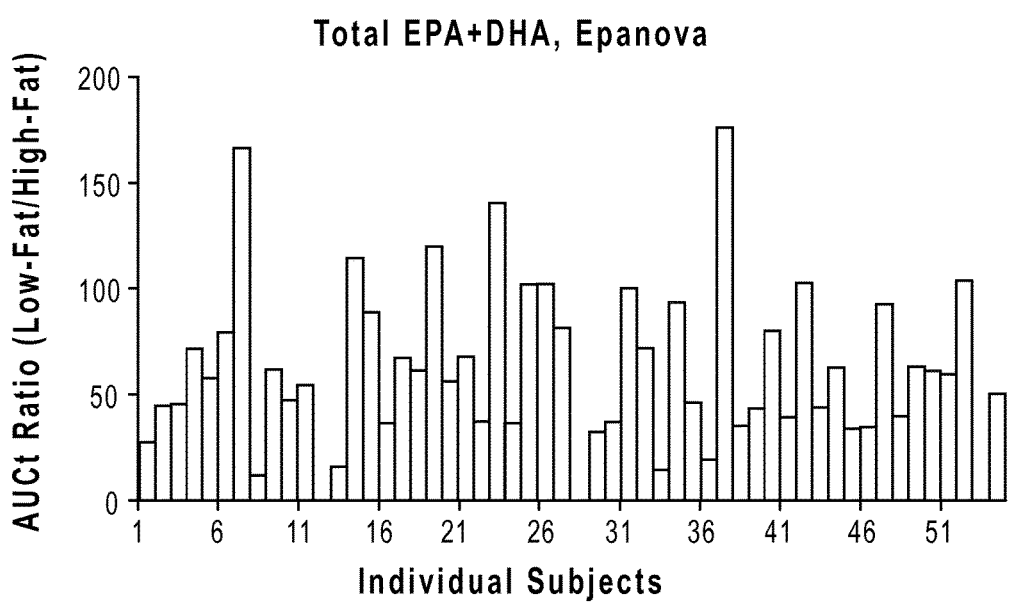

FIGS. 10A and 10B present individual subject $AUC_{0-t}$ responses during the low-fat and high-fat diets expressed as the ratio (%) of low-fat $AUC_{0-t}$ to high-fat $AUC_{0-t}$. Negative ratios were not plotted.

Figure 11:
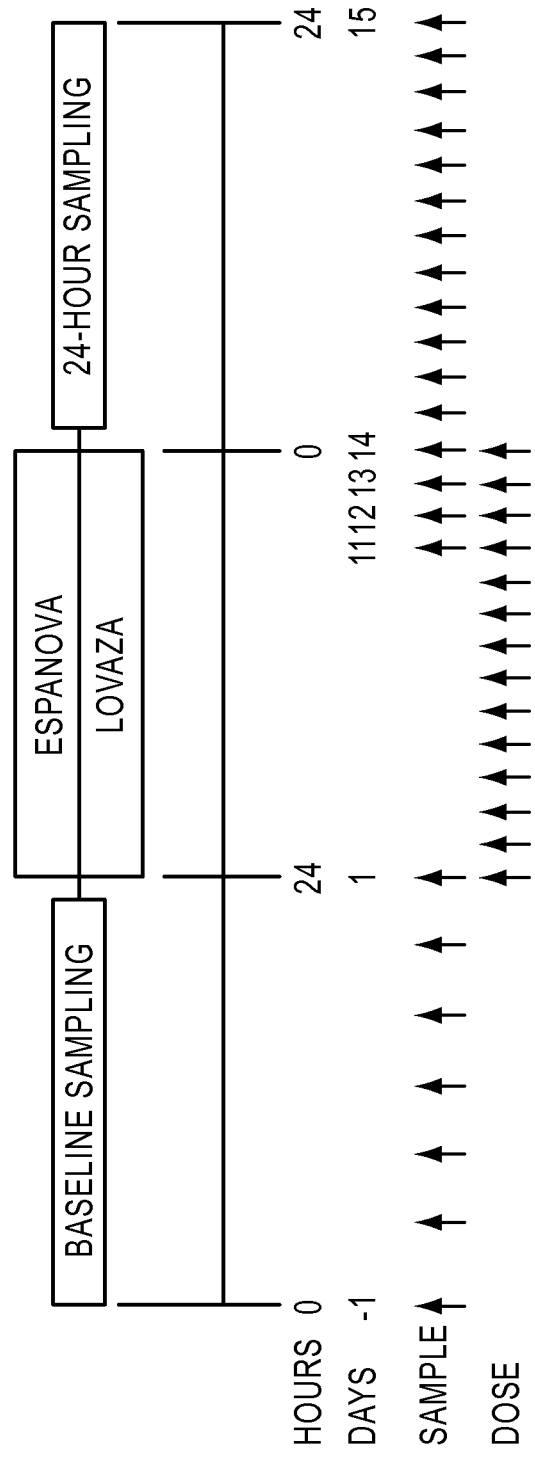

FIG. 11 is a treatment flow diagram illustrating the design of the 14 day comparative bioavailability trial further described in Example 8 (timeline not to scale).

Figure 12A:
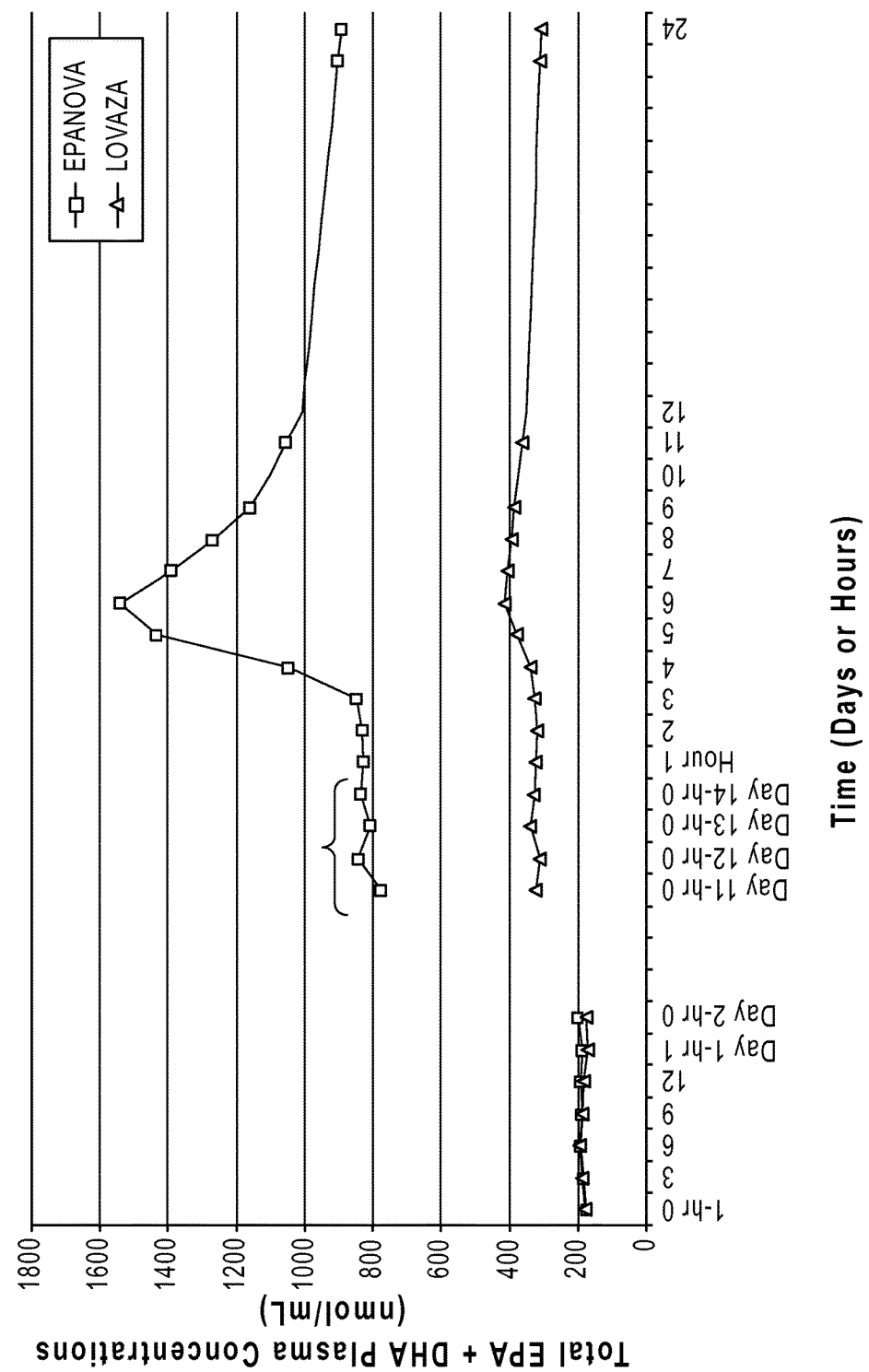

FIG. 12A plots the mean unadjusted total EPA+DHA concentrations versus time (linear scale) for treatment with Lovaza® vs. treatment with Epanova® in the 14 day comparative bioavailability trial further described in Example 8.

Figure 12B:
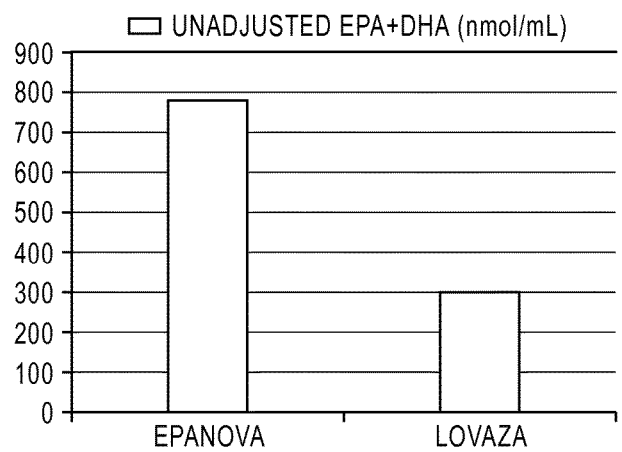

FIG. 12B is a histogram showing the difference in unadjusted EPA+DHA (nmol/mL) for the points bracketed in FIG. 12A.

Figure 13:
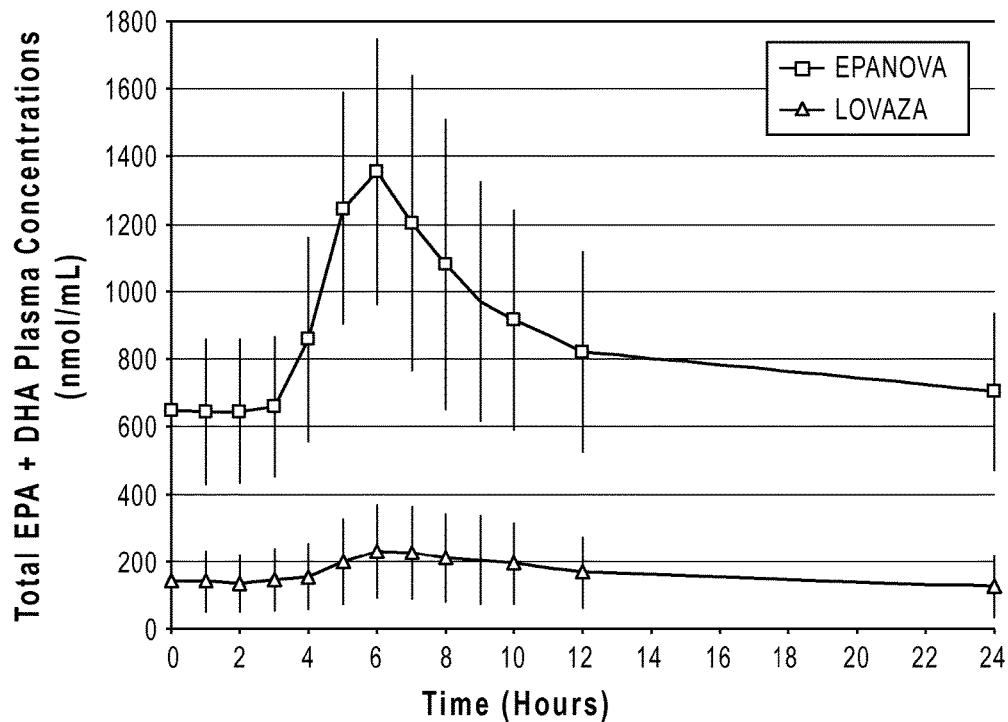

FIG. 13 plots EPA+DHA mean base-line adjusted plasma total EPA+DHA concentrations versus time (linear scale) for treatment with Lovaza® vs. treatment with Epanova® in the 14 day comparative bioavailability study.

Figure 14A:
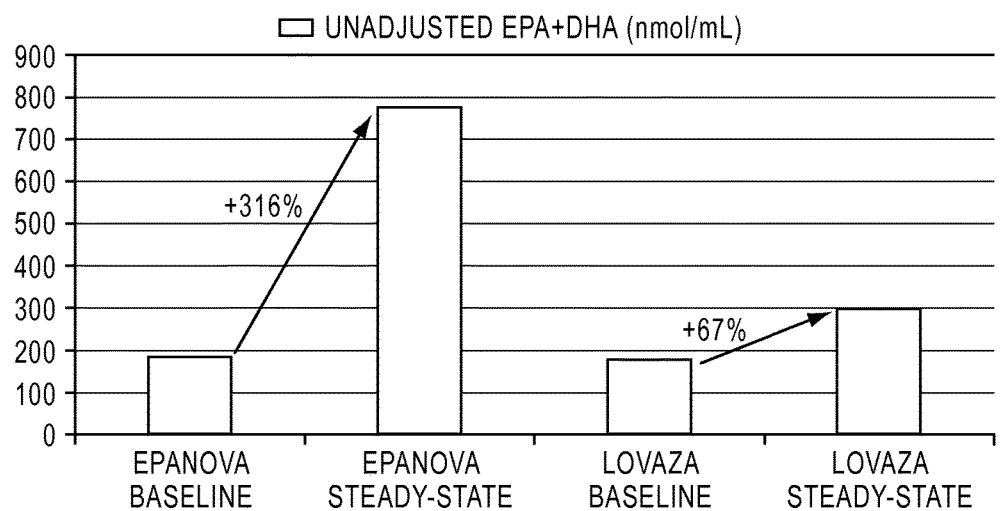

FIG. 14A is a histogram that plots the increases from baseline to steady state in unadjusted blood levels for EPA+DHA in the Lovaza® and Epanova® arms of the 14 day comparative bioavailability study.

Figure 14B:
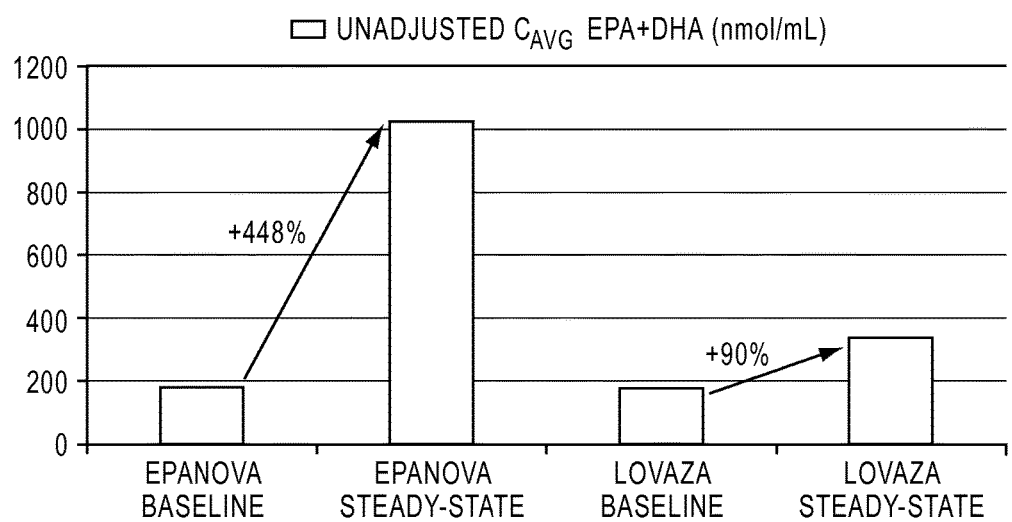

FIG. 14B is a histogram that plots the increases from baseline to steady state in unadjusted $C_{avg}$ for EPA+DHA in the Lovaza® and Epanova® arms of the 14 day comparative bioavailability study.

Figure 15A:
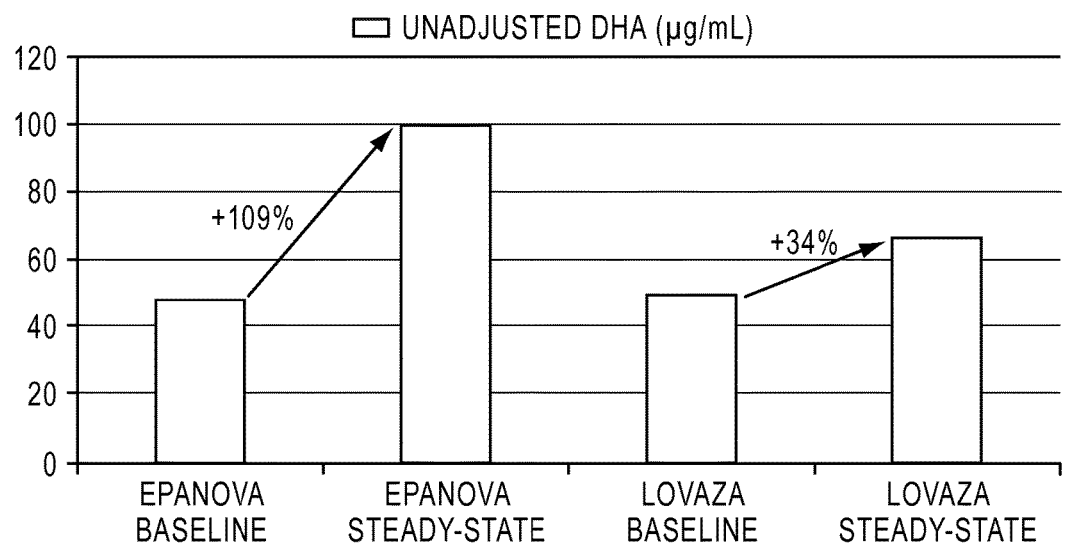

FIG. 15A is a histogram that plots the increases from baseline to steady state for total blood levels of DHA in the Lovaza® and Epanova® arms of the 14 day comparative bioavailability study.

Figure 15B:
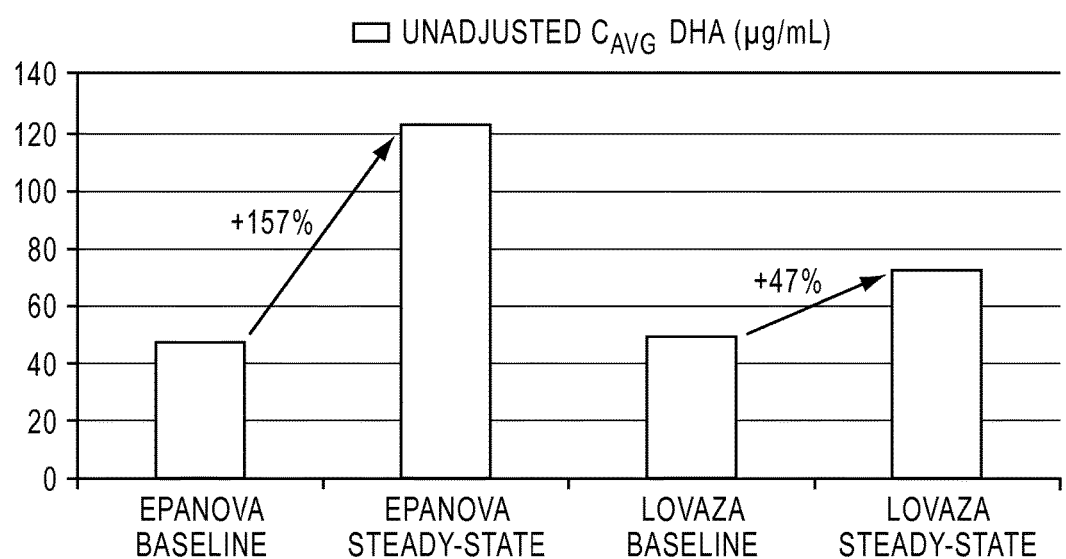

FIG. 15B is a histogram that plots the increases from baseline to steady state for DHA $C_{avg}$ levels in the Epanova® cohort compared to Lovaza® cohort in the 14 day comparative bioavailability study.

Figure 16A:
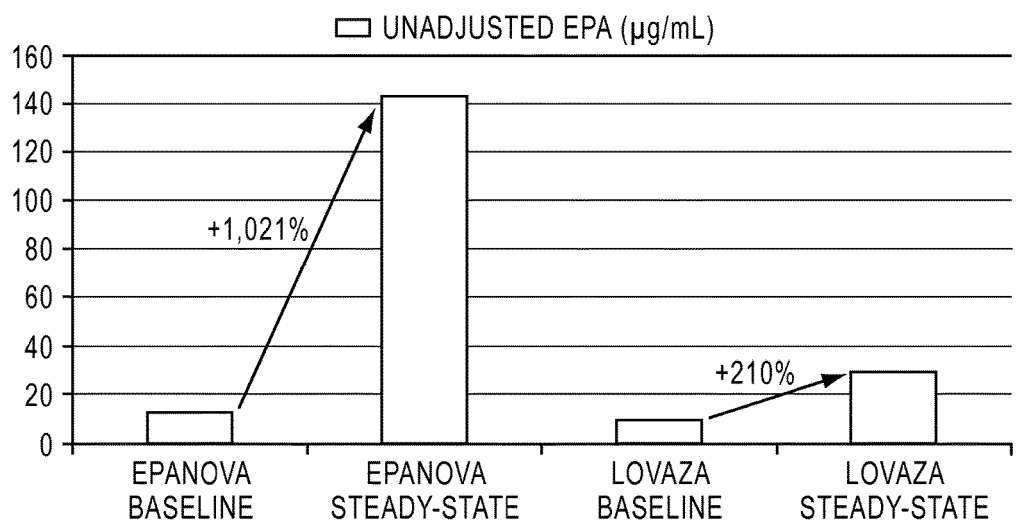

FIG. 16A is a histogram that plots the increases from baseline to steady state for total EPA levels in blood in the Lovaza® and Epanova® arms of the 14 day comparative bioavailability study.

Figure 16B:
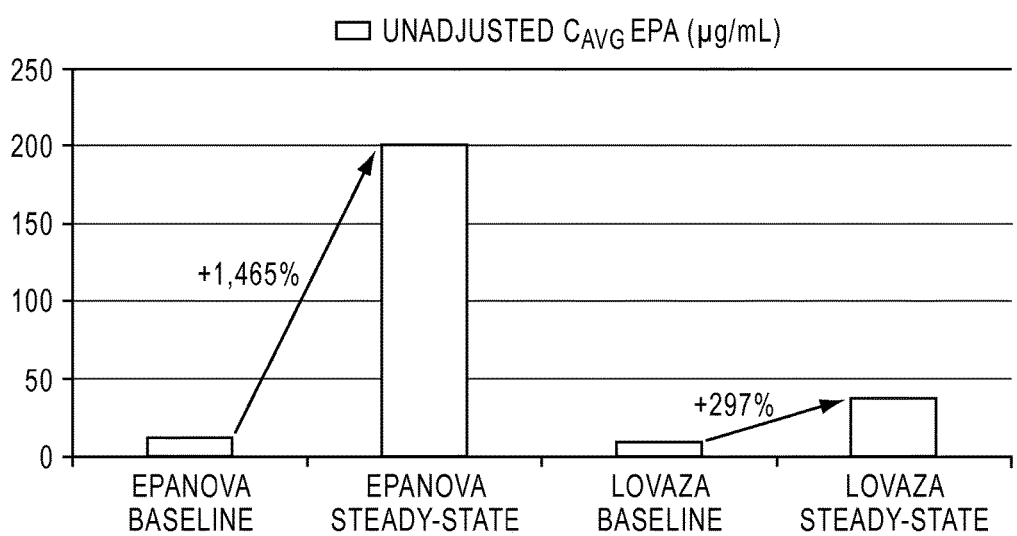

FIG. 16B plots the increases from baseline to steady state for EPA $C_{avg}$ levels in the Epanova® and Lovaza® cohorts in the 14 day comparative bioavailability study.

Figure 17:
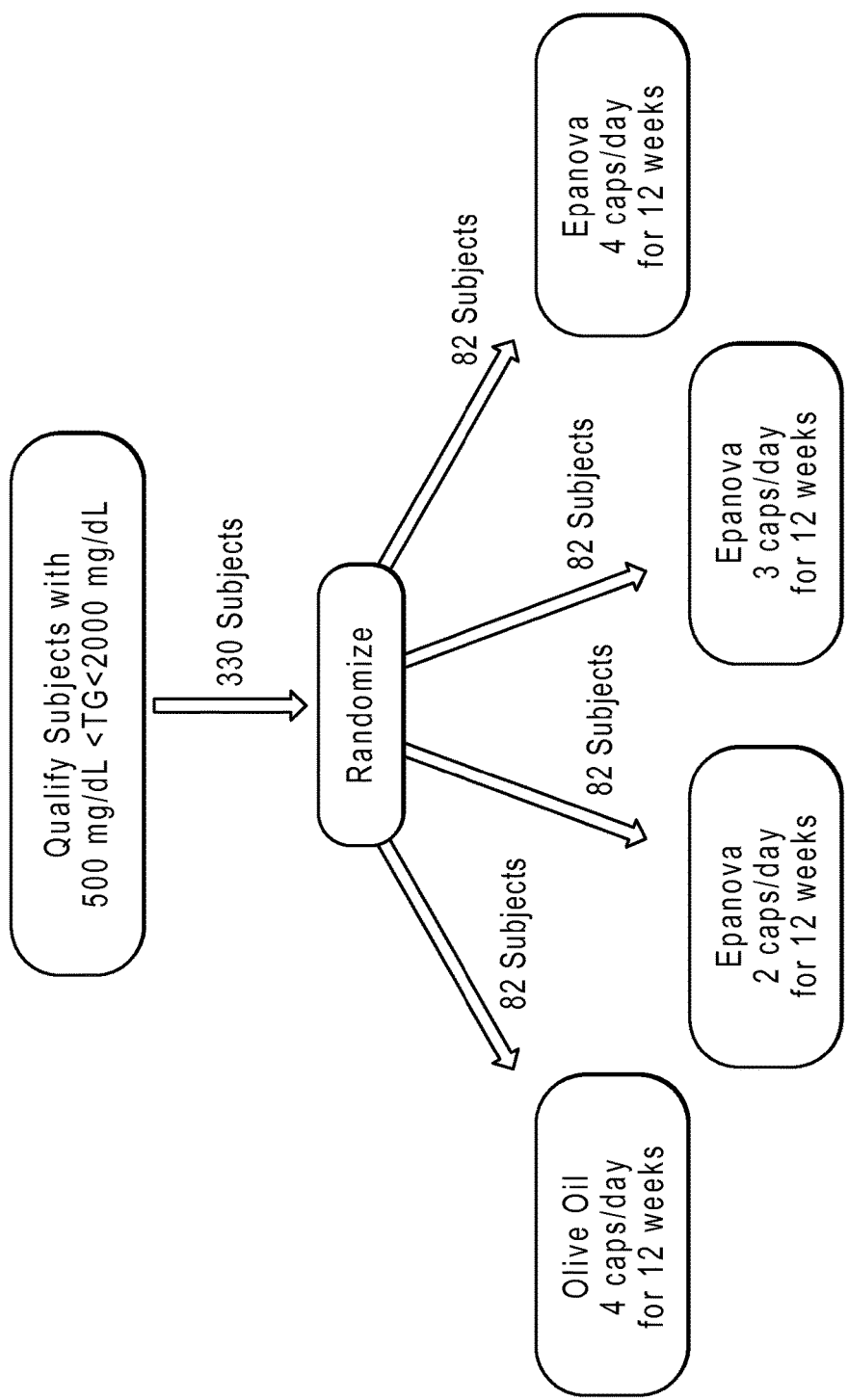

FIG. 17 provides a treatment flow diagram illustrating the design of the EVOLVE study, further described in Example 10.

Figure 18:
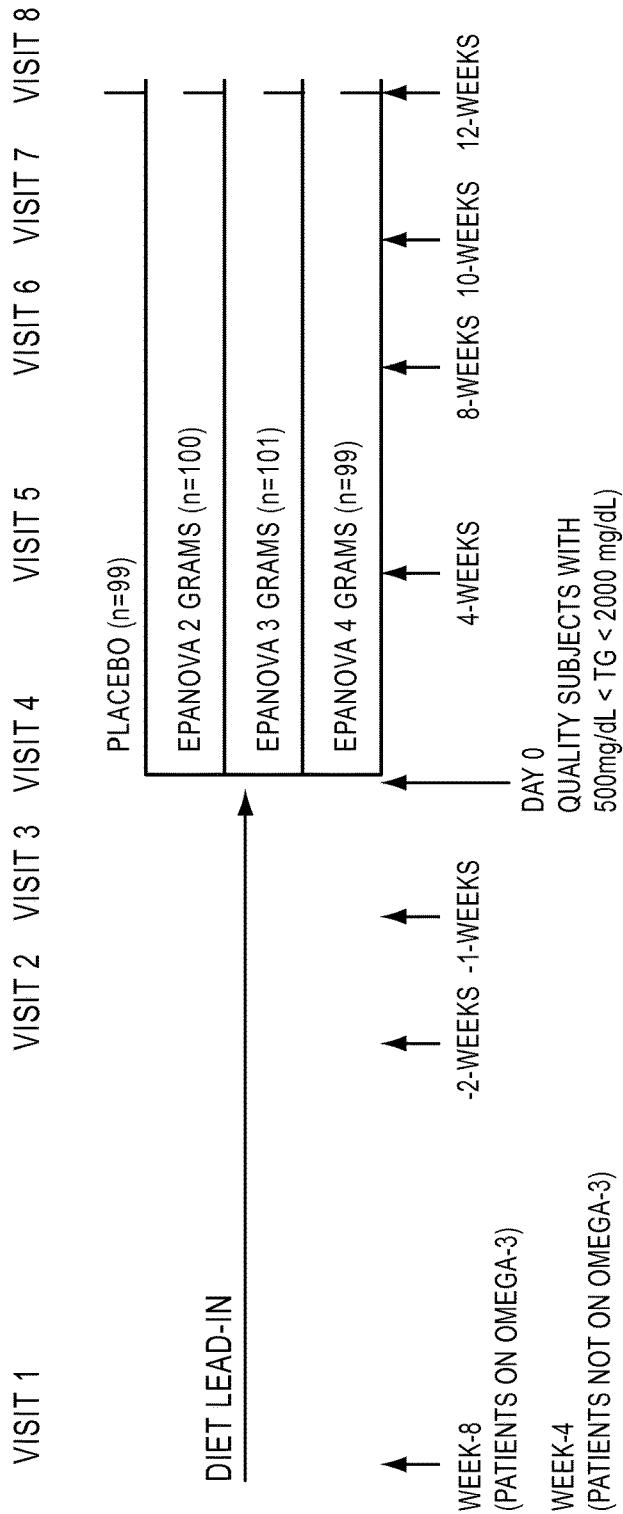

FIG. 18 summarizes the EVOLVE trial design in greater detail, further identifying the timing of study visits.

Figure 19:
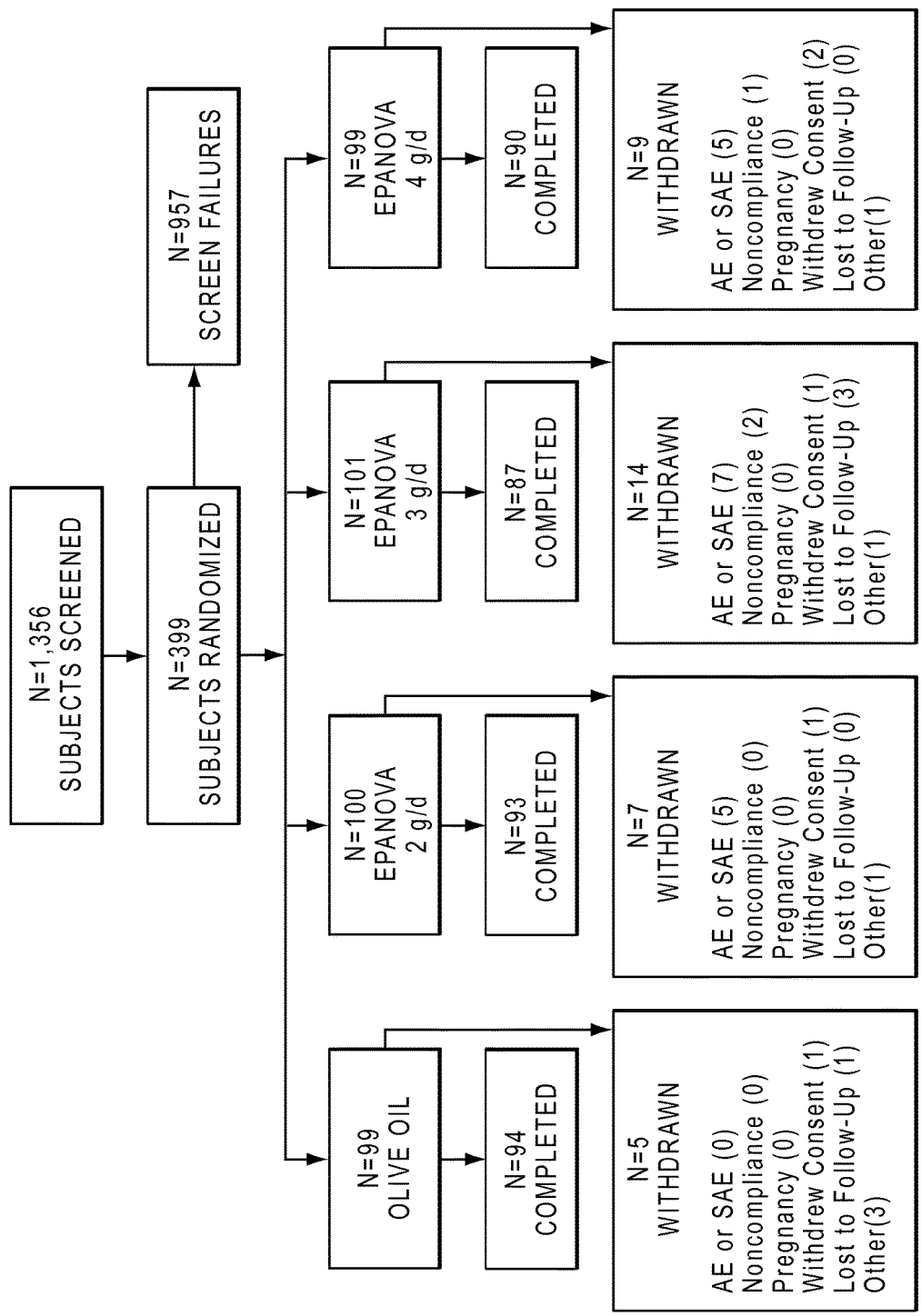

FIG. 19 shows the disposition of subjects in the EVOLVE trial.

FIGS. 20A-20D display average baseline and end-of-treatment ("EOT") plasma levels (in µg/mL) for EPA (FIG. 20A), DHA (FIG. 20B), DPA (FIG. 20C) and AA (FIG. 20D), for each of the treatment arms in the EVOLVE trial.

Figure 20A:
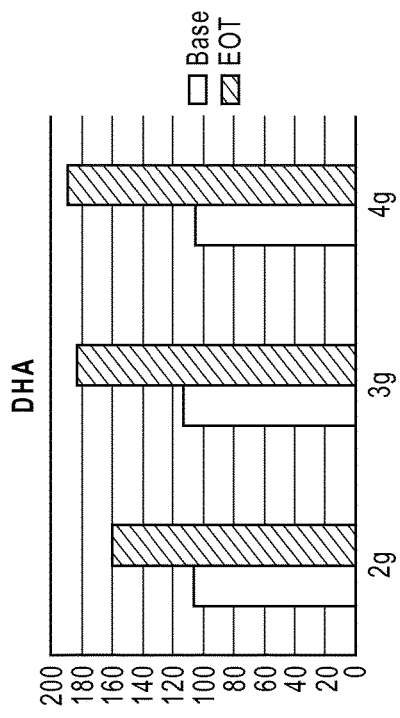
Figure 20B:
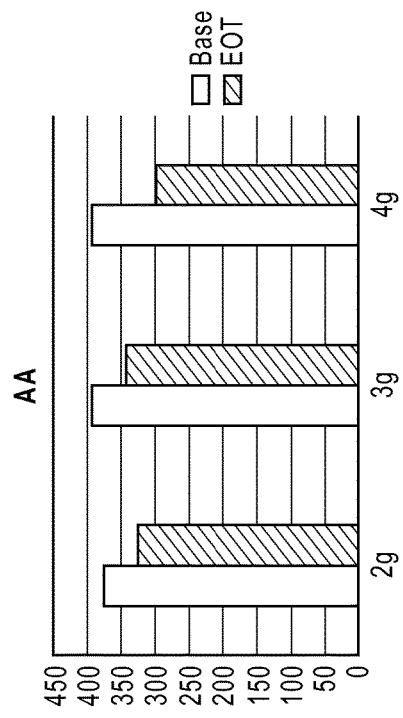
Figure 20C:
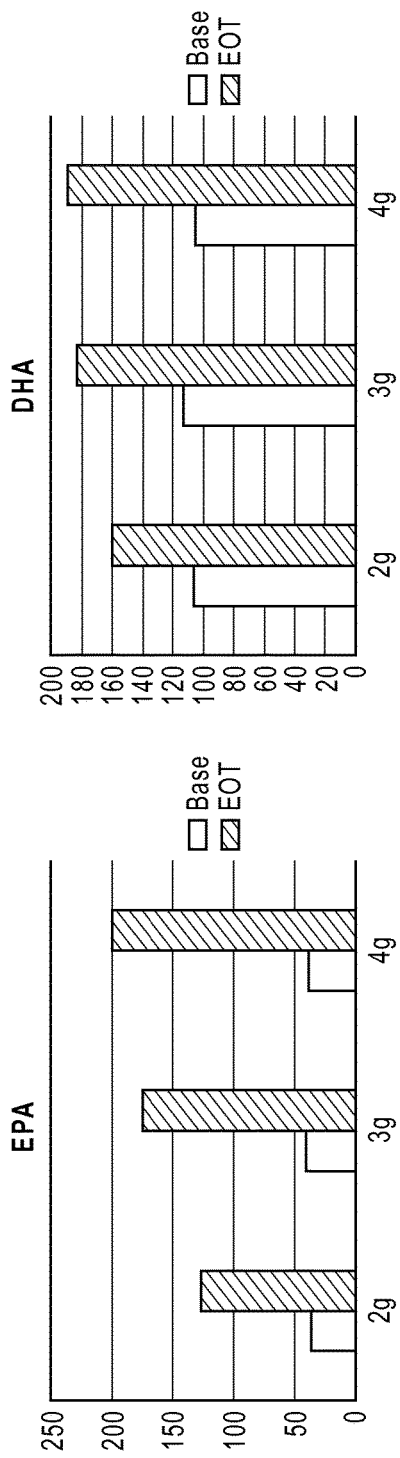
Figure 20D:
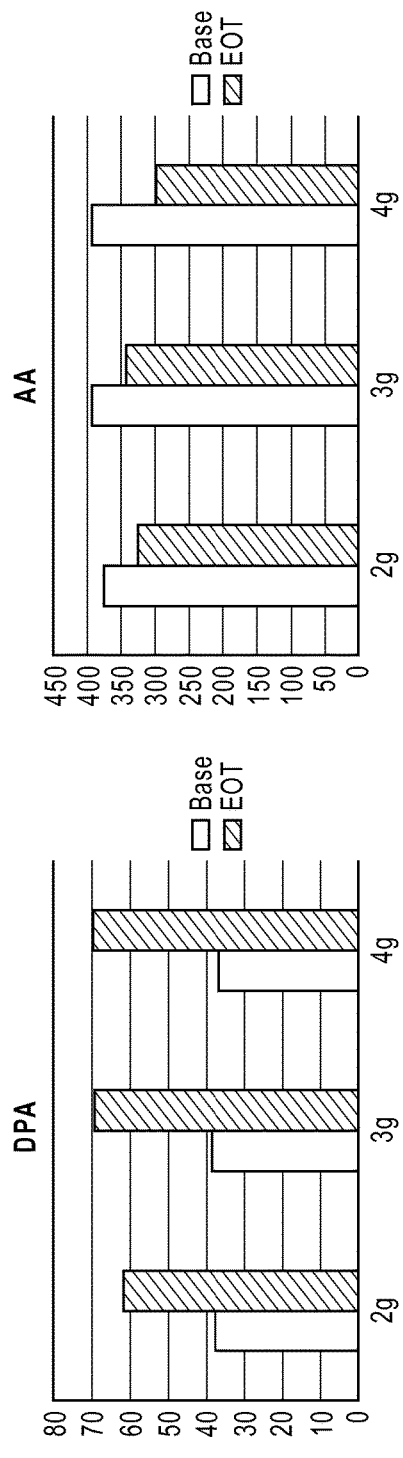
Figure 20E:
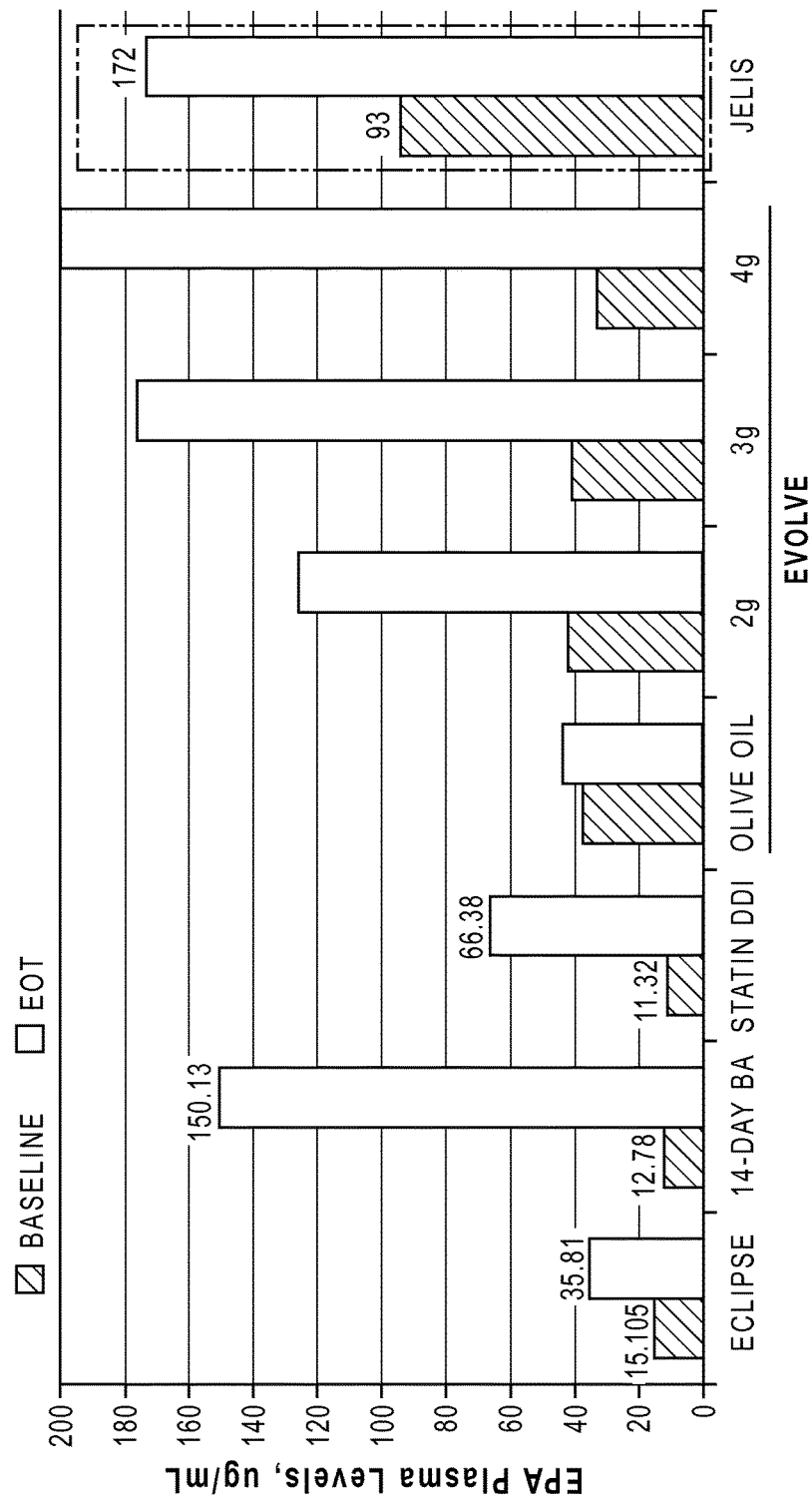

FIG. 20E compares average baseline and EOT EPA levels for the ECLIPSE trial described in Example 7, the 14-day bioavailability study described in Example 8, a statin drug-drug interaction study ("STATIN DDI") described in Example 11, each treatment arm as well as the control arm of the EVOLVE trial described in Example 10, and values earlier reported in the literature for the unrelated JELIS trial ("JELIS"), which used a different omega-3 composition.

FIGS. 21A-21D plot median baseline and end-of-treatment ("EOT") plasma levels (in µg/mL) for EPA (FIG. 21A), DHA (FIG. 21B), DPA (FIG. 21C), and AA (FIG. 21D) in the EVOLVE trial.

Figure 22A:
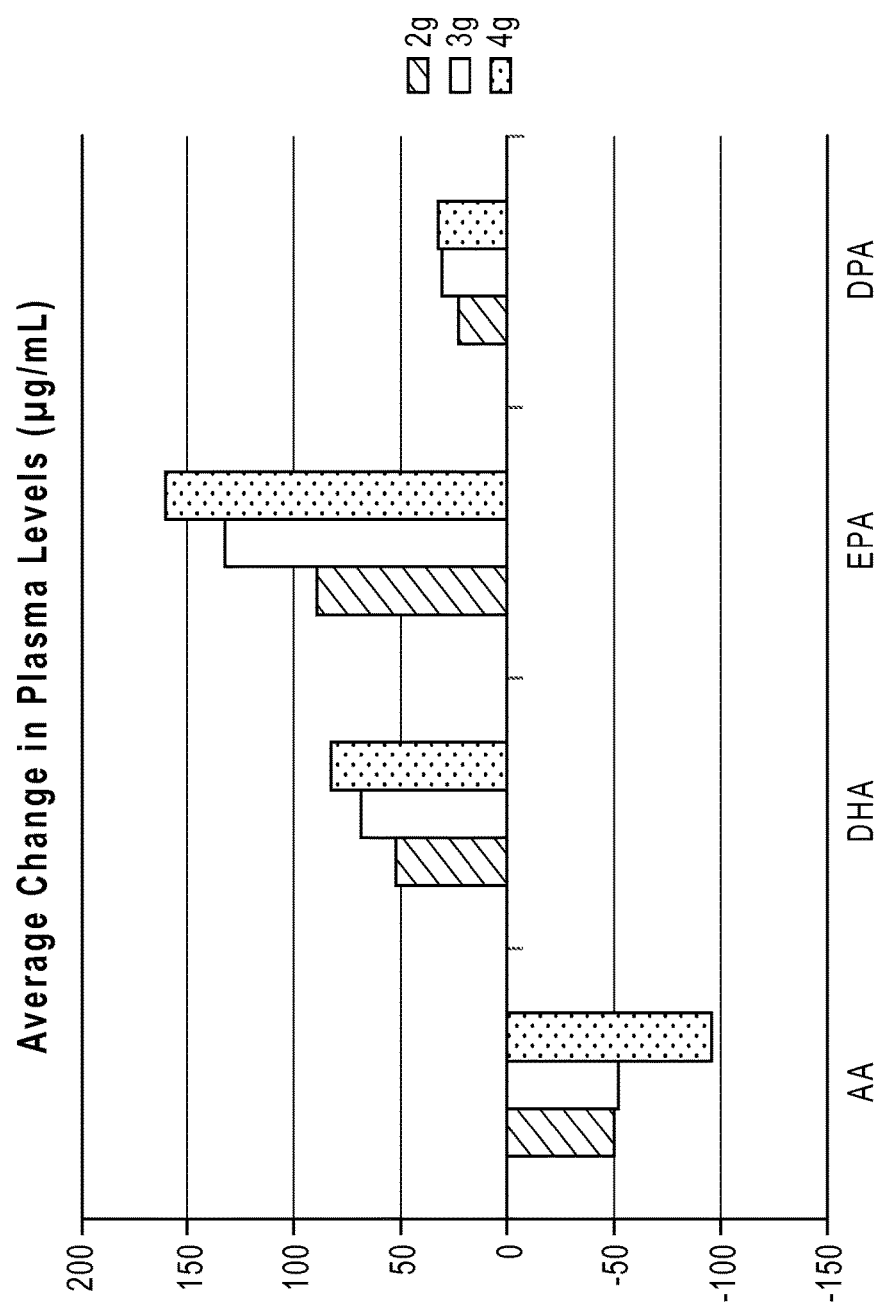
Figure 22B:
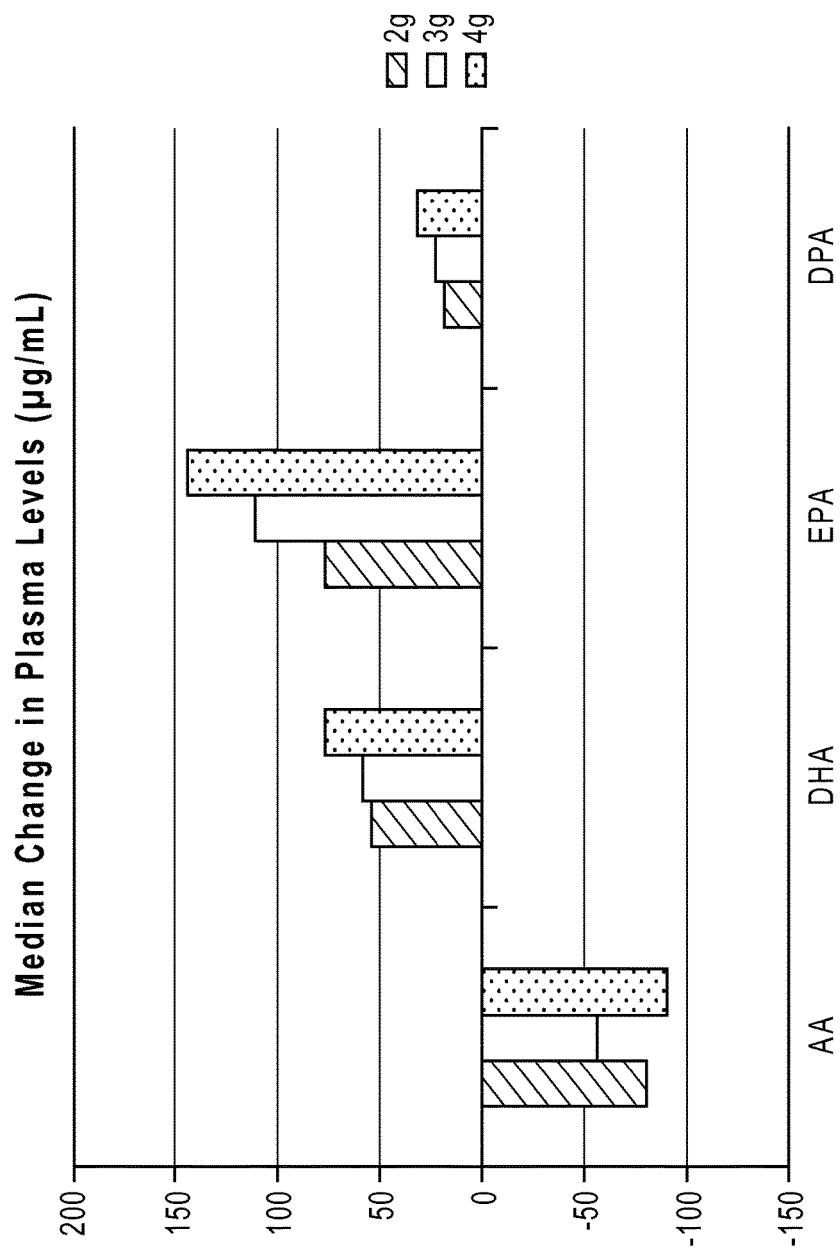

FIGS. 22A and 22B plot change from baseline to EOT in absolute plasma levels (in µg/mL) of AA, DHA, EPA, and DPA, for each of the treatment arms of the EVOLVE trial. FIG. 22A plots average changes; FIG. 22B plots median changes.

Figure 23B:
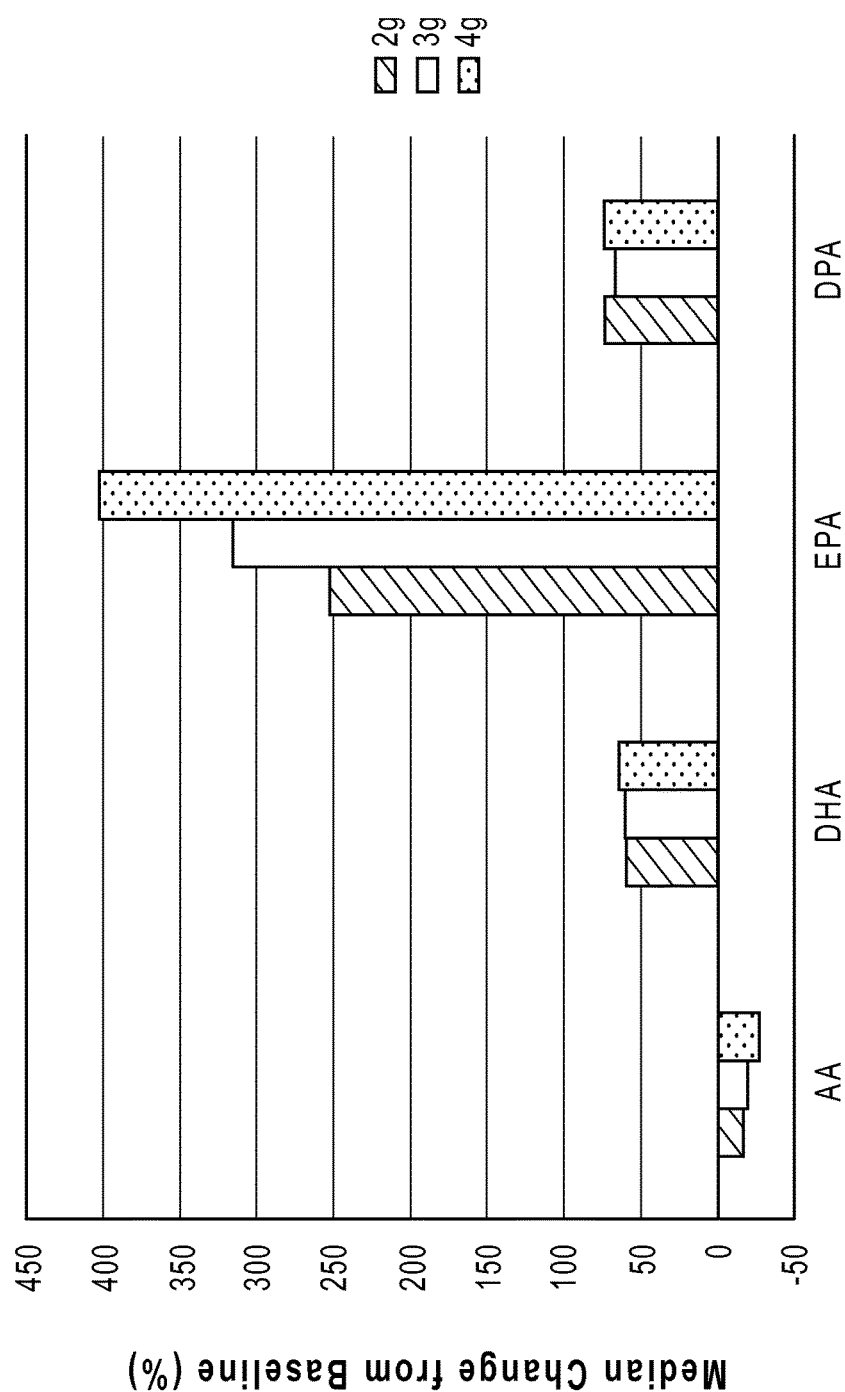

FIG. 23A plots average change from baseline to EOT, as percentage of baseline value, for AA, DHA, EPA, and DPA in each of the treatment arms of the EVOLVE trial. FIG. 23B plots median percent change from baseline to EOT.

Figure 24A:
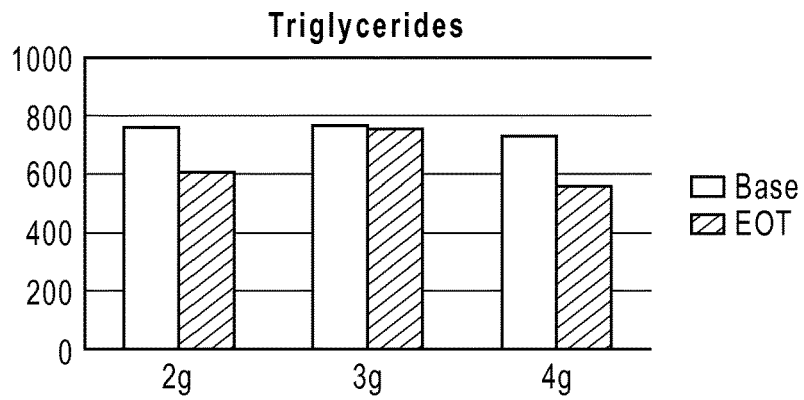
Figure 24B:
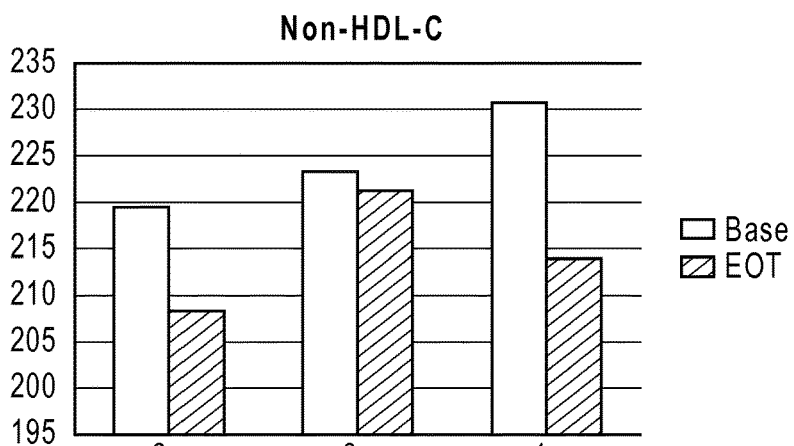
Figure 24C:
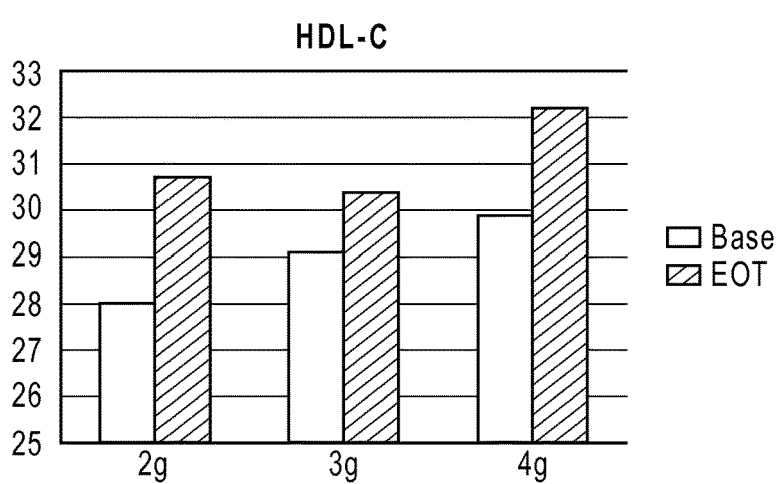
Figure 24D:
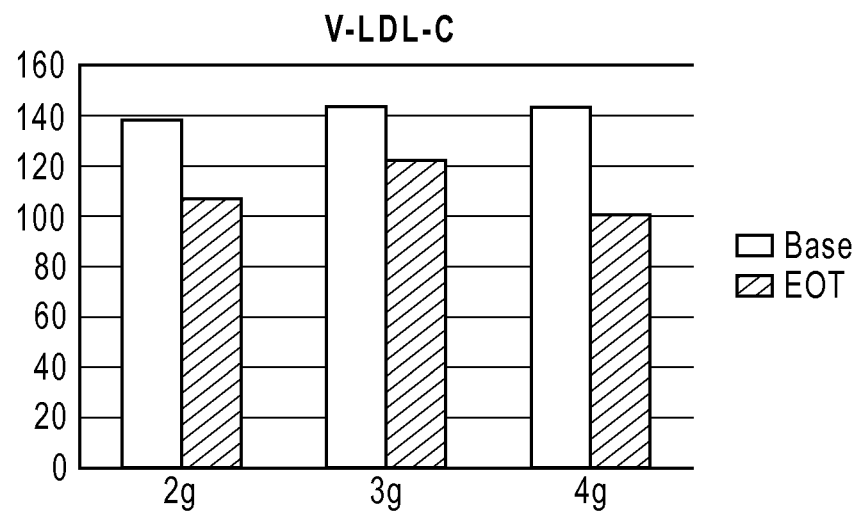
Figure 24E:
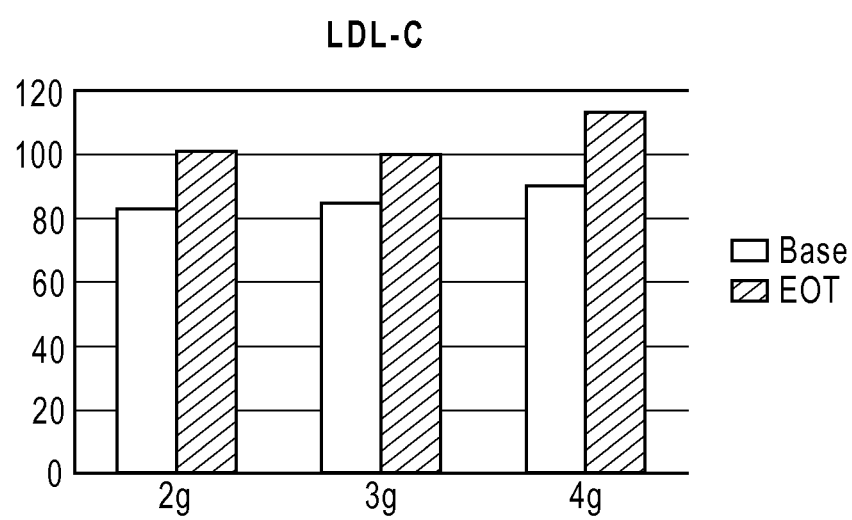

FIGS. 24A-24I plot average baseline and EOT plasma levels (in mg/dL, with the exception of LpPLA2, shown in ng/mL) in the EVOLVE trial for triglycerides (FIG. 24A), Non-HDL-C (FIG. 24B), HDL-C (FIG. 24C), V-LDL-C (FIG. 24D), LDL-C (FIG. 24E), ApoB (FIG. 24F), ApoCIII (FIG. 24G), RLP (FIG. 24H), LpPLA2 (FIG. 24I).

Figure 25A:
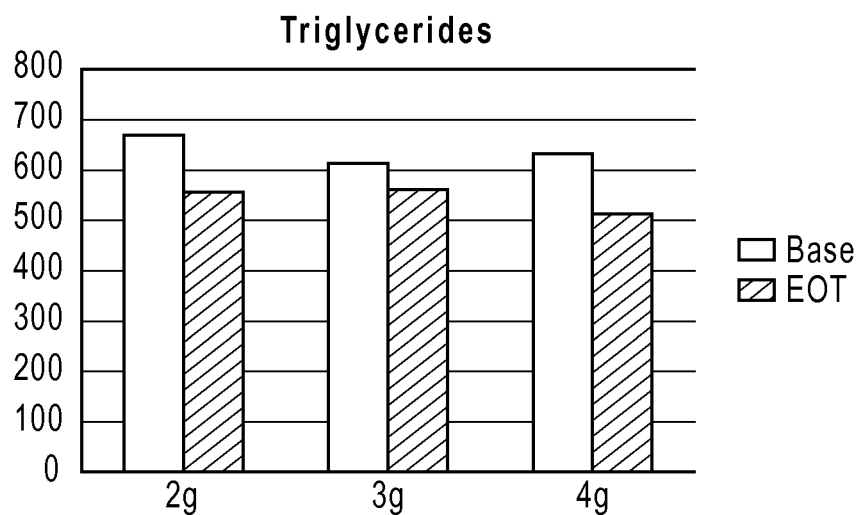
Figure 25B:
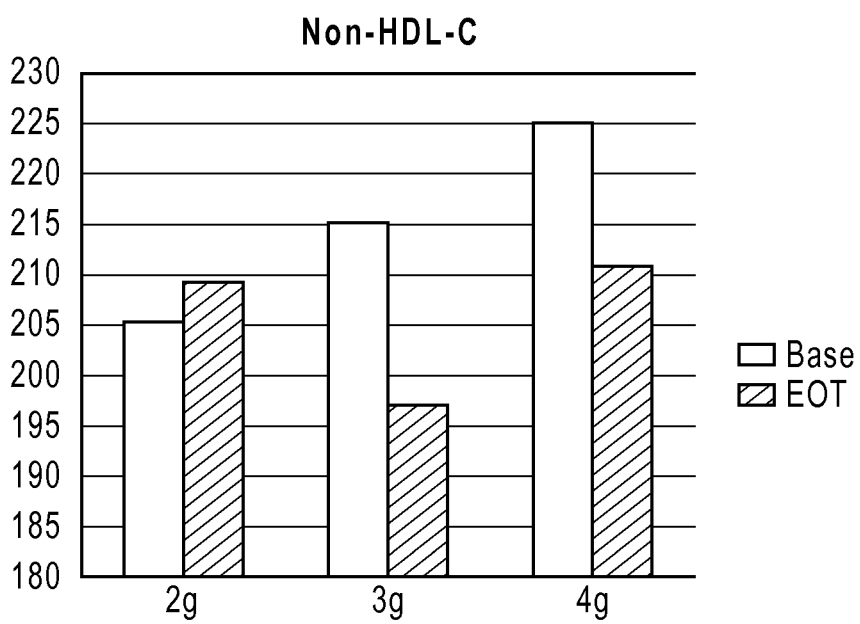
Figure 25C:
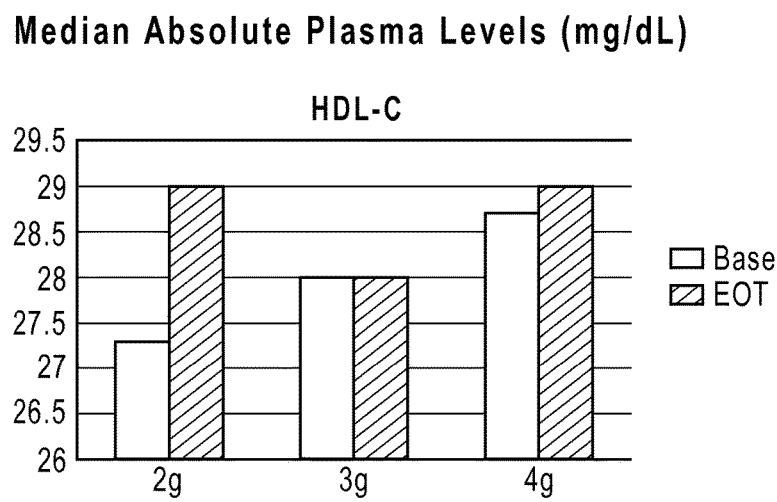
Figure 25D:
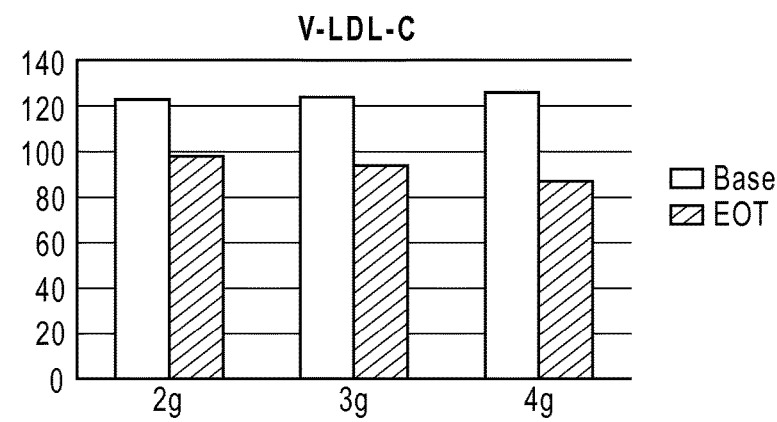
Figure 25E:
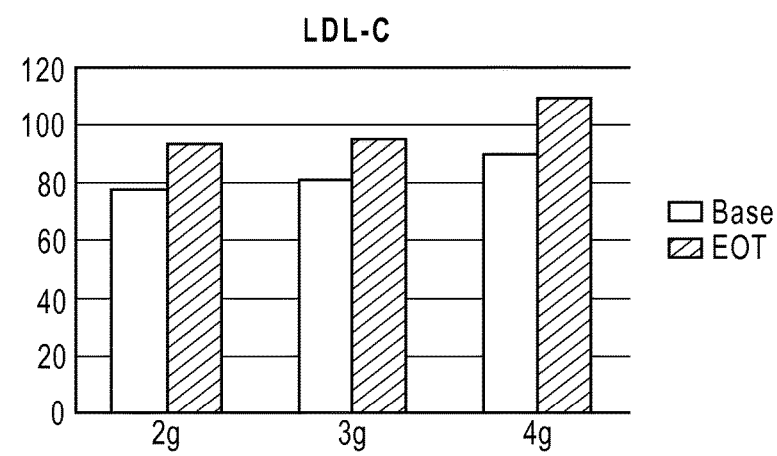

FIGS. 25A-25I plot median baseline and EOT plasma levels (in mg/dL, with the exception of LpPLA2, shown in ng/mL) in the EVOLVE trial for triglycerides (FIG. 25A), Non-HDL-C (FIG. 25B), HDL-C (FIG. 25C), V-LDL-C (FIG. 25D), LDL-C (FIG. 25E), ApoB (FIG. 25F), ApoCIII (FIG. 25G), RLP (FIG. 25H), LpPLA2 (FIG. 25I).

Figure 26A:
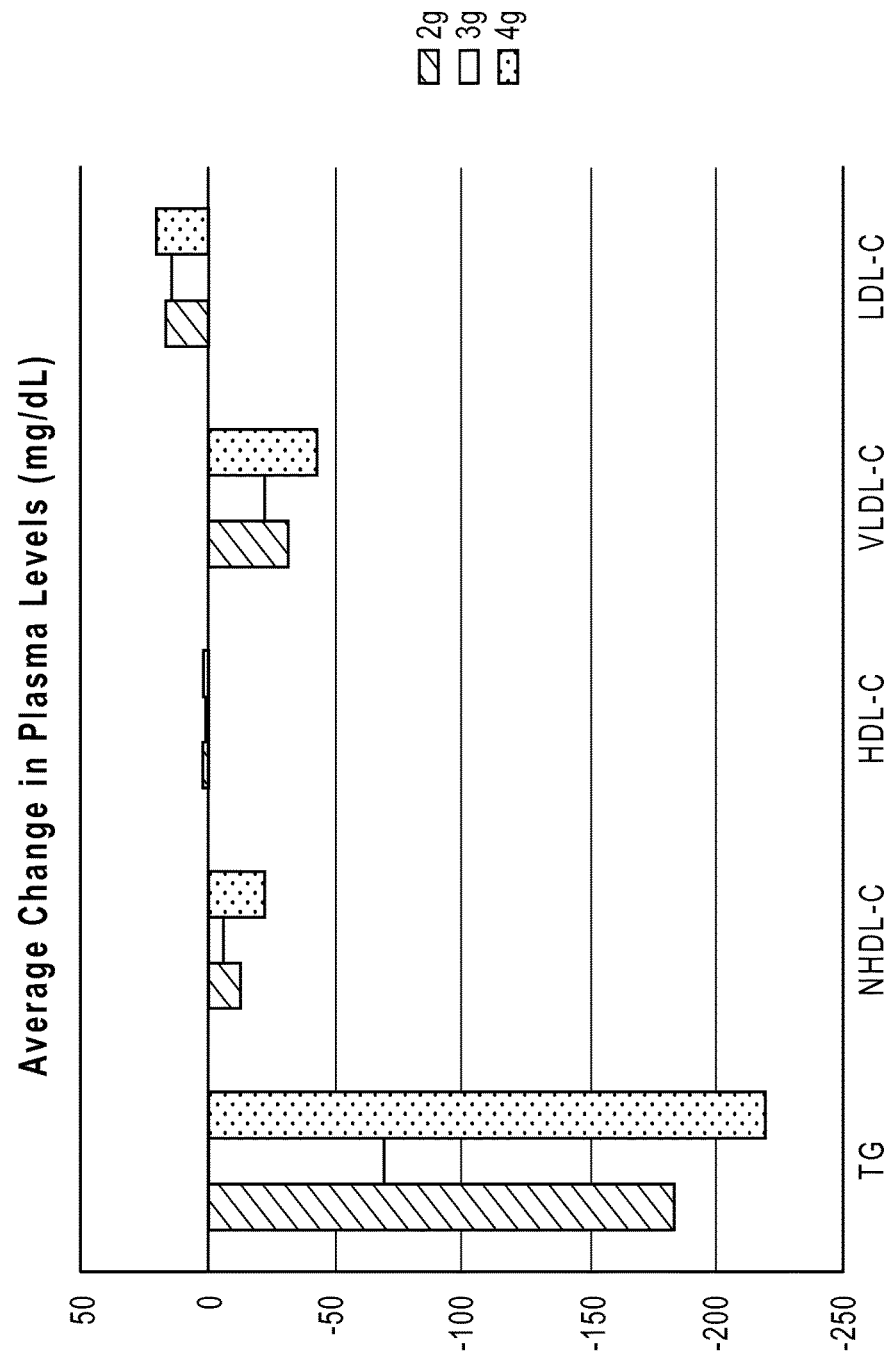
Figure 26B:
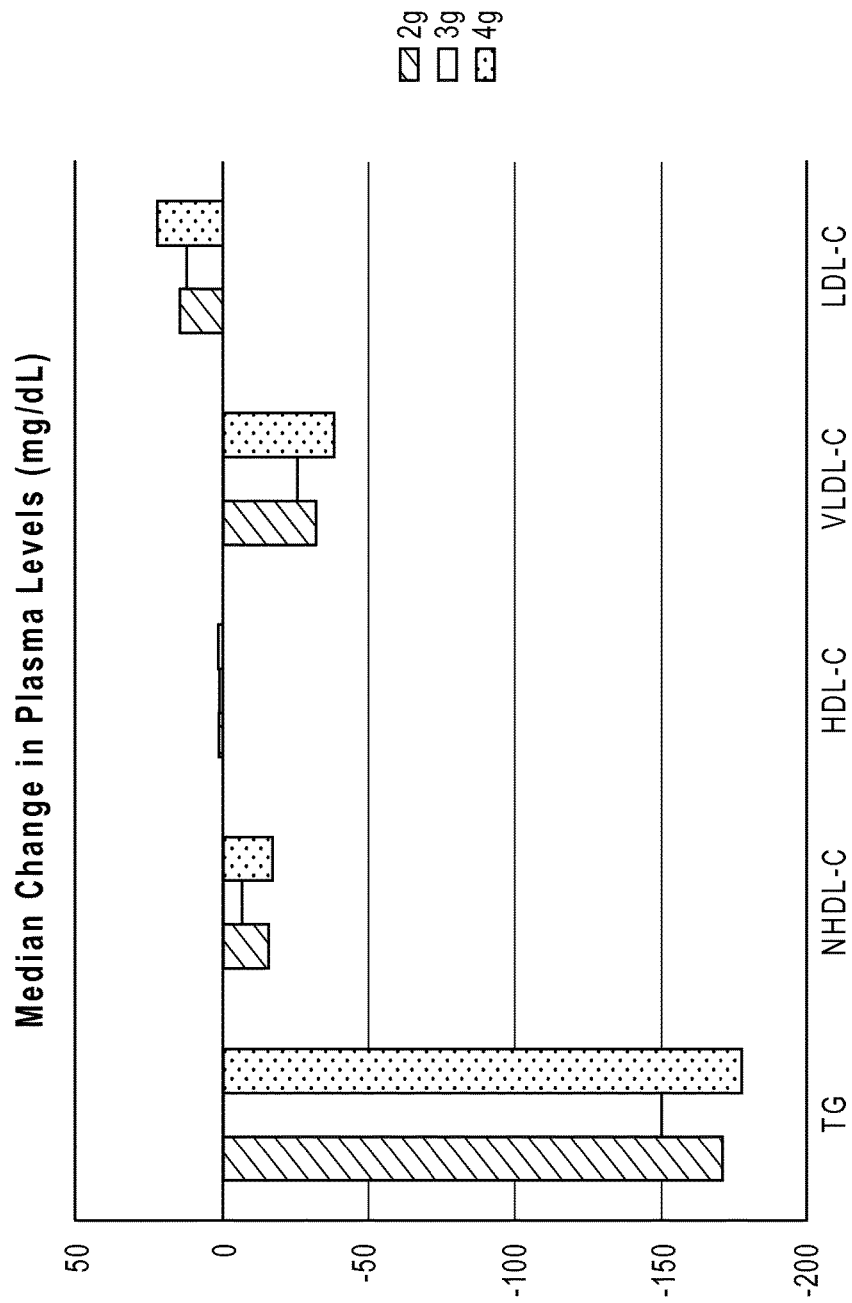

FIGS. 26A and 26B plot change from baseline to EOT in absolute plasma levels (in mg/dL) in the EVOLVE trial of triglycerides ("TG"), Non-HDL-C ("NHDL-C"), HDL-C, VLDL-C, and LDL-C for each of the treatment arms of the EVOLVE trial, with FIG. 26A plotting average change and FIG. 26B showing median change.

Figure 27:
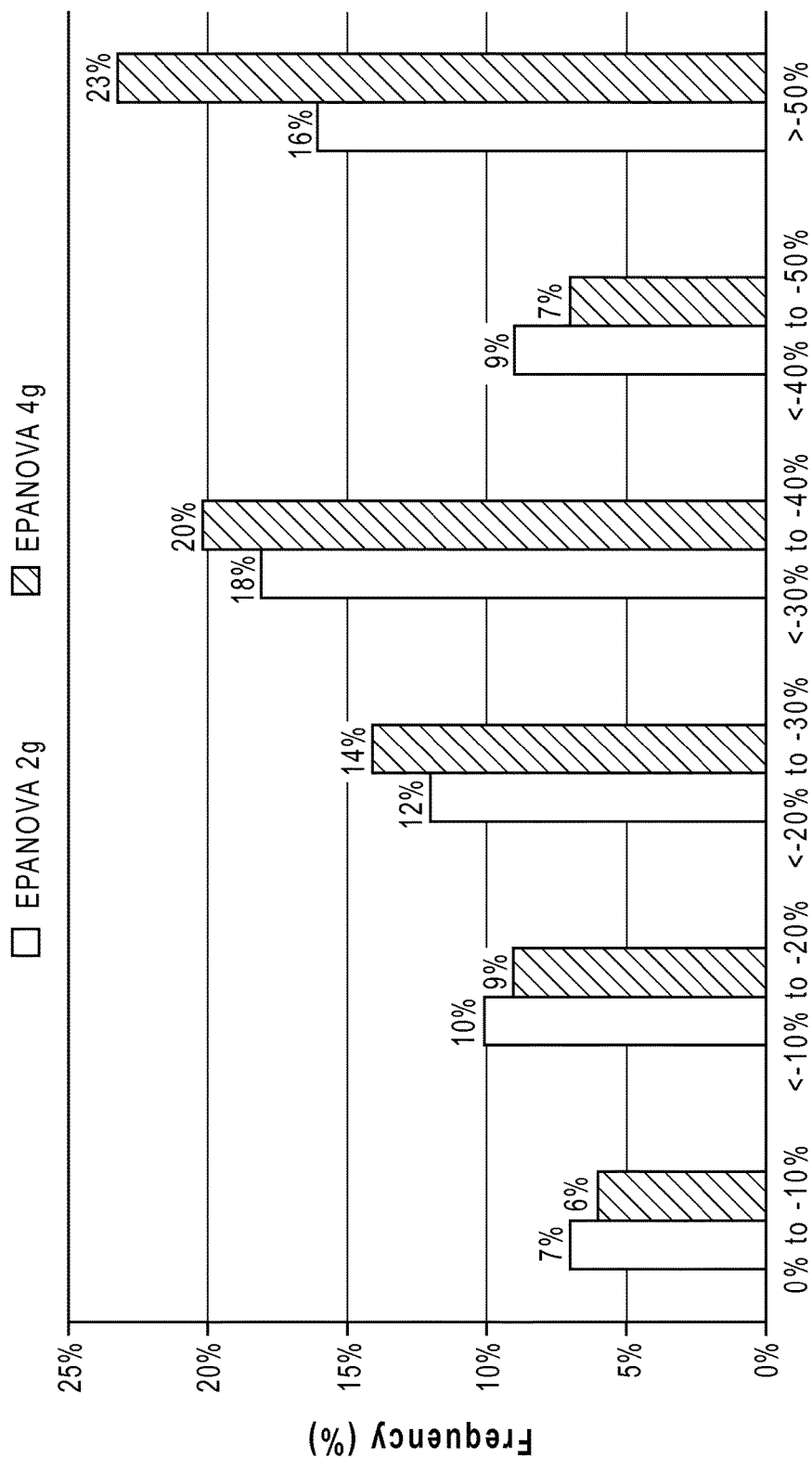

FIG. 27 plots the percentage of subjects in the EVOLVE trial, given by the Y-axis, for whom triglyceride levels were reduced by the indicated percentage, given by the X-axis, for 2 g dose and 4 g dose of Epanova®.

Figure 28A:
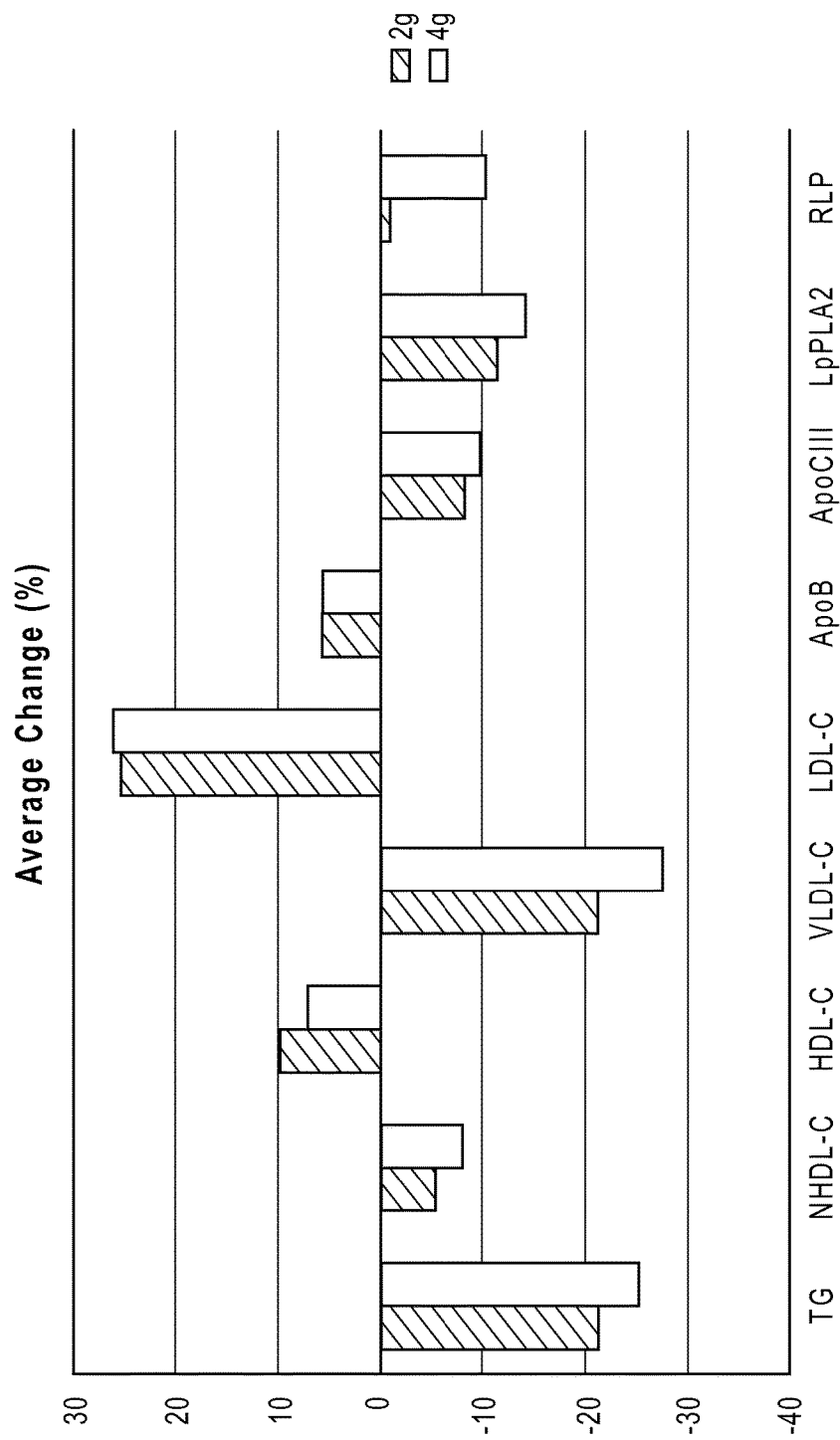
Figure 28B:
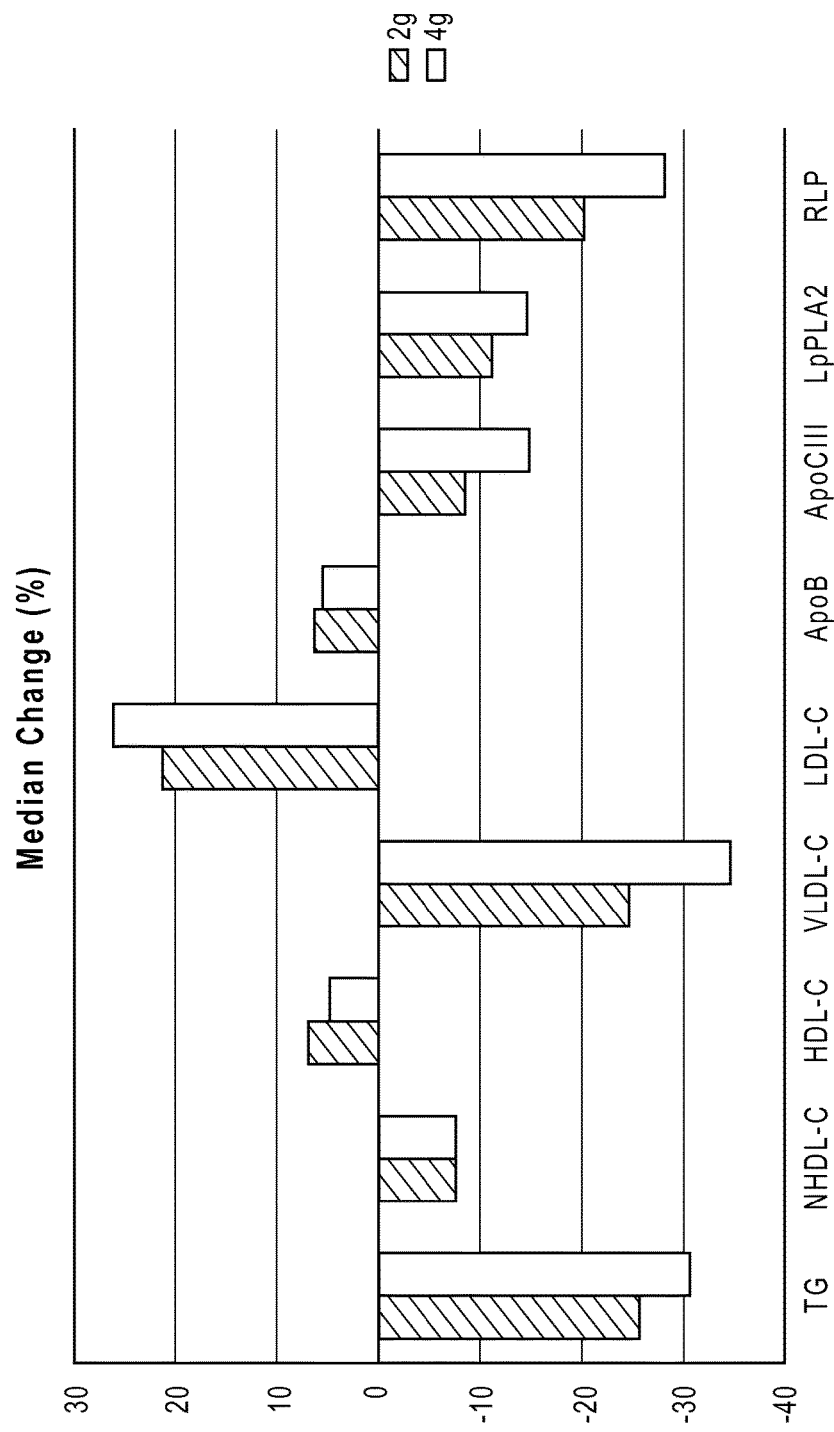

FIG. 28A plots average change from baseline to EOT, as percentage of baseline value, for TG, non-HDL-c ("NHDL-C"), HDL-C, VLDL-C, LDL-C, ApoB, ApoCIII, LpLPA2, and RLP in each of the treatment arms of the EVOLVE trial, with FIG. 28B plotting median percent change from baseline to EOT.

Figure 29:
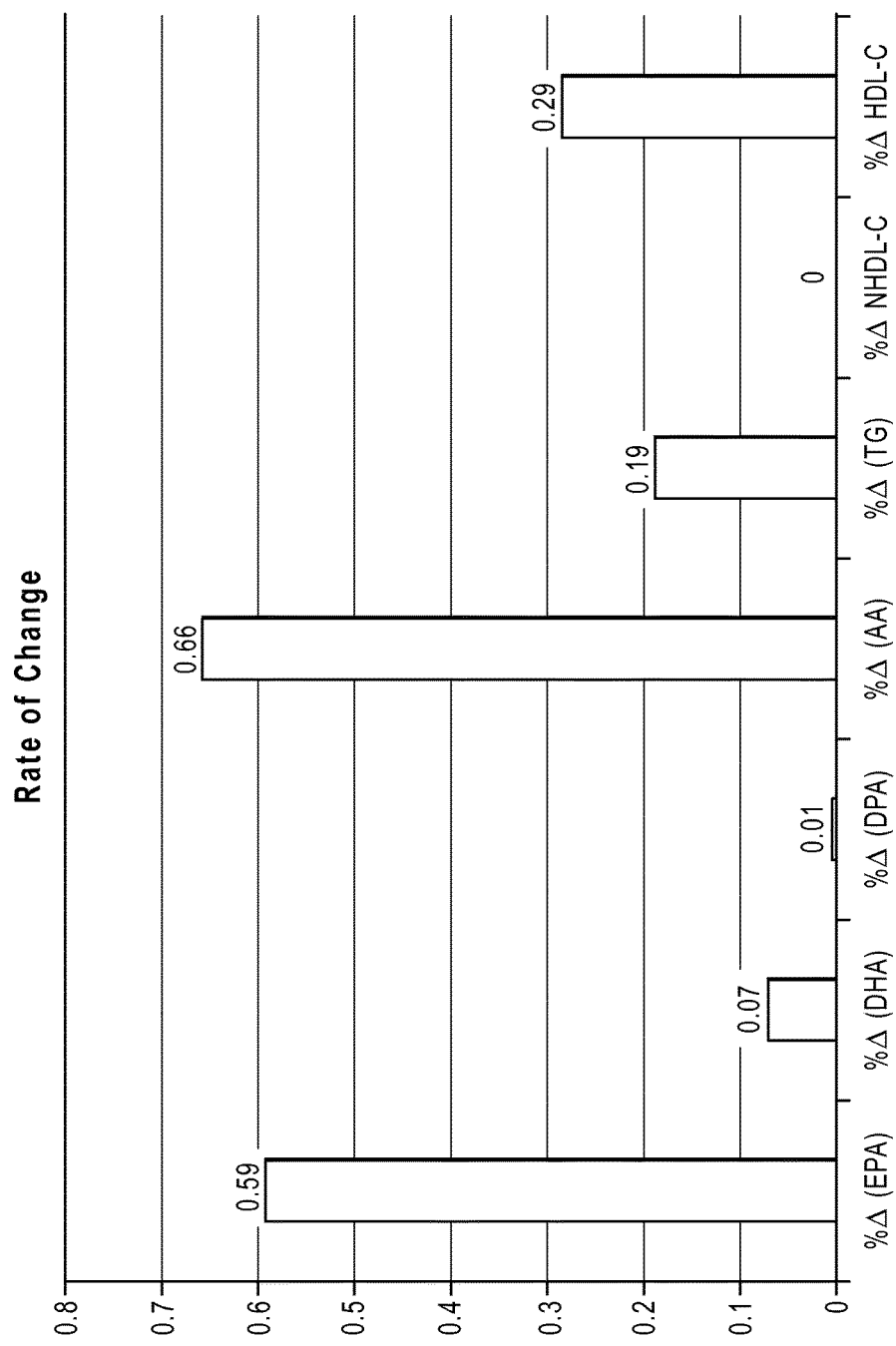

FIG. 29 plots the rate of change (absolute value) of the median percentage change from baseline in plasma levels of EPA, DHA, DPA, AA, TG, NHDL-C, and HDL-C between 2 g and 4 g doses of Epanova® in the EVOLVE trial.

Figure 30:
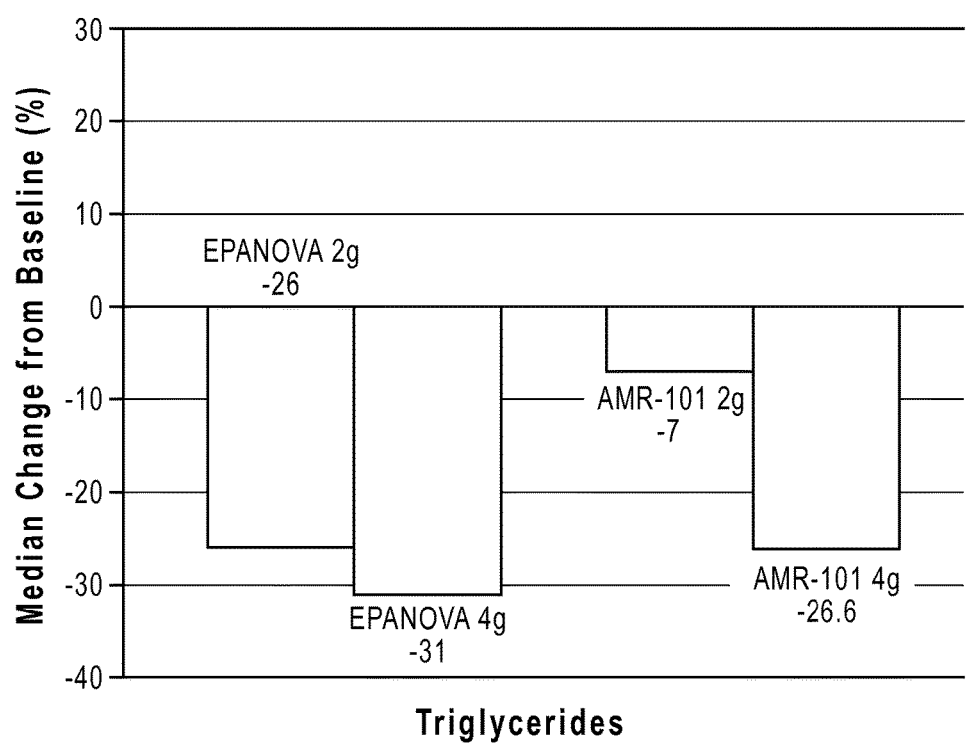

FIG. 30 illustrates comparative data for Epanova®, as measured in the EVOLVE trial, and data reported by others for AMR-101 (Vascepa), at the indicated doses, with respect to TG levels.

Figure 31:
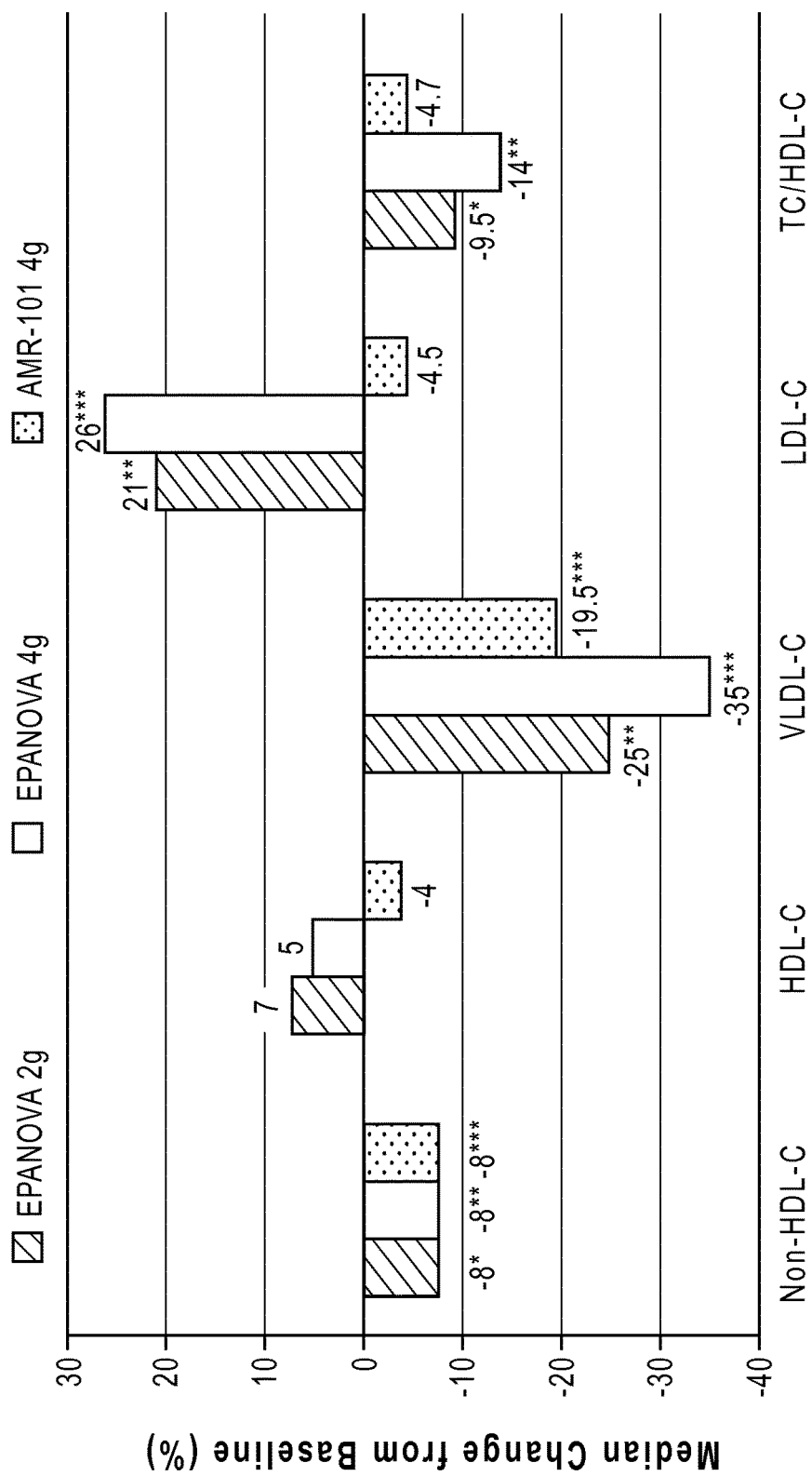

FIG. 31 illustrates comparative data for Epanova®, as measured in the EVOLVE trial, and AMR-101 (Vascepa), with respect to various blood lipid parameters. Data for AMR-101 were reported by others. (*) indicates a p value of less than 0.05, () indicates a p value of less than 0.01, and (*) indicates a p value of less than 0.001.

Figure 32:
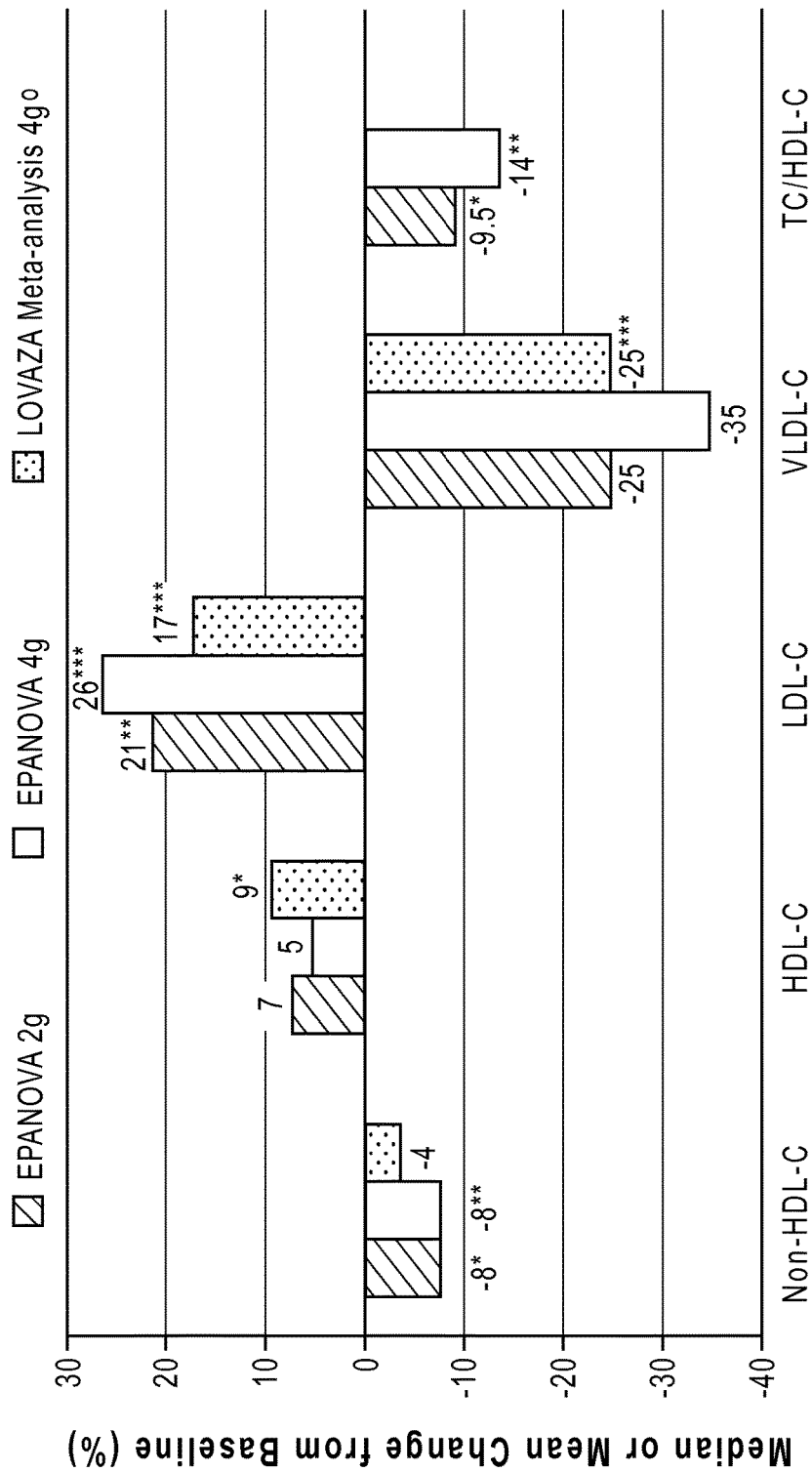

FIG. 32 illustrates comparative data for Epanova® 2 g and 4 g doses, as determined in the EVOLVE trial, and Lovaza® 4 g dose, with respect to various blood lipid parameters. Data for Lovaza® were reported by others. (*) indicates a p value of less than 0.05, () indicates a p value of less than 0.01, and (*) indicates a p value of less than 0.001.

Figure 33:
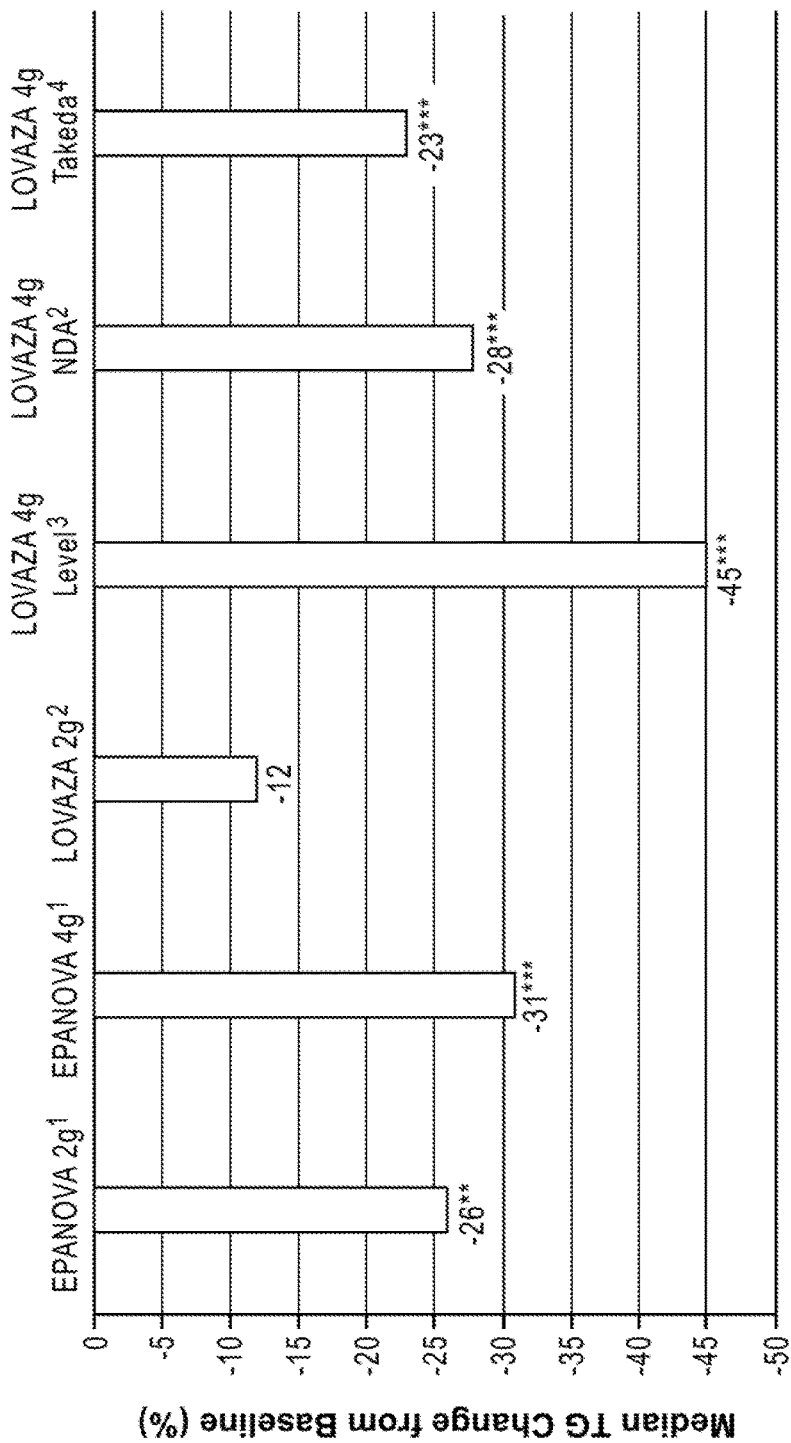

FIG. 33 illustrates comparative data for Epanova® 2 g and 4 g doses, as assessed in the EVOLVE trial, and Lovaza® 4 g dose, as reported by others, with respect to TG levels. The superscripts indicate data sourced from (1) EVOLVE trial, (2) a meta-analysis from the Lovaza® New Drug Application ("NDA") (3) Lovaza® FDA-approved product Label and (4) Takeda study. (*) indicates a p value of less than 0.05, () indicates a p value of less than 0.01, and (*) indicates a p value of less than 0.001.

Figure 34:
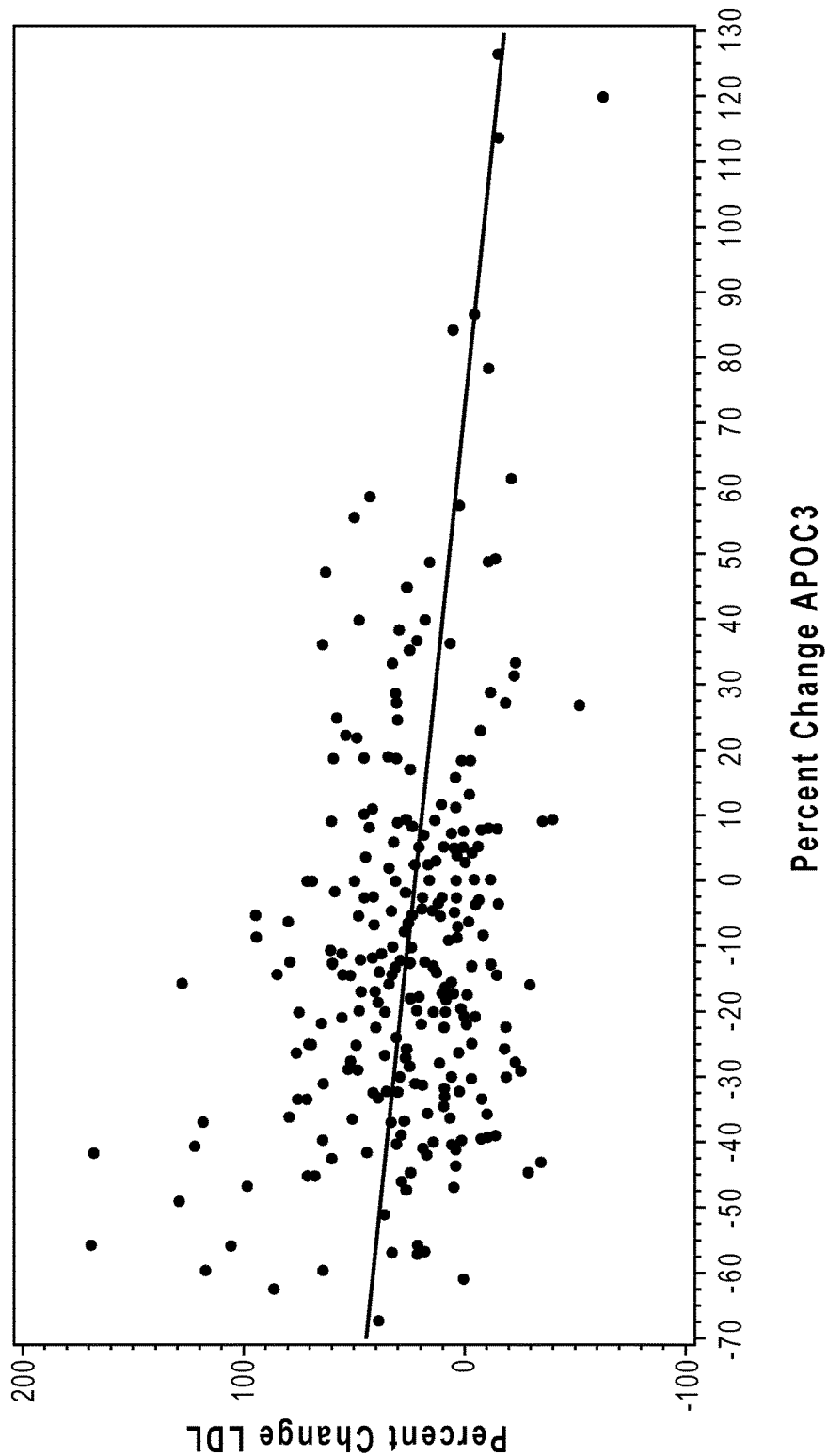

FIG. 34 plots the correlation between percent change in LDL and percent change in ApoCIII, as measured in the EVOLVE trial.

Figure 35:
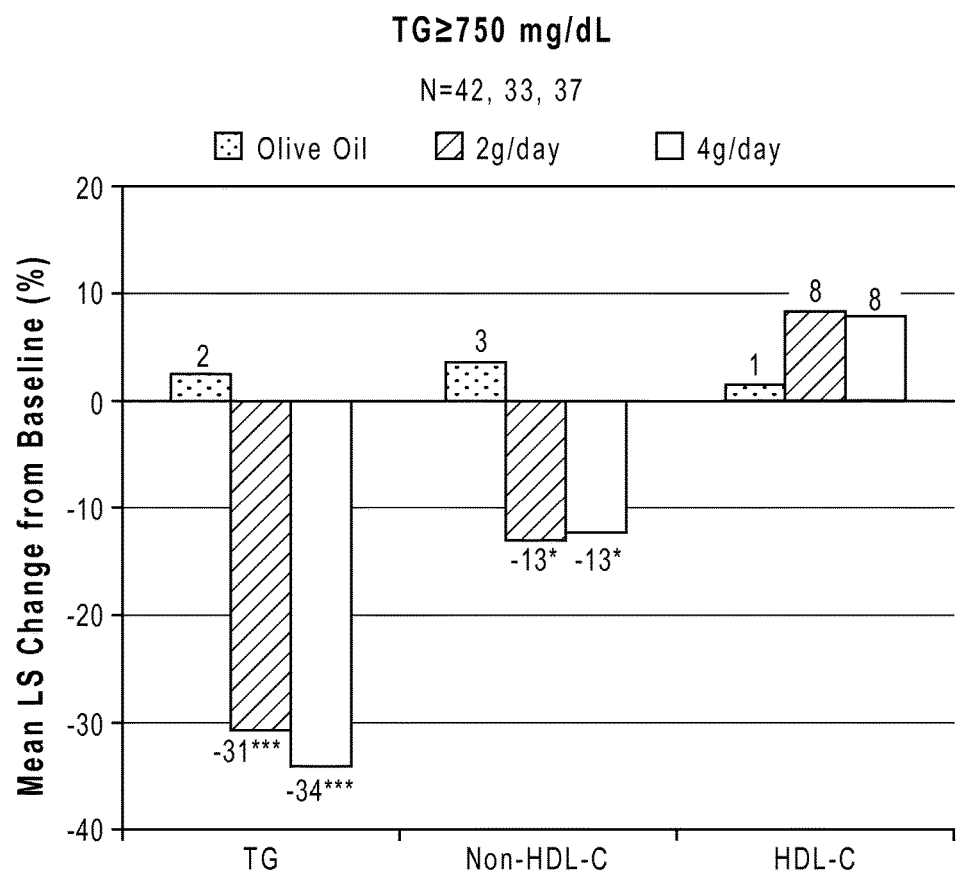

FIG. 35 plots the least squares (LS) mean percentage change from baseline for the subset of EVOLVE trial subjects having TG baseline levels greater than or equal to 750 mg/dL, for the indicated treatment arms of the EVOLVE study, as further described in Example 10. (*) indicates a p value of less than 0.05, () indicates a p value of less than 0.01, and (*) indicates a p value of less than 0.001.

Figure 36:
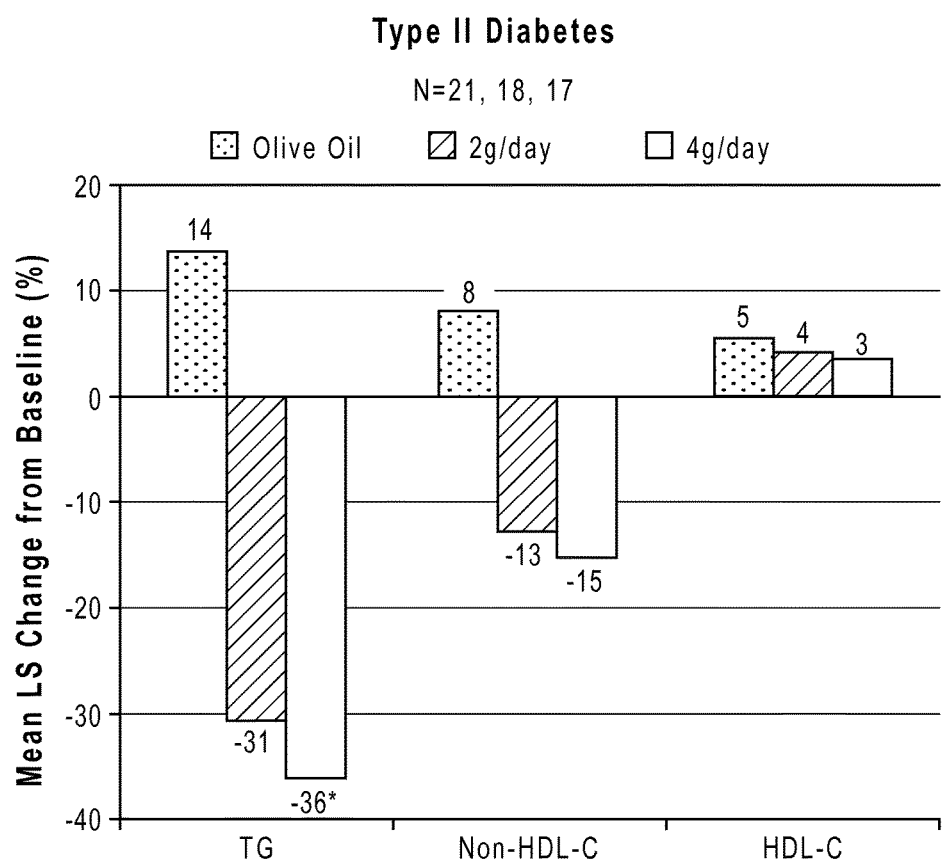

FIG. 36 plots the least squares (LS) mean percentage change from baseline for the subset of subjects having Type II diabetes, for the indicated treatment arms of the EVOLVE study, as described in Example 10. (*) indicates a p value of less than 0.05, () indicates a p value of less than 0.01, and (*) indicates a p value of less than 0.001.

Figure 37:
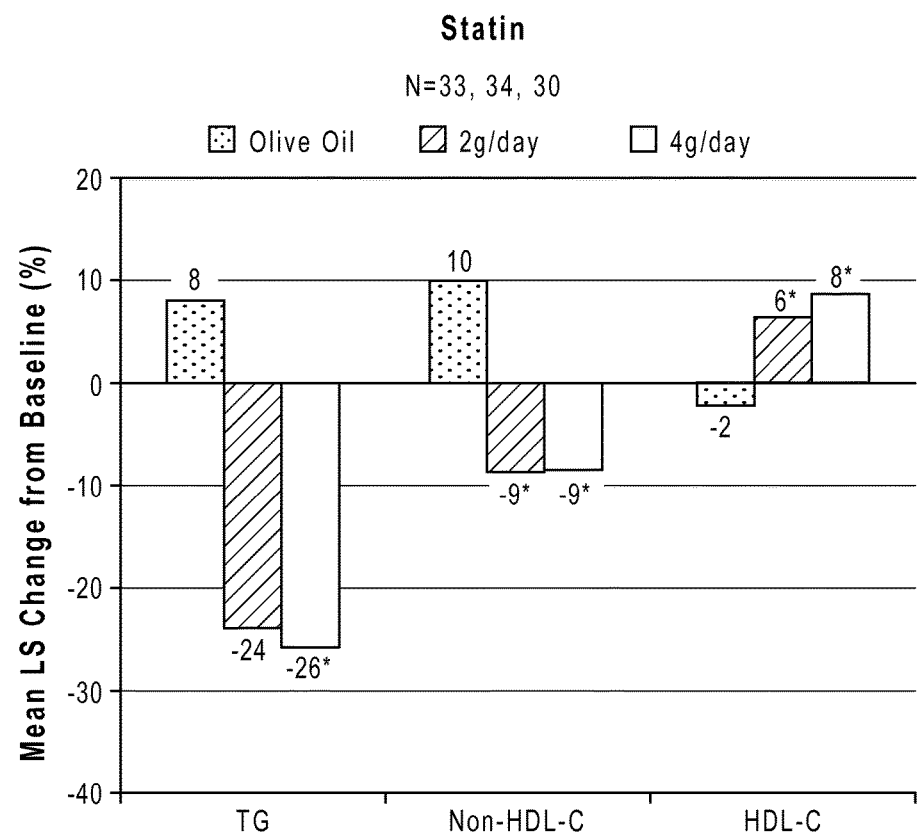

FIG. 37 plots the least squares (LS) mean percentage change from baseline for the subset of subjects undergoing concurrent statin therapy, for the indicated treatment arms of the EVOLVE study, as described in Example 10. (*) indicates a p value of less than 0.05, () indicates a p value of less than 0.01, and (*) indicates a p value of less than 0.001.

Figure 38:
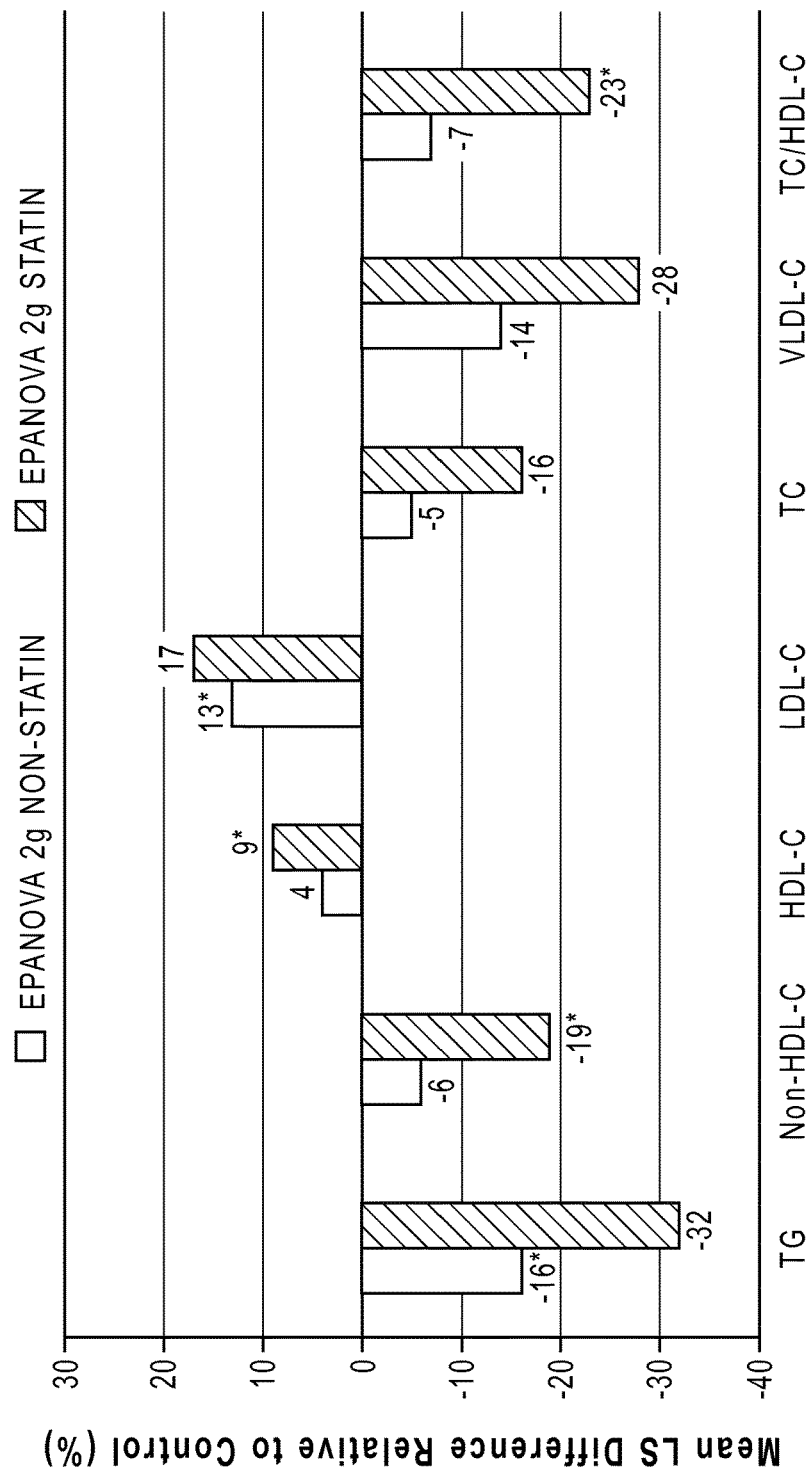

FIG. 38 plots the least squares (LS) mean percentage difference relative to control for triglycerides ("TG"), non-HDL-cholesterol ("NHDL-C"), HDL-C, LDL-C, TC, VLDL-C, and TC/HDL-C, comparing subjects from the EVOLVE study described in Example 10 who either received (STATIN) or did not receive (NON-STATIN) statin therapy concurrent with treatment with the 2 g dose of Epanova®. (*) indicates a p value of less than 0.05, () indicates a p value of less than 0.01, and (*) indicates a p value of less than 0.001.

Figure 39:
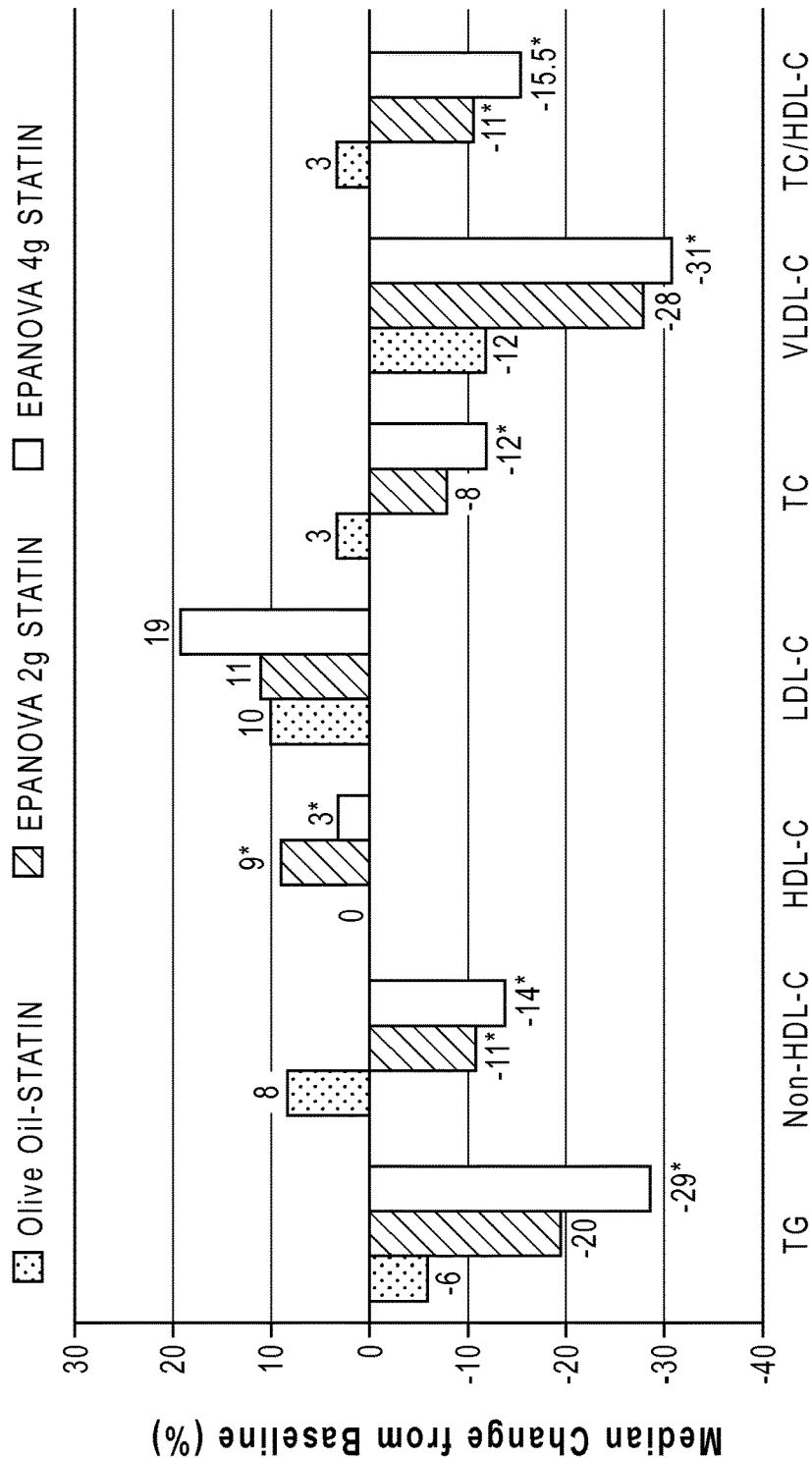

FIG. 39 plots the median percent change from baseline for TG, NHDL-C, HDL-C, LDL-C, TC, VLDL-C, and TC/HDL-C for the subset of subjects undergoing concurrent statin therapy, in the indicated treatment arms of the EVOLVE study, further described in Example 10. (*) indicates a p value of less than 0.05, () indicates a p value of less than 0.01, and (*) indicates a p value of less than 0.001.

Figure 40:
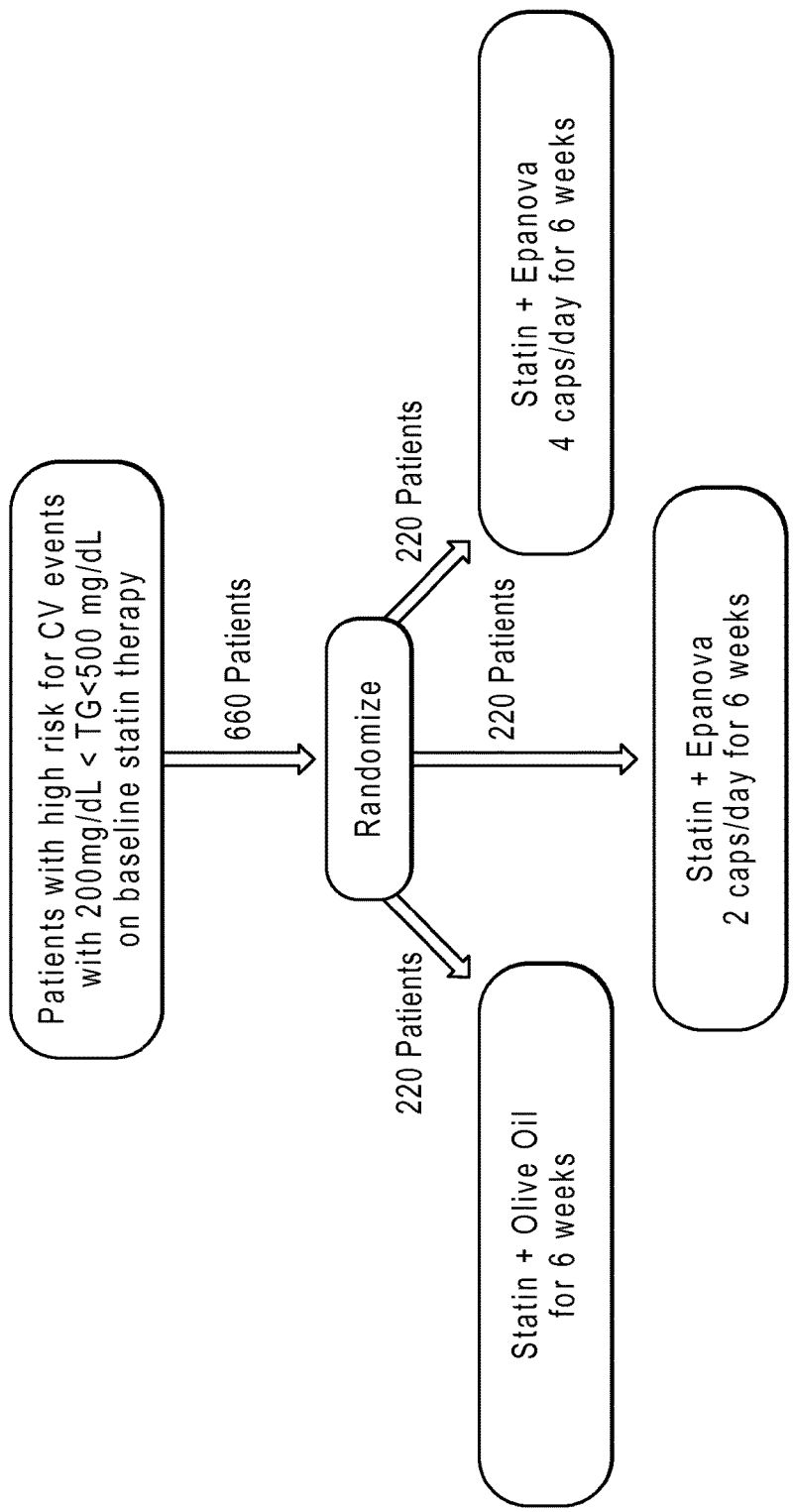

FIG. 40 provides a treatment flow diagram illustrating the design of the ESPRIT study, further described in Example 12.

Figure 41:
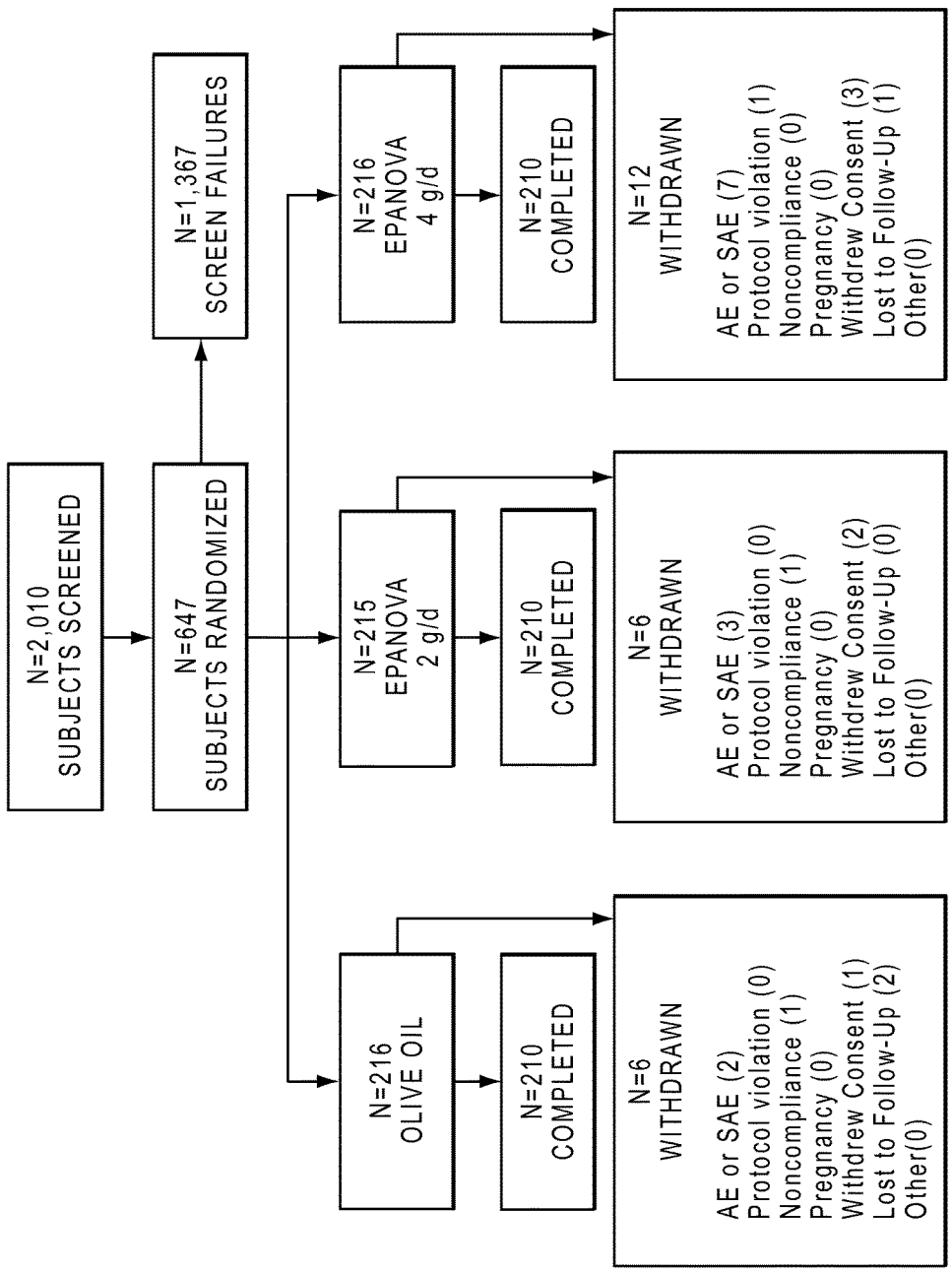

FIG. 41 shows the disposition of subjects in the ESPRIT trial.

Figure 42A:
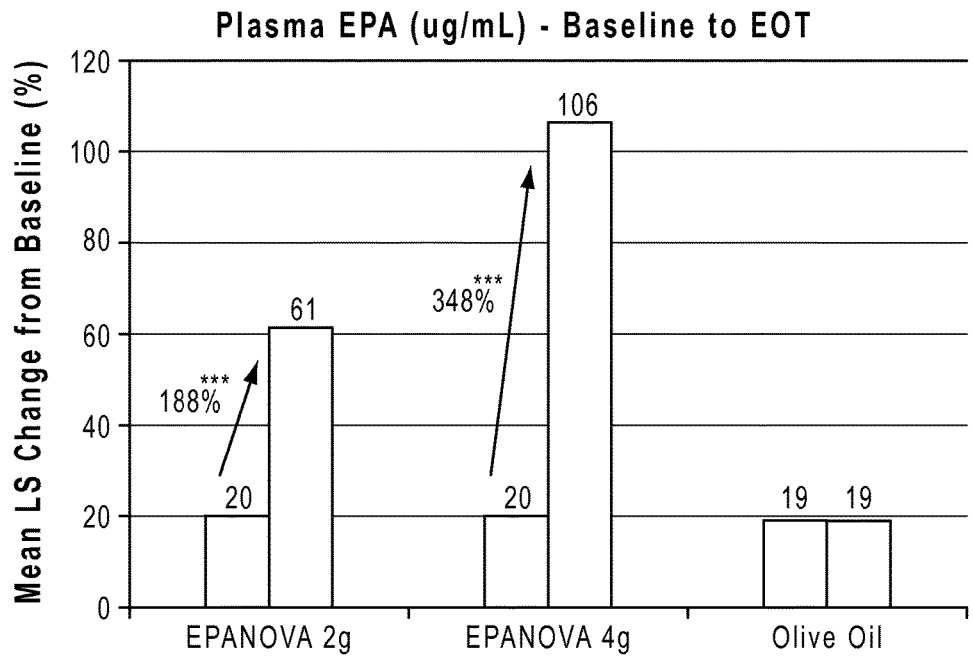
Figure 42B:
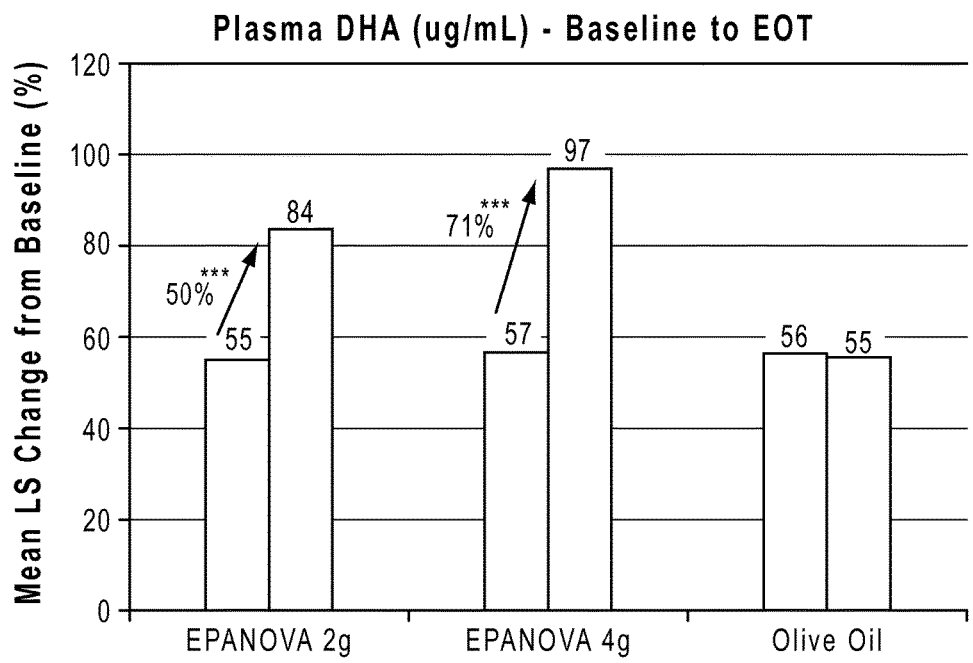

FIGS. 42A and 42B plot the median LS percentage change from baseline for EPA (FIG. 42A) and DHA (FIG. 42B) from the ESPRIT study, further described in Example 12. (*) indicates a p value of less than 0.05, () indicates a p value of less than 0.01, and (*) indicates a p value of less than 0.001.

Figure 43:
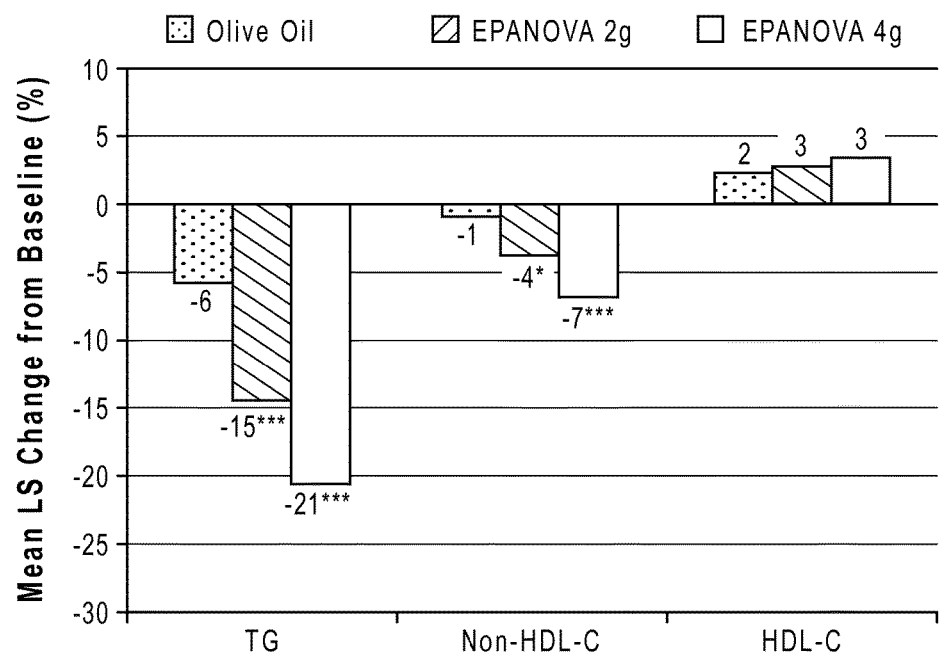

FIG. 43 plots mean LS percentage change from baseline for TG, Non-HDL-C, and HDL-C. Data shown are from the ESPRIT study, further described in Example 12. (*) indicates a p value of less than 0.05, () indicates a p value of less than 0.01, and (*) indicates a p value of less than 0.001.

Figure 44:
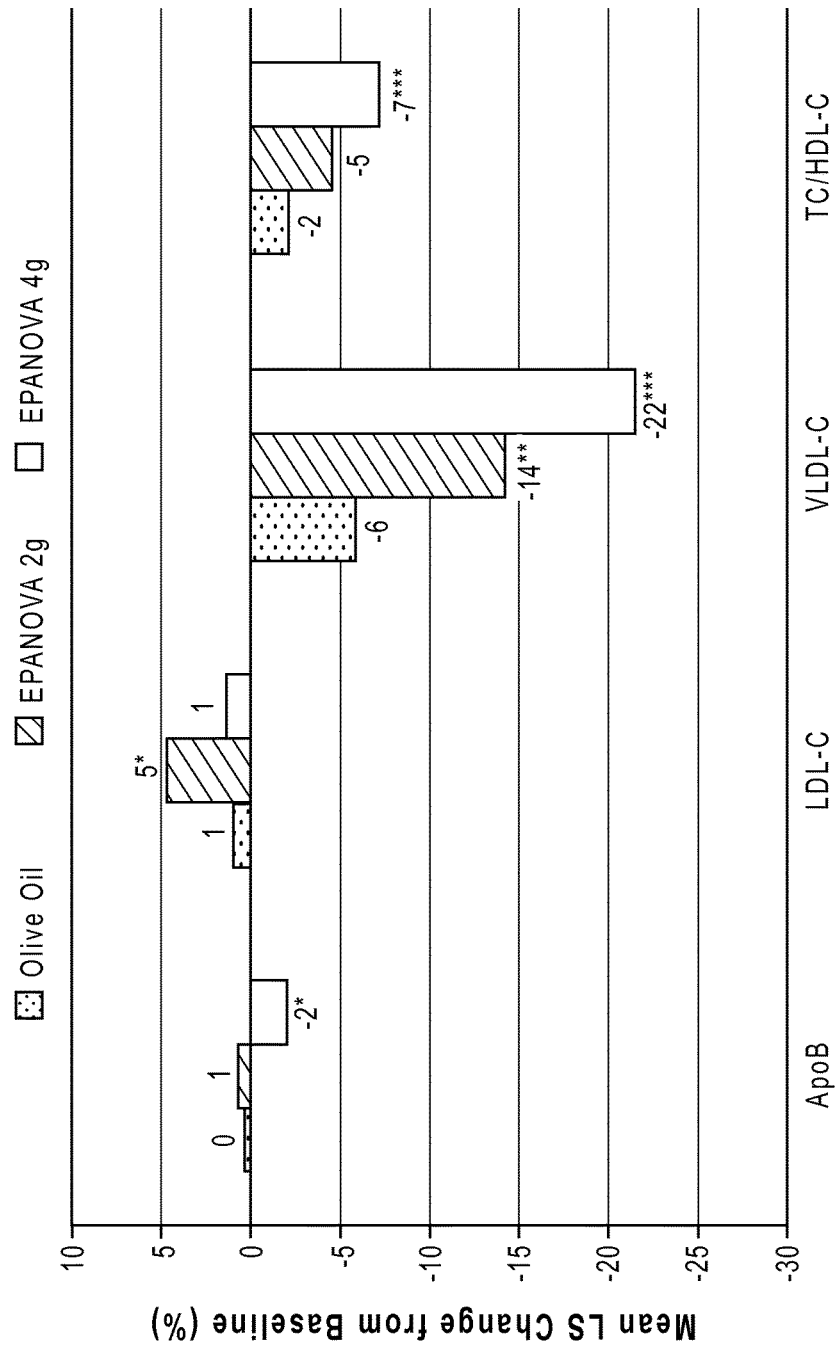

FIG. 44 plots mean LS percentage change from baseline for ApoB, LDL-C, VLDL-C, and TC/HDL-C. Data shown are from the ESPRIT study, further described in Example 12. (*) indicates a p value of less than 0.05, () indicates a p value of less than 0.01, and (*) indicates a p value of less than 0.001.

Figure 45:
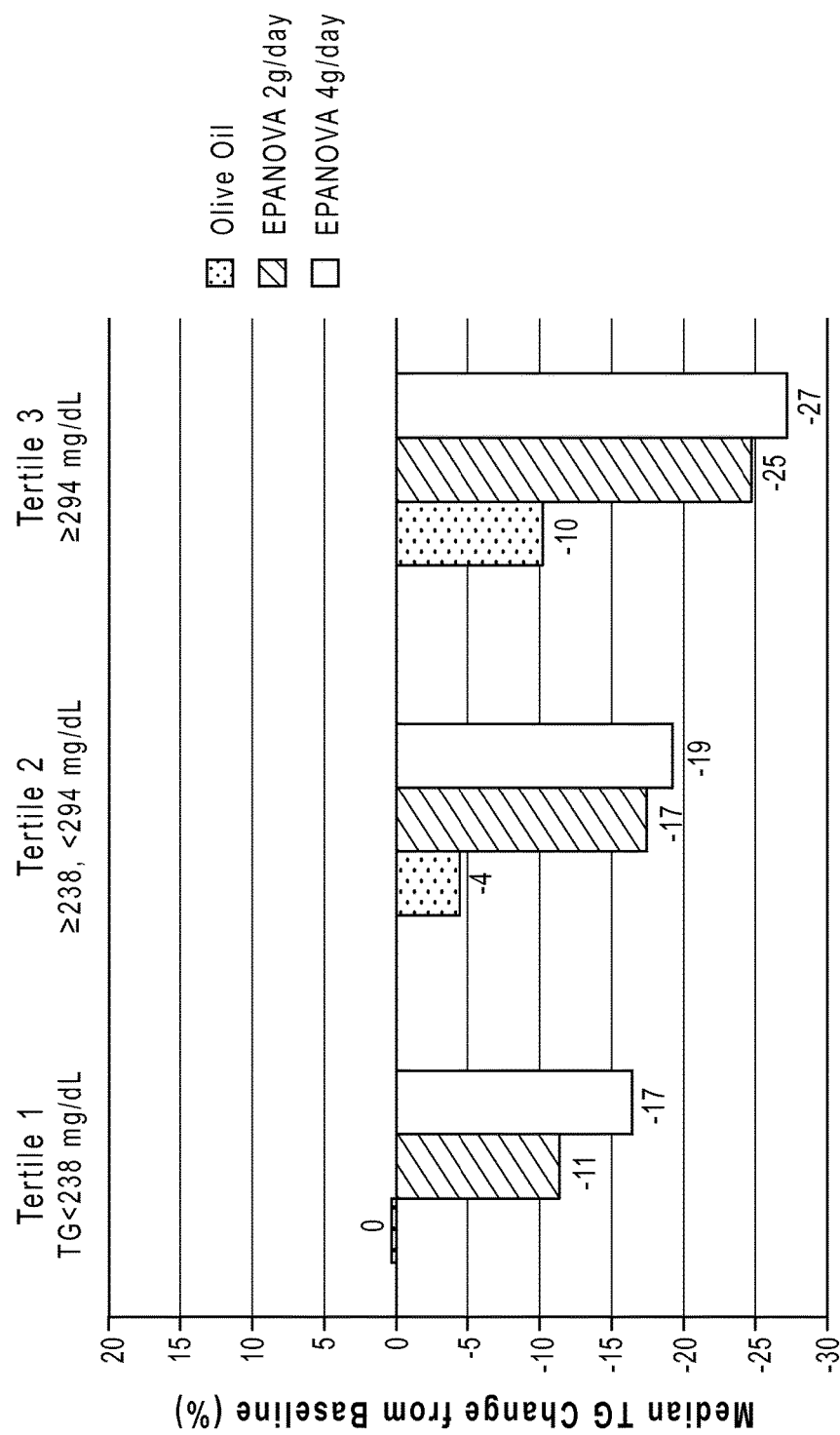

FIG. 45 plots median percentage change from baseline for TG, with subjects grouped into tertiles by baseline TG levels, for subjects in the ESPRIT trial.

Figure 46:
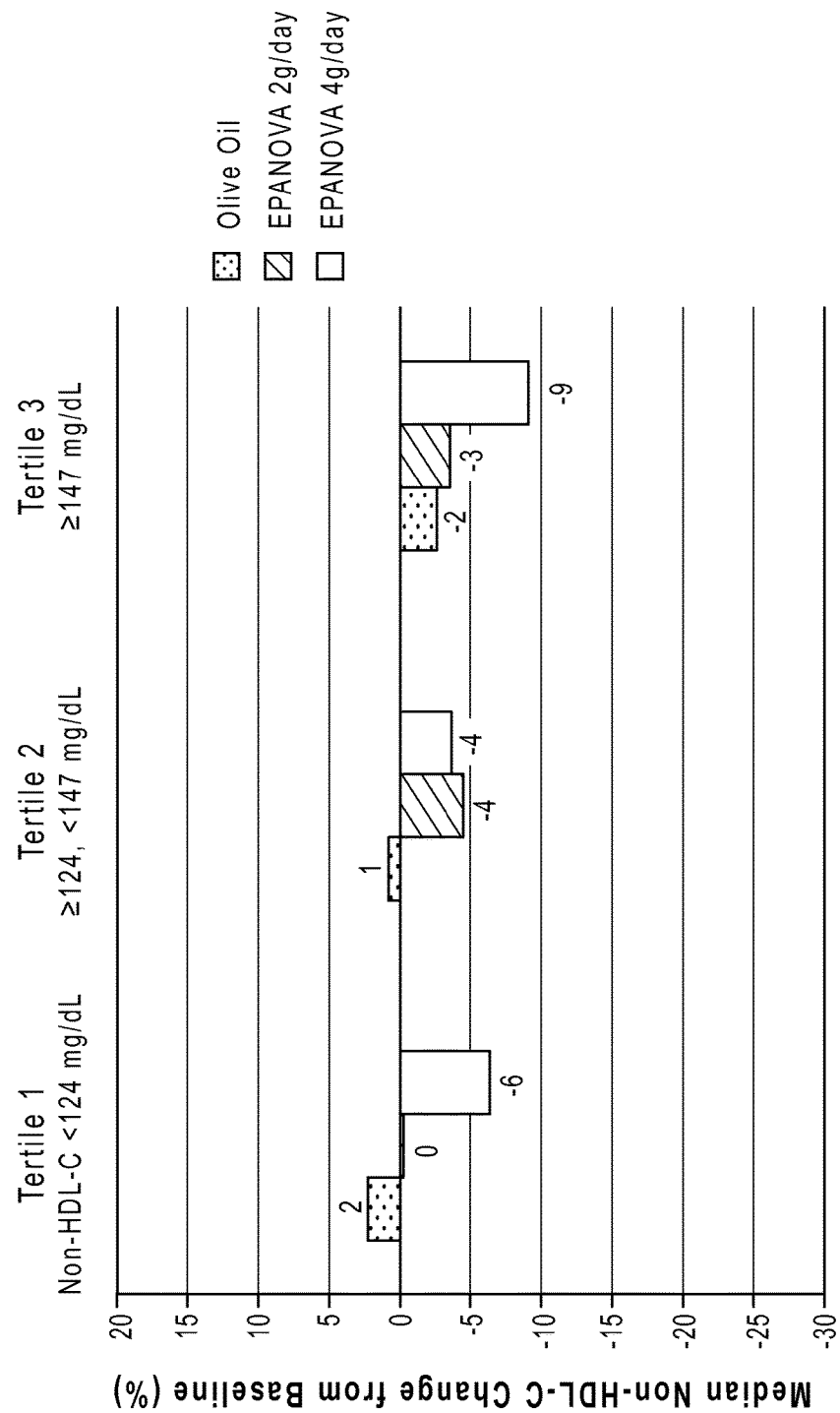

FIG. 46 plots median percentage change from baseline for Non-HDL-C, with subjects grouped into tertiles by baseline Non-HDL-C levels, for subjects in the ESPRIT trial.

Figure 47:
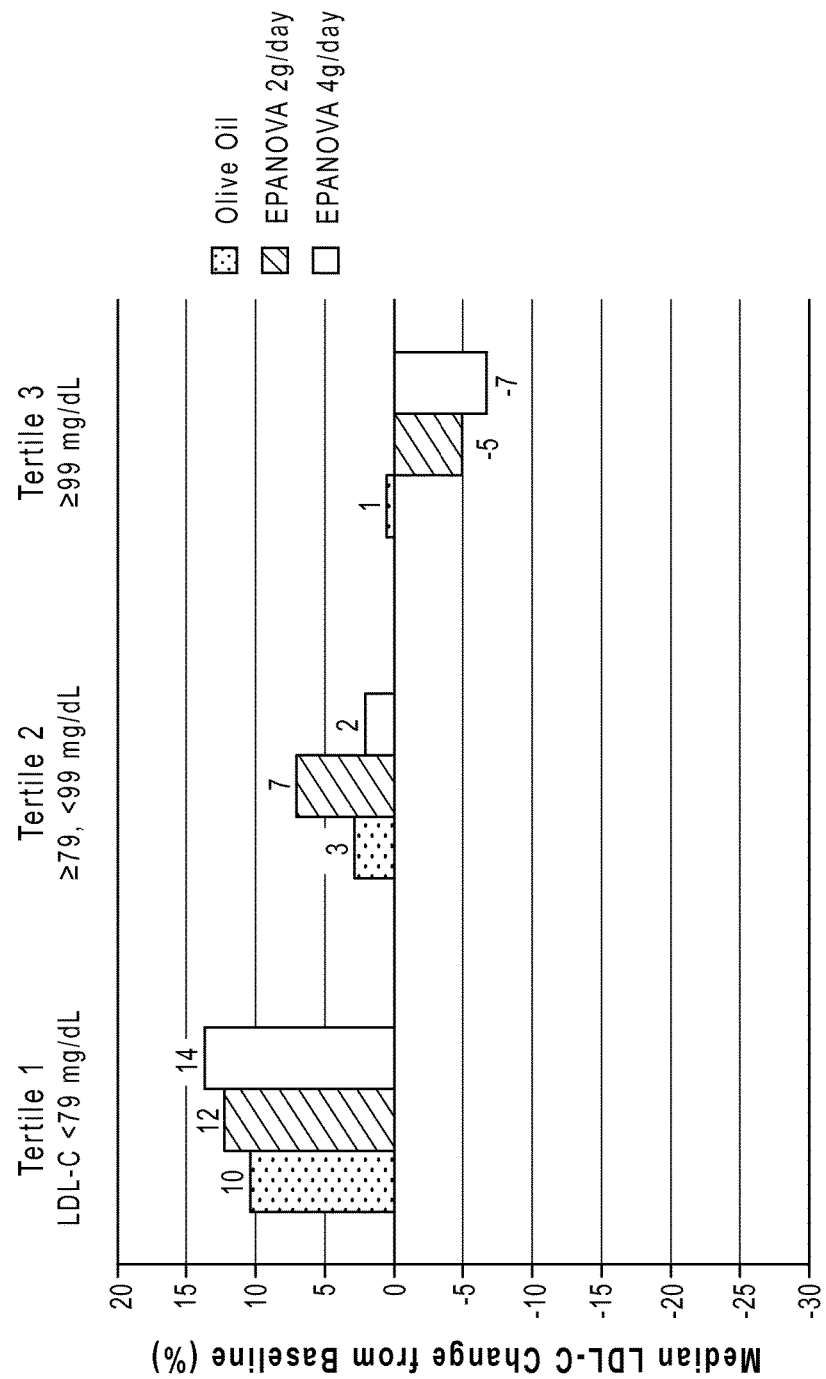

FIG. 47 plots median percentage change from baseline for LDL-C, with subjects grouped into tertiles by baseline LDL-C levels, for subjects in the ESPRIT trial.

Figure 48:
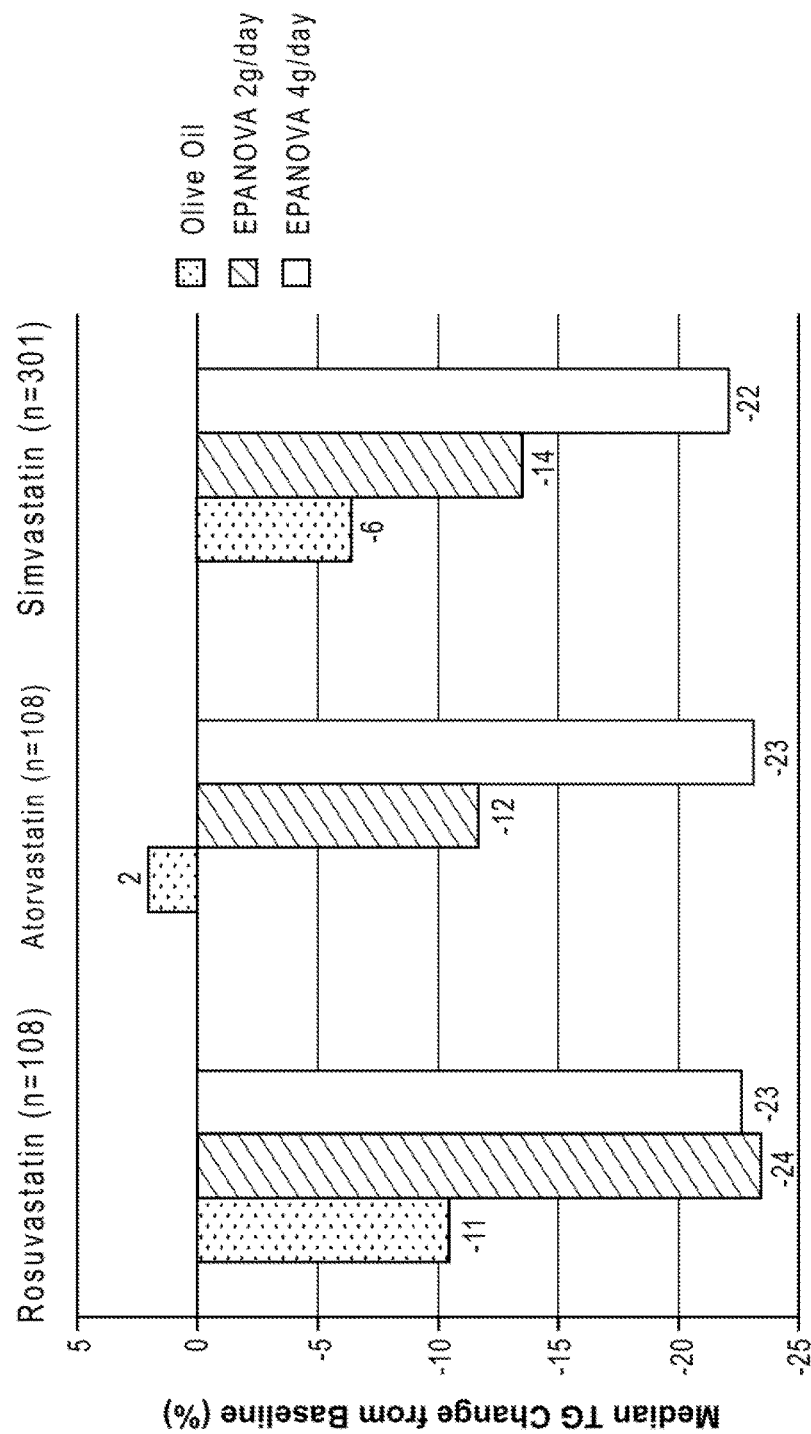

FIG. 48 plots median percentage change from baseline for TG for each of the treatment arms of the ESPRIT trial, with subjects grouped according to the identity of the statin taken in concurrent therapy.

Figure 49:
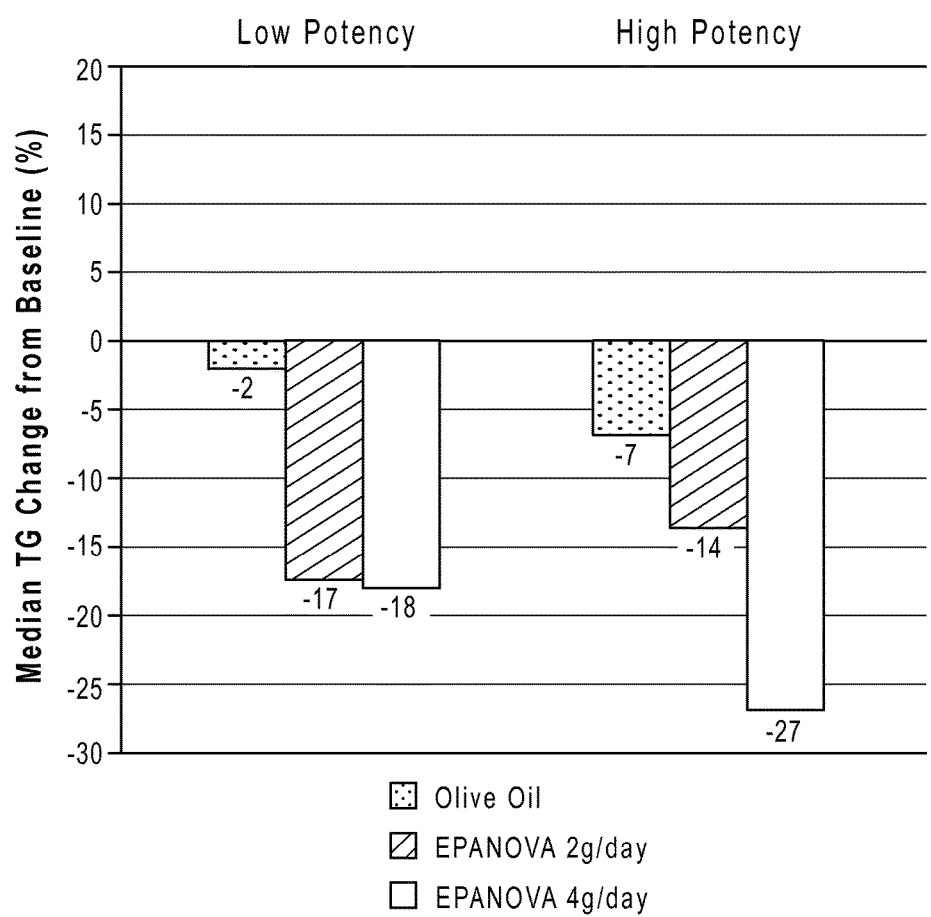

FIG. 49 plots median percentage change from baseline for TG for each of the treatment arms of the ESPRIT trial, with subjects grouped into two groups according to low or high potency concurrent statin therapy.

Figure 50:
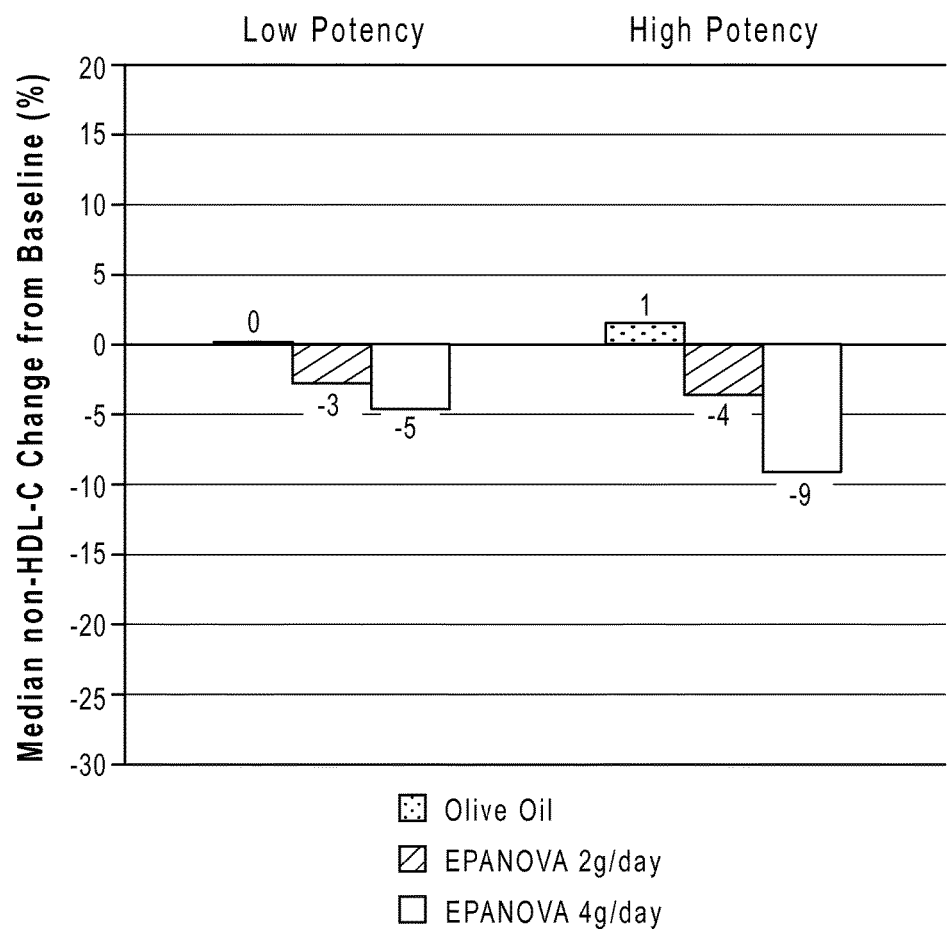

FIG. 50 plots median percentage change from baseline for Non-HDL-C for each of the treatment arms of the ESPRIT trial, with subjects grouped according to low or high potency concurrent statin therapy.

Figure 51:
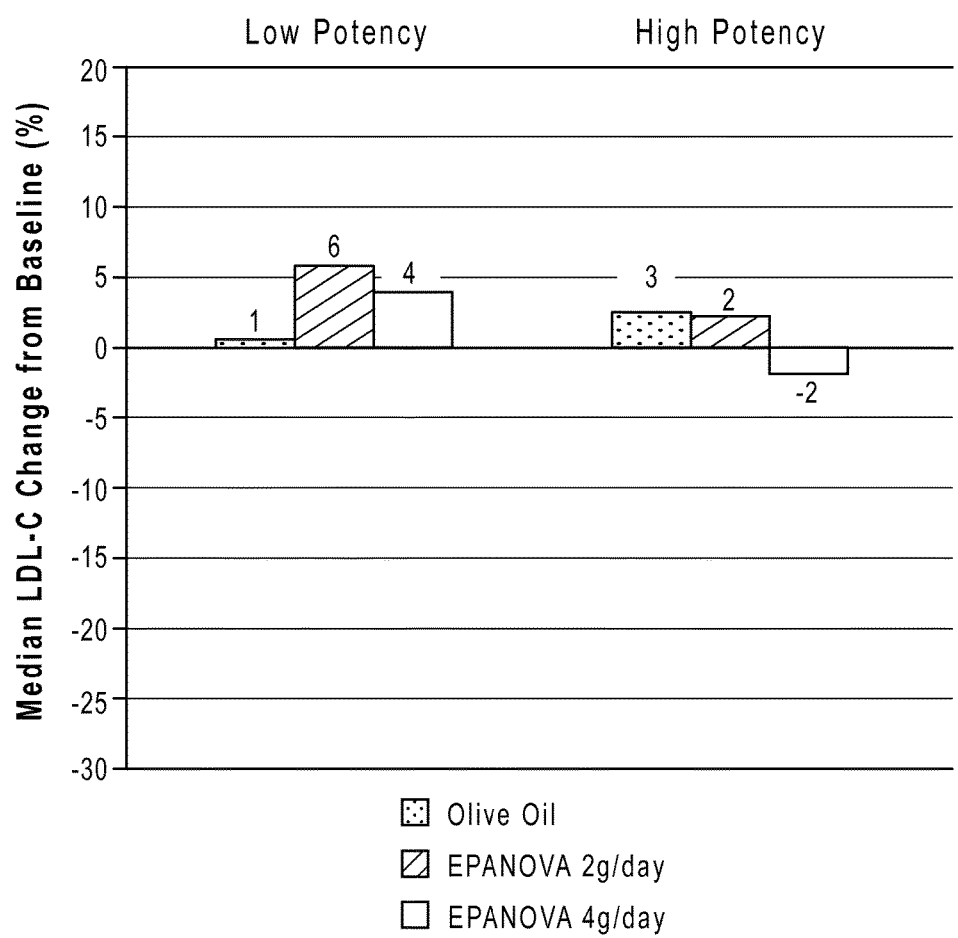

FIG. 51 plots median percentage change from baseline for LDL-C for each of the treatment arms of the ESPRIT trial, with subjects grouped into two groups according to low or high potency concurrent statin therapy.

Figure 52:
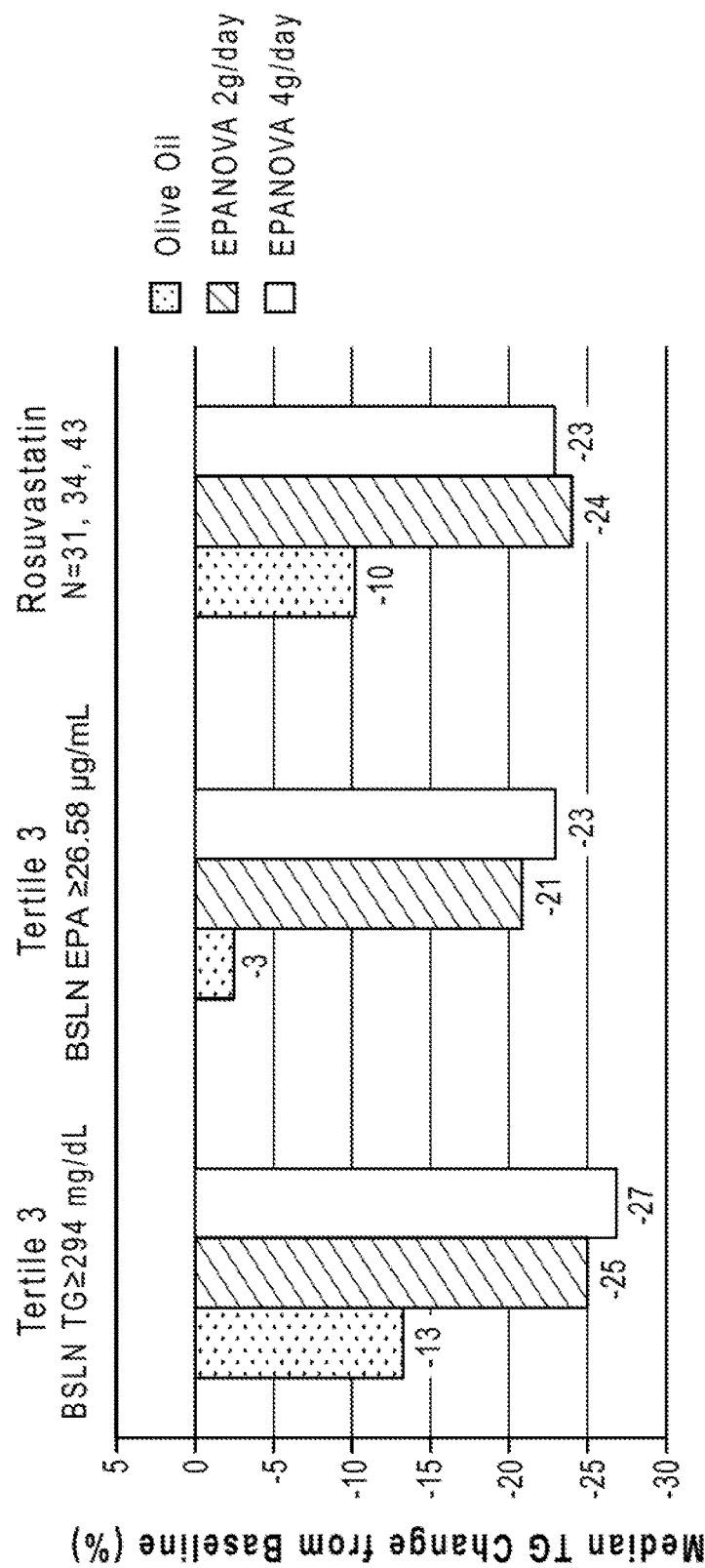

FIG. 52 plots median percentage change from baseline for TG, with subjects in each treatment arm of the ESPRIT trial grouped into three groups according to high baseline TG, high baseline EPA, or concurrent rosuvastatin therapy.

Figure 53:
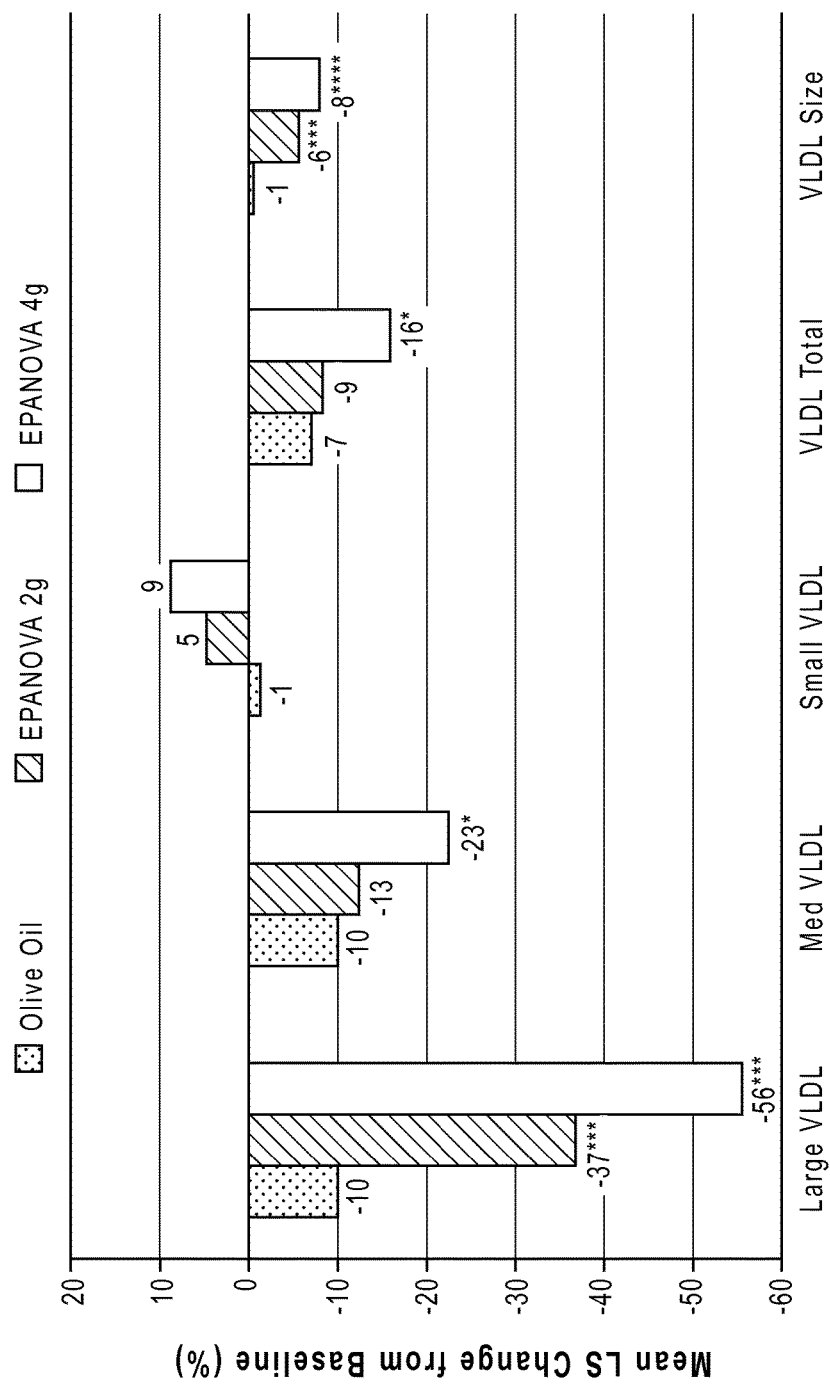

FIG. 53 plots mean LS percentage change in particle size distribution from baseline for V-LDL particles grouped by size, as determined in the ESPRIT trial. (*) indicates a p value of less than 0.05, () indicates a p value of less than 0.01, and (*) indicates a p value of less than 0.001.

Figure 54:
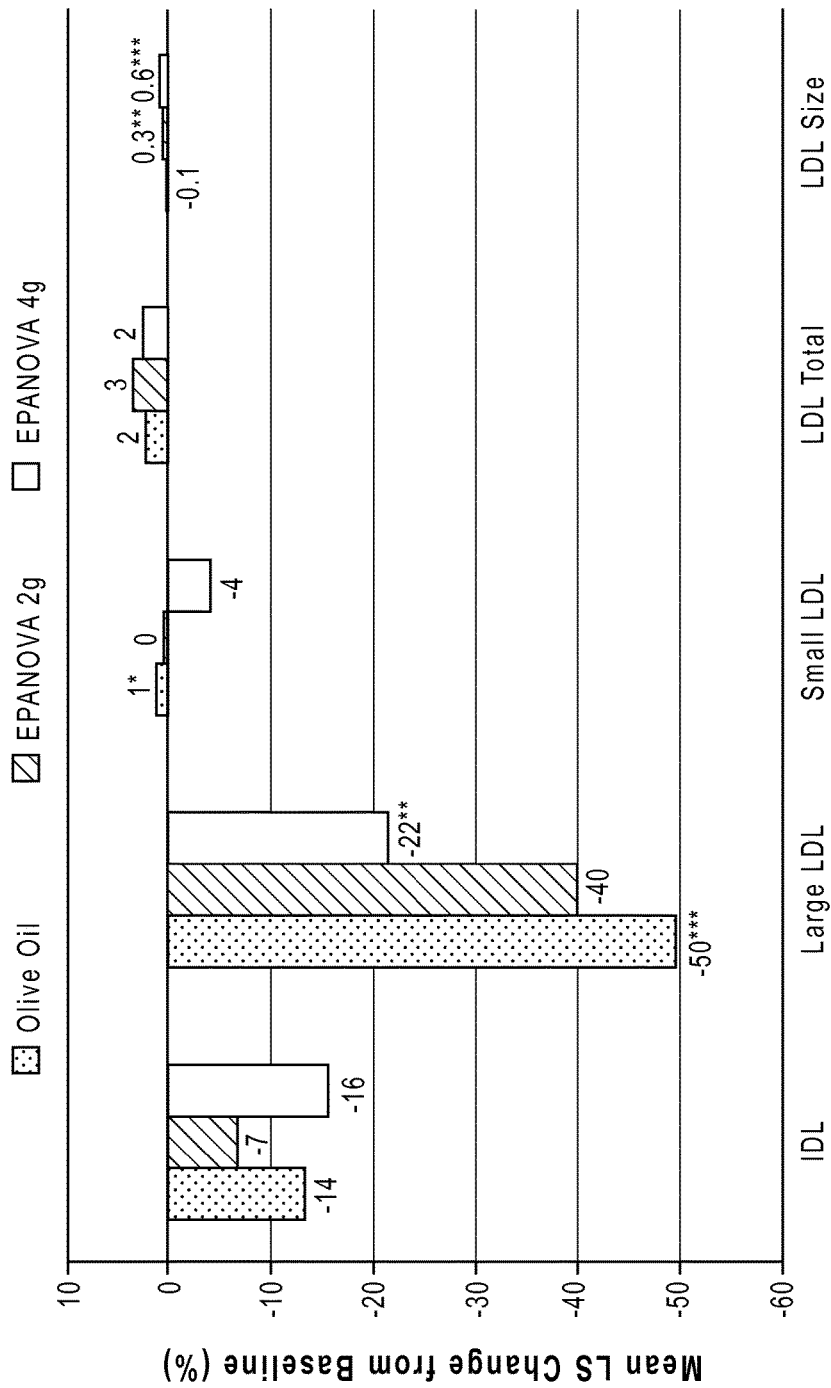

FIG. 54 plots mean LS percentage change in particle size distribution from baseline for LDL particles grouped by size for each of the treatment arms of the ESPRIT trial. (*) indicates a p value of less than 0.05, () indicates a p value of less than 0.01, and (*) indicates a p value of less than 0.001.

Figure 55:
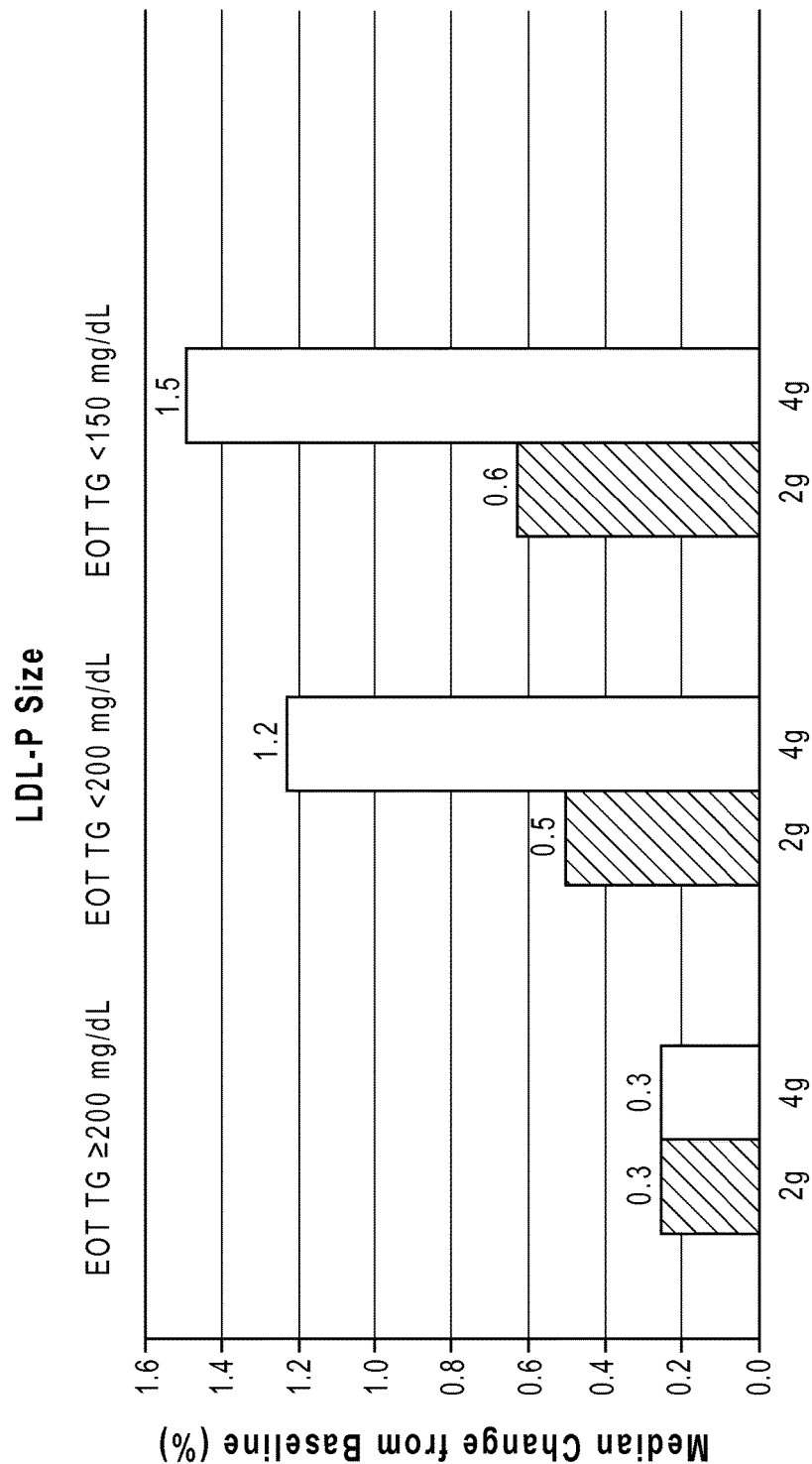

FIG. 55 plots LS median percentage change in LDL particle size, with subjects grouped into three groups according to ESPRIT EOT triglyceride levels.

Figure 56A:
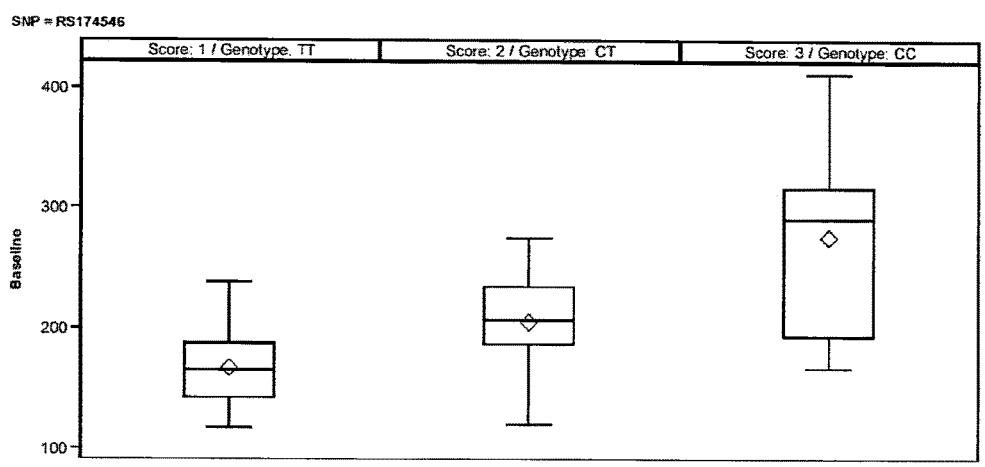
Figure 56B:
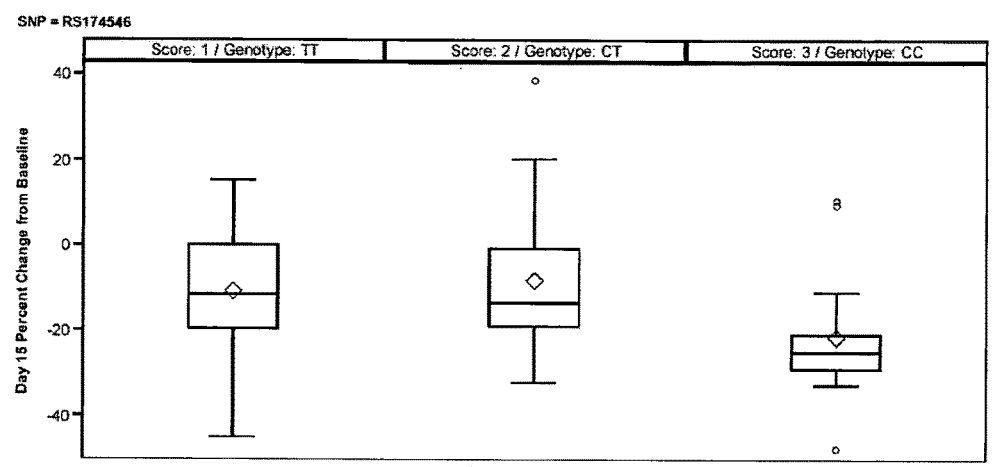

FIG. 56A depicts baseline arachidonic acid (AA) plasma levels (in μg/mL) for subjects in the clinical trial further described in Example 11, grouped according to genotype at the rs174546 SNP. FIG. 56B depicts percent change from baseline in AA plasma levels at day 15 of treatment with Epanova®, grouped according to genotype at the rs174546 SNP. For each genotype, the interquartile range is indicated by a box, the median is indicated by a horizontal line in the interior of the interquartile box, and the mean is represented by a diamond. Outliers are represented by open circles. The whiskers extend to the minimum and maximum non-outlier value. Score 1 identifies subjects who are homozygous at the major allele; Score 3 identifies subjects homozygous at the minor allele; and Score 2 represents heterozygotes.

5. DETAILED DESCRIPTION

5.1. Overview: Pharmaceutical Compositions of Omega-3 Polyunsaturated Fatty Acids in Free Acid Form that are Unexpectedly Enriched in DPA have Exceptional Clinical Efficacy Urea inclusion complexation (clathration) is a standard step often used in the refining of fish oils to remove saturated and mono-unsaturated long chain fatty acids, thus enriching for desired long chain omega-3 polyunsaturated fatty acids in the resulting composition. Despite long usage, however, and studies designed to characterize the effects of various physiochemical parameters on the process, the degree to which urea complexation enriches individual species of long chain polyunsaturated fatty acids remains unpredictable. This residual unpredictability in the urea complexation procedure, coupled with the potential for generating impermissibly high levels of ethyl carbamate, which would obligate additional processing, initially militated in favor of omitting urea complexation from the commercial scale refining process to be used for producing pharmaceutical grade compositions of omega-3 PUFAs in free acid form meeting certain desired compositional specifications.

However, as further described in Example 1, early efforts to develop a urea-free commercial scale process made clear that such processes could not reliably produce batches with a composition that met required specifications. Accordingly, a process using urea complexation was sought, and it was discovered that strict compositional control on the PUFA species present in the intermediate ethyl ester feedstock, coupled with use of an algorithmically-determined amount of urea, could reliably produce batches meeting the required specifications, and without exceeding acceptable ethyl carbamate limits.

As described in Example 2, four exemplary production batches of polyunsaturated fatty acids in free acid form were prepared using a urea complexation step. Strict compositional controls were applied to the ethyl ester intermediate feedstock, using only batches in which specified species of polyunsaturated fatty acids fell within defined range limits, and urea amounts were used that fell within the range required by the urea calculator algorithm. All four production batches of the pharmaceutical composition were determined to meet the desired compositional specifications.

As expected, the urea complexation step substantially decreased the percentage of saturated fatty acids and monounsaturated fatty acids in the resulting composition, thereby substantially enriching for polyunsaturated fatty acids. See FIG. 3A. Unexpectedly, however, performing urea complexation using urea amounts falling within the algorithmically-determined range had differential effects on enrichment of particular species of omega-3 polyunsaturated fatty acids and omega-6 polyunsaturated fatty acids.

As described below in Example 3, the omega-3 docosapentaenoic acid species, DPA (C22:5 n-3), was found to be enriched, whereas the corresponding omega-6 species, with identical chain length and degree of unsaturation, docosapentaenoic acid (C22:5 n-6), was reduced in prevalence. The divergent effect of urea complexation on enrichment of these two isomers—in conjunction with differences in their relative concentrations in the ethyl ester intermediate feedstock—resulted in a log order difference in their concentrations in the final, free acid, pharmaceutical composition ("API").

Further production batches were prepared, and as described in Example 4, compositional analysis of 10 batches of API demonstrated reproducibly elevated levels of DPA in the final composition. As described in Example 5, compositional analysis of 21 batches prepared using urea complexation demonstrated a reproducible 10-fold difference in the concentration of the omega-3 species, DPA, as compared to its omega-6 isomer, docosapentaenoic acid (C22:5 n-6).

At an average concentration of 4.44% (a/a) across 21 production batches, DPA is the third most prevalent species of polyunsaturated fatty acid in the API, exceeded only by EPA and DHA. At this level, the DPA concentration is also approximately 10-fold greater than that reported for an earlier pharmaceutical composition of omega-3 polyunsaturated fatty acids in free acid form, termed Purepa, in which DPA was reported to be present at a level of 0.5%. See Belluzzi et al., *Dig. Dis. Sci.* 39(12): 2589-2594 (1994).

Figure 1:
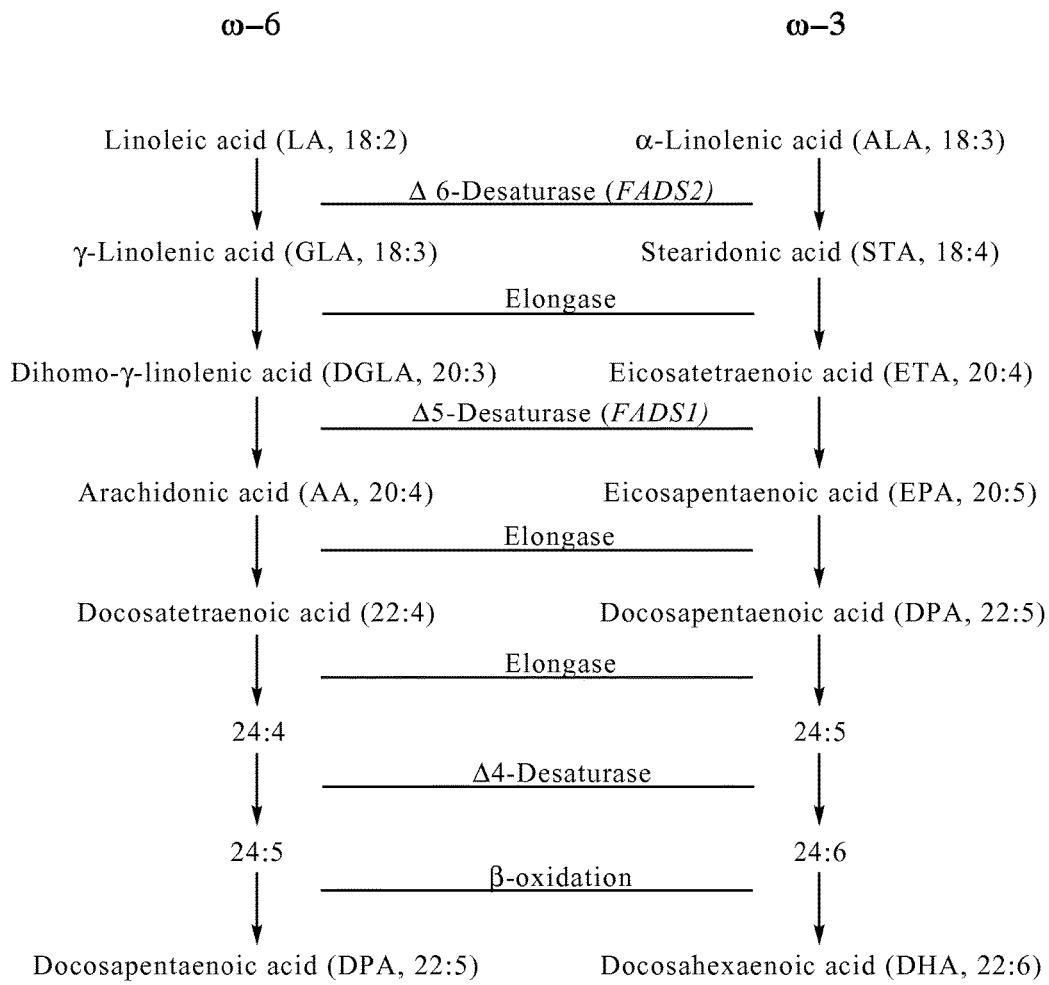
FIG. 1 shows the known human pathways for biosynthesis of omega-3 and omega-6 long-chain polyunsaturated fatty acids from intermediate (medium) chain length essential fatty acids.

Although DPA is an intermediate in the biosynthetic pathway from EPA to DHA (see FIG. 1), surprisingly little is known about the DPA's specific biological effects. To clarify the potential contribution of DPA to clinical efficacy of the pharmaceutical composition, gene expression profiling experiments were conducted using HepG2 hepatocarcinoma cells.

As further described in Example 6, DPA's effects on hepatic cell gene expression predict greater clinical efficacy of DPA-enriched compositions.

The gene expression profiling experiments demonstrated that DPA has significant biological activity at relevant in vitro concentrations. These effects are markedly different from those seen with EPA and with DHA.

At relevant concentration, DPA was observed to affect expression of genes in multiple metabolic pathways, including genes in categories known to be relevant to the clinical effects of omega-3 polyunsaturated fatty acids: genes involved in lipid metabolism, genes involved in cardiovascular physiology, and genes involved in inflammation. Significant second-order effects are also predicted, given the changes observed in the expression of genes that encode proteins that themselves affect gene expression, and in genes encoding proteins that affect post-transcriptional modification.

Specific effects on expression of several genes involved in lipid metabolism suggest that DPA, at an analogous in vivo concentration, should contribute to improvement in various clinically-relevant lipid parameters. In particular, the observed DPA-driven upregulation of ACADSB, the short/branched chain acyl-CoA dehydrogenase, predicts lower serum triglyceride levels; DPA-driven downregulation of HMGCR, analogous to inhibition of the encoded HMG-CoA-reductase enzyme by statins, would be predicted to lead to favorable decreases in the total cholesterol:HDL ratio; and DPA downregulation of SQLE, a rate-limiting step in sterol synthesis, analogously predicts reductions in total cholesterol levels.

The expression profiling experiments also demonstrated a dose threshold for DPA's effects. The lower concentration tested, chosen to mimic the 10-fold lower concentration of DPA in the earlier free acid omega-3 formulation, Purepa, affected the expression of 10-fold fewer genes than the higher DPA concentration, chosen to mimic the exposure expected from the pharmaceutical compositions described herein, demonstrating that the lower DPA concentration provides subthreshold exposure, and would be expected to provide a subtherapeutic dose in vivo.

Human clinical trials confirmed the exceptional clinical efficacy of the DPA-enriched pharmaceutical composition of omega-3 polyunsaturated fatty acids in free acid form.

Example 7 presents the results of the ECLIPSE clinical trial, an open-label, single dose, randomized 4-way-crossover study comparing the bioavailability of a 4 g dose of Lovaza® to bioavailability of a 4 g dose of the DPA-enriched pharmaceutical composition of omega-3 PUFA in free acid form described herein (hereinafter, "Epanova®"), under both high fat and low fat dietary conditions. According to the FDA-approved product label, each 1-gram capsule of Lovaza® contains at least 900 mg of the ethyl esters of omega-3 fatty acids sourced from fish oils, predominantly a combination of ethyl esters of eicosapentaenoic acid (EPA— approximately 465 mg) and docosahexaenoic acid (DHA— approximately 375 mg). The batch of Epanova® used in the trial comprised 57.3% (a/a) EPA, 19.6% (a/a) DHA, and 6.2% (a/a) DPA, each substantially in free acid form.

The baseline-adjusted change in total EPA+DHA and individual EPA and DHA absorption profiles (AUC) with Epanova® (omega-3 PUFAs in free acid form) were significantly greater than with Lovaza® (omega-3-PUFA ethyl esters) during the high-fat diet period and dramatically better during the low-fat diet period. Furthermore, there was a profound impact of fat content of the meals on the bioavailability of Lovaza®, whereas the bioavailability of Epanova® was much more predictable, due to only modest food effect.

The superior fat-independent bioavailability of Epanova® over Lovaza® is clinically important, in view of the NCEP ATP III recommendation that subjects with hypertriglyceridemia and dyslipidemias adhere to a low-fat diet during adjunct therapy.

Example 8 presents results from a 14-day bioavailability study, which demonstrated that the increase in bioavailability observed in the single-dose ECLIPSE trial is maintained, even enhanced, over 2 weeks of dosing. In addition, disaggregated subject-specific data demonstrated that the subject with least response to Epanova® still had a greater day-14 EPA+DHA $C_{max}$ than the subject with best response to Lovaza®.

Example 10 presents the results of the EVOLVE trial, a 12-week, double-blind, olive oil-controlled study of patients selected on the basis of high triglyceride levels, in the range of 500-2,000 mg/dL (severe hypertriglyceridemia). The primary study endpoint was percent change in plasma triglyceride levels from baseline to end-of-treatment ("EOT"). The secondary endpoint was percent change in plasma non-HDL cholesterol ("non-HDL-C") from baseline to EOT.

As can be seen from FIGS. 20-23, 12 week treatment with Epanova® caused dramatic increases in plasma levels of EPA, DHA, and DPA.

Increases in plasma levels of EPA, DHA, and DPA were accompanied by significant reductions in plasma AA levels, with the 4 g dosage regimen effecting an average reduction of 18%, a median reduction of 25.9%, and a least squares ("LS") mean reduction of 23.2%. These decreases in plasma arachidonic acid levels were observed despite the administration of exogenous arachidonic acid, which was present at 2.446% (a/a) in the Epanova® batch used in this trial.

The increase in EPA plasma levels with concomitant reduction in AA plasma levels caused a significant improvement in the EPA/AA ratio, from approximately 0.10 at baseline to approximately 0.67 (average) and 0.62 (median) at end-of-treatment ("EOT") at the 4 g dose. The EPA/AA ratio has been reported to constitute an independent risk factor for coronary atherosclerosis, Nakamua & Maegawa, *Endocrine Abstracts* (2012) 29 OC19.1, with lower ratios associated with progression in coronary atherosclerosis in statin-treated patients with coronary artery disease, Nozue et al., *Am J Cardiol.* 2013 Jan. 1; 111(1):6-1 (ePub ahead of print).

Furthermore, treatment with Epanova® resulted in substantial reductions in triglyceride levels (see FIGS. 26A and 26B), reductions in non-HDL-C and VLDL-C, and increase in HDL-C. LDL-C levels were elevated, an observation that may be attributed to an increase in LDL particle size upon treatment (discussed further in Example 12).

The EVOLVE trial also demonstrated that Apolipoprotein CIII (ApoCIII) was significantly reduced by Epanova® treatment. Elevated levels of ApoCIII have been found to be an independent predictor for cardiovascular heart disease (CHD) risk, whereas genetically reduced levels of ApoCIII have been associated with protection from CHD, and have also been correlated with increase in longevity.

The extremely high bioavailability of the omega-3 PUFAs in Epanova® revealed previously unknown, and unexpected, differences in pharmacokinetic response among the various PUFA species.

FIG. 29 plots the rate of change in the median percentage change from baseline in plasma levels of EPA, DHA, DPA, AA, TG, non-HDL-C, and HDL-C (absolute value) between 2 g and 4 g doses of Epanova®. With little or no increase in plasma levels of DHA and DPA upon doubling of the Epanova® dose from 2 g to 4 g per day, the rate of change (slope) in the median percentage change from baseline is near zero, predicting little further increase in DHA and DPA plasma levels would be achieved if dose is further increased. Similar plateauing of response was seen in triglyceride levels, HDL-C levels, and non-HDL-C levels (data not shown).

By contrast, the rate of change for EPA remains high, with a slope of 0.59; further increase in EPA plasma levels is expected to be obtained by increasing Epanova® dosage above 4 g per day. Significantly, the rate of change (decrease) in AA levels upon doubling the Epanova® dose from 2 g to 4 g per day is even higher than that for EPA; further reductions in AA plasma levels are expected as Epanova® dosage is increased above 4 g/day. Epanova® thus exhibits unprecedented potency in ability to elevate EPA levels, reduce AA levels, and improve the EPA:AA ratio.

As shown in FIG. 38, a subset of subjects in the 2 g treatment arm of the EVOLVE trial who were receiving concurrent statin therapy displayed greater magnitudes of percentage changes (mean LS difference), relative to control, for TG, non-HDL-C, HDL-C, LDL-C, TC, VLDL-C, and TC/HDL-C, when compared to those subjects in the 2 g treatment arm who did not receive concurrent statin therapy. Subjects receiving concurrent statin therapy showed a dose-dependent response to Epanova®, as shown in comparative data for Epanova® 2 g and Epanova® 4 g displayed in FIG. 39.

Example 12 describes the ESPRIT clinical trial, which was conducted to study patients on baseline statin therapy with triglyceride levels between 200-500 mg/dL, lower than the patients with severe hypertriglyceridemia enrolled in the EVOLVE study described in Example 10.

Dose-dependent reductions in triglycerides, reductions in non-HDL-C, and increases in HDL-C, were observed, when compared to olive oil placebo (see FIG. 43). Furthermore, dose-dependent reductions in VLDL-C and TC/HDL-C were observed (see FIG. 44). Taken together, the results (summarized in FIGS. 42-44) demonstrate efficacy of Epanova® as an add-on to statin therapy in patients with triglyceride levels between 200-500 mg/dL.

FIGS. 45-52 illustrate that Epanova® is efficacious as an add-on to both low-potency and high-potency statins, in a range of baseline patient conditions. As seen from FIG. 48, the reductions in TG levels were observed for patients who received concurrent rosuvastatin, atorvastatin, and simvastatin therapy. Statistically significant effects on triglycerides, non-HDL-C, and LDL-C levels were observed regardless whether low potency or high potency statins were co-administered, as shown in FIGS. 49-51.

5.2. DPA-Enriched Omega-3 Compositions in Free Acid Form

Accordingly, in a first aspect, improved compositions of polyunsaturated fatty acids ("PUFAs") in free acid form are provided. In various embodiments, the composition is a pharmaceutical composition suitable for oral administration. In a variety of embodiments, the composition is a neutraceutical composition suitable for oral administration.

The composition comprises a plurality of species of omega-3 PUFA, each present substantially in free acid form.

The composition comprises eicosapentaenoic acid (C20:5 n-3) ("EPA," also known as timnodonic acid), docosahexaenoic acid (C22:6 n-3) ("DHA," also known as cervonic acid), and docosapentaenoic acid (C22:5 n-3) ("DPA", also known as clupanodonic acid), each substantially in free acid form.

The composition comprises EPA in an amount, calculated as a percentage by area on GC chromatogram of all fatty acids in the composition, of at least about 45% ("45% (a/a)"). In various embodiments, the composition comprises EPA in an amount of at least about 46% (a/a) 47% (a/a), 48% (a/a), 49% (a/a), or at least about 50% (a/a). In certain embodiments, the composition comprises EPA in an amount of at least about 51% (a/a), at least about 52% (a/a), at least about 53% (a/a), at least about 54% (a/a), at least about 55% (a/a), at least about 56% (a/a), at least about 57% (a/a), at least about 58% (a/a), even at least about 59% (a/a), at least about 60% (a/a), at least about 61% (a/a), 62% (a/a), 63% (a/a), 64% (a/a), or 65% (a/a).

In certain embodiments, the composition comprises EPA in an amount of about 45 to about 65% (a/a). In particular embodiments, EPA is present in an amount of about 50 to about 60% (a/a). In various embodiments, EPA is present in an amount of about 52 to about 58.0% (a/a). In some embodiments, EPA is present in an amount of about 55% (a/a) to about 56% (a/a). In some embodiments, EPA is present in an amount of about 55% (a/a).

In various embodiments, the composition comprises EPA in an amount, calculated as a percentage by mass of all fatty acids in the composition ("% (m/m)"), of about 50% (m/m) to about 60% (m/m). In certain embodiments, EPA is present in an amount of about 55% (m/m).

The composition comprises DHA in an amount of at least about 13% (a/a). In various embodiments, the composition comprises DHA in an amount of at least about 14% (a/a), at least about 15% (a/a), at least about 16% (a/a), at least about 17% (a/a), at least about 18% (a/a), at least about 19% (a/a), or at least about 20% (a/a). In selected embodiments, the composition comprises DHA in an amount of at least about 21% (a/a), at least about 22% (a/a), at least about 23% (a/a), at least about 24% (a/a), even at least about 25% (a/a).

In various embodiments, the composition comprises DHA in an amount of about 13% (a/a) to about 25% (a/a). In certain embodiments, DHA is present in an amount of about 15% (a/a) to about 25% (a/a). In several embodiments, DHA is present in an amount of about 17% (a/a) to about 23% (a/a). In certain embodiments, DHA is present in an amount of about 19% (a/a) to about 20% (a/a).

In various embodiments, the compositions comprise DHA in an amount of about 15% (m/m) to about 25% (m/m). In certain embodiments, DHA is present in an amount of about 17% (m/m) to about 23% (m/m). In certain embodiments, DHA is present in an amount of about 20% (m/m).

The composition comprises DPA in an amount of at least about 1% (a/a). In various embodiments, the composition comprises DPA in an amount of at least about 1.5% (a/a), 2% (a/a), 2.5% (a/a), 3% (a/a), 3.5% (a/a), 4% (a/a), 4.5% (a/a), even at least about 5% (a/a). In selected embodiments, the composition comprises DPA in an amount of at least about 6% (a/a), at least about 7% (a/a), at least about 8% (a/a), or at least about 9% (a/a).

In a variety of embodiments, the composition comprises DPA in an amount of about 1% (a/a) to about 8% (a/a). In certain embodiments, the composition comprises DPA in an amount of about 2% (a/a) to about 7% (a/a). In selected embodiments, the composition comprises DPA in an amount of about 3% (a/a) to about 6% (a/a). In particular embodiments, the composition comprises DPA in an amount of about 4% (a/a) to about 5% (a/a).

In various embodiments, the composition comprises DPA, calculated as a percentage by mass of all fatty acids in the composition, in an amount of no less than about 1% (m/m). In various embodiments, the composition comprises DPA in an amount of about 1% (m/m) to about 8% (m/m). In particular embodiments, the composition comprises DPA in an amount of no more than about 10% (m/m).

The composition comprises EPA and DHA in a total amount of at least about 60% (a/a). In various embodiments, the composition comprises EPA and DHA in a total amount of at least about 61% (a/a), 62% (a/a), 63% (a/a), 64% (a/a), 65% (a/a), 66% (a/a), 67% (a/a), 68% (a/a), 69% (a/a), or at least about 70% (a/a). In particular embodiments, the composition comprise EPA and DHA in a total amount off at least about 71% (a/a), 72% (a/a), 73% (a/a), 74% (a/a), 75% (a/a), 76% (a/a), 77% (a/a), 78% (a/a), 79% (a/a), even at least about 80% (a/a). In certain embodiments, the composition comprises EPA and DHA in total amount of at least about 81% (a/a), 82% (a/a), at least about 83% (a/a), 84% (a/a), even at least about 85% (a/a).

In various embodiments, the composition comprises EPA and DHA in an amount of about 70.0% (m/m) to about 80.0% (m/m). In certain embodiments, the composition comprises about 75% (m/m) EPA plus DHA.

The composition comprises EPA, DHA, and DPA in a total amount of at least about 61% (a/a). In typical embodiments, the composition comprises EPA, DHA, and DPA in a total amount of at least about 62% (a/a), 63% (a/a), 64% (a/a), 65% (a/a), 66% (a/a), at least about 67% (a/a), at least about 68% (a/a), at least about 69% (a/a), or at least about 70% (a/a). In certain embodiments, the composition comprises EPA, DHA, and DPA in a total amount of at least about 71% (a/a), 72% (a/a), 73% (a/a), 74% (a/a), 75% (a/a), 76% (a/a), 77% (a/a), 78% (a/a), 79% (a/a), 80% (a/a), even at least about 81% (a/a), 82% (a/a), 83% (a/a), 84% (a/a), 85% (a/a), 86% (a/a), 87% (a/a), even at least about 88% (a/a).

In various embodiments, the composition comprises EPA, DHA, and DPA in a total amount of between about 70% (a/a) to about 90% (a/a).

In a particular series of embodiments, EPA is present in an amount of about 55% (a/a) to about 56% (a/a); DHA is present in an amount of about 19% (a/a) to about 20% (a/a); and DPA is present in an amount of about 4% (a/a) to about 5% (a/a).

In certain embodiments, the composition further comprises one or more omega-3 polyunsaturated fatty acid species selected from the group consisting of: α-linolenic acid (C18:3 n-3), moroctic acid (C18:4 n-3, also known as stearidonic acid), eicosatrienoic acid (C20:3 n-3), eicosatetraenoic acid (C20:4 n-3), and heneicosapentaenoic acid (C21:5 n-3).

In particular embodiments, the composition comprises EPA, DHA, DPA, and moroctic acid, each substantially in the free acid form. In a variety of embodiments, the composition comprises EPA, DHA, DPA, moroctic acid, and heneicosapentaenoic acid, each substantially in the free acid form. In specific embodiments, the composition comprises EPA, DHA, DPA, moroctic acid, heneicosapentaenoic acid, and eicosatetraenoic acid, each substantially in the free acid form. In selected embodiments, the composition comprises EPA, DHA, DPA, α-linolenic acid (C18:3 n-3), moroctic acid (C18:4 n-3), eicosatrienoic acid (C20:3 n-3), eicosatetraenoic acid (C20:4 n-3), and heneicosapentaenoic acid (C21:5 n-3).

In various embodiments, total omega-3 fatty acids—defined as the sum of alpha-linolenic acid (C18:3 n-3), moroctic acid (C18:4 n-3), eicosatrienoic acid (C20:3 n-3), eicosatetraenoic acid (C20:4 n-3), eicosapentaenoic acid (EPA) (C20:5 n-3), heneicosapentaenoic acid (C21:5 n-3), docosapentaenoic acid (C22:5 n-3) and docosahexaenoic acid (DHA) (C22:6 n-3)—constitute from about 80% (a/a) to about 95% (a/a) of all fatty acids in the composition. In a variety of embodiments, total omega-3 fatty acids constitute from about 80-about 95% (m/m) of all fatty acids in the composition.

In various embodiments, the composition further comprises one or more species of omega-6 PUFA, each present substantially in the free acid form.

In certain embodiments, the composition comprises one or more species of omega-6 PUFA selected from the group consisting of linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6, also known as osbond acid).

In particular embodiments, the composition comprises linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6), each present substantially in the free acid form.

In various embodiments, AA is present in an amount of no more than about 5% (a/a) of the fatty acids in the composition. In certain embodiments, AA comprises no more than about 4.5% (a/a) of the fatty acids in the composition. In particular embodiments, AA is present in an amount of no more than about 4% (a/a) of the fatty acids in the composition.

In certain embodiments, AA is present in an amount of no more than about 5% (m/m) of the fatty acids in the composition. In certain embodiments, AA comprises no more than about 4.5% (m/m) of the fatty acids in the composition. In particular embodiments, AA is present in an amount of no more than about 4% (m/m) of the fatty acids in the composition.

In certain embodiments, total omega-6 polyunsaturated fatty acids—defined as the sum of linoleic acid (C18:2 n-6), gamma-linolenic acid (C18:3 n-6), eicosadienoic acid (C20:2 n-6), dihomo-gamma-linolenic acid (C20:3 n-6), arachidonic acid (C20:4 n-6) and docosapentaenoic acid (C22:5 n-6)—comprise no more than about 10% (a/a) of the fatty acids in the composition. In certain embodiments, total omega-6 polyunsaturated fatty acids—defined as the sum of linoleic acid (C18:2 n-6), gamma-linolenic acid (C18:3 n-6), eicosadienoic acid (C20:2 n-6), dihomo-gamma-linolenic acid (C20:3 n-6), arachidonic acid (C20:4 n-6) and docosapentaenoic acid (C22:5 n-6)—comprise no more than about 10% (m/m) of the fatty acids in the composition.

In specific embodiments, the composition is given by Table 11, with each species of PUFA identified therein falling within the range of about −3SD to about +3 SD of the respectively recited average. In certain embodiments, each species of PUFA identified therein falls within the range of about −2SD to about +2 SD of the respectively recited average. In certain embodiments, each species falls within the range of about −1SD to about +1SD of the respectively recited average.

In selected embodiments, the composition is given by Table 13, with each species of PUFA identified therein falling within the range of about −3SD to about +3 SD of the respectively recited average. In certain embodiments, each species falls within the range of about −2SD to about +2 SD of the respectively recited average. In certain embodiments, each PUFA species falls within the range of about −1SD to about +1SD of the respectively recited average.

In certain embodiments, polyunsaturated fatty acids other than omega-3 and omega-6 polyunsaturated fatty acids are present in an amount of no more than about 5% (a/a). In various embodiments, polyunsaturated fatty acids other than omega-3 and omega-6 polyunsaturated fatty acids are present in an amount of no more than about 5% (m/m).

In a variety of embodiments, at least 90% of each of the plurality of species of omega-3 PUFA in the composition is in the free acid form. In certain embodiments, at least 91%, at least 92%, at least 93%, at least 94%, at least 95%, at least 96%, at least 97%, at least 98%, even at least 99% of each species of omega-3 PUFA in the composition is present in the free acid form. In exemplary embodiments, at least 90% of the total omega-3 polyunsaturated fatty acid content in the composition is present in the free acid form. In certain embodiments, at least 91%, at least 92%, at least 93%, at least 94%, at least 95%, at least 96%, at least 97%, at least 98%, even at least 99% of the total omega-3 polyunsaturated fatty acid content in the composition is present in the free acid form.

In various embodiments, at least 90% of each of the plurality of species of omega-6 PUFA in the composition is in the free acid form. In certain embodiments, at least 91%, at least 92%, at least 93%, at least 94%, at least 95%, at least 96%, at least 97%, at least 98%, even at least 99% of each species of omega-6 PUFA in the composition is present in the free acid form. In exemplary embodiments, at least 90% of the total omega-6 polyunsaturated fatty acid content in the composition is present in the free acid form.

In various embodiments, at least 90% of the total polyunsaturated fatty acid in the composition is present in the free acid form. In certain embodiments, at least 91%, at least 92%, at least 93%, at least 94%, at least 95%, at least 96%, at least 97%, at least 98%, even at least 99% of the total polyunsaturated fatty acid in the composition is present in the free acid form.

The composition comprises, in typical embodiments, no more than about 3.0% (a/a) saturated fatty acids and no more than about 5.0% (a/a) mono-unsaturated fatty acids. In various embodiments, the composition comprises no more than about 3.0% (m/m) saturated fatty acids and no more than about 5.0% (m/m) mono-unsaturated fatty acids.

In typical embodiments, the composition usefully further comprises an antioxidant. In certain embodiments, the antioxidant is butylated hydroxyanisole (BHA). In some embodiments, the antioxidant is alpha-tocopherol. In some embodiments, alpha-tocopherol is present in an amount of about 0.20-about 0.40% (m/m). In various embodiments, alpha-tocopherol is present in an amount of about 0.25-about 0.35% (m/m). In particular embodiments, alpha-tocopherol is present in an amount of about 0.27-about 0.33% (m/m).

In typical embodiments, the composition comprises no more than about 0.1 ppm ethyl carbamate. In some embodiments, the composition comprises no more than 0.1 ppm ethyl carbamate. In various embodiments, the composition comprises less than 0.1 ppm ethyl carbamate.

5.3. Unit Dosage Forms

In another aspect, the pharmaceutical or neutraceutical composition of DPA-enriched omega-3 PUFAs in free acid form described in Section 5.2 above is usefully packaged in unit dosage forms for oral administration.

In particular embodiments, the dosage form is a capsule. In certain embodiments, the dosage form is a gelatin capsule. In particular embodiments, the gelatin capsule is a hard gelatin capsule. In other embodiments, the dosage form is a soft gelatin capsule.

In various embodiments, the capsule comprises Type A gelatin. In some embodiments, the capsule comprises both Type A and Type B gelatin. Sources of collagen for the production of either type A or type B gelatin include, but are not limited to, cows, pigs and fish.

In various embodiments, the capsule is a soft gelatin capsule comprising sufficient porcine Type A gelatin such that the capsule disintegrates within a time period of not more than 30 minutes in purified water at 37° C. after storage for at least 3 months at 40° C. In certain embodiments, the capsule is a soft gelatin capsule comprising sufficient porcine Type A gelatin such that the capsule disintegrates within a time period of not more than 30 minutes in purified water at 37° C. after storage for 6 months at 40° C. In certain embodiments, the capsule is a soft gelatin capsule comprising sufficient porcine Type A gelatin such that the capsule disintegrates within a time period of not more than 30 minutes in purified water at 37° C. after storage for 12 months at 40° C.

In various embodiments, the capsule is a soft gelatin capsule comprising sufficient porcine Type A gelatin such that the capsule disintegrates within a time period of not more than 30 minutes in purified water at 37° C. after storage for at least 3 months at 30° C. In certain embodiments, the capsule is a soft gelatin capsule comprising sufficient porcine Type A gelatin such that the capsule disintegrates within a time period of not more than 30 minutes in purified water at 37° C. after storage for 6 months at 30° C. In some embodiments, the capsule is a soft gelatin capsule comprising sufficient porcine Type A gelatin such that the capsule disintegrates within a time period of not more than 30 minutes in purified water at 37° C. after storage for 12 months at 30° C.

In certain embodiments, the capsule is a soft gelatin capsule comprising a mixture of porcine type A gelatin and a type B gelatin. In various such embodiments, at least 1%, 2%, 3%, 4%, 5%, 10%, 15%, 20%, 25%, 30%, 40% even at least about 50% (w/w) of the gelatin is porcine type A gelatin. In selected embodiments, at least about 55%, 60%, 65%, 70%, 75% (w/w) of the gelatin is porcine type A gelatin. In particular embodiments, at least 80%, 85%, 90%, even 95% (w/w) of the gelatin is porcine type A gelatin.

In various embodiments, the capsule is a soft gelatin capsule in which the gelatin consists essentially of porcine type A gelatin.

In some embodiments, the capsule is a reduced cross-linked gelatin capsule, such as those described in U.S. Pat. No. 7,485,323, incorporated herein by reference in its entirety.

In certain embodiments, the capsule comprises succinylated gelatin.

In a variety of embodiments, capsules are made from substances that are not animal by-products, such as agar-agar, carrageenan, pectin, konjak, guar gum, food starch, modified corn starch, potato starch, and tapioca. Non-animal sources of materials that can be used to make capsules useful in the oral unit dosage forms described herein are described in U.S. Patent Publication No. 2011/0117180, incorporated herein by reference. In some embodiments, Vegicaps® Capsules (Catalent) are used.

In certain capsular oral unit dosage form embodiments, the capsule is uncoated.

In other capsular oral unit dosage form embodiments, the capsule is coated.

In certain coated capsule embodiments, the fatty acid composition is released in a time-dependent manner. In various embodiments, there is no substantial release of the PUFA composition for at least 30 minutes after ingestion. In certain embodiments, there is no substantial release of the PUFA composition for at least 30 minutes when release is tested in vitro. In certain embodiments, no more than about 20% of the PUFA composition is released within the first 30 minutes when tested in vitro. In selected embodiments, no more than about 25%, 30%, even no more than about 35% of the PUFA composition is released within the first 30 minutes, when tested in vitro. In particular embodiments, in vitro release properties are assessed according to the procedures described in provisional patent application No. 61/749,124, filed Jan. 4, 2013, titled "Method of release testing for omega-3 polyunsaturated fatty acids," by Bharat Mehta, the disclosure of which is incorporated herein by reference in its entirety.

In particular embodiments, substantial quantities of the PUFA composition are released by about 60 minutes after ingestion. In certain embodiments, substantial quantities of the PUFA composition are released by about 60 minutes when tested in vitro. In selected embodiments, at least about 40% of the PUFA composition is released by about 60 minutes, when tested in vitro. In various embodiments, at least about 45%, 50%, 55%, 60%, even at least about 65% of the PUFA composition is released by about 60 minutes, when tested in vitro. In particular embodiments, in vitro release properties are assessed according to the procedures described in provisional patent application No. 61/749,123, filed Jan. 4, 2013, titled "Method of release testing for omega-3 polyunsaturated fatty acids," by Mehta, the disclosure of which is incorporated herein by reference in its entirety.

In certain embodiments, capsules are coated as described in U.S. Pat. Nos. 5,792,795 and 5,948,818, the disclosures of which are incorporated herein by reference. In various coated embodiments, the coating is a poly(ethylacrylate-methylacrylate) copolymer. In some embodiments, the coating is Eudragit NE 30-D (Evonik Industries AG), which has an average molecular weight of about 800,000.

In other coated capsule embodiments, the capsule is coated with an enteric coating that protects the capsule from dissolution or disintegration in the stomach but dissolves at pH values encountered in the small intestine.

In various embodiments, the oral unit dosage form contains from about 100 mg to about 2000 mg of the PUFA composition. In some embodiments, the oral dosage form contains about 250 mg of the PUFA composition. In some embodiments, the oral dosage form contains about 500 mg of the PUFA composition. In certain embodiments, the oral dosage form contains about 750 mg of the PUFA composition. In some embodiments, the oral dosage form contains about 1000 mg of the PUFA composition. In other embodiments, the oral dosage form contains about 1500 mg of the PUFA composition. In certain embodiments, the unit dosage form contains nonintegral weight amounts of PUFA composition between 100 mg and 2000 mg.

5.4. Dosage Kits

In another aspect, a plurality of unit dosage forms as above-described may usefully be packaged together in a dosage kit to increase ease of use and patient compliance.

In certain embodiments, the dosage kit is a bottle. In other embodiments, the plurality of dosage forms is packaged in blister packs, a plurality of which blister packs may optionally be packaged together in a box or other enclosure. Typically, whether in a bottle or one or more blister packs, the plurality of unit dosage forms is sufficient for 30 days, 60 days, or 90 days of dosing. Thus, in selected embodiments, the unit dosage form is a capsule containing approximately one gram of pharmaceutical composition as described above, and the dosage kit comprises 30, 60, 90, 120, 150, 180, 240, 270, or 300 such capsules.

In various embodiments, the plurality of unit dosage forms is packaged under an inert gas, such as nitrogen or a noble gas, or is packaged under vacuum.

5.5. Methods of Treatment

In another aspect, methods of treatment are provided.

5.5.1. Treatment of Severe Hypertriglyceridemia (>500 mg/dL)

In a first series of treatment embodiments, methods of treating severe hypertriglyceridemia are provided.

The methods comprise orally administering the pharmaceutical composition described in Section 5.2 above to a patient having pre-treatment serum or plasma triglyceride levels ≥500 mg/dL, in an amount and for a duration sufficient to reduce serum or plasma triglyceride levels below pre-treatment levels. In typical embodiments, each dose of the pharmaceutical composition is administered as one or as a plurality of the unit dosage forms described in Section 5.3, above.

In various embodiments, the pharmaceutical composition is administered in an amount and for a duration effective to reduce serum or plasma triglyceride levels by at least about 5%, 6%, 7%, 8%, or at least about 9% below pre-treatment levels. In certain embodiments, the composition is administered in an amount and for a duration effective to reduce serum or plasma triglyceride levels by at least 10%, 11%, 12%, 13%, 14%, 15%, 16%, 17%, 18% or 19% below pre-treatment levels. In particular embodiments, the composition is administered in an amount and for a duration effective to reduce serum or plasma triglyceride levels by at least about 20% below pre-treatment levels. In various embodiments, the pharmaceutical composition is administered in an amount and for a duration effective to reduce serum or plasma triglycerides by at least about 25%, 30%, 35%, 40%, 45%, even at least about 50% below pre-treatment levels.

In a series of embodiments, the pharmaceutical composition is administered in an amount and for a duration effective to reduce serum or plasma triglyceride levels by at least about 50 mg/dL, 60 mg/dL, 70 mg/dL, 80 mg/dL, 90 mg/dL, even at least about 100 mg/dL. In certain embodiments, the composition is administered in an amount and for a duration effective to reduce serum or plasma triglyceride levels by at least about 110 mg/dL, 120 mg/dL, 130 mg/dL, 140 mg/dL, even at least about 150 mg/dL. In specific embodiments, the pharmaceutical composition is administered in an amount and for a duration effective to reduce serum or plasma triglyceride levels by at least about 160 mg/dL, 170 mg/dL, 180 mg/dL, even at least about 190 mg/dL or 200 mg/dL.

In some embodiments, the pharmaceutical composition is administered in an amount and for a duration effective to decrease non-HDL-c levels by at least about 1%, 2%, 3%, 4%, 5%, 6%, 7%, 8%, 9%, even at least about 10% below pre-treatment levels.

In various embodiments, the pharmaceutical composition is administered in an amount and for a duration effective to increase HDL-c levels by at least about 1% above pre-treatment levels. In certain embodiments, the pharmaceutical composition is administered in an amount and for a duration sufficient to increase HDL-c by at least about 2%, 3%, 4%, even at least about 5%, 6%, 7%, 8%, 9%, or 10% above pre-treatment levels.

In certain embodiments, the pharmaceutical composition is administered in an amount and for a duration effective to reduce the total cholesterol:HDL-c ("TC/HDL") ratio by at least about 1% below pre-treatment levels. In some embodiments, the pharmaceutical composition is administered in an amount and for a duration sufficient to reduce the TC/HDL ratio by at least about 2%, 3%, 4%, 5%, 6%, 7%, 8%, even at least about 9% or at least about 10% below pre-treatment levels.

In some embodiments, the pharmaceutical composition is administered in an amount and for a duration effective to decrease VLDL-c levels by at least about 5%, 6%, 7%, 8%, 9%, or at least about 10% below pre-treatment levels. In certain embodiments, the pharmaceutical composition is administered in an amount and for a duration sufficient to decrease VLDL-c levels by at least about 11%, 12%, 13%, 14%, 15%, 16%, 17%, even at least about 18%, 19%, or 20% below pre-treatment levels. In particular embodiments, the pharmaceutical composition is administered in an amount and for a duration sufficient to decrease VLDL-c levels by at least about 21%, 22%, 23%, 24%, even at least about 25% below pre-treatment levels.

In a variety of embodiments, the pharmaceutical composition is administered in an amount and for a duration effective to decrease ApoCIII levels. In certain embodiments, the pharmaceutical composition is administered in an amount and for a duration sufficient to decrease ApoCIII levels by at least about 1%, 2%, 3%, 4%, 5%, 6%, 7%, even at least about 8%, 9% or 10% below pre-treatment levels.

In some embodiments, the pharmaceutical composition is administered in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In certain embodiments, the effective amount is at least about 2 g per day. In various embodiments, the effective amount is at least about 3 g per day. In particular embodiments, the effective amount is at least about 4 g per day. In typical embodiments, the effective amount is about 2 g per day. In certain embodiments, the effective amount is about 4 g per day.

In typical embodiments, the pharmaceutical composition is administered for at least 30 days. In certain embodiments, the pharmaceutical composition is administered for at least 60 days. In particular embodiments, the pharmaceutical composition is administered for at least 90 days, 120 days, 180 days, 240 days, or at least 360 days. In certain embodiments, the pharmaceutical composition is administered indefinitely.

In some embodiments, the pharmaceutical composition is administered daily. In other embodiments, the pharmaceutical composition is administered every other day.

In particular embodiments, the daily dosage of pharmaceutical composition is administered in a single daily dose. In other embodiments, the pharmaceutical composition is administered in divided doses, with the daily dose divided into two administrations, three administrations, or even four administrations, over the course of the day.

In certain embodiments, the pharmaceutical composition is administered with food. In certain embodiments, the pharmaceutical composition is administered with a low fat meal. In other embodiments, the pharmaceutical composition is administered without food. In certain embodiments, the pharmaceutical composition is administered in the fasting state.

The methods, in certain embodiments, further comprising administering a statin. In particular embodiments, the statin is selected from the group consisting of: pravastatin, lovastatin, simvastatin, atorvastatin, fluvastatin, rosuvastatin, tenivastatin, and pitavastatin.

5.5.2. Treatment of Hypertriglyceridemia (200-500 mg/dL)

In another series of treatment embodiments, methods of treating patients who have pre-treatment serum or plasma triglyceride levels of about 200 mg/dL to about 500 mg/dL are provided. In certain embodiments, the patients are already on statin therapy; in these patients, the pre-treatment serum or plasma triglyceride levels are those measured during statin treatment, prior to administration of the pharmaceutical compositions described in Section 5.2 above.

The method comprises orally administering an effective amount of a statin, and further administering the pharmaceutical composition described in Section 5.2 herein, orally, in an amount and for a duration sufficient to lower serum or plasma triglyceride levels below levels measured prior to treatment with the pharmaceutical composition described herein. The pharmaceutical composition described in Section 5.2 and the statin need not be administered at the same time, with the same dosage schedule, or even on the same days. It is sufficient that the two be administered in sufficient temporal proximity that the patient receives therapeutic benefit concurrently from both.

In certain embodiments, the pharmaceutical composition described in Section 5.2 is administered in an amount and for a duration sufficient to reduce serum or plasma triglyceride levels by at least about 5% below pre-treatment levels. In various embodiments, the pharmaceutical composition is administered in an amount and for a duration sufficient to reduce serum or plasma triglyceride levels by at least about 6%, 7%, 8%, 9%, 10%, 11%, 12%, 13%, 14%, 15%, even at least about 16%, 17%, 18%, 19%, or at least about 20% below pre-treatment levels.

In some embodiments, the pharmaceutical composition described in Section 5.2 herein is administered in an amount and for a duration sufficient to reduce non-HDL-cholesterol by at least about 1%, at least about 2%, at least about 3%, 4%, 5%, even at least about 7%, 8%, 9%, or at least about 10% below pre-treatment levels.

In a series of embodiments, the pharmaceutical composition described in Section 5.2 herein is administered in an amount and for a duration sufficient to raise HDL-c levels by at last about 1%, 2%, 3% or more above pre-treatment levels.

In some embodiments, the pharmaceutical composition is administered in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In various embodiments, the pharmaceutical composition described in Section 5.2 herein is administered in unit dosage forms as described in Section 5.3 above.

In various embodiments, the pharmaceutical composition is administered in an amount of at least about 1 g per day. In some embodiments, the pharmaceutical composition is administered in an amount of at least about 2 g/day. In certain embodiments, the pharmaceutical composition is administered in an amount of at least about 3 g/day. In particular embodiments, the pharmaceutical composition is administered in an amount of at least about 4 g/day. In typical embodiments, the pharmaceutical composition is administered in an amount of about 2 g/day. In certain embodiments, the pharmaceutical composition is administered in an amount of about 3 g/day or about 4 g per day.

5.5.3. Treatment to Increase Plasma EPA:AA Ratios

Methods are also provided for increasing the EPA:AA ratio, without regard to the patient's pre-treatment plasma triglyceride levels. The methods comprise administering the pharmaceutical composition described in Section 5.2 herein to a patient having an EPA:AA ratio below about 0.25, in an amount and for duration sufficient to increase the patient's EPA:AA ratio to at least about 0.25. In some embodiments, the pharmaceutical composition is administered in an amount and for a duration sufficient to increase the patient's EPA:AA ratio to at least about 0.3, at least about 0.35, at least about 0.40, at least about 0.45, at least about 0.50, even to a level of at least about 0.55, 0.60, 0.61, 0.62, 0.63, 0.64, or 0.65.

In certain embodiments, the method comprises administering the pharmaceutical composition in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In various embodiments, the pharmaceutical composition described in Section 5.2 herein is administered in unit dosage forms as described in Section 5.3 above.

In various embodiments, the pharmaceutical composition is administered in an amount of at least about 1 g per day. In some embodiments, the pharmaceutical composition is administered in an amount of at least about 2 g/day. In certain embodiments, the pharmaceutical composition is administered in an amount of at least about 3 g/day. In particular embodiments, the pharmaceutical composition is administered in an amount of at least about 4 g/day. In typical embodiments, the pharmaceutical composition is administered in an amount of about 2 g/day. In certain embodiments, the pharmaceutical composition is administered in an amount of about 3 g/day or about 4 g per day.

5.5.4. Treatment to Lower Serum or Plasma ApoCIII Levels

Methods are also provided for decreasing a patient's serum or plasma ApoCIII levels, without regard to the patient's pre-treatment plasma triglyceride levels. The methods comprise administering the pharmaceutical composition described in Section 5.2 herein to a patient in need of lower ApoCIII levels, in an amount and for duration sufficient to decrease the patient's serum or plasma ApoCIII levels. In typical embodiments, the patient is at risk for cardiovascular heart disease.

In certain embodiments, the pharmaceutical composition is administered in an amount and for a duration sufficient to decrease ApoCIII levels by at least about 1%, 2%, 3%, 4%, 5%, 6%, 7%, even at least about 8%, 9% or 10% below pre-treatment levels.

5.5.5. Other Methods of Treatment

In another aspect, the pharmaceutical compositions described herein is used to treat other disorders, including one or more of nonalcoholic steatohepatitis (NASH), hyperlipoproteinemia, including type III hyperlipoproteinemia, and metabolic syndrome.

In certain embodiments, the pharmaceutical composition is used to reduce resistance to platelet aggregation inhibitors, such as Plavix, including use in the methods described in U.S. patent application Ser. No. 13/620,312, the disclosure of which is incorporated herein by reference in its entirety.

5.6. Process

In another aspect, an improved process is presented for refining fish oil into pharmaceutical compositions comprising PUFAs in free acid form, and particularly for refining fish oil into the pharmaceutical compositions described in Section 5.2 herein.

5.6.1. Preparation of Intermediate Feedstock

The intermediate feedstock is prepared by transesterification of the body oil obtained from fish, for example fish from families Engraulidae, Clupeidae and Scombridae, by standard techniques well-known in the art, with process parameters adjusted so as to achieve a composition falling within the tolerances described in section 5.6.2 immediately below.

Suitable standard process steps are described, e.g., in U.S. Pat. Nos. 5,656,667; 5,719,302; 5,945,318; 6,204,401; 6,518,049; 6,528,669; 7,491,522; 7,550,613; 7,678,930; 7,718,698; 7,732,488 and in U.S. Pat. Nos. 5,472,705; 5,750,572; 5,776,978; 5,869,714; 7,541,480; 7,553,870; and 7,619,002, incorporated herein by reference.

In an exemplary process, a crude triglyceride oil is extracted from fish, such as anchovy, sardine, mackerel and menhaden. The crude triglyceride oil is then alkali refined, e.g. using sodium hydroxide, and deodorized, polished, and dried. The PUFAs are then converted to esters, such as methyl esters or ethyl esters, by transesterification. Transesterification can be performed, for example, by ethanolysis in the presence of ethanol and sodium ethoxide to produce ethyl esters. Transesterification is followed by at least one round, typically a plurality of rounds, of distillation.

In another exemplary process, triglyceride oil is alkali refined and deodorized, transesterified with ethanol, such as by ethanolysis in the presence of ethanol and sodium ethoxide, and then subject to one or more rounds of fractional distillation.

Figure 2:
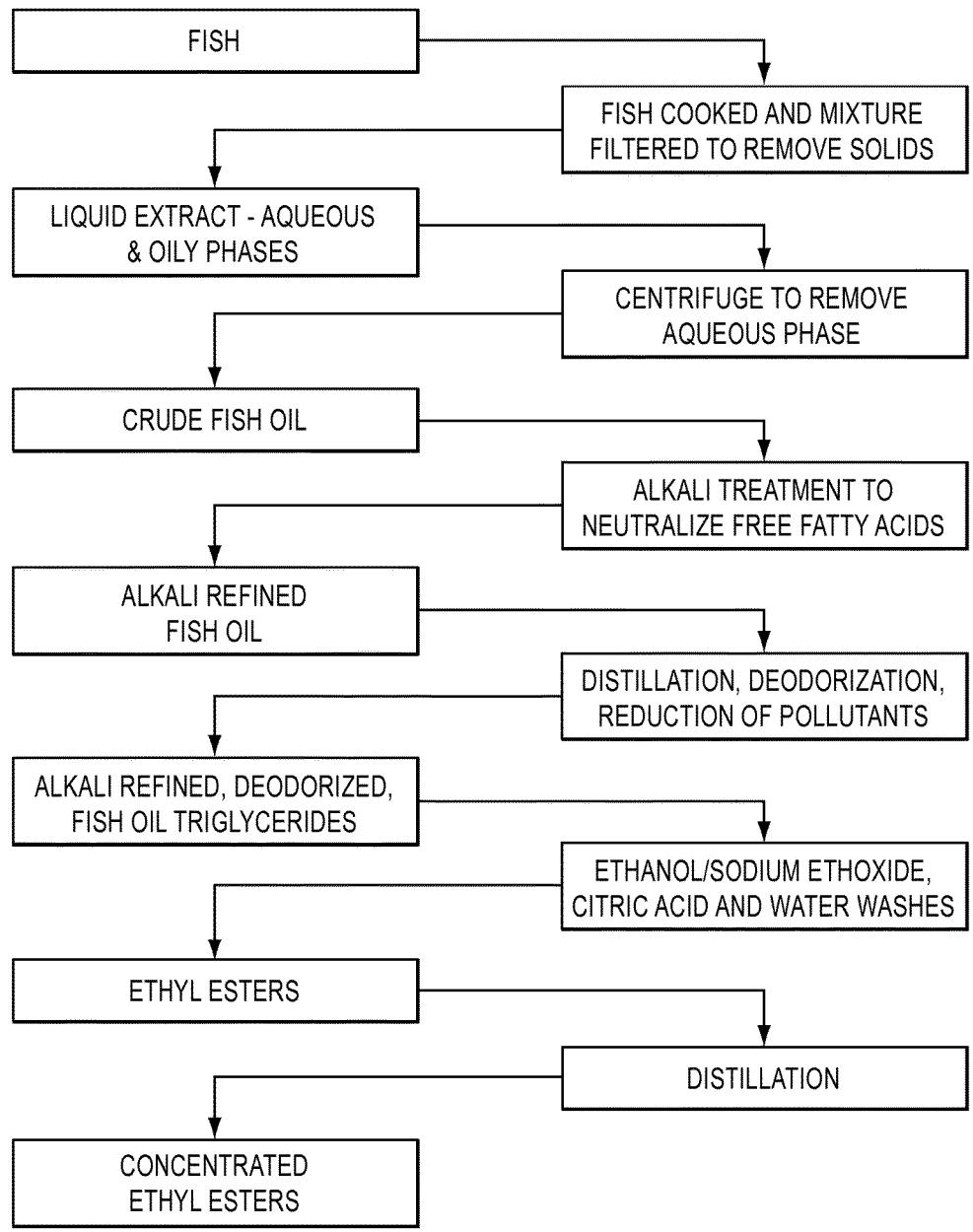
FIG. 2 is flow chart of an exemplary process for preparing an intermediate feedstock of PUFA ethyl esters.

FIG. 2 presents a flow chart of an exemplary process for producing the intermediate feedstock. In this process, fish are cooked in water and the resulting mixture of liquids and solids are filtered and the liquid portion centrifuged to remove the aqueous phase. The oily fraction remaining from the preceding step is treated with alkali to neutralize any free fatty acids present, followed by water washing. Thereafter, alkali refined fish oil in the triglyceride form is deodorized and environmental pollutants reduced, e.g. by distillation. The dried deodorized fish oil is converted to the ethyl ester form using reaction with ethanol, catalyzed by the use of sodium ethoxide. After completion of the reaction, the excess ethanol is removed by distillation and the ethyl esters washed with a citric acid solution and then with water. In this exemplary process, the ethyl esters are distilled to achieve the required concentration of EPA ethyl ester (EPA-EE) and DHA ethyl ester (DHA-EE) for use as an intermediate feedstock. In some embodiments, multiple rounds of distillation are performed. The exact conditions used are adjusted depending on the composition of the input ethyl ester composition in order to achieve the required concentration of EPA-EE and DHA-EE for the intermediate feedstock, as detailed in section 5.6.2 immediately below.

Alternatives to these process steps are well known, and may be used as appropriate so long as the resulting intermediate feedstock composition falls within the tolerances defined in section 5.6.2 immediately below.

5.6.2. Intermediate Feedstock Composition

The intermediate feedstock composition comprises a plurality of species of omega-3 PUFAs, each present substantially in the form of an ethyl ester.

The intermediate feedstock composition comprises EPA, DHA, and DPA, each substantially in the form of an ethyl ester.

In various embodiments, the intermediate feedstock composition comprises EPA ethyl ester (EPA-EE), DHA-EE, and DPA-EE, in an amount, calculated as a percentage by area on GC chromatogram of all fatty acid ethyl esters in the composition, falling within the range of −3SD to +3 SD of the averages respectively recited in Table 9. In certain embodiments, each of EPA-EE, DHA-EE, and DPA-EE falls within −2SD to +2 SD of the respectively recited average. In certain embodiments, each of EPA-EE, DHA-EE, and DPA-EE falls with −1SD to +1SD of the respectively recited average. In certain embodiments, the intermediate feedstock composition comprises EPA-EE, DHA-EE, and DPA-EE within the range set by their respective minima and maxima area percentages among the batches described in Table 8.

In certain embodiments, the composition further comprises one or more omega-3 polyunsaturated fatty acids, each substantially in the form of the ethyl ester, selected from the group consisting of: α-linolenic acid (C18:3 n-3), moroctic acid (C18:4 n-3), eicosatrienoic acid (C20:3 n-3), eicosatetraenoic acid (C20:4 n-3), and heneicosapentaenoic acid (C21:5 n-3). In various embodiments, the one or more further species of omega-3-EE, if present, is present in an amount, calculated as a percentage by area on GC chromatogram of all fatty acid ethyl esters in the composition, falling within the range of −3SD to +3 SD of the averages respectively recited in Table 9. In certain embodiments, each species falls within −2SD to +2 SD of the respectively recited average. In certain embodiments, each species falls with −1SD to +1SD of the respectively recited average. In certain embodiments, the one or more further species of omega-3-EE, if present, is present in an amount, calculated as a percentage by area on GC chromatogram of all fatty acid ethyl esters in the composition, falling within the range set by their respective minima and maxima area percentages among the batches described in Table 8.

In certain embodiments, the intermediate feedstock composition also comprises at least one species of omega-6 PUFA. In various embodiments, the composition comprises ethyl esters of one or more omega-6 polyunsaturated fatty acid selected from the group consisting of: linoleic acid (C18:2 n-6), gamma-linolenic acid (C18:3 n-6), eicosadienoic acid (C20:3 n-6), dihomo-gamma-linolenic acid ("DGLA") (C20:3 n-6), arachidonic acid (C20:4 n-6) ("AA"), and docosapentaenoic acid (C22:5 n-6). Each species of omega-6 PUFA is present substantially in ethyl ester form.

In various embodiments, the one or more species of omega-6-EE, if present, is present in an amount, calculated as a percentage by area on GC chromatogram of all fatty acid ethyl esters in the composition, falling within the range of −3SD to +3 SD of the averages respectively recited in Table 9. In certain embodiments, each species falls within −2SD to +2 SD of the respectively recited average. In certain embodiments, each species falls with −1SD to +1SD of the respectively recited average. In certain embodiments, the one or more further species of omega-3-EE, if present, is present in an amount, calculated as a percentage by area on GC chromatogram of all fatty acid ethyl esters in the composition, falling within the range set by their respective minima and maxima area percentages among the batches described in Table 8.

5.6.3. Urea Complexation

Intermediate transesterified feedstock having a composition as above-defined is subjected to urea inclusion complexation. In typical embodiments, the amount of urea used for complexation falls within an algorithmically-determined range.

Thus, in another aspect, an improved process is presented for refining fish oil into pharmaceutical compositions comprising PUFAs in free acid form, particularly for refining fish oil into the pharmaceutical compositions described herein. The improvement comprises subjecting an intermediate feedstock of transesterified fish oil comprising the ethyl esters of various omega-3 and omega-6 PUFA species in defined percentage ranges to a step of urea inclusion complexation, wherein the amount of urea used for complexation is within the range calculated according to (i) formula I(a), or (ii) according to formula I(b), or (iii) according to both formula I(a) and formula I(b) with the urea amount set to a value within the range set by, and inclusive of, the results of formulae I(a) and I(b), such as an average thereof, wherein the formulae are as follows:

$$[\text{Urea}] = F_{enrichment\text{-}DHA} * ((DHA_{target} - DHA\text{-}EE_{input}) / DHA\text{-}EE_{input})) \quad \text{(Ia)}$$

$$[\text{Urea}] = F_{enrichment\text{-}EPA} * ((EPA_{target} - EPA\text{-}EE_{input}) / EPA\text{-}EE_{input})) \quad \text{(Ib).}$$

The DHA and EPA target values are selected based on the desired final composition. The enrichment factors, $F_{enrichment\text{-}DHA}$ and $F_{enrichment\text{-}EPA}$, can be the same or different. In a typical embodiment, $F_{enrichment\text{-}DHA}$ and $F_{enrichment\text{-}EPA}$ are the same, with a value of about 100/0.34, or about 300.

Using the algorithmically determined amount of urea, complexation is performed according to standard techniques. See, e.g., U.S. Pat. Nos. 4,377,526; 5,106,542; 5,243,046; 5,679,809; 5,945,318; 6,528,669; 6,664,405; 7,541,480; 7,709,668; and 8,003,813, the disclosures of which are incorporated herein by reference.

In an exemplary embodiment, the intermediate feedstock is mixed with a solution of urea in ethanol. The complexation is carried out at 60° C.-80° C., the mixture is then cooled, and the mixture is thereafter filtered or centrifuged to remove urea complexes. Ethanol is removed by distillation and the oil washed several times with water.

5.6.4. Post-Complexation Finishing

Following removal of urea complexes, the uncomplexed PUFA esters are hydrolyzed to free fatty acids by standard techniques. The composition is further purified by distillation, either before or after hydrolysis, and further finished using one or more of the following standard techniques: treatment with active carbon, chromatographic purification, solvent removal, bleaching, e.g. with bleaching earth, and supercritical extraction. Antioxidants, such as BHA or α-tocopherol, are added.

6. EXAMPLES

6.1. Example 1: Urea Complexation is Required for Reliable Production of Omega-3 PUFA Compositions in Free Acid Form that Meet Specification Requirements Urea inclusion complexation (clathration) is a standard step often used in the refining of fish oils to remove saturated and mono-unsaturated long chain fatty acids, thus enriching for desired long chain omega-3 polyunsaturated fatty acids in the resulting composition. Despite long usage, however (see, e.g., U.S. Pat. No. 4,377,526), and studies designed to characterize the effects of various physiochemical parameters on the process (see, e.g., Hayes et al., "Triangular Phase Diagrams To Predict The Fractionation Of Free Fatty Acid Mixtures Via Urea Complex Formation," *Separation Sci. Technol.* 36(1):45-58 (2001) and Hayes, "Purification of Free Fatty Acids via Urea Inclusion Compounds," in *Handbook of Functional Lipids* (Taylor & Francis Group) (2005)), the degree to which urea complexation enriches individual species of long chain polyunsaturated fatty acids, including species of both omega-3 PUFAs, and omega-6 PUFAs, remains unpredictable. This residual unpredictability in the urea complexation procedure, and the potential for urea complexation to generate impermissible levels of ethyl carbamate, which would obligate further processing, initially militated in favor of omitting urea complexation from the commercial scale refining process to be used for producing pharmaceutical grade compositions of omega-3 PUFAs in free acid form meeting the specifications set forth in Table 1, below.

TABLE 1

| Initial Target Specifications | |
|---|---|
| Parameter (all species to be present as free acid) | Specification limit |
| EPA | 50.0-60.0% (m/m) |
| DHA | 15.0-25.0% (m/m) |
| EPA + DHA | 70.0-80.0% (m/m) |
| Total omega-3 fatty acids | 80.0-90.0% (m/m) |
| Arachidonic Acid | nmt 4.5% (a/a) |
| Saturated fatty acids | nmt 3.0% (a/a) |
| Mono-unsaturated fatty acids | nmt 5.0% (a/a) |
| Omega-6 fatty acids | nmt 10.0% (a/a) |
| Other unsaturated fatty acids | nmt 5.0% (a/a) |
| Total unidentified above 0.1% | nmt 2.0% (a/a) |

"(m/m)"—percentage, by weight, of all fatty acids in the composition

"(a/a)"—percentage by area on gas chromatogram of all fatty acids in the composition "nmt"—"no more than".

Early efforts to develop a urea-free process, however, demonstrated that such processes could not reliably produce pharmaceutical compositions on a commercial scale that met the required target compositional specification. Table 2, below, presents data on two such lots. Values that fell outside of the desired specification range are underlined.

TABLE 2

| Parameter (all species to be present as free acid) | Specification limit | Batch 1 (non-winterized) | | Batch 2 (winterized) | |
|---|---|---|---|---|---|
| | | (m/m) | (a/a) | (m/m) | (a/a) |
| EPA | 50.0-60.0% (m/m) | <u>49.0</u> | 51.5 | <u>49.8</u> | 53.0 |
| DHA | 15.0-25.0% (m/m) | 19.6 | 20.3 | 19.6 | 20.9 |
| EPA + DHA | 70.0-80.0% (m/m) | <u>68.3</u> | 71.8 | <u>69.4</u> | 73.9 |
| Total omega-3 fatty acids | 80.0-90.0% (m/m) | <u>78.0</u> | 81.2 | <u>79.3</u> | 83.7 |
| Arachidonic Acid | nmt 4.5% (a/a) | 2.8 | 2.8 | 2.9 | 2.8 |
| Saturated fatty acids | nmt 3.0% (a/a) | 1.9 | 2.6 | 0.6 | 0.5 |
| Mono-unsaturated fatty acids | nmt 5.0% (a/a) | <u>6.6</u> | 5.1 | <u>6.7</u> | 5.1 |
| Omega-6 fatty acids | nmt 10.0% (a/a) | 4.2 | 5.3 | 4.3 | 5.2 |
| Other unsaturated fatty acids | nmt 5.0% (a/a) | 2.7 | 0.3 | 2.1 | 0.4 |
| Total unidentified above 0.1% | nmt 2.0% (a/a) | <u>5.4</u> | <u>5.5</u> | <u>6.3</u> | <u>5.4</u> |

Accordingly, a process using urea complexation was sought, and it was discovered that strict compositional control on the PUFA species present in the intermediate ethyl ester feedstock, coupled with use of urea amounts within ranges set algorithmically, could reliably produce pharmaceutical compositions meeting the specifications set forth in Table 1 without exceeding acceptable ethyl carbamate limits.

The compositional requirements for the intermediate ethyl ester feedstock are presented in Section 5.6.2 and Examples 2 and 4. See Tables 3-6, 8-9.

The optimal amount of urea required to be used was found to be determined by (i) formula I(a), or (ii) according to formula I(b), or (iii) according to both formula I(a) and formula I(b), with the urea amount set to a value within the range set by, and inclusive of, the results of formulae I(a) and I(b), such as the average of the two results, wherein the formulae are as follows:

$$[\text{Urea}] = F_{enrichment-DHA} * ((DHA_{target} - DHA\text{-}EE_{input}) / DHA\text{-}EE_{input})) \quad (Ia)$$

$$[\text{Urea}] = F_{enrichment-EPA} * ((EPA_{target} - EPA\text{-}EE_{input}) / EPA\text{-}EE_{input})) \quad (Ib).$$

The enrichment factors, $F_{enrichment-DHA}$ and $F_{enrichment-EPA}$, can be the same or different. A typical value, using the intermediate feedstock batches described in Examples 2 and 4, has been found to be about 100/0.34 (i.e., about 300) for both.

6.2. Example 2: Compositional Analysis of Four Exemplary Production Batches Produced Using Controlled Urea Complexation Confirm that Specification Requirements were Met Four exemplary production batches of polyunsaturated fatty acids in free acid form were prepared. Strict compositional controls were applied to the ethyl ester intermediate feedstock, using only batches in which specified species of polyunsaturated fatty acids fell within defined range limits. Urea amounts to be used for complexation at production scale were first determined empirically at lab scale, using small test batches of the ethyl ester intermediate feedstock and varying the concentration of urea, thereby varying the oil:urea:ethanol ratio. The optimal concentration suggested by the test scale determinations was confirmed to fall within the range required by the algorithm described in Example 1, and used for production scale manufacture.

The composition of the intermediate transesterified feedstock and the final pharmaceutical composition ("active pharmaceutical ingredient", or "API"), was determined by gas chromatography. Results are compiled in Tables 3-6, below.

TABLE 3

| PUFA species | | Intermediate Feedstock (transesterified ethyl esters) | API (final free fatty acid composition) |
|---|---|---|---|
| (common name) | (identity) | (% a/a) | (% a/a) |
| linoleic acid | 18:2 n-6 | 0.54 | 0.55 |
| gamma-linolenic acid | 18:3 n-6 | 0.00 | 0.15 |
| α-linolenic acid | 18:3 n-3 | 0.45 | 0.39 |
| moroctic acid | 18:4 n-3 | 1.52 | 1.70 |
| eicosadienoic acid | 20:2 n-6 | 0.00 | 0.10 |
| dihomo-gamma-linolenic acid | 20:3 n-6 | 0.47 | 0.35 |
| arachidonic acid (AA) | 20:4 n-6 | 2.11 | 2.43 |
| eicosatrienoic acid | 20:3 n-3 | 0.00 | 0.15 |
| eicosatetraenoic acid | 20:4 n-3 | 1.78 | 2.18 |
| eicosapentaenoic acid (EPA) | 20:5 n-3 | 49.42 | 57.25 |
| heneicosapentaenoic acid | 21:5 n-3 | 2.32 | 2.79 |
| docosapentaenoic acid | 22:5 n-6 | 0.71 | 0.83 |
| docosapentaenoic acid (DPA) | 22:5 n-3 | 5.80 | 6.23 |
| docosahexaenoic acid (DHA) | 22:6 n-3 | 17.09 | 19.58 |
| Aggregate Metrics | | | |
| Total % | | 99.41 | 98.43 |
| PUFAs % | | 82.77 | 96.30 |
| Total Omega 3 | | 78.37 | 90.26 |
| Total Omega 6 | | 3.83 | 4.41 |
| Remaining PUFAs | | 0.57 | 1.63 |
| Saturates % | | 4.34 | 0.35 |
| Mono-unsaturates % | | 12.30 | 1.34 |
| Unknowns % | | 0.60 | 0.42 |

TABLE 4

| PUFA species | | Intermediate Feedstock (transesterified ethyl esters) | API (final free fatty acid composition) |
|---|---|---|---|
| (common name) | (identity) | (% a/a) | (% a/a) |
| linoleic acid | 18:2 n-6 | 0.54 | 0.49 |
| gamma-linolenic acid | 18:3 n-6 | 0.00 | 0.14 |
| α-linolenic acid | 18:3 n-3 | 0.45 | 0.34 |
| moroctic acid | 18:4 n-3 | 1.52 | 1.67 |
| eicosadienoic acid | 20:2 n-6 | 0.00 | 0.13 |
| dihomo-gamma-linolenic acid | 20:3 n-6 | 0.47 | 0.39 |
| arachidonic acid (AA) | 20:4 n-6 | 2.11 | 2.45 |
| eicosatrienoic acid | 20:3 n-3 | 0.00 | 0.25 |
| eicosatetraenoic acid | 20:4 n-3 | 1.78 | 2.02 |
| eicosapentaenoic acid (EPA) | 20:5 n-3 | 49.42 | 57.64 |
| heneicosapentaenoic acid | 21:5 n-3 | 2.32 | 2.75 |
| docosapentaenoic acid | 22:5 n-6 | 0.71 | 0.79 |
| docosapentaenoic acid (DPA) | 22:5 n-3 | 5.80 | 6.22 |
| docosahexaenoic acid (DHA) | 22:6 n-3 | 17.09 | 19.65 |
| Aggregate Metrics | | | |
| Total % | | 99.41 | 98.60 |
| PUFAs % | | 82.77 | 96.35 |
| Total Omega 3 | | 78.37 | 90.54 |
| Total Omega 6 | | 3.83 | 4.38 |
| Remaining PUFAs | | 0.57 | 1.43 |
| Saturates % | | 4.34 | 0.31 |
| Mono-unsaturates % | | 12.30 | 1.25 |
| Unknown % | | 0.60 | 0.69 |

TABLE 5

| PUFA species | | Intermediate Feedstock (transesterified ethyl esters) | API (final free fatty acid composition) |
|---|---|---|---|
| (common name) | (identity) | (% a/a) | (% a/a) |
| linoleic acid | 18:2 n-6 | 0.54 | 0.59 |
| gamma-linolenic acid | 18:3 n-6 | 0.00 | 0.12 |
| α-linolenic acid | 18:3 n-3 | 0.38 | 0.38 |
| moroctic acid | 18:4 n-3 | 1.09 | 1.16 |
| eicosadienoic acid | 20:2 n-6 | 0.00 | 0.12 |
| dihomo-gamma-linolenic acid | 20:3 n-6 | 0.57 | 0.45 |
| arachidonic acid | 20:4 n-6 | 2.42 | 2.84 |
| eicosatrienoic acid | 20:3 n-3 | 0.00 | 0.22 |
| eicosatetraenoic acid | 20:4 n-3 | 1.97 | 2.11 |
| eicosapentaenoic acid (EPA) | 20:5 n-3 | 49.20 | 55.81 |

TABLE 5-continued

| PUFA species (common name) | (identity) | Intermediate Feedstock (transesterified ethyl esters) (% a/a) | API (final free fatty acid composition) (% a/a) |
|---|---|---|---|
| heneicosapentaenoic acid | 21:5 n-3 | 2.30 | 2.72 |
| docosapentaenoic acid | 22:5 n-6 | 0.64 | 0.13 |
| docosapentaenoic acid (DPA) | 22:5 n-3 | 5.06 | 5.46 |
| docosahexaenoic acid (DHA) | 22:6 n-3 | 17.64 | 19.45 |
| Aggregate Metrics | | | |
| Total % | | 99.60 | 98.76 |
| PUFAs % | | 82.48 | 93.77 |
| Total Omega 3 | | 77.64 | 87.31 |
| Total Omega 6 | | 4.36 | 4.24 |
| Remaining PUFAs | | 0.48 | 2.22 |
| Saturates % | | 5.15 | 0.24 |
| Mono-unsaturates % | | 11.98 | 2.97 |
| Unknowns % | | 0.40 | 1.79 |

TABLE 6

| PUFA species (common name) | (identity) | Intermediate Feedstock (transesterified ethyl esters) (% a/a) | API (final free fatty acid composition) (% a/a) |
|---|---|---|---|
| linoleic acid | 18:2 n-6 | 0.55 | 0.55 |
| gamma-linolenic acid | 18:3 n-6 | 0.00 | 0.12 |
| α-linolenic acid | 18:3 n-3 | 0.38 | 0.37 |
| moroctic acid | 18:4 n-3 | 1.13 | 1.26 |
| eicosadienoic acid | 20:2 n-6 | 0.36 | 0.00 |
| dihomo-gamma-linolenic acid | 20:3 n-6 | 0.56 | 0.42 |
| arachidonic acid (AA) | 20:4 n-6 | 2.43 | 2.86 |
| eicosatrienoic acid | 20:3 n-3 | 0.00 | 0.16 |
| eicosatetraenoic acid | 20:4 n-3 | 1.82 | 2.09 |
| eicosapentaenoic acid (EPA) | 20:5 n-3 | 48.84 | 57.08 |
| heneicosapentaenoic acid | 21:5 n-3 | 2.28 | 2.78 |
| docosapentaenoic acid | 22:5 n-6 | 0.63 | 0.10 |
| docosapentaenoic acid (DPA) | 22:5 n-3 | 5.02 | 5.49 |
| docosahexaenoic acid (DHA) | 22:6 n-3 | 17.61 | 20.00 |
| Aggregate Metrics | | | |
| Total % | | 99.49 | 98.74 |
| PUFAs % | | 82.11 | 94.94 |
| Total Omega 3 | | 77.09 | 89.22 |
| Total Omega 6 | | 4.53 | 4.05 |
| Remaining PUFAs | | 0.49 | 1.67 |
| Saturates % | | 5.42 | 0.40 |
| Mono-unsaturates % | | 11.96 | 1.57 |
| Unknowns % | | 0.51 | 1.84 |

All four production batches of API met the compositional specifications set forth in Table 1, above.

6.3. Example 3: Controlled Urea Complexation Differentially Enriches Selected Omega-3 and Omega-6 Species As expected, the urea complexation step substantially decreased the percentage of saturated fatty acids and mono-unsaturated fatty acids in the resulting composition, thereby substantially enriching for polyunsaturated fatty acids. See Tables 3-6, and FIG. 3A. Unexpectedly, however, performing urea complexation using urea amounts falling within the algorithmically-determined range had a differential effect on enrichment of individual species of omega-3 polyunsaturated fatty acids and omega-6 polyunsaturated fatty acids.

Table 7 provides a qualitative assessment of enrichment of various species of polyunsaturated fatty acid, comparing prevalence in the ethyl ester intermediate feedstock to that in the free acid API, averaged across the four production batches described in Tables 3-6. See also FIG. 3B.

TABLE 7

| Polyunsaturated fatty acid species | Qualitative effect of controlled urea complexation |
|---|---|
| linoleic acid (C18:2 n-6) | neutral |
| gamma-linolenic acid (C18:3 n-6) | enriched |
| α-linolenic acid (C18:3 n-3) | reduced |
| moroctic acid (C18:4 n-3) | enriched |
| eicosadienoic acid (C20:2 n-6) | neutral |
| dihomo-gamma-linolenic acid (C20:3 n-6) | reduced |
| arachidonic acid (C20:4 n-6) (AA) | enriched |
| eicosatrienoic acid (C20:3 n-3) | enriched |
| eicosatetraenoic acid (C20:4 n-3) | enriched |
| eicosapentaenoic acid (C20:5 n-3) (EPA) | enriched |
| heneicosapentaenoic acid (C21:5 n-3) | enriched |
| docosapentaenoic acid (C22:5 n-6) | reduced |
| docosapentaenoic acid (C22:5 n-3) (DPA) | enriched |
| docosahexaenoic acid (C22:6 n-3) (DHA) | enriched |

Although omega-3 polyunsaturated fatty acids, as a class, are substantially enriched, the effect of urea complexation on omega-6 PUFAs, as a class, is not as predictable. On average, the omega-6 species DGLA and docosapentaenoic acid are reduced in prevalence; gamma-linolenic acid and arachidonic acid are increased; and there is little or no effect on linolenic acid and eicosadienoic acid.

We noted, in particular, that the omega-3 docosapentaenoic acid species, DPA (C22:5 n-3), is enriched, whereas the corresponding omega-6 species, with identical chain length and degree of unsaturation, docosapentaenoic acid (C22:5 n-6), is reduced in prevalence. The divergent effect of urea complexation on enrichment of these two isomers—in conjunction with differences in their relative concentrations in the ethyl ester intermediate feed stock—results in a log order difference in their concentrations in the final, free acid, API. Averaging across the four batches of API presented in Tables 3-6, the omega-3 docosapentaenoic acid species, DPA, is present in the final API at 5.85% (a/a), whereas the omega-6 docosapentaenoic acid species is present at an average concentration of 0.46% (a/a).

At an average concentration of 5.85% (a/a), DPA is the third most prevalent species of polyunsaturated fatty acid in the API, exceeded only by EPA and DHA. At this level, the DPA concentration is also 10-fold greater than that reported for an earlier pharmaceutical composition of omega-3 polyunsaturated fatty acids in free acid form, termed Purepa, in which DPA was reported to be present at a level of 0.5%. See Belluzzi et al., *Dig. Dis. Sci.* 39(12): 2589-2594 (1994).

6.4. Example 4: Compositional Analysis of Ten (10) Exemplary Production Batches of API Demonstrates Reproducibly Elevated Levels of DPA Further production batches were prepared according to the methods described in Example 2.

Data from ten (10) batches of API, inclusive of the four batches described in Tables 3-6 in Example 2, produced from eight (8) different batches of intermediate transesterified (ethyl ester) feedstock, are presented in the tables below.

The composition of each of the intermediate feedstock batches is shown in Table 8. Table 9 presents the average ("AVG"), standard deviation ("STDEV", "SD"), and Delta ("Δ", the absolute difference between +1 SD and −1 SD, +2 SD and −2 SD, etc.) across the 8 batches of intermediate feedstock for each of the listed (ethyl ester) species. The composition of each of the ten batches of final API is shown in Table 10, below; Table 11 presents the average, standard deviation, and Delta values for each of the listed (free acid) species across the 10 batches of API.

TABLE 8

Intermediate (Ethyl Ester) Feedstock Batches

| Identity | Common name | Batch 1 | Batch 2 | Batch 3 | Batch 4 | Batch 5 | Batch 6 | Batch 7 | Batch 8 |
|---|---|---|---|---|---|---|---|---|---|
| | BV No. | 319021 | 319553 | 319554 | 320613 | 320766 | 320941 | 320824 | 320862 |
| | ONC No. | 22581 | 24876 | 24906 | 27008 | 27824 | 27824 | 28069 | 28139 |
| | | area % | area % | area % | area % | area % | area % | area % | area % |
| C18:2(n-6) | Linoleic acid | 0.552 | 0.516 | 0.522 | 0.571 | 0.689 | 0.712 | 0.657 | 0.611 |
| C18:3(n-6) | Gamma-linolenic acid | 0.166 | 0.146 | 0.141 | 0.157 | 0.253 | 0.218 | 0.283 | 0.159 |
| C18:3(n-3) | α-Linolenic acid | 0.379 | 0.368 | 0.351 | 0.422 | 0.516 | 0.498 | 0.419 | 0.491 |
| C18:4(n-3) | Moroctic acid | 1.403 | 0.991 | 1.008 | 1.100 | 1.432 | 1.462 | 1.372 | 1.505 |
| C20:2(n-6) | Eicosadienoic acid | 0.156 | 0.181 | 0.194 | 0.167 | 0.423 | 0.366 | 0.274 | 0.212 |
| C20:3(n-6) | Dihomo-gamma-linolenic acid | 0.314 | 0.384 | 0.421 | 0.376 | 0.415 | 0.473 | 0.446 | 0.398 |
| C20:4(n-6) | Arachidonic acid | 1.977 | 2.362 | 2.316 | 2.805 | 2.867 | 2.884 | 3.306 | 2.152 |
| C20:3(n-3) | Eicosatrienoic acid | 0.171 | 0.200 | 0.216 | 0.181 | 0.270 | 0.223 | 0.220 | 0.245 |
| C20:4(n-3) | Eicosatetraenoic acid | 1.855 | 1.908 | 1.870 | 1.653 | 2.159 | 2.142 | 1.896 | 2.132 |
| C20:5(n-3) | EPA | 46.131 | 45.698 | 44.908 | 45.317 | 45.131 | 45.675 | 45.416 | 46.185 |
| C21:5(n-3) | Heneicosapentaenoic acid | 2.239 | 2.105 | 2.156 | 2.165 | 1.763 | 1.761 | 2.140 | 2.407 |
| C22:5(n-6) | Docosapentaenoic acid | 0.658 | 0.575 | 0.556 | 0.508 | 0.535 | 0.524 | 0.509 | 0.572 |
| C22:5(n-3) | DPA | 5.341 | 4.634 | 4.598 | 5.178 | 2.858 | 2.874 | 4.324 | 4.834 |
| C22:6(n-3) | DHA | 15.875 | 16.102 | 15.997 | 15.700 | 16.861 | 17.046 | 16.128 | 16.852 |

TABLE 9

Intermediate (Ethyl Ester) Feedstock
8 batch statistics

| Identity | Common name | AVG | SD | −3SD | −2SD | −1SD | +1SD | +2SD | +3SD | 1SD Δ | 2SD Δ | 3SD Δ |
|---|---|---|---|---|---|---|---|---|---|---|---|---|
| C18:2(n-6) | Linoleic acid | 0.60 | 0.08 | 0.38 | 0.45 | 0.53 | 0.68 | 0.76 | 0.83 | 0.15 | 0.30 | 0.45 |
| C18:3(n-6) | Gamma-linolenic acid | 0.19 | 0.05 | 0.03 | 0.08 | 0.14 | 0.24 | 0.30 | 0.35 | 0.11 | 0.22 | 0.32 |
| C18:3(n-3) | α-Linolenic acid | 0.43 | 0.06 | 0.24 | 0.30 | 0.37 | 0.49 | 0.56 | 0.62 | 0.13 | 0.26 | 0.38 |
| C18:4(n-3) | Moroctic acid | 1.28 | 0.21 | 0.64 | 0.86 | 1.07 | 1.50 | 1.71 | 1.93 | 0.43 | 0.86 | 1.28 |
| C20:2(n-6) | Eicosadienoic acid | 0.25 | 0.10 | −0.05 | 0.05 | 0.15 | 0.35 | 0.45 | 0.54 | 0.20 | 0.40 | 0.60 |
| C20:3(n-6) | Dihomo-gamma-linolenic acid | 0.40 | 0.05 | 0.26 | 0.31 | 0.36 | 0.45 | 0.50 | 0.55 | 0.10 | 0.19 | 0.29 |
| C20:4(n-6) | Arachidonic acid | 2.58 | 0.45 | 1.23 | 1.68 | 2.13 | 3.03 | 3.48 | 3.93 | 0.90 | 1.80 | 2.70 |
| C20:3(n-3) | Eicosatrienoic acid | 0.22 | 0.03 | 0.12 | 0.15 | 0.18 | 0.25 | 0.28 | 0.31 | 0.07 | 0.13 | 0.19 |
| C20:4(n-3) | Eicosatetraenoic acid | 1.95 | 0.18 | 1.42 | 1.60 | 1.77 | 2.13 | 2.31 | 2.49 | 0.36 | 0.71 | 1.07 |
| C20:5(n-3) | EPA | 45.56 | 0.45 | 44.20 | 44.65 | 45.10 | 46.01 | 46.46 | 46.92 | 0.91 | 1.81 | 2.72 |
| C21:5(n-3) | Heneicosapentaenoic acid | 2.09 | 0.22 | 1.42 | 1.64 | 1.87 | 2.32 | 2.54 | 2.76 | 0.45 | 0.90 | 1.34 |
| C22:5(n-6) | Docosapentaenoic acid | 0.56 | 0.05 | 0.41 | 0.46 | 0.51 | 0.60 | 0.65 | 0.70 | 0.10 | 0.20 | 0.30 |
| C22:5(n-3) | DPA | 4.33 | 0.96 | 1.45 | 2.41 | 3.37 | 5.29 | 6.25 | 7.21 | 1.92 | 3.84 | 5.76 |
| C22:6(n-3) | DHA | 16.32 | 0.52 | 14.77 | 15.29 | 15.80 | 16.84 | 17.36 | 17.87 | 1.04 | 2.07 | 3.10 |

TABLE 10

Final (free acid) API Batches

| Identity | Common name | Batch 1 | Batch 2 | Batch 3 | Batch 4 | Batch 5 | Batch 6 | Batch 7 | Batch 8 | Batch 9 | Batch 10 |
|---|---|---|---|---|---|---|---|---|---|---|---|
| | | API Batch # | | | | | | | | | |
| | | 36355 | 36395 | 37225 | 37289 | 38151 | 38154 | 38157 | 38300 | 38303 | 38306 |
| | | Intermediate Batch # | | | | | | | | | |
| | | 1 | 1 | 2 | 3 | 4 | 4 | 5 | 7 | 8 | 6 |
| | | area % | area % | area % | area % | area % | area % | area % | area % | area % | area % |
| C18:2(n-6) | Linoleic acid | 0.55 | 0.49 | 0.59 | 0.55 | 0.60 | 0.61 | 0.78 | 0.62 | 0.53 | 0.72 |
| C18:3(n-6) | Gamma-linolenic acid | 0.15 | 0.14 | 0.12 | 0.12 | 0.17 | 0.16 | 0.16 | 0.22 | 0.15 | 0.15 |
| C18:3(n-3) | α-Linolenic acid | 0.39 | 0.34 | 0.38 | 0.37 | 0.45 | 0.45 | 0.55 | 0.41 | 0.44 | 0.50 |
| C18:4(n-3) | Moroctic acid | 1.70 | 1.67 | 1.16 | 1.26 | 1.37 | 1.37 | 1.87 | 1.65 | 1.77 | 1.81 |
| C20:2(n-6) | Eicosadienoic acid | 0.10 | 0.13 | 0.12 | 0.09 | 0.10 | 0.10 | 0.27 | 0.12 | 0.11 | 0.12 |
| C20:3(n-6) | Dihomo-gamma-linolenic acid | 0.35 | 0.39 | 0.45 | 0.42 | 0.42 | 0.45 | 0.52 | 0.51 | 0.42 | 0.51 |
| C20:4(n-6) | Arachidonic acid | 2.43 | 2.45 | 2.84 | 2.86 | 3.50 | 3.50 | 3.64 | 4.02 | 2.57 | 3.60 |
| C20:3(n-3) | Eicosatrienoic acid | 0.15 | 0.25 | 0.22 | 0.16 | 0.20 | 0.17 | 0.25 | 0.18 | 0.17 | 0.23 |
| C20:4(n-3) | Eicosatetraenoic acid | 2.18 | 2.02 | 2.11 | 2.09 | 1.96 | 1.90 | 2.64 | 2.13 | 2.34 | 2.54 |
| C20:5(n-3) | EPA | 57.25 | 57.64 | 55.81 | 57.08 | 56.25 | 56.38 | 56.88 | 56.30 | 56.72 | 57.15 |
| C21:5(n-3) | Heneicosapentaenoic acid | 2.79 | 2.75 | 2.72 | 2.78 | 2.68 | 2.60 | 2.15 | 2.57 | 2.88 | 2.18 |
| C22:5(n-6) | Docosapentaenoic acid | 0.20 | 0.17 | 0.72 | 0.71 | 0.61 | 0.62 | 0.66 | 0.63 | 0.71 | 0.66 |
| C22:5(n-3) | DPA | 6.23 | 6.22 | 5.46 | 5.49 | 6.12 | 5.97 | 3.41 | 5.15 | 5.59 | 3.43 |
| C22:6(n-3) | DHA | 19.58 | 19.65 | 19.45 | 20.00 | 19.16 | 18.79 | 20.60 | 20.10 | 20.97 | 21.01 |

TABLE 11

Final (free acid) API 10 batch statistics

| Identity | Common name | AVG | SD | −3 SD | −2 SD | −1 SD | +1 SD | +2 SD | +3 SD | 1SD Δ | 2SD Δ | 3SD Δ |
|---|---|---|---|---|---|---|---|---|---|---|---|---|
| C18:2(n-6) | Linoleic acid | 0.61 | 0.09 | 0.34 | 0.43 | 0.52 | 0.69 | 0.78 | 0.87 | 0.18 | 0.35 | 0.53 |
| C18:3(n-6) | Gamma-linolenic acid | 0.15 | 0.03 | 0.07 | 0.10 | 0.13 | 0.18 | 0.21 | 0.24 | 0.06 | 0.11 | 0.17 |
| C18:3(n-3) | α-Linolenic acid | 0.43 | 0.06 | 0.23 | 0.30 | 0.36 | 0.49 | 0.56 | 0.62 | 0.13 | 0.26 | 0.39 |
| C18:4(n-3) | Moroctic acid | 1.56 | 0.25 | 0.81 | 1.06 | 1.31 | 1.81 | 2.06 | 2.31 | 0.50 | 1.00 | 1.50 |
| C20:2(n-6) | Eicosadienoic acid | 0.13 | 0.05 | −0.03 | 0.02 | 0.07 | 0.18 | 0.23 | 0.29 | 0.11 | 0.21 | 0.32 |
| C20:3(n-6) | Dihomo-gamma-linolenic acid | 0.44 | 0.06 | 0.28 | 0.33 | 0.39 | 0.50 | 0.56 | 0.61 | 0.11 | 0.22 | 0.33 |
| C20:4(n-6) | Arachidonic acid | 3.14 | 0.58 | 1.41 | 1.99 | 2.57 | 3.72 | 4.29 | 4.87 | 1.15 | 2.30 | 3.46 |
| C20:3(n-3) | Eicosatrienoic acid | 0.20 | 0.04 | 0.08 | 0.12 | 0.16 | 0.24 | 0.28 | 0.32 | 0.08 | 0.16 | 0.24 |
| C20:4(n-3) | Eicosatetraenoic acid | 2.19 | 0.24 | 1.46 | 1.71 | 1.95 | 2.43 | 2.68 | 2.92 | 0.49 | 0.97 | 1.46 |
| C20:5(n-3) | Eicosapentaenoic acid (EPA) | 56.74 | 0.56 | 55.07 | 55.63 | 56.19 | 57.30 | 57.86 | 58.42 | 1.12 | 2.23 | 3.34 |
| C21:5(n-3) | Heneicosapentaenoic acid | 2.61 | 0.25 | 1.85 | 2.11 | 2.36 | 2.86 | 3.12 | 3.37 | 0.51 | 1.01 | 1.52 |
| C22:5(n-6) | Docosapentaenoic acid | 0.57 | 0.21 | −0.05 | 0.16 | 0.36 | 0.78 | 0.98 | 1.19 | 0.41 | 0.83 | 1.24 |
| C22:5(n-3) | Docosapentaenoic acid (DPA) | 5.31 | 1.06 | 2.13 | 3.19 | 4.25 | 6.37 | 7.42 | 8.48 | 2.12 | 4.23 | 6.35 |
| C22:6(n-3) | Docosahexaenoic acid (DHA) | 19.93 | 0.75 | 17.68 | 18.43 | 19.18 | 20.68 | 21.43 | 22.18 | 1.50 | 2.99 | 4.49 |

As is evident from Table 11, the log order difference in relative concentration in the API of the omega-3 docosapentaenoic acid species, DPA (C22:5 n-3), and the omega-6 docosapentaenoic acid isomer (C22:5 n-6), is maintained—at 5.31% (a/a) for DPA (C22:5 n-3) vs. 0.57% (a/a) for docosapentaenoic acid (C22:5 n-6)—as is the 10-fold increase in concentration of DPA as compared to the earlier omega-3 free acid Purepa formulation reported in Belluzzi et al. (5.31 vs. 0.5%).

6.5. Example 5: Compositional Analysis of 21 Exemplary Production Batches Demonstrates Reproducibly Elevated Levels of DPA The high absolute and relative concentration of the omega-3 docosapentaenoic acid species, DPA, has now been observed across 21 batches of API produced using urea complexation, as summarized in Tables 12 and 13, below.

TABLE 12

Final (free acid) API 21 batch statistics

| Identity | Common name | Min % (a/a) | Max % (a/a) | AVG % (a/a) |
|---|---|---|---|---|
| C18:2(n-6) | Linoleic acid | 0.49 | 1.00 | 0.74 |
| C18:3(n-6) | Gamma-linolenic acid | 0.12 | 0.52 | 0.24 |
| C18:3(n-3) | a-Linolenic acid | 0.34 | 0.83 | 0.54 |
| C18:4(n-3) | Stearidonic (moroctic) acid | 1.16 | 5.83 | 2.83 |
| C20:2(n-6) | Eicosadienoic acid | 0.10 | 0.27 | 0.15 |
| C20:3(n-6) | Dihomo-gamma-linolenic acid | 0.24 | 0.52 | 0.40 |

TABLE 12-continued

Final (free acid) API
21 batch statistics

| Identity | Common name | Min % (a/a) | Max % (a/a) | AVG % (a/a) |
|---|---|---|---|---|
| C20:4(n-6) | Arachidonic acid (AA) | 2.32 | 4.02 | 3.17 |
| C20:3(n-3) | Eicosatrienoic acid | 0.10 | 0.25 | 0.16 |
| C20:4(n-3) | Eicosatetraenoic acid | 1.40 | 2.82 | 2.13 |
| C20:5(n-3) | Eicosapentaenoic (timnodonic) acid (EPA) | 48.61 | 57.64 | 55.40 |
| C21:5(n-3) | Heneicosapentaenoic acid | 1.81 | 2.88 | 2.33 |
| C22:5(n-6) | Docosapentaenoic acid | 0.17 | 0.73 | 0.58 |
| C22:5(n-3) | Docosapentaenoic acid (DPA) | 2.77 | 6.23 | 4.44 |
| C22:6(n-3) | Cervonic acid (DHA) | 15.99 | 21.78 | 19.35 |

TABLE 13

Final (free acid) API
21 batch statistics

| Identity | Common name | AVG % (a/a) | SD | -3SD | -2SD | -1SD | +1SD | +2SD | +3SD | 1SD Δ | 2SD Δ | 3SD Δ |
|---|---|---|---|---|---|---|---|---|---|---|---|---|
| C18:2(n-6) | Linoleic acid | 0.74 | 0.16 | 0.26 | 0.42 | 0.58 | 0.90 | 1.07 | 1.23 | 0.32 | 0.65 | 0.97 |
| C18:3(n-6) | Gamma-linolenic acid | 0.24 | 0.11 | -0.09 | 0.02 | 0.13 | 0.35 | 0.46 | 0.58 | 0.22 | 0.44 | 0.66 |
| C18:3(n-3) | α-Linolenic acid | 0.54 | 0.15 | 0.09 | 0.24 | 0.39 | 0.69 | 0.84 | 0.99 | 0.30 | 0.60 | 0.90 |
| C18:4(n-3) | Stearidonic (moroctic) acid | 2.83 | 1.49 | -1.63 | -0.15 | 1.34 | 4.31 | 5.80 | 7.28 | 2.97 | 5.94 | 8.92 |
| C20:2(n-6) | Eicosadienoic acid | 0.15 | 0.04 | 0.02 | 0.07 | 0.11 | 0.20 | 0.24 | 0.28 | 0.09 | 0.17 | 0.26 |
| C20:3(n-6) | Dihomo-gamma-linolenic acid | 0.40 | 0.07 | 0.18 | 0.25 | 0.32 | 0.47 | 0.55 | 0.62 | 0.15 | 0.30 | 0.45 |
| C20:4(n-6) | Arachidonic acid | 3.17 | 0.51 | 1.65 | 2.16 | 2.67 | 3.68 | 4.19 | 4.70 | 1.01 | 2.03 | 3.04 |
| C20:3(n-3) | Eicosatrienoic acid | 0.16 | 0.05 | 0.01 | 0.06 | 0.11 | 0.21 | 0.26 | 0.31 | 0.10 | 0.20 | 0.31 |
| C20:4(n-3) | Eicosatetraenoic acid | 2.13 | 0.41 | 0.92 | 1.32 | 1.73 | 2.54 | 2.94 | 3.35 | 0.81 | 1.62 | 2.43 |
| C20:5(n-3) | Timnodonic acid (EPA) | 55.40 | 2.13 | 49.00 | 51.13 | 53.27 | 57.53 | 59.66 | 61.80 | 4.26 | 8.53 | 12.79 |
| C21:5(n-3) | Heneicosapentaenoic acid | 2.33 | 0.34 | 1.29 | 1.64 | 1.98 | 2.67 | 3.02 | 3.36 | 0.69 | 1.38 | 2.07 |
| C22:5(n-6) | Docosapentaenoic acid | 0.58 | 0.16 | 0.11 | 0.27 | 0.43 | 0.74 | 0.90 | 1.06 | 0.31 | 0.63 | 0.94 |
| C22:5(n-3) | Docosapentaenoic acid (DPA) | 4.44 | 1.16 | 0.98 | 2.13 | 3.29 | 5.60 | 6.75 | 7.91 | 2.31 | 4.62 | 6.93 |
| C22:6(n-3) | Cervonic acid (DHA) | 19.35 | 1.69 | 14.28 | 15.97 | 17.66 | 21.04 | 22.73 | 24.42 | 3.38 | 6.76 | 10.14 |

6.6. Example 6: DPA's Effects on Hepatic Cell Gene Expression Predict Greater Clinical Efficacy of DPA-Enriched Compositions DPA is the third most prevalent species of polyunsaturated fatty acid in the pharmaceutical compositions analyzed in the examples above, and is present at a concentration 10-fold that in Purepa, an earlier pharmaceutical composition of omega-3 polyunsaturated fatty acids in free acid form. Although DPA is an intermediate in the biosynthetic pathway from EPA to DHA (see FIG. 1), surprisingly little is known about the DPA's specific biological effects. See Kaur et al., "Docosapentaenoic acid (22:5n-3): a review of its biological effects," Prog. Lipid Res. 50:28-34 (2011). To clarify the potential contribution of DPA to clinical efficacy of the pharmaceutical composition, gene expression profiling experiments were conducted.

6.6.1. Methods

Cell Culture and Treatment—
Hep G2 hepatocarcinoma cells were cultured in serum-free Dulbecco's Modified Eagle's Medium (DMEM) (Sigma-Aldrich) with 4.5 g/l glucose, 1-glutamine, $NaHCO_3$ and pyridoxine HCl supplemented with 1% (vol/vol) non-essential amino acids, 1% Na-pyruvate, 1% penicillin/streptomycin, and 10% (vol/vol) fatty acid-free bovine serum albumin (BSA), all purchased from Gibco BRL.

Cell cultures were transferred weekly by trypsinization and incubated at 37° C. in a humidified incubator containing 5% $CO_2$. After 5 weeks of cell culture, EPA (eicosapentaenoic acid, lot #0439708-2, Cayman Chemicals), DPA (docosapentaenoic acid, lot 163481-26, Cayman Chemicals), and DHA (docosahexaenoic acid, lot 0437083-5, Cayman Chemicals), diluted immediately before use in serum free DMEM, were added to triplicate wells (250,000 cells/well) at the final effective concentrations set forth in Table 14, below.

Ratios of EPA (at 100 µM), DHA (at 40 µM), and DPA (at 11 µM) were chosen to approximate the ratios of EPA, DHA, and DPA in the pharmaceutical compositions (API) described in Section 5.2 and Example 5 (see Tables 12 and 13). Absolute concentrations were chosen to best approximate—within the constraint imposed by the desired compositional ratios and constraints imposed by the culture conditions—the plasma ranges observed in the 2 g and 4 g treatment arms of the EVOLVE trial (see Example 10). The lower DPA concentration (1 µM) was chosen to approximate the systemic exposure that would be expected from use of the earlier pharmaceutical composition of omega-3 polyunsaturated fatty acids in free acid form, termed Purepa, in which DPA was reported to be present at a level 1/10 that seen in the current pharmaceutical composition.

The HepG2 cells were incubated with the identified fatty acid (EPA, DHA, DPA, or specified mixtures) for a total of 48 hours prior to cell harvest and RNA extraction.

TABLE 14

| Sample # | PUFA species | Final concentration per well | Well | RNA quality (260/280) |
|---|---|---|---|---|
| GL 01 | EPA | 30 μM | a | 2.0 |
| GL 02 | EPA | 30 μM | b | 2.1 |
| GL 03 | EPA | 30 μM | c | 2.0 |
| GL 04 | EPA | 100 μM | a | 1.98 |
| GL 05 | EPA | 100 μM | b | 2.05 |
| GL 06 | EPA | 100 μM | c | 2.0 |
| GL 07 | DHA | 12 μM | a | 2.0 |
| GL 08 | DHA | 12 μM | b | 2.04 |
| GL 09 | DHA | 12 μM | c | 2.0 |
| GL 10 | DHA | 40 uM | a | 2.0 |
| GL 11 | DHA | 40 uM | b | 2.0 |
| GL 12 | DHA | 40 uM | c | 2.11 |
| GL 13 | DPA | 0.3 μM | a | 2.07 |
| GL 14 | DPA | 0.3 μM | b | 2.0 |
| GL 15 | DPA | 0.3 μM | c | 2.0 |
| GL 16 | DPA | 3.0 μM | a | 2.09 |
| GL 17 | DPA | 3.0 μM | b | 2.0 |
| GL 18 | DPA | 3.0 μM | c | 1.99 |
| GL 19 | DPA | 1 μM | a | 2.2 |
| GL 20 | DPA | 1 μM | b | 2.03 |
| GL 21 | DPA | 1 μM | c | 2.03 |
| GL 22 | DPA | 11 μM | a | 2.0 |
| GL 23 | DPA | 11 μM | b | 2.08 |
| GL 24 | DPA | 11 μM | c | 2.06 |
| GL 25 | EPA:DHA:DPA 100:40:1(50:20:0.5) | total 200 μM | a | 2.05 |
| GL 26 | EPA:DHA:DPA 100:40:1(50:20:0.5) | total 200 μM | b | 2.0 |
| GL 27 | EPA:DHA:DPA 100:40:1(50:20:0.5) | total 200 μM | c | 2.0 |
| GL 28 | EPA:DHA:DPA 100:40:11 (50:20:5.5) | total 200 μM | a | 2.0 |
| GL 29 | EPA:DHA:DPA 100:40:11 (50:20:5.5) | total 200 μM | b | 2.06 |
| GL 30 | EPA:DHA:DPA 100:40:11 (50:20:5.5) | total 200 μM | c | 2.07 |
| GL 31 | EPA:DHA:DPA 30:12:0.3 (50:20:0.5) | total 60 μM | a | 2.07 |
| GL 32 | EPA:DHA:DPA 30:12:0.3 (50:20:0.5) | total 60 μM | b | 2.13 |
| GL 33 | EPA:DHA:DPA 30:12:0.3 (50:20:0.5) | total 60 μM | c | 2.05 |
| GL 34 | EPA:DHA:DPA 30:12:3 (50:20:5.5) | total 60 μM | a | 2.0 |
| GL 35 | EPA:DHA:DPA 30:12:3 (50:20:5.5) | total 60 μM | b | 2.12 |
| GL 36 | EPA:DHA:DPA 30:12:3 (50:20:5.5) | total 60 μM | c | 2.01 |
| GL 37 | BSA (fatty acid free) |  | a | 2.03 |
| GL 38 | BSA (fatty acid free) |  | b | 2.00 |
| GL 39 | BSA(fatty acid free) |  | c | 2.00 |

Cell Harvest and RNA Isolation—

Total RNA was isolated using TRIzol, according to manufacturer's instructions (Invitrogen). RNA quality was assessed with a Nanodrop 8000 Spectrophotometer (Thermo Scientific). As set forth in Table 14, above, each of the RNA extractions for each treatment had a 260/280 ratio between 2.0 and 2.2. RNA was then further purified with Qiagen RNeasy columns. From 300 ng of total RNA per prep, the Illumina TotalPrep RNA Amplification kit (Ambion) was used to generate amplified biotinylated cRNA after reverse transcription by the Eberwine procedure. Aliquots of the treated and control RNA samples were sent to a gene expression core lab for analysis. The remainder of the total RNA samples were stored at −70° C.

Expression Assay and Data Analysis—

Specific transcripts within the biotinylated cRNA were measured by fluorescent imaging after direct hybridization to Illumina HT-12 bead arrays, v.4.0. Gene expression data were analyzed using Ingenuity® iReport™ software (Ingenuity Systems, Redwood City, Calif.).

6.6.2. Results

6.6.2.1. Expression Profiling Demonstrates that DPA has Biological Effects Different from EPA and DHA Although DPA is an intermediate in the biosynthetic pathway from EPA to DHA, and although DPA is known to retroconvert to EPA in vivo, Kaur et al., *Prog. Lipid Res.* 50:28-34 (2011), we observed markedly different effects on hepatic cell gene expression after incubating with DPA, as compared to effects seen with EPA and with DHA.

For a high-level assessment of similarities and differences in effects on gene expression, we used the Ingenuity® iReport™ software to query the gene expression data for the top 5 responses, ranked by the Ingenuity® iReport™ algorithm, seen after exposure to each of EPA (100 μM), DHA (40 μM), and DPA (11 μM), within various curated categories of genes. Results are cumulated in Table 15, below. An analogous assessment, using a different categorization, is presented in Table 16, which follows. Symbols used are: "□"—attribute is unique to the specified fatty acid species; "□"—attribute is shared with another fatty acid species; and "♦"—attribute was commonly observed with all 3 fatty acid species.

TABLE 15

| | EPA | DHA | DPA |
|---|---|---|---|
| Diseases and Disorders | | | |
| Cancer | ♦ | ♦ | ♦ |
| Connective Tissue Disorders | □ | | |
| Dermatological Diseases and Conditions | | □ | □ |
| Developmental Disorder | | □ | |
| Hematological Disease | | | □ |
| Immunological Disease | □ | | |
| Infectious Disease | ♦ | ♦ | ♦ |
| Inflammatory Disease | □ | | |
| Renal and Urological Disease | | □ | |
| Reproductive System Disease | | | □ |
| Molecular and Cellular Functions | | | |
| Cellular Compromise | □ | | |
| Cell Death and Survival | □ | □ | |
| Cellular Development | ♦ | ♦ | ♦ |
| Cellular Function and Maintenance | □ | | |
| Cellular Growth and Proliferation | ♦ | ♦ | ♦ |
| Cellular Movement | □ | | |
| Cell-To-Cell Signaling and Interaction | | □ | □ |
| Gene Expression | | □ | |
| RNA Post-Transcriptional Modification | | □ | |
| Physiological System Development and Function | | | |
| Connective Tissue Development and Function | | □ | |
| Hematological System Development and Function | □ | | □ |
| Hematopoiesis | □ | | |
| Immune Cell Trafficking | | | □ |
| Lymphoid Tissue Structure and Development | □ | | |
| Reproductive System Development and Function | □ | □ | |
| Skeletal and Muscular System Development and Function | | □ | |
| Tissue Development | | □ | □ |
| Tissue Morphology | | | □ |
| Tumor Morphology | ♦ | ♦ | ♦ |
| Top Canonical Pathways | | | |
| CD27 Signaling in Lymphocytes | | | |
| IL-17A Signaling in Airway Cells | | □ | □ |
| IL-17A Signaling in Gastric Cells | | □ | □ |
| IL-8 Signaling | □ | | |

TABLE 15-continued

| | EPA | DHA | DPA |
|---|---|---|---|
| IMLP Signaling of Neutrophils | □ | | |
| Role of IL-17F in Allergic Inflammatory Airway Diseases | | □ | |
| Role of IL-17A in Arthritis | ♦ | ♦ | ♦ |
| Role of IL-17A in Psoriasis | | □ | □ |
| Role of Macrophages, Fibroblasts and Endothelial Cells in Rheumatoid Arthritis | □ | | |
| TREM1 Signaling | □ | | |

TABLE 16

| | EPA | DHA | DPA |
|---|---|---|---|
| Tox Lists | | | |
| Cardiac Hypertrophy | □ | | |
| Hepatic Cholestasis | ♦ | ♦ | ♦ |
| Hepatic Stellate Cell Activation | | □ | |
| Increases Transmembrane Potential of Mitochondria and Mitochondrial Membrane | | | □ |
| Liver Necrosis/Cell Death | □ | | |
| Liver Proliferation | □ | □ | |
| Mechanism of Gene Regulation by Peroxisome Proliferators via PPARα | | □ | |
| PPARα/RXRα Activation | | □ | □ |
| Primary Glomerulonephritis Biomarker Panel (Human) | | □ | |
| Renal Necrosis/Cell Death | □ | □ | |
| Clinical Chemistry and Hematology | | | |
| Increased Levels of Albumin | | | □ |
| Increased Levels of Creatinine | ♦ | ♦ | ♦ |
| Increased Levels of Hematocrit | □ | | |
| Increased Levels of Red Blood Cells | □ | □ | |
| Cardiotoxicity | | | |
| Cardiac Arrhythmia | | | □ |
| Cardiac Damage | □ | | |
| Cardiac Dysfunction | | □ | |
| Cardiac Fibrosis | | □ | □ |
| Cardiac Hypertrophy | ♦ | ♦ | ♦ |
| Cardiac Inflammation | ♦ | ♦ | ♦ |
| Cardiac Necrosis/Cell Death | □ | | □ |
| Cardiac Proliferation | | □ | |
| Congenital Heart Anomaly | | | □ |
| Hepatotoxicity | | | |
| Biliary Hyperplasia | | | □ |
| Liver Cholestasis | ♦ | ♦ | ♦ |
| Liver Damage | □ | | |
| Liver Enlargement | | □ | □ |
| Liver Hepatitis | | □ | □ |
| Liver Inflammation | ♦ | ♦ | ♦ |
| Liver Necrosis/Cell Death | □ | | |
| Liver Proliferation | □ | □ | |
| Nephrotoxicity | | | |
| Renal Damage | □ | □ | |
| Renal Hydronephrosis | | | □ |
| Renal Inflammation | ♦ | ♦ | ♦ |
| Renal Necrosis/Cell Death | ♦ | ♦ | ♦ |
| Renal Nephritis | ♦ | ♦ | ♦ |
| Renal Proliferation | ♦ | ♦ | ♦ |

The data highlight marked differences in the effects of DPA, EPA, and DHA, across multiple categories.

Differences in the effects on gene expression were also observed using a different analysis, in which the specific genes most significantly up-regulated and down-regulated by each of EPA (100 μM), DHA (40 μM) and DPA (11 μM) were identified. The data are respectively compiled in Tables 17 (up-regulated genes) and 18 (down-regulated genes) below. Symbols used are: "→"—expression affected at both DPA concentrations; "□" expression regulated in common with another fatty acid species, identified in parentheses; "♦" gene regulated by all three fatty acid species.

TABLE 17 top genes up-regulated

| fatty acid species | μM Conc. | genes | |
|---|---|---|---|
| DPA | 11 | ↑ MST1 (includes EG: 15235) | □□(DHA) |
| | | ↑ MGC16121 | □ |
| | | ↑ AMT | □ |
| | | ↑ AHSA2 | □♦ |
| | | ↑ SRSF1 | □□(EPA) |
| | | ↑ HNRNPA2B1 | |
| | | ↑ ALDOC | |
| | | ↑ TOP3B | |
| | | ↑ STK36 | |
| | | ↑ SRSF5 | |
| DHA | 40 | ↑ HIST2AA3/HIST2H2AA4 | □(EPA) |
| | | ↑ AHSA2 | ♦ |
| | | ↑ MT1X | |
| | | ↑ SNORA62 | |
| | | ↑ HIST1H3A (includes others) | |
| | | ↑ MST1 (includes EG: 15235) | □(DPA) |
| | | ↑ HIST2H2AC | |
| | | ↑ LOX | □(EPA) |
| | | ↑ LSMD1 | |
| | | ↑ MRPS34 | |
| EPA | 100 | ↑ HIST2H2BE (includes others) | |
| | | ↑ AHSA2 | ♦ |
| | | ↑ SRSF1 | □(DPA) |
| | | ↑ RGS2 (includes EG: 19735) | |
| | | ↑ HIST2H2AA3/HIST2H2AA4 | □(DHA) |
| | | ↑ MAT2A | |
| | | ↑ ZNF91 | |
| | | ↑ HIST1H3A (includes others) | □(DHA) |
| | | ↑ LOX | □(DHA) |
| | | ↑ GNAI3 | |

TABLE 18 top genes down-regulated

| fatty acid species | μM Conc. | Genes | |
|---|---|---|---|
| DPA | 11 | ↓ IL8 | ♦ |
| | | ↓ CDKN2AIPNL | ♦ |
| | | ↓ CATSPER2 | □♦ |
| | | ↓ CCBE1 | □(DHA) |
| | | ↓ ALPP | □(DHA) |
| | | ↓ CCL20 | ♦ |
| | | ↓ DDX51 | □(DHA) |
| | | ↓ QRFPR | |
| | | ↓ ZNF14 | |
| | | ↓ RELB | □(EPA) |
| DHA | 40 | ↓ CATSPER2 | ♦ |
| | | ↓ IL8 | ♦ |
| | | ↓ CCL20 | ♦ |
| | | ↓ CDKN2AIPNL | ♦ |
| | | ↓ MAP2K2 | |
| | | ↓ DDX51 | □(DPA) |
| | | ↓ CCBE1 | □(DPA) |
| | | ↓ JOSD1 | |
| | | ↓ ALPP | □(DPA) |
| | | ↓ ZNF652 | |
| EPA | 100 | ↓ IL8 | ♦ |
| | | ↓ CCL20 | ♦ |
| | | ↓ NFKBIA | |
| | | ↓ IER3 | |
| | | ↓ RELB | □(DPA) |
| | | ↓ CATSPER2 | ♦ |
| | | ↓ CDKN2AIPNL | ♦ |
| | | ↓ G0S2 | |
| | | ↓ ZFP38 | |
| | | ↓ HERDSPUD1 | |

Differences in the effects of DPA, EPA, and DHA were also readily be seen by comparing the genes whose expression is uniquely affected by each of the species of omega-3 PUFA.

TABLE 19

Top genes uniquely regulated by DPA (11 μM)

| Gene | EPA | DHA | DPA |
|---|---|---|---|
| 1. ALDOC | | | ↑ |
| 2. AMT | | | ↑ |
| 3. HNRNPA2B1 | | | ↑ |
| 4. MGC16121 | | | ↑ |
| 5. PRKCD | | | ← |
| 6. RELA (inhibited) | | | ← |
| 7. SRSF5 | | | ↑ |
| 8. STK36 | | | ↑ |
| 9. TLR7 (inhibited) | | | ← |
| 10. TOP3B | | | ↑ |
| 11. QRFPR | | | ↓ |
| 12. ZNF14 | | | ↑ |

TABLE 20

Top genes uniquely regulated by DHA (40 μM)

| Gene | EPA | DHA | DPA |
|---|---|---|---|
| 1. FOXO3 | | ← | |
| 2. LSMD1 | | ↑ | |
| 3. MAP2K2 | | ↓ | |
| 4. MRPS34 | | ↑ | |
| 5. MT1X | | ↑ | |
| 6. NFKB1 | | ← | |
| 7. SNORA62 | | ↑ | |
| 8. TNFSF11 | | ← | |
| 9. ZNF652 | | ↓ | |

TABLE 21

Top genes uniquely regulated by EPA (100 μM)

| Gene | EPA | DHA | DPA |
|---|---|---|---|
| 1. Beta-estradiol (inhibited) | ← | | |
| 2. GNAI3 | ↑ | | |
| 3. G0S2 | ↓ | | |
| 4. HERPUD1 | ↓ | | |
| 5. HIST2H2BE (includes others) | ↑ | | |
| 6. IL2 (inhibited) | ← | | |
| 7. IER3 | ↓ | | |
| 8. Lipopolysaccharide (inhibited) | ← | | |
| 9. MAT2A | ↑ | | |
| 10. NFkB (complex) (inhibited) | ← | | |
| 11. NFKBIA | ↓ | | |
| 12. RGS2 (includes EG: 19735) | ↑ | | |

Differences in the effects of DPA, EPA, and DHA on gene expression can also be seen by comparing the genes whose expression is most significantly affected by at least two of the species of polyunsaturated fatty acid.

TABLE 22

Top genes commonly regulated by DHA and DPA

| Gene | EPA | DHA | DPA |
|---|---|---|---|
| 1. AHSA2 | ↑ | ↑ | ↑ |
| 2. ALPP | | ↓ | ↓ |
| 3. CATSPER2 | | ↓ | ↓ |
| 4. CCL20 | | ↓ | ↓ |
| 5. CDKN2AIPNL | ↓ | ↓ | ↓ |
| 6. CCBE | | ↓ | ↓ |
| 7. DDX51 | | ↓ | ↓ |
| 8. IL8 | ↓ | ↓ | ↓ |
| 9. MST1 (includes EG: 15235) | | ↑ | ↑ |

TABLE 23

Top genes commonly regulated by EPA and DPA

| Gene | EPA | DHA | DPA |
|---|---|---|---|
| 1. AHSA2 | ↑ | ↑ | ↑ |
| 2. CATSPER2 | ↓ | ↓ | ↓ |
| 3. CCL20 | ↓ | ↓ | ↓ |
| 4. CDKN2AIPNL | ↓ | ↓ | ↓ |
| 5. IL8 | ↓ | ↓ | ↓ |
| 6. RELB | ↓ | | ↓ |
| 7. SRSF1 | ↑ | | ↑ |

These analyses collectively demonstrate that there are marked differences in the effects of EPA, DHA, and DPA across multiple physiological, pharmacological, and biochemical categories. EPA, DHA, and DPA are not identical in effect; the particular species that are present in an omega-3 PUFA composition clearly matter to the physiological effects that the composition will have upon administration.

6.6.2.2. DPA has Significant Activity at Higher, but not Lower, Concentration

Two concentrations of DPA were assessed. As noted above, the higher DPA concentration (at 11 μM), was chosen so that ratios of EPA (at 100 μM), DHA (at 40 μM), and DPA (at 11 μM) would approximate the ratios of EPA, DHA, and DPA in the pharmaceutical compositions (API) described in Section 5.2 and Example 5, with absolute concentrations chosen to best approximate—within the constraint imposed by the desired compositional ratio and constraints imposed by the culture conditions—the plasma ranges observed in the treatment arms of the EVOLVE trial (see Example 10). The lower DPA concentration (1 μM) was chosen to approximate the systemic exposure that would be expected from use of the earlier pharmaceutical composition of omega-3 polyunsaturated fatty acids in free acid form, termed Purepa, in which DPA was reported to be present at a level 1/10 that seen in the current pharmaceutical composition.

Overall, 310 genes were uniquely responsive to the higher, but not the lower, DPA level. The large number of genes that show statistically significant changes in gene expression predicts that DPA will have meaningful biological effects when the higher concentration is reached in vivo. By contrast, the lower DPA concentration is clearly a sub-threshold dose, at least with respect to regulation of these 310 genes, and far less a response would be expected at this lower in vivo plasma concentration.

When effects were assessed on genes that are broadly categorized by the iReport™ software as affecting molecular and cellular function, two subcategories uniquely appear within the top 5, ranked by the Ingenuity® iReport™ algorithm, at the higher, but not lower DPA, concentration—those involved in gene expression, and those affecting RNA post-transcriptional modification. Given the potential for pleiotropic second-order effects caused by changes in the expression of genes that encode proteins that themselves affect gene expression, and in genes encoding proteins that affect post-transcriptional modification, these results suggest that DPA is capable of modulating a large number of metabolic pathways at the higher, but not lower, concentration.

The threshold dose effect can also be seen by focusing on three categories of genes known to be relevant to the clinical effects of omega-3 polyunsaturated fatty acids: genes involved in lipid metabolism, genes involved in cardiovascular physiology, and genes involved in inflammation (assignment of genes to the identified categories performed automatically by the iReport™ software). Results are tabulated in Table 24, below.

TABLE 24

| | Total gene responses Low [DPA] | Total gene responses High [DPA] | Gene responses in common |
|---|---|---|---|
| Lipid metabolism | 2 | 22 | 0 |
| Cardiovascular | 10 | 51 | 6 |
| Inflammatory | 18 | 22 | 4 |

As shown in Table 24, only 2 genes involved in lipid metabolism were responsive to the 1 µM concentration of DPA, whereas 22 lipid metabolism genes uniquely responded with statistically significant change in expression upon incubation in the presence of 11 µM DPA. Focusing on lipid metabolism, 1 µM DPA is clearly a sub-threshold dose, whereas 11 µM has significant effects.

A greater number of genes proved responsive to the 1 µM DPA dose in the cardiovascular physiology category, and we observed a five-fold (rather than 10-fold) increase in number of genes affected at 11 µM DPA. An even greater number of genes involved in inflammatory pathways were responsive to 1 µM DPA, with only a minor increase in gene number observed at 11 µM.

The 11 µM in vitro concentration is lower than the ~90 µM plasma concentration observed in the 4 g/day EVOLVE patients. See Example 10. The results thus predict that a clinically-relevant dose of the DPA-enriched compositions described in Section 5.2 and Example 5 (see Table 12 and 13) will have significant metabolic effects, including effects on lipid metabolism, cardiovascular physiology, and inflammation. Few, if any, of these DPA-specific effects would be expected at the 10-fold lower DPA levels seen in the earlier Purepa preparation.

6.6.2.3. DPA, at Higher Concentration, Affects Expression of Multiple Lipid Metabolism Genes The 22 lipid metabolism genes that demonstrate statistically significant changes in expression at the 11 µM DPA concentration, but not 1 µM concentration, are identified in Table 25, below.

TABLE 25

Lipid Metabolism Genes Responsive to 11 µM DPA

| Symbol | Entrez Gene Name | Entrez Gene ID for Human | Fold Change | Drug(s) known to affect expression |
|---|---|---|---|---|
| APOA2 | apolipoprotein A-II | 336 | −1.229 | |
| CD83 | CD83 molecule | 9308 | −1.629 | |
| DGAT1 | diacylglycerol O-acyltransferase 1 | 8694 | 1.602 | omacor |
| DNAJB1 | DnaJ (Hsp40) homolog, subfamily B, member 1 | 3337 | −1.489 | |
| FGFR3 | fibroblast growth factor receptor 3 | 2261 | 1.336 | pazopanib |
| GNAI3 | guanine nucleotide binding protein (G protein), alpha inhibiting activity polypeptide 3 | 2773 | 1.455 | |
| IL8 | interleukin 8 | 3576 | −2.535 | |
| IL32 | interleukin 32 | 9235 | −1.629 | |
| IL18 (includes EG: 16173) | interleukin 18 (interferon-gamma-inducing factor) | 3606 | −1.347 | |
| IP6K1 | inositol hexakisphosphate kinase 1 | 9807 | −1.242 | |
| IP6K2 | inositol hexakisphosphate kinase 2 | 51447 | 1.319 | |
| KIT | v-kit Hardy-Zuckerman 4 feline sarcoma viral oncogene homolog | 3815 | 1.239 | dasatinib, sunitinib, pazopanib, tivozanib, OSI-930, telatinib, tandutinib, imatinib, sorafenib |
| NFKB1 | nuclear factor of kappa light polypeptide gene enhancer in B-cells 1 | 4790 | −1.386 | |
| PDPN (includes EG: 10630) | podoplanin | 10630 | −1.307 | |
| PGF | placental growth factor | 5228 | −1.284 | aflibercept |
| PIP4K2B | phosphatidylinositol-5-phosphate 4-kinase, type II, beta | 8396 | −1.578 | |
| PLA2G16 | phospholipase A2, group XVI | 11145 | −1.337 | |
| PLIN5 | perilipin 5 | 440503 | −1.371 | |
| PTGR2 | prostaglandin reductase 2 | 145482 | −1.416 | |
| PTX3 | pentraxin 3, long | 5806 | −1.536 | |
| RGS2 (includes EG: 19735) | regulator of G-protein signaling 2, 24 kDa | 5997 | 1.289 | |
| STIP1 | stress-induced-phosphoprotein 1 | 10963 | −1.469 | |

DPA's effects on expression of several of these genes suggest that DPA, at analogous in vivo concentration, should lead to improvement in various clinically-relevant lipid parameters.

For example, DPA at 11 µM upregulates ACADSB, the short/branched chain acyl-CoA dehydrogenase. The ACADSB gene product is involved in breakdown of triglycerides; upregulation would be expected to result in lower serum triglyceride levels. HMGCR, which is downregulated, encodes HMG-CoA reductase, the rate-limiting enzyme for cholesterol synthesis and the target for statin inhibition. Thus, analogous to statin action, downregulation of expression of the HMGCR gene by DPA should lead to favorable decreases in the total cholesterol:HDL ratio. SQLE, which is also downregulated, encodes squalene epoxidase, which catalyzes the first oxygenation step in sterol biosynthesis and is thought to be one of the rate-limiting enzymes in this pathway. Downregulation of SQLE should also lead to reduced total cholesterol levels.

6.6.2.4. Summary of Expression Profiling Results

Our expression profiling experiments using a hepatic cell line demonstrate that DPA has significant biological activity at a concentration that approximates the plasma levels observed in human patients administered a 4 g daily dose of an exemplary batch of the DPA-enriched pharmaceutical composition.

At this concentration, DPA affects expression of genes in multiple metabolic pathways, including genes in categories known to be relevant to the clinical effects of omega-3 polyunsaturated fatty acids: genes involved in lipid metabolism, genes involved in cardiovascular physiology, and genes involved in inflammation. Significant second-order effects are expected, given the changes we observed in the expression of genes that encode proteins that themselves affect gene expression, and in genes encoding proteins that affect post-transcriptional modification.

Specific effects on expression of several genes involved in lipid metabolism suggest that DPA, at analogous in vivo concentration, should lead to improvement in various clinically-relevant lipid parameters. In particular, we observed DPA-driven upregulation of ACADSB, the short/branched chain acyl-CoA dehydrogenase, expected to result in lower serum triglyceride levels; downregulation of HMGCR, which, like treatment with statins, should lead to favorable decreases in the total cholesterol:HDL ratio; and downregulation in SQLE, which should analogously lead to reduced total cholesterol levels.

These effects are distinguishable from those observed with EPA and DHA.

Our experiments demonstrated statistically significant dose-dependent effects for DPA, with the lower concentration, chosen to mimic the 10-fold lower concentration of DPA in an earlier free acid omega-3 formulation, affecting 10-fold fewer genes than the higher DPA concentration, chosen to mimic the plasma exposure observed in a clinical trial of the DPA-enriched pharmaceutical compositions described here. At least with respect to the 300 genes uniquely regulated by the higher DPA concentration—notably including genes beneficially affecting lipid metabolism—the lower DPA concentration provides subthreshold exposure, and would be expected to provide a subtherapeutic dose in vivo.

6.7. Example 7: ECLIPSE Clinical Trial

6.7.1. Drug Agents

Lovaza®-Prescription Lovaza® capsules were acquired through commercial US sources. According to the FDA-approved product label, each 1-gram capsule of Lovaza® contains at least 900 mg of the ethyl esters of omega-3 fatty acids sourced from fish oils, predominantly a combination of ethyl esters of eicosapentaenoic acid (EPA—approximately 465 mg) and docosahexaenoic acid (DHA—approximately 375 mg). Independent compositional analysis was not performed.

STUDY DRUG (Epanova®)—Type A porcine soft gelatin capsules coated with Eudragit NE 30-D (Evonik Industries AG) were prepared, each containing one gram of a PUFA composition in which the polyunsaturated fatty acids are present in the form of free fatty acids ("API"). The encapsulated API had the composition set forth in Table 26.

TABLE 26

| PUFA species | | API |
|---|---|---|
| (common name) | (carbon chain length: number double bonds, omega series) | (final free fatty acid composition) (% a/a) |
| linoleic acid | 18:2 n-6 | 0.55 |
| gamma-linolenic acid | 18:3 n-6 | 0.15 |
| α-linolenic acid | 18:3 n-3 | 0.39 |
| moroctic acid | 18:4 n-3 | 1.70 |
| eicosadienoic acid | 20:2 n-6 | 0.10 |
| dihomo-gamma-linolenic acid (DGLA) | 20:3 n-6 | 0.35 |
| arachidonic acid (AA) | 20:4 n-6 | 2.43 |
| eicosatrienoic acid | 20:3 n-3 | 0.15 |
| eicosatetraenoic acid | 20:4 n-3 | 2.18 |
| eicosapentaenoic acid (EPA) | 20:5 n-3 | 57.25 |
| heneicosapentaenoic acid | 21:5 n-3 | 2.79 |
| docosapentaenoic acid | 22:5 n-6 | 0.83 |
| docosapentaenoic acid (DPA) | 22:5 n-3 | 6.23 |
| docosahexaenoic acid (DHA) | 22:6 n-3 | 19.58 |
| Total % | | 98.43 |
| PUFAs % | | 96.30 |
| Total Omega 3 | | 90.26 |
| Total Omega 6 | | 4.41 |
| Remaining PUFAs | | 1.63 |
| Saturates % | | 0.35 |
| Mono-unsaturates % | | 1.35 |
| Unknowns % | | 0.42 |

6.7.2. Study Design

An open-label, single dose, randomized, 4-way crossover study of bioavailability was conducted with two different treatments: 4 grams of Epanova® or 4 g of Lovaza®, each administered with a low-fat and high-fat meal to 54 healthy adults. FIG. 4 provides a treatment flow diagram illustrating the design of the study: briefly, after a washout period, subjects were randomized to one of two treatment sequences:

(i) Epanova® (low fat)→Lovaza® (low-fat)→Epanova® (high-fat)→Lovaza® (high fat), or
(ii) Lovaza® (low-fat)→Epanova® (low-fat)→Lovaza® (high-fat)→Epanova® (high-fat).

Low-fat period meals (periods 1 and 2): no breakfast (fasting); no-fat lunch (0 g fat; 600 kcal) after the 4-hour blood draw; low-fat dinner (9 g fat; 900 kcal) after the 12-hour blood draw. Low-fat food items were: fat-free yogurt, fruit cup, fat-free Fig Newtons, Lean Cuisine meal.

High-fat period meals (periods 3 and 4): high-fat breakfast (20 g fat; 600 kcal) immediately after the 0.5 hour blood draw; high-fat lunch (30 g fat; 900 kcal) after the 4-hour blood draw; and high-fat dinner (30 g fat; 900 kcal) after the 12-hour blood draw. High-fat food items were: breakfast sandwich & powdered mini-donuts; cheese pizza; potato chips; and cheese and ham panini.

Pre-trial screening washout requirements were: 60 days for fish oil, EPA or DHA supplements or fortified foods; 7 days for fish, flaxseed, perilla seed, hemp, spirulina, or black currant oils, statins, bile acid sequestrants, cholesterol absorption inhibitors or fibrates. The crossover washout period was at least 7 days.

The evening before the in-clinic visit, subjects consumed a low-fat dinner 12 hours before time 0 of each treatment period (9 g fat; 900 kcal). Investigational product (Epanova® or LOVAZA®) was administered in the morning after the pre-dose blood draws (time 0). Pharmacokinetic blood sampling for each 2-day treatment period at −1.0, −0.5 and 0 hours (pre-dosing) and post-dosing at 1, 2, 3, 4, 5, 6, 7, 8, 10 and 12 hours (+/−5 minutes) for the $1^{st}$ day and at 24 hours (+/−15 min) for the $2^{nd}$ day.

6.7.3. Pharmacokinetic and Statistical Analyses

The following pharmacokinetic parameters for EPA and DHA plasma concentrations were calculated for the baseline-adjusted change in total and individual EPA and DHA concentrations by standard noncompartmental methods: $AUC_{0-t}$, $AUC_{0-inf}$, $C_{max}$, and $T_{max}$.

The primary determinants of bioavailability: ln-transformed area under the plasma concentration versus time curve ($AUC_t$) and maximum measured plasma concentration ($C_{max}$) over a 24-hour interval for the baseline-adjusted change in total and individual EPA and DHA concentrations.

Plasma concentrations were baseline-adjusted prior to the calculation of pharmacokinetic parameters. Figures are plotted for the baseline-adjusted change in geometric means (ln-transformed).

Analysis of variance (ANOVA) was used to evaluate the ln-transformed pharmacokinetic parameters for differences due to treatments, period, dosing sequence and subjects within sequence.

Ratios of means were calculated using the least square means for ln-transformed $AUC_{0-t}$, $AUC_{0-inf}$ and $C_{max}$.

The ratios of means and their 90% confidence intervals are to lie above the upper limit of 125.00% for $AUC_{0-t}$, $AUC_{0-inf}$ and $C_{max}$ in order to show Epanova® has superior relative bioavailability compared to Lovaza® with regards to diet.

6.7.4. Results

Study population—The study enrolled 54 healthy adults, 41 males (75.9%) and 13 females (24.1%), aged 21 to 77. All of the treatment periods were completed by 51 subjects (94.4%), with 53 subjects (98.1%) completing the low fat portion of the study. The population was predominantly Black or African-American (66.7%) with 31.5% White and 1.8% Asian.

Bioavailability—FIG. 5 compares the bioavailability of total EPA+DHA (baseline-adjusted change) following a single dose (4 g) of Lovaza® during the high-fat and low-fat periods (fasted dose conditions), confirming that the bioavailability of Lovaza® is significantly decreased with the low-fat diet. The baseline-adjusted change in total plasma EPA+DHA levels show that the $AUC_t$ for Lovaza® in the low-fat meal period is decreased by 83.3% compared to Lovaza® in the high-fat meal period: 661.6 vs 3959.5 nmol-h/mL, respectively (p<0.0001) (LS mean data in Table 27, below). $C_{MAX}$ of Lovaza® in the low-fat period decreased by 80.6% compared to the high-fat period (p<0.0001) and the $T_{MAX}$ increased 62% in the low-fat period compared to the high-fat period (10.2 vs. 6.3 hrs, respectively; p=0.0001).

TABLE 27

| Bioavailability Parameter | Least Square Mean | | Ratio of Means (%) | P-value[a] | Intra Subject C.V. %[b] | 90% Confidence Interval Limits (%) | |
|---|---|---|---|---|---|---|---|
| | Low-Fat | High-Fat | | | | Lower | Upper |
| Baseline-Adjusted Change | | | | | | | |
| $AUC_t$ (nmol · hr/mL) | 661.63 | 3959.52 | 16.7 | <0.0001 | 69.1 | 3.47 | 29.95 |
| $C_{max}$ (nmol/mL) | 86.89 | 448.63 | 19.4 | <0.0001 | 70.7 | 5.50 | 33.23 |
| $T_{max}$ (hr) | 10.19 | 6.28 | 162.3 | 0.0001 | 54.5 | 138.32 | 186.24 |
| Baseline-Adjusted Change (Ln-transformed) Data (Geometric Means) | | | | | | | |
| Ln $AUC_t$ (nmol · hr/mL) | 652.06 | 3468.17 | 18.8 | <0.0001 | 55.3 | 15.72 | 22.49 |
| Ln $C_{max}$ (nmol/mL) | 60.61 | 398.07 | 15.2 | <0.0001 | 69.2 | 12.35 | 18.78 |

N = 53
[a]p-value is for the Least Square (LS) Mean Difference between Epanova ® and Lovaza ® from the ANOVA model
[b]covariance %

FIG. 6 compares the bioavailability of total EPA+DHA (baseline-adjusted change) during the high-fat period following a single dose (4 g) of Lovaza® versus a single dose (4 g) of Epanova®, demonstrating that in the high-fat meal periods, in which the bioavailability of Lovaza® was confirmed to be greatest, the bioavailability EPA+DHA was nonetheless significantly greater when administered in free fatty acid form (Epanova®) than as the corresponding ethyl ester omega-3 composition (Lovaza®) (p<0.0007).

FIG. 7 compares the bioavailability of total EPA+DHA (baseline-adjusted change) following a single dose of Epanova® vs. Lovaza® during the low-fat diet period, demonstrating that the baseline-adjusted change in total plasma EPA+DHA levels show a 4.6-fold greater $AUC_t$ for Epanova® than Lovaza® during low-fat meal periods: 3077.8 vs. 668.9 nmol-h/mL, respectively (p<0.0001) (LS mean data in Table 28, below). $C_{max}$ of Epanova® is 3.2-fold greater than Lovaza® (p<0.0001) and $T_{max}$ is 20% shorter than LOVAZA® (8 vs 10 hrs, respectively; p=0.0138).

TABLE 28

| Bioavailability Parameter | Least Square Mean | | Ratio of Means (%) | P-value[a] | Intra Subject C.V. %[b] | Inter Subject C.V. %[b] | 90% Confidence Interval Limits (%) | |
|---|---|---|---|---|---|---|---|---|
| | Epanova® | Lovaza® | | | | | Lower | Upper |
| Baseline-Adjusted Change | | | | | | | | |
| $AUC_t$ (nmol · hr/mL) | 3077.83 | 668.95 | 460.10 | <0.0001 | 62.9 | 253 | 402.77 | 517.42 |
| $C_{max}$ (nmol/mL) | 277.58 | 86.35 | 321.46 | <0.0001 | 71.6 | 48.9 | 27236 | 370.56 |
| $T_{max}$ (hr) | 8.08 | 10.21 | 79.23 | 0.0138 | 45.8 | 24.6 | 65.60 | 92.86 |
| Baseline-Adjusted Change (Ln-transformed) Data (Geometric Means) | | | | | | | | |
| Ln $AUC_t$ (nmol · hr/mL) | 2651.41 | 658.09 | 402.90 | <0.0001 | 63.9 | 243 | 329.71 | 492.33 |
| Ln $C_{max}$ (nmol/mL) | 225.79 | 60.70 | 371.95 | <0.0001 | 66.3 | 42.7 | 304.37 | 454.53 |

N = 53
[a] p-value is for the Least Square (LS) Mean Difference between Epanova ® and Lovaza ® from the ANOVA model
[b] covariance %

FIG. 8 compares the bioavailability of EPA (baseline-adjusted change) following a single dose of Epanova® vs. Lovaza® during the low-fat diet period, showing a 13.5-fold greater $AUC_t$ for Epanova® than Lovaza® during low-fat meal periods: 578.2 vs. 42.7 µg·h/mL, respectively (p<0.0001) (LS mean data are presented in Table 29, below). $C_{MAX}$ of Epanova® is 5.6-fold greater than Lovaza® (p<0.0001) and $T_{MAX}$ is 12% shorter than Lovaza® (8 vs. 9 hours, respective; p=0.2605).

Lovaza® during the low-fat diet period, showing a 2.2-fold greater $AUC_t$ for Epanova® than Lovaza® during low-fat meal periods: 383.1 vs 173.4 µg·hr/mL, respectively (p<0.0001) (LS mean data presented in Table 30, below). $C_{max}$ of Epanova® is 1.9-fold greater than Lovaza® (p<0.0001) and $T_{MAX}$ is 21% shorter than Lovaza® (8 vs. 11 hours, respectively; p=0.0148). The 2.2-fold greater DHA

TABLE 29

| Bioavailability Parameter | Least Square Mean | | Ratio of Means (%) | P-value[a] | Intra Subject C.V. %[b] | Inter Subject C.V. %[b] | 90% Confidence Interval Limits (%) | |
|---|---|---|---|---|---|---|---|---|
| | Epanova® | Lovaza® | | | | | Lower | Upper |
| Baseline-Adjusted Change | | | | | | | | |
| $AUC_t$ (µg · hr/mL) | 578.22 | 42.67 | 1355.1 | <0.0001 | 80.8 | 18.2 | 1163.8 | 1546.4 |
| $C_{max}$ (µg/mL) | 52.64 | 9.45 | 557.0 | <0.0001 | 83.9 | 49.8 | 467.32 | 646.68 |
| $T_{max}$ (hr) | 8.06 | 9.13 | 88.28 | 02605 | 54.7 | 25.8 | 71.02 | 105.54 |
| Baseline-Adjusted Change (Ln-transformed) Data (Geometric Means) | | | | | | | | |
| Ln $AUC_t$ (µg · hr/mL) | 495.66 | 48.65 | 457.09 | <0.0001 | 93.0 | 23.5 | 713.46 | 1283.9 |
| Ln $C_{max}$ (µg/mL) | 39.02 | 4.66 | 837.53 | <0.0001 | 102.1 | 52.3 | 630.85 | 1111.9 |

N = 53
[a] p-value is for the Least Square (LS) Mean Difference between Epanova ® and Lovaza ® from the ANOVA model
[b] Covariance %

FIG. 9 compares the bioavailability of DHA (baseline-adjusted change) following a single dose of Epanova® vs. bioavailability in Epanova® vs Lovaza® occurred despite there being 42% less DHA in the Epanova® formulation.

TABLE 30

| Bioavailability Parameter | Least Square Mean | | Ratio of Means (%) | P-value[a] | Intra Subject C.V. %[b] | Inter Subject C.V. %[b] | 90% Confidence Interval Limits (%) | |
|---|---|---|---|---|---|---|---|---|
| | Epanova® | Lovaza® | | | | | Lower | Upper |
| Baseline-Adjusted Change | | | | | | | | |
| $AUC_t$ (µg · hr/mL) | 383.06 | 173.40 | 220.91 | <0.0001 | 55.2 | 32.1 | 192.10 | 249.72 |
| $C_{max}$ (µg/mL) | 35.50 | 19.19 | 185.02 | <0.0001 | 66.0 | 48.3 | 154.43 | 215.61 |
| $T_{max}$ (hr) | 8.45 | 10.72 | 78.84 | 0.0148 | 47.3 | 24.0 | 64.82 | 92.87 |
| Baseline-Adjusted Change (Ln-transformed) Data (Geometric Means) | | | | | | | | |
| Ln $AUC_t$ (µg · hr/mL) | 337.09 | 162.19 | 207.84 | <0.0001 | 61.3 | 21.4 | 171.98 | 251.17 |
| Ln $C_{max}$ (µg/mL) | 30.17 | 15.00 | 201.14 | <0.0001 | 52.5 | 42.2 | 170.73 | 236.96 |

N = 53
[a] p-value is for the Least Square (LS) Mean Difference between Epanova ® and Lovaza ® from the ANOVA model
[b] covariance %

FIGS. 10A and 10B present individual subject $AUC_{0-t}$ responses during the low-fat and high diets expressed as the ratio (%) of low-fat $AUC_{0-t}$ to high-fat $AUC_{0-t}$. Negative ratios were not plotted. The data show that during the low-fat diet period, 30 of 54 (56%) subjects on Epanova® (free fatty acids) versus 3 of 52 (6%) on Lovaza® (ethyl esters) maintained an $AUC_t$ that was ≥50% of the respective high-fat diet period $AUC_t$.

A total of 51 adverse events were reported by 29 subjects. The most common adverse events were headaches (10 subjects) and loose stools or diarrhea (9 subjects). All adverse events were mild in severity, and none were serious. There were no clinically significant changes in laboratory, vital sign or physical assessments.

6.7.5. Conclusions

The baseline-adjusted change in total EPA+DHA and individual EPA and DHA absorption profiles (AUC) with Epanova® (omega-3 PUFAs in free acid form) were significantly greater than with Lovaza® (omega-3-PUFA ethyl esters) during the high-fat diet period and dramatically better during the low-fat diet period. Furthermore, there was a very profound impact of fat content of the meals on the bioavailability of Lovaza®, whereas the bioavailability of Epanova® was much more predictable due to only a modest food effect. The superior fat-independent bioavailability of Epanova® over Lovaza® is clinically important as subjects with severely elevated triglycerides require a very low-fat diet. These findings demonstrate a significant therapeutic advantage of free fatty acid Omega-3 composition for treatment of severe hypertriglyceridemia in view of the NCEP ATP III recommendation to have these subjects adhere to a low-fat diet during adjunct therapy.

6.8. Example 8: 14 Day Comparative Bioavailability Trial

To determine whether the effects observed after a single dose were maintained after repeat dosing, a longer term study was performed. FIG. 11 is a treatment flow diagram illustrating the design of the 14 day comparative bioavailability trial, in which study drug (Lovaza® or Epanova®) was consumed with a low fat breakfast. In contrast, doses were given fasting in the low fat arm of the original ECLIPSE trial described in Example 7.

Changes from baseline to steady state in EPA and DHA levels in the Lovaza® arm of the 14 day comparative bioavailability were consistent with prior studies, as shown in Table 31, which presents the mean percentage change in EPA and DHA in the identified prior studies.

TABLE 31

| | Prior third party studies | | | |
|---|---|---|---|---|
| Drug | Study | No. Subjects | No. Weeks | Δ EPA (%) | Δ DHA (%) |
| omega-3 ethyl ester | CK85-013 | 17 | 8 | 276 | 34 |
| | CK85-014 | 54 | 12 | 300 | 50 |
| | CK85-017 | 29 | 12 | 300 | 50 |
| | CK85-019 | 26 | 12 | 200 | 29 |
| | CK85-022 | 30 | 12 | 233 | 23 |
| | CK85-023 | 28 | 12 | 139 | 11 |
| | CK85-95014 | 30 | 24 | 260 | 54 |
| | CK85-95009 | 22 | 16 | 173 | −10* |
| | CK85-94010 | 20 | 6 | 202 | 77** |
| | CK85-95011 | 49 | 12 | 361** | 59 |
| | CK85-95012 | 6 | 6 | 156* | 40 |

EPA range (% Δ): (156* - - - 209 - - - 361**)
DHA range (% Δ): (−10* - - - 34 - - - 77**)

FIG. 12A plots the mean un-adjusted total EPA+DHA concentrations versus time (linear scale), both for treatment with Lovaza® and treatment with Epanova®. FIG. 12B is a histogram showing the difference in unadjusted EPA+DHA (nmol/mL) for the time points bracketed in FIG. 12A. FIGS. 12A and 12B demonstrate that after 14-days of dosing, accumulation of EPA+DHA from Epanova® was 2.6 fold higher than Lovaza® in subjects maintained on a low-fat diet.

FIG. 13 plots mean baseline-adjusted plasma total EPA+DHA concentrations versus time (linear scale) for treatment with Lovaza® vs. treatment with Epanova® in the 14 day comparative bioavailability study, demonstrating that after 14-days of dosing with a low-fat meal, EPA+DHA levels ($AUC_{0-24}$) from Epanova® were 5.8 fold higher than Lovaza® in subjects maintained on a low-fat diet.

FIG. 14A is a histogram that plots the increases from baseline to steady state in unadjusted blood levels for EPA+DHA in the Lovaza® and Epanova® arms of the 14 day comparative bioavailability study, demonstrating that blood levels of EPA+DHA increased 316% from baseline to steady-state in the Epanova® cohort compared to 66% in the Lovaza® cohort. FIG. 14B is a histogram that plots the increases from baseline to steady state in unadjusted $C_{avg}$ for EPA+DHA in the Lovaza® and Epanova® arms of the 14 day comparative bioavailability study, demonstrating that average concentration ($C_{avg}$) levels of EPA+DHA increased 448% from baseline in the Epanova® cohort compared to 90% in the Lovaza® cohort.

FIG. 15A is a histogram that plots the increases from baseline to steady state for total blood levels of DHA in the Lovaza® and Epanova® arms of the 14 day comparative bioavailability study, demonstrating that levels of DHA increased 109% from baseline to steady-state in the Epanova® cohort compared to 34% in the Lovaza® cohort. FIG. 15B plots the increases from baseline to steady state for DHA $C_{avg}$ levels in the Epanova® cohort compared to Lovaza® cohort in the 14 day comparative bioavailability study, and demonstrates that average concentration ($C_{avg}$) levels of DHA increased 157% from baseline in the Epanova® cohort compared to 47% in the Lovaza® cohort.

FIG. 16A is a histogram that plots the increases from baseline to steady state for total EPA levels in blood in the Lovaza® and Epanova® arms of the 14 day comparative bioavailability study, and demonstrates that Levels of EPA increased 1021% from baseline to steady-state in the Epanova® cohort compared to 210% in the Lovaza® cohort. FIG. 16B plots the average concentration increases from baseline to steady-state, and demonstrates that $C_{avg}$ levels of EPA increased 1,465% from baseline in the Epanova® cohort compared to 297% in the Lovaza® cohort.

The data demonstrate that the increase in bioavailability observed after single dosing in the ECLIPSE trial is maintained, even enhanced, over the longer term (2 weeks). In addition, disaggregated subject-specific data (not shown)

demonstrate that the subject with least response to Epanova® still had a greater day 14 EPA+DHA $C_{max}$ than the subject with best response to Lovaza®.

The increased $C_{avg}$ and total blood levels of clinically relevant omega-3 PUFA species achieved with Epanova® as compared to Lovaza® predicts significantly improved efficacy in lowering serum triglyceride levels and in reducing cardiovascular risk.

6.9. Example 9: 13 Week Rat Study

This study compared omega-3 exposure and its effects on serum lipid levels in rats treated with equivalent doses of Epanova® or LOVAZA® for 13 weeks.

The Sprague Dawley rat was selected for this study because it was the rat strain used in the toxicology program conducted with Lovaza®, and thus permitted direct comparison of the data from the present study with Epanova® to publicly available rat toxicity data in the Lovaza® Summary Basis of Approval. The study design provided a robust toxicology evaluation of Epanova® with dose selections based upon the publicly available rat toxicity data for Lovaza® (maximum tolerated dose=2000 mg/kg). The Sprague Dawley rats provide a model that is recognized to predict the effects of omega-3 PUFAs on lipid changes for triglycerides and total cholesterol in human subjects. Results at 13 weeks are shown in Table 32, below.

PLACEBO—Capsules were prepared containing olive oil for use as a control.

6.10.2. Study Design

A 12-week double-blind, olive oil-controlled, study was performed in the United States, Denmark, Hungary, India, Netherlands, Russia, and Ukraine. Subjects were selected on the basis of high triglyceride levels, in the range of 500-2,000 mg/dL. Subjects were randomly selected to receive 2, 3, or 4 grams of Epanova®, or 4 grams of olive oil as placebo. The general trial design is illustrated in FIG. 17, with FIG. 18 providing a more detailed treatment flow diagram further identifying the timing of study visits. The primary study endpoint was percent change in plasma triglyceride levels from baseline to end-of-treatment ("EOT"). The secondary endpoint was percent change in plasma non-HDL-cholesterol ("Non-HDL-C") from baseline to EOT.

6.10.3. Results

FIG. 19 shows the disposition of all subjects, with "AE" abbreviating "adverse event" and "SAE" abbreviating "serious adverse event."

A total of 1,356 subjects were initially screened, and of these, 399 were selected to participate in the study. Of the 399 subjects, 99 received olive oil placebo, 100 received

TABLE 32

| Treatment | Sex | DHA exposure[a] | | EPA exposure[a] | | TGs | Cholesterol |
|---|---|---|---|---|---|---|---|
| | | $AUC_{(0-t)}$ (μg · hr/mL) | $C_{max}$ (μg/mL) | $AUC_{(0-t)}$ (μg · hr/mL) | $C_{max}$ (μg/mL) | (% difference from control) | (% difference from control) |
| Epanova ® | M | 15.56 | 1.82 | 14.02 | 2.15 | −32 | −45 |
| | F | 13.00 | 2.05 | 9.50 | 1.38 | −53 | −41 |
| | Both | 14.28 | 1.94 | 11.76 | 1.77 | −43 | −43 |
| Lovaza ® | M | 6.55 | 0.47 | 7.57 | 0.73 | −14 | −25 |
| | F | 4.97 | 0.40 | 6.04 | 0.55 | −38 | −36 |
| | Both | 5.76 | 0.43 | 6.81 | 0.64 | −26 | −31 |

$AUC_{(0-t)}$ Area under plasma concentration time curve to the last sample time. Measure of systemic exposure
$C_{max}$ Maximum plasma concentration
[a] Dose normalized values based on estimated doses of DHA and EPA As shown in Table 32, Epanova® provided not only markedly higher maximum plasma concentrations ($C_{max}$) of DHA and EPA than Lovaza®, but also provided markedly higher $AUC_{(0-t)}$ for the two omega-3 species; $AUC_{(0-t)}$ is a measure of systemic exposure. The greater bioavailability and long term systemic exposure of these two omega-3 PUFA species with Epanova® therapy resulted in long term differences in lipid lowering efficacy, with Epanova® effecting substantially greater reductions in plasma triglycerides and in total cholesterol than was seen with LOVAZA®. The compositions described herein thus provide greater efficacy with respect to two clinically important cardiovascular parameters.

6.10. Example 10: Evolve Trial

6.10.1. Drug Agents

STUDY DRUG (Epanova®)—Type A porcine soft gelatin capsules were prepared, each containing one gram (1 g) of a PUFA composition comprising omega-3 PUFAs in free acid form ("API"). The capsules were coated with Eudragit NE 30-D (Evonik Industries AG). The API had the composition given in batch 2 of Table 10 (see Example 4, above).

Epanova® 2 g/day; 101 received Epanova® 3 g/day; and 99 received Epanova® 4 g/day. Table 33 shows average triglyceride (TO) and cholesterol measurements for the subjects at randomization (prior to treatment), in comparison to desirable levels as described by the Third Report of the Expert Panel on Detection, Evaluation, and Treatment of High Blood Cholesterol in Adults (Adult Treatment Panel produced by the National Heart Lung and Blood Institute.

TABLE 33

| | Desirable | Patients randomized for trial | | | |
|---|---|---|---|---|---|
| Parameter | (mg/dL)[1] | 4 g/day | 3 g/day | 2 g/day | Olive Oil |
| TG | <150 | 655 | 715 | 717 | 686 |
| HDL-C | >40 | 29 | 28 | 27 | 29 |
| LDL-C | <100 | 90 | 81 | 77 | 78 |
| Non-HDL-C | <130 | 225 | 215 | 205 | 215 |
| VLDL-C | <30 | 126 | 124 | 123 | 125 |

[1] NCEP ATP III, September 2002

Of the patients receiving olive oil, five total were withdrawn from the study due to the following reasons: withdrawn consent (1), lost to follow-up (1), and other reasons (3). Of the patients receiving Epanova® 2 g/day, seven total were withdrawn due to the following reasons: adverse effects (5), withdrawn consent (1), and other reasons (1). Of the patients receiving Epanova® 3 g/day, 14 total were withdrawn due to: adverse effects (7), noncompliance (2), withdrawn consent (1), lost to follow-up (3), and other reasons (1). Of the patients receiving Epanova® 4 g/day, 9 were withdrawn, due to: adverse effects (5), noncompliance (1), withdrawn consent (2), and other reasons (1).

Epanova® achieved the primary endpoint of triglyceride reduction and the secondary endpoint of reduction of non-HDL cholesterol (total cholesterol level minus the level of HDL-cholesterol) ("non-HDL-C") at all doses, and produced statistically significant reductions in multiple established markers of atherogenicity: Apo B, Apo CIII, RLP, and LpPLA2. In patients on concomitant statin therapy, Epanova® provided additive efficacy on key lipid parameters: TG; non-HDL-C; HLD-c; total cholesterol (TC); and TC/HDL-C.

Plasma levels of EPA, DHA, and DPA—the three species of omega-3 lc-PUFA in greatest abundance in Epanova®—were measured at baseline and at end-of treatment (EOT), as were plasma levels of the omega-6 lc-PUFA, arachidonic acid (AA). Table 34, below, separately tabulates average baseline, median baseline, average end-of-treatment (EOT), and median EOT plasma levels for EPA, DHA, DPA, and AA, as well as TG, NHDL-C, HDL-C, VLDL-C, and LDL-C.

Baseline plasma levels of EPA, DHA, DPA, and AA indicate effective randomization of subjects among the treatment arms. EPA:AA ratios at baseline were about 0.10 (see Table 37, below).

FIGS. 20A-20E plot the average baseline and end-of-treatment ("EOT") plasma levels (in µg/mL) for EPA (FIG. 20A), DHA (FIG. 20B), DPA (FIG. 20C) and AA (FIG. 20D), for each of the treatment arms in the EVOLVE trial. FIG. 20E compares average baseline and EOT EPA levels for each treatment arm and the control (olive oil) arm to values earlier reported for ECLIPSE (see Example 7), 14-day bioavailability study (see Example 8), a statin drug-drug-interaction study (Statin DDI), and the unrelated JELIS trial conducted by others with a different omega-3 PUFA formulation ("JELIS"). Note that the Japanese subjects in the JELIS trial had higher baseline EPA levels. FIGS. 21A-21D plot median baseline and end-of-treatment (EOT) plasma levels (in µg/mL) for EPA (FIG. 21A), DHA (FIG. 21B), DPA (FIG. 21C), and AA (FIG. 21D).

TABLE 34

(Baseline and EOT absolute plasma levels)

| | | Baseline (Average) | EOT (Average) | Baseline (Median) | EOT (Median) |
|---|---|---|---|---|---|
| EPA (µg/mL) | 2 g | 36.6 | 126.8 | 26.7 | 104 |
| | 3 g | 41.4 | 174.7 | 30.7 | 141.9 |
| | 4 g | 38.9 | 199.7 | 25.7 | 170 |
| DHA (µg/mL) | 2 g | 106.6 | 159.9 | 93.5 | 148.3 |
| | 3 g | 113.7 | 183.6 | 97.4 | 156.9 |
| | 4 g | 104.8 | 188.8 | 91.8 | 169.1 |
| DPA (µg/mL) | 2 g | 37.6 | 61.77 | 35.23 | 54.59 |
| | 3 g | 38.71 | 69.36 | 34.71 | 58.56 |
| | 4 g | 36.84 | 69.73 | 32.53 | 66.03 |
| AA (µg/mL) | 2 g | 377.9 | 327.4 | 358.4 | 279.2 |
| | 3 g | 394.9 | 344 | 368.8 | 313.8 |
| | 4 g | 393.9 | 298.1 | 363.4 | 274.2 |
| TG (mg/dL) | 2 g | 760.1 | 608.7 | 669 | 554 |
| | 3 g | 766.9 | 754.5 | 612 | 560.8 |
| | 4 g | 730.5 | 557.2 | 631 | 511 |
| Non-HDL-C (mg/dL) | 2 g | 219.6 | 208.2 | 205.3 | 209.3 |
| | 3 g | 223.4 | 221.5 | 215.3 | 197 |
| | 4 g | 230.7 | 214.1 | 225 | 211 |
| HDL-C (mg/dL) | 2 g | 28 | 30.7 | 27.3 | 29 |
| | 3 g | 29.1 | 30.4 | 28 | 28 |
| | 4 g | 29.9 | 32.2 | 28.7 | 29 |
| V-LDL-C (mg/dL) | 2 g | 138.1 | 106.9 | 123.3 | 98 |
| | 3 g | 143 | 121.5 | 124 | 93.8 |
| | 4 g | 143.9 | 100.7 | 126 | 87 |
| LDL-C (mg/dL) | 2 g | 83.1 | 101.3 | 77.3 | 93.3 |
| | 3 g | 84.9 | 99.7 | 81 | 95 |
| | 4 g | 90.4 | 113.4 | 90.3 | 109.5 |
| ApoB (mg/dL) | 2 g | 115.6 | 121.1 | 114 | 120 |
| | 3 g | 114.5 | 116 | 112 | 115 |
| | 4 g | 119.3 | 126.6 | 118 | 121.5 |
| ApoCIII (mg/dL) | 2 g | 26.5 | 24.3 | 22 | 21 |
| | 3 g | 27.8 | 25 | 27 | 21 |
| | 4 g | 27.5 | 22.7 | 27 | 21 |
| RLP (mg/dL) | 2 g | 55.5 | 49.7 | 49.7 | 37 |
| | 3 g | 62.7 | 54.4 | 54.4 | 34.5 |
| | 4 g | 58.1 | 43.4 | 43.4 | 33 |
| LpPLA2 (ng/mL) | 2 g | 270.6 | 236.7 | 266 | 225 |
| | 3 g | 271.2 | 241.4 | 244.5 | 223.5 |
| | 4 g | 266.9 | 223.2 | 249 | 208 |

Table 35, below, tabulates the average change and the median change in absolute plasma levels from baseline to EOT for EPA, DHA, DPA, and AA, as well as TG, NHDL-C, HDL-C, VLDL-C, and LDL-C.

TABLE 35

| | AA (µg/mL) | EPA (µg/mL) | DPA (µg/mL) | DHA (µg/mL) | TG (mg/dL) | non-HDL-C (mg/dL) | HDL-C (mg/dL) | VLDL-C (mg/dL) | LDL-C (mg/dL) |
|---|---|---|---|---|---|---|---|---|---|
| average change from baseline to EOT | | | | | | | | | |
| 2 g | −50.5 | 90.2 | 24.17 | 53.3 | −183.6 | −13.3 | 2.6 | −31.2 | 18 |
| 3 g | −50.9 | 133.3 | 30.65 | 69.9 | −69 | −6.1 | 1.7 | −21.9 | 15.5 |
| 4 g | −95.8 | 160.8 | 32.89 | 84 | −220.2 | −21.9 | 2.1 | −42.5 | 21.7 |
| median change from baseline to EOT | | | | | | | | | |
| 2 g | −79.2 | 77.3 | 19.36 | 54.8 | −172.2 | −16 | 1.7 | −31.5 | 14.8 |
| 3 g | −55 | 111.2 | 23.85 | 59.5 | −150.1 | −6.7 | 1.8 | −25.3 | 11.9 |
| 4 g | −89.2 | 144.3 | 33.5 | 77.3 | −178 | −17 | 1.7 | −37.7 | 22.3 |

FIGS. 22A, 22B, 26A, and 26B plot the data in the table above, showing the change from baseline to EOT in absolute plasma levels (in μg/mL) of AA, DHA, EPA, and DPA for each of the treatment arms of the EVOLVE trial, with FIG. 22A plotting average change and FIG. 22B showing median change from baseline.

Table 36A, below, separately tabulates average, median, and least squares mean percentage change from baseline to EOT in plasma levels of EPA, DHA, DPA, and AA, as well as TG, NHDL-C, HDL-C, VLDL-C, and LDL-C, for each of the treatment arms of the EVOLVE trial.

Table 36B, below, separately tabulates average, median, and least squares mean percentage change from baseline to EOT in plasma levels of ApoB, ApoCIII, LpPLA2, and RLP, for each of the treatment arms of the EVOLVE trial.

TABLE 36A

|  | AA (μg/mL) | EPA (μg/mL) | DPA (μg/mL) | DHA (μg/mL) | TG (mg/dL) | n-HDL-C (mg/dL) | HDL-C (mg/dL) | VLDL-C (mg/dL) | LDL-C (mg/dL) |
|---|---|---|---|---|---|---|---|---|---|
| average percentage change from baseline to EOT ||||||||||
| 2 g | −10.5 | 410.8 | 86.08 | 69 | −21.2 | −5.4 | 10 | −21.2 | 25.6 |
| 3 g | −11.2 | 538.1 | 96.59 | 88.4 | −14.1 | −3.4 | 5.6 | −18.6 | 20 |
| 4 g | −18 | 778.3 | 131.66 | 106 | −25.2 | −8 | 7.2 | −27.5 | 26.2 |
| median percentage change from baseline to EOT ||||||||||
| 2 g | −15.6 | 253.9 | 75.3 | 61.2 | −25.8 | −7.7 | 7 | −24.7 | 21.4 |
| 3 g | −17.9 | 317 | 68.6 | 61.9 | −21.7 | −3.2 | 6.2 | −21.5 | 15.5 |
| 4 g | −25.9 | 404.8 | 74.87 | 65.5 | −30.7 | −7.7 | 5 | −34.7 | 26.2 |
| LS mean percentage change ||||||||||
| 2 g | −15.14 | 267.04 | — | 56.72 | −26.47 | −7.77 | 7.46 | −27.05 | 19.35 |
| 3 g | −15.98 | 331.86 | — | 64.07 | −24.38 | −6.49 | 3.33 | −25.62 | 13.94 |
| 4 g | −23.2 | 406.32 | — | 71.77 | −31.1 | −9.76 | 5.71 | −33.23 | 19.36 |

TABLE 36B

|  | ApoB | ApoCIII | LpPLA2 | RLP |
|---|---|---|---|---|
| average percentage change from baseline to EOT |||||
| 2 g | 5.9 | −8.3 | −11.3 | −0.9 |
| 3 g | 4.6 | −8.5 | −8.8 | −6.9 |
| 4 g | 5.7 | −9.8 | −14.1 | −10.3 |
| median percentage change from baseline to EOT |||||
| 2 g | 6.3 | −8.7 | −11.3 | −20.2 |
| 3 g | 5.6 | −12.8 | −9.5 | −16.2 |
| 4 g | 5.7 | −15 | −14.6 | −28.2 |
| LS mean change (%) |||||
| 2 g | 3.84 | −10.87 | −14.93 | −20.67 |
| 3 g | 2.28 | −12.16 | −11.06 | −22.63 |
| 4 g | 3.78 | −14.39 | −17.17 | −27.52 |

FIG. 23A plots the average change from baseline to EOT, as percentage of baseline value, for AA, DHA, EPA, and DPA in each of the treatment arms of the EVOLVE trial, and FIG. 23B plots the median percent change from baseline to EOT.

Table 37 below presents EPA/AA ratios at beginning and end-of-treatment for each of the treatment arms of the EVOLVE trial.

TABLE 37

| | EPA/AA ratios | |
|---|---|---|
| | baseline | EOT |
| average |||
| 2 g | 0.096851 | 0.387294 |
| 3 g | 0.104837 | 0.507849 |
| 4 g | 0.098756 | 0.669909 |
| median |||
| 2 g | 0.074498 | 0.372493 |
| 3 g | 0.083243 | 0.452199 |
| 4 g | 0.070721 | 0.619985 |

As can be seen from Tables 35 and 36A and FIGS. 20-23, 12 week treatment with Epanova® caused dramatic increases in plasma levels of EPA, DHA, and DPA. For example, at the 2 g dose, the average percentage change from baseline to EOT in EPA plasma levels was 411%; at the 4 g dose, 778%. Median percentage change in EPA plasma levels were respectively 254% and 405%. At the 2 g dose, the average percentage change from baseline to EOT in DHA plasma levels was 69%; at the 4 g dose, the average percentage change was 106%. Median percentage change in DHA plasma levels appear less dramatic, with a 61.2% change at 2 g Epanova®, and 65.5% change at 4 g.

Increases in plasma levels of EPA, DHA, and DPA were accompanied by significant reductions in plasma AA levels, with the 4 g dosage regimen effecting an average reduction of 95.8 μg/mL and median reduction of 89.2 μg/mL, which correspond to an average percentage reduction of 18%, a median percentage change of 25.9%, and a LS mean change of 23.2%. It should be noted that the decrease in plasma arachidonic acid levels was observed despite exogenous administration of arachidonic acid, which was present at 2.446% (a/a) in the Epanova® batch used in this trial.

The increase in EPA plasma levels and concomitant reduction in AA plasma levels cause a significant improvement in the EPA/AA ratio, as shown in Table 37, from approximately 0.10 at baseline to approximately 0.67 (average) and 0.62 (median) at EOT at the 4 g dose.

Furthermore, treatment with Epanova® resulted in substantial reductions in TG levels, as shown in FIG. 26A and FIG. 26B which plot the average and median, respectively, for the absolute change from baseline. FIG. 27 illustrates the percentage of subjects who exhibited 0-10% reduction in TG, 10-20% reduction in TG, 20-30% reduction in TG, 30-40% reduction in TG, 40-50% reduction in TG, and greater than 50% reduction in TG, for Epanova® 2 g and 4 g doses.

FIG. 26A and FIG. 26B also show that non-HDL-C and VLDL-C were reduced, while HDL-C was elevated. LDL-C levels were also elevated, a measurement that is likely due to an increase in LDL particle size upon treatment (discussed further in Example 12). Average and median percentage changes are displayed in FIG. 28A and FIG. 28B, respectively.

Absolute average baseline and EOT levels are plotted in FIGS. 24A-24I for TG (FIG. 24A), Non-HDL-C (FIG. 24B), HDL-C (FIG. 24C), V-LDL-C (FIG. 24D), LDL-C (FIG. 24E), ApoB (FIG. 24F), ApoCIII (FIG. 24G), RLP (FIG. 24H), and LpPLA2 (FIG. 24I). Absolute median baseline and EOT levels are plotted in FIGS. 25A-25I for TG (FIG. 25A), Non-HDL-C (FIG. 25B), HDL-C (FIG. 25C), V-LDL-C (FIG. 25D), LDL-C (FIG. 25E), ApoB (FIG. 25F), ApoCIII (FIG. 25G), RLP (FIG. 25H), and LpPLA2 (FIG. 25I).

The extremely high bioavailability of the omega-3 PUFAs in Epanova® revealed differences in pharmacokinetic response among the various plasma species. FIG. 29 plots the rate of change in the median percentage change from baseline in plasma levels of EPA, DHA, DPA, AA, TG, non-HDL-C, and HDL-C (absolute value) between 2 g and 4 g doses of Epanova®. Table 38, below, tabulates the results:

TABLE 38

| (rate of change in median percentage change from baseline) (absolute value) | | | | | | |
|---|---|---|---|---|---|---|
| EPA | DHA | DPA | AA | TG | non-HDL-C | HDL-C |
| 0.59432847 | 0.07026143 | 0.00571049 | 0.66025641 | 0.189922 | 0 | 0.285714 |

Given little or no increase in plasma levels of DHA and DPA upon doubling of the Epanova® dose from 2 g to 4 g per day, the rate of change (slope) in the median percentage change from baseline is near zero, predicting little further increase in DHA and DPA plasma levels will be seen upon further increase in dose. Similar plateauing of response is seen in triglyceride levels, HDL-C levels, and non-HDL-C levels (data not shown).

By contrast, the rate of change for EPA remains high, with a slope of 0.59; further increase in EPA plasma levels is expected to be obtained by increasing Epanova® dosage above 4 g/day. Significantly, the rate of change in AA levels upon doubling the Epanova® dose from 2 g to 4 g per day is even higher than that for EPA; further reductions in AA plasma levels are expected as Epanova® dosage is increased above 4 g/day. Epanova® thus exhibits unprecedented potency in ability to reduce AA levels.

Summary of the results of the EVOLVE trial are tabulated in Table 39, below.

TABLE 39

| | OO (n = 98) | | 2 gram (n = 99) | | | | 3 gram (n = 97) | | | | 4 gram (n = 99) | | | |
|---|---|---|---|---|---|---|---|---|---|---|---|---|---|---|
| | Baseline (mg/dL) | % Δ | Baseline (mg/dL) | % Δ | p-value | LSM difference rel. to OO | Baseline (mg/dL) | % Δ | p-value | LSM difference rel. to OO | Baseline (mg/dL) | % Δ | p-value | LSM difference |
| TG | 686.3 | −10.4 | 717 | −25.8 | 0.003 | −22.1 | 715 | −21.7 | 0.021 | −20 | 655 | −30.7 | <0.001 | −26.7 |
| Non-HDL-C | 214.5 | −0.9 | 205.3 | −7.7 | 0.018 | −10.3 | 215.3 | −3.2 | 0.042 | −9 | 225 | −7.7 | 0.002 | −12.2 |
| HDL-C | 28.7 | 2.2 | 27.3 | 7 | 0.088 | 5.5 | 28 | 6.2 | 0.127 | 1.4 | 28.7 | 5 | 0.127 | 3.7 |
| TC/HDL-C | 8.8 | −1.9 | 8.8 | −9.5 | 0.024 | −11.8 | 8.8 | −7.2 | 0.137 | −7.7 | 9 | −14.1 | 0.004 | −12.9 |
| LDL-C | 78.2 | 9.8 | 77.3 | 21.4 | 0.003 | 16.2 | 81 | 15.5 | 0.092 | 10.8 | 90.3 | 26.2 | <0.001 | 16.3 |
| VLDL-C | 124.5 | −11.3 | 123.3 | −24.7 | 0.006 | −18.4 | 124 | −21.5 | 0.017 | −17 | 126 | −34.7 | <0.001 | −24.6 |
| ApoB | 110 | 2.3 | 114 | 6.3 | 0.344 | 3 | 112 | 5.6 | 0.834 | 1.4 | 118 | 5.7 | 0.449 | 2.9 |

The EVOLVE trial also demonstrated that Apolipoprotein CIII (ApoCIII) was significantly reduced by Epanova® treatment. ApoCIII inhibits lipoprotein lipase activity and hepatic uptake of triglyceride-rich lipoproteins. Elevated levels of ApoCIII have been found to be an independent predictor for cardiovascular heart disease (CHD) risk while genetically reduced ApoCIII is associated with protection from CHD.

triglycerides present in chylomicrons to free fatty acids, and impairment of LPL is known to be associated with severe hypertriglyceridemia (Fojo and Brewer, 1992, *J. of Int. Med.* 231:669-677). Subjects who exhibit a substantial increase in EPA following treatment with Epanova®, accompanied by a minor change in clinical parameters such as triglyceride levels, AA levels, etc., can be classified as non-responders. Such subjects can be removed from treatment with Epanova®.

TABLE 40

| COUNTRY of the subject | Dose | BMI | BASELINE TG (mg/dL) | EOT TG (mg/dL) | TG % change from baseline | BASELINE EPA (mcg/mL) | EOT EPA (mcg/mL) | EPA % change from baseline | Baseline HbA1c | EOT HbA1c |
|---|---|---|---|---|---|---|---|---|---|---|
| Hungary | 2 | 32.4 | 778 | 831 | 6.8 | 18.4 | 171.4 | 832 | 7.3 | 8.1 |
| Hungary | 2 | 33.4 | 924 | 937 | 1.4 | 11.4 | 133.6 | 1067 | 5.9 | 6.2 |
| Hungary | 2 | 36.2 | 782 | 803 | 2.6 | 12.5 | 173.6 | 1288 | 6.0 | 5.6 |
| Russia | 2 | 31.2 | 857 | 1723 | 101.1 | 22.1 | 243.7 | 1001 | 5.6 | 6.2 |
| Netherlands | 2 | 27.1 | 511 | 589 | 15.2 | 15.4 | 257.4 | 1572 | 5.0 | 5.0 |
| India | 2 | 25.1 | 460 | 544 | 18.4 | 4.6 | 79.9 | 1632 | 6.7 | 6.6 |
| US | 3 | 34.6 | 1047 | 1077 | 2.8 | 16.7 | 273.7 | 1543 | 6 | 5.6 |
| US | 3 | 36 | 622 | 687 | 10.3 | 16.4 | 193.8 | 1080 | 6.6 | 7.2 |
| US | 3 | 31 | 838 | 870 | 3.8 | 14.3 | 151.2 | 961 | 5.6 | 6.1 |
| US | 3 | 40.8 | 888 | 995 | 12 | 61.8 | 650.6 | 953 | 8 | 8.7 |
| Hungary | 3 | 36.3 | 484 | 463 | −4.3 | 10.1 | 185.3 | 1740 | 6.1 | 6.0 |
| Hungary | 3 | 29.6 | 647 | 627 | −3.1 | 8.6 | 110.3 | 1177 | 6.2 | 6.3 |
| Hungary | 3 | 36.6 | 851 | 1016 | 19.3 | 10.4 | 94.4 | 811 | 8.2 | 8.6 |
| Hungary | 3 | 28.6 | 707 | 730 | 3.2 | 8.3 | 408.5 | 4827 | 5.8 | 6 |
| Hungary | 3 | 32.8 | 2158 | 2273 | 5.3 | 24.5 | 480.1 | 1863 | 5.6 | 5.1 |
| Hungary | 3 | 31.7 | 1034 | 992 | −4.1 | 10.6 | 280.5 | 2538 | 5.3 | 5.5 |
| Hungary | 3 | 34.8 | 976 | 1110 | 13.7 | 22.4 | 224.8 | 905 | 7.3 | 7.9 |
| Hungary | 3 | 28.8 | 728 | 1210 | 66.1 | 22.4 | 289 | 1071 | 7.1 | 7.9 |
| Ukraine | 3 | 36.2 | 1664 | 10317 | 520.1 | 91.9 | 1238.8 | 1248 | 8.1 | 10.8 |
| Hungary | 4 | 30.1 | 714 | 702 | −1.7 | 11.1 | 256.7 | 2214 | 5.1 | 5.4 |
| Hungary | 4 | 31.7 | 785 | 1300 | 65.6 | 11.7 | 466 | 3886 | 8.5 | 10.9 |
| Hungary | 4 | 27.3 | 513 | 527 | 2.6 | 16.6 | 198.3 | 1093 | 7.8 | 8 |
| Hungary | 4 | 31.9 | 508 | 625 | 23.2 | 3.5 | 198.4 | 5504 | 6 | 7.3 |
| Ukraine | 4 | 33.6 | 563 | 589 | −2.5 | 34.9 | 327.9 | 841 | 7 | 7.3 |
| Russia | 4 | 29.7 | 664 | 702 | 5.7 | 38.2 | 795.2 | 1984 | 5.5 | 5.1 |
| Russia | 4 | 41.6 | 483 | 504 | 4.3 | 10.9 | 231.1 | 2026 | 6.2 | 6.3 |
| India | 4 | 32.8 | 839 | 1721 | 105.0 | 13.8 | 1066.6 | 7624 | 5.6 | 5.2 |

Omega-3 fatty acid formulations containing DHA have been shown to increase LDL-C in patients with severe hypertriglyceridemia (Kelley et al., 2009, *J. Nutrition*, 139 (3):495-501). This effect on LDL-C is postulated to be a result of increased lipoprotein particle size (Davidson et al., 2009, *J. Clin. Lipidology*, 3(5):332-340). Clinical data suggest that eicosapentaenoic acid (EPA) alone, at a dose which lowers triglycerides to a similar extent as EPA+DHA, does not raise LDL-C, but also fails to lower ApoCIII (Homma et al., 1991, *Atherosclerosis*, 91(1):145-153).

FIG. 34 shows the correlation between percent change in LDL and percent change in ApoCIII for data from the EVOLVE trial. A Pearson correlation coefficient of −0.28 was obtained when these data were fit using a linear regression, demonstrating that increases in LDL correlated with decreases in ApoCIII upon treatment with Epanova®. These results are consistent with previous reports of increased LDL upon administration of DHA, an observation that may be attributed to increased lipoprotein particle size. The effects of Epanova® on lipoprotein particle size are discussed further in Example 12, below.

A subset of subjects, shown in Table 40, exhibited a greater than 800% increase in EPA with less than 5% decrease in triglyceride levels. This failure to respond can likely be attributed to a deficiency or functional defect in the Type 1 lipoprotein lipase (LPL) enzyme. LPL hydrolyzes

6.11. Example 11: Statin Drug-Drug Interaction Trial

6.11.1. Drug Agents

STUDY DRUG (Epanova®)—Type A porcine soft gelatin capsules were prepared, each containing one gram (1 g) of a PUFA composition comprising omega-3 PUFAs in free acid form ("API"). The capsules were coated with Eudragit NE 30-D (Evonik Industries AG). The API had the composition given in batch 3 of Table 9 (see Example 4, above).

STUDY DRUG (Zocor®)—40 mg tablets of simvastatin produced by Merck Sharp & Dohme Ltd. were obtained from a commercial source.

STUDY DRUG (Aspirin®)—81 mg enteric-coated tablets produced by Bayer HealthCare Pharmaceuticals were obtained from a commercial source.

6.11.2. Study Design

An open-label, randomized, 2-way crossover study was designed to evaluate the effect of multiple doses of Epanova® on the multiple-dose pharmacokinetics of simvastatin in healthy normal subjects. Low dose aspirin (81 mg) was also be administered daily in both study arms.

Treatment condition "A" consisted of co-administration of an oral dose of 40 mg of simvastatin (1 tablet), 81 mg of aspirin (1 tablet) and 4 g (4 capsules) of Epanova®, once a day (every 24 hours) with 240 mL of water on the mornings of Days 1 to 14, for a total of 14 doses, under fasting conditions. Treatment condition "B" consisted of administration of an oral dose of 40 mg of simvastatin (1 tablet) and 81 mg of aspirin (1 tablet) once a day (every 24 hours) with 240 mL of water on the mornings of Days 1 to 14, for a total of 14 doses, under fasting conditions. There was a 14 day washout between treatments.

A total of 52 subjects were enrolled and randomized with respect to order of treatment. Of these, 46 participants were Hispanic.

Blood was drawn for plasma fatty acid levels (EPA, DHA, AA) at check-in (day −1) and at check-out (day 15) following the treatment arm with Epanova® (treatment "A"). Genotyping was performed at various previously identified SNPs, including SNPs in the FADS1 gene (e.g. rs174546), including a SNP associated with conversion of DGLA to AA (SNP rs174537), the FADS2 gene, and Scd-1 gene.

6.11.3. Results

Average baseline and end-of-treatment ("EOT") plasma levels (in µg/mL) for EPA levels are shown in FIG. 20E.

FIG. 56 shows arachidonic acid (AA) plasma levels for subjects grouped according to genotype at the rs174546 SNP, at (A) baseline (in µg/mL), and (B) day 15 of treatment with Epanova® (in percent change from baseline). For each genotype, the interquartile range is indicated by a box, the median is indicated by a horizontal line in the interior of the interquartile box, and the mean is represented by a diamond. Outliers are represented by open circles. The whiskers extend to the minimum and maximum non-outlier value. Score 1 identifies subjects who are homozygous at the major allele; Score 3 identifies subjects homozygous at the minor allele; and Score 2 represents heterozygotes.

Prior to treatment, the Hispanic population had a higher prevalence of TT homozygotes (41%) compared to CC homozygotes (24%) for SNP rs174546. This corresponded to significantly different baseline levels of EPA (CC=18 µg/mL; CT=11 µg/mL; TT=7 µg/mL, p<0.0001) and arachidonic acid (AA) (CC=266 µg/mL; CT=202 µg/mL; TT=167 p<0.0001) across genotypes.

In response to treatment with Epanova®, a substantial increase in EPA was observed, with the largest percent increase in the TT genotype (TT: 1054%, CT: 573%, CC: 253%).

6.12. Example 12: ESPRIT Trial

6.12.1. Drug Agents

STUDY DRUG (Epanova®)—Type A porcine soft gelatin capsules were prepared, each containing one gram (1 g) of a PUFA composition comprising omega-3 PUFAs in free acid form ("API"). The capsules were coated with Eudragit NE 30-D (Evonik Industries AG). The API had the composition given in batch 3 of Table 9 (see Example 4, above).

PLACEBO—Capsules were prepared containing olive oil for use as a control.

6.12.2. Study Design

As shown in FIG. 38, a subset of subjects in the 2 g treatment arm of the EVOLVE trial who were receiving concurrent statin therapy displayed greater magnitudes of percentage changes (mean LS difference), relative to control, for TG, non-HDL-C, HDL-C, LDL-C, TC, VLDL-C, and TC/HDL-C, when compared to those subjects in the 2 g treatment arm who did not receive concurrent statin therapy. Subjects receiving concurrent statin therapy showed a dose-dependent response to Epanova®, as shown in comparative data for Epanova® 2 g and Epanova® 4 g displayed in FIG. 39.

As a follow-on to the enhanced efficacy observed for Epanova® in conjunction with statin therapy, the ESPRIT clinical trial was conducted to study patients on baseline statin therapy. As shown in FIG. 40, patients were selected for the ESPRIT study based on TG levels between 200-500 mg/dL and baseline statin therapy. Of the 660 patients who were selected for the trial, 220 were treated with olive oil placebo, 220 were treated with Epanova® 2 g dose, and 220 were treated with Epanova® 4 g dose. All placebo and Epanova® treatments were administered in addition to the baseline statin therapy.

Table 41, below, shows the baseline levels for TG, HDL-C, LDL-C, non-HDL-C, and VLDL-C for subjects in the ESPRIT trial, in comparison to desirable levels as described by the Third Report of the Expert Panel on Detection, Evaluation, and Treatment of High Blood Cholesterol in Adults (Adult Treatment Panel III), issued by the National Heart Lung and Blood Institute.

TABLE 41

| | Baseline levels | | | |
|---|---|---|---|---|
| | Desirable (mg/dL) | 2 g/day | 4 g/day | Olive Oil (OO) |
| TG | <150 | 265 | 265 | 269 |
| HDL-C | >40 | 38 | 37 | 38 |
| LDL-C | <100 | 92 | 91 | 87 |
| Non-HDL-C | <130 | 139 | 135 | 132 |
| VLDL-C | <30 | 42 | 43 | 42 |

6.12.3. Results

FIG. 41 illustrates the patient disposition for the ESPRIT trial, showing that 6 patients were withdrawn from the placebo arm, 6 patients were withdrawn from the 2 g treatment arm, and 12 patients were withdrawn from the 4 g treatment arm. The number of patients who experienced adverse effects (AE) was low overall, with 2 in the placebo arm, 3 in the 2 g treatment arm, and 7 in the 4 g treatment arm.

Patients in the ESPRIT trial exhibited significant percentage changes in plasma EPA and DHA levels, as shown in FIG. 42A and FIG. 42B, respectively. These patients also demonstrated dose-dependent reductions in TG, reductions in non-HDL-C, and increases in HDL-C, compared to olive oil placebo (see FIG. 43). Furthermore, dose-dependent reductions in VLDL-C and TC/HDL-C were observed (see FIG. 44). Taken together, the results of FIGS. 42-44 demonstrate efficacy of Epanova® as an add-on to statin therapy.

Further details of the results of the ESPRIT trial are presented in FIGS. 45-52, demonstrating that Epanova® is efficacious as an add-on to both low-potency and high-potency statins, in a range of baseline patient conditions. FIG. 45 shows the results for median TG percentage change from baseline for three tertiles of patients, partitioned by baseline TG levels. FIG. 46 shows the results for median non-HDL-C percentage change from baseline for three tertiles of patients, partitioned by baseline non-HDL-C levels. FIG. 47 shows the results for median LDL-C percentage change from baseline for three tertiles of patients, partitioned by baseline LDL-C levels.

As seen from FIG. 48, the reductions in TG levels were observed for patients who received concurrent rosuvastatin, atorvastatin, and simvastatin therapy. Statistically significant effects on triglycerides, non-HDL-C, and LDL-C levels were observed regardless of whether low potency or high potency statins were co-administered, as shown in FIGS. 49-51.

FIG. 52 compares median percentage changes from baseline for triglycerides for (A) patients having higher TG baseline levels (≥294 mg/dL), (B) patients having high baseline EPA levels (≥26.58 μg/mL), and (C) patients receiving concurrent rosuvastatin therapy. The results show that the Epanova® 2 g dose works similarly to the 4 g dose in those patient populations shown in FIG. 52.

The increased LDL-C levels observed upon treatment with Epanova® were consistent with observed increased lipoprotein particle size. Large VLDL, medium VLDL, small VLDL, VLDL total, and VLDL size were measured for placebo and each of the treatment arms of the ESPRIT trial. The results are displayed in FIG. 53 and show that Epanova® treatment resulted in decreased amounts of large VLDL particles and correspondingly increased amounts of small VLDL particles. Decreased VLDL particle size was observed, as shown in FIG. 53, together with increases in LDL particle size, as shown in FIG. 54. Shown in FIG. 55, as end-of-treatment TG levels decreased, percentage increases in LDL-P size were larger. Taken together, FIGS. 53-55 demonstrate that Epanova® treatment resulted in increased lipoprotein particle size, an observation that can account for the observed increased LDL-C.

Table 42, below, summarizes the results of the ESPRIT trial.

TABLE 42

| | | Olive Oil (OO) | | | 4 g/day* | | | | | 2 g/day* | | | | |
|---|---|---|---|---|---|---|---|---|---|---|---|---|---|---|
| | | Base | EOT | %Δ | Base | EOT | %Δ | p-value | diff | Base | EOT | %Δ | p-value | diff |
| Non-HDL-C | median | 132 | 134 | 1 | 135 | 129 | −6 | <0.001 | −6 | 139 | 133 | −3 | 0.037 | −3 |
| | mean | 135 | 136 | 1 | 139 | 132 | −5 | | | 140 | 136 | −2 | | |
| TG | median | 269 | 260 | −4 | 265 | 215 | −21 | <0.001 | −15 | 265 | 222 | −15 | <0.001 | −9 |
| | mean | 280 | 268 | −3 | 287 | 233 | −18 | | | 284 | 244 | −14 | | |
| HDL-C | median | 38 | 38 | 2 | 37 | 38 | 3 | 0.988 | 1 | 38 | 39 | 2 | 0.988 | 0 |
| | mean | 39 | 40 | 3 | 39 | 40 | 4 | | | 39 | 40 | 3 | | |
| LDL-C | median | 87 | 91 | 2 | 91 | 92 | 1 | 0.647 | 0 | 92 | 95 | 5 | 0.025 | 4 |
| | mean | 92 | 93 | 4 | 94 | 94 | 4 | | | 92 | 97 | 6 | | |
| VLDL-C | median | 42 | 41 | −3 | 43 | 33 | −20 | <0.001 | −16 | 42 | 37 | −12 | 0.008 | −8 |
| | mean | 46 | 44 | 3 | 47 | 38 | −14 | | | 47 | 40 | −10 | | |
| TC | median | 174 | 174 | 1 | 170 | 167 | −4 | <0.001 | −4 | 177 | 174 | −1 | 0.049 | −2 |
| | mean | 174 | 176 | 1 | 178 | 172 | −3 | | | 179 | 176 | −1 | | |
| TC/HDL-C | median | 5 | 5 | −2 | 5 | 4 | −7 | 0.001 | −5 | 5 | 5 | −4 | 0.119 | −3 |
| | mean | 5 | 5 | −1 | 5 | 5 | −6 | | | 5 | 5 | −3 | | |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating hypertriglyceridemia, comprising orally administering to a patient having pre-treatment serum or plasma triglyceride levels of about 200 mg/dL to about 500 mg/dL a therapeutically effective amount of a pharmaceutical composition comprising:
   eicosapentaenoic acid (EPA), in an amount of 50% to 60% by weight;
   docosahexaenoic acid (DHA), in an amount of 17% to 23% by weight; and
   docosapentaenoic acid (C22:5 n-3) (DPA), in an amount of 1% to 8% by weight;
   wherein at least 90% by weight of the polyunsaturated fatty acid in the composition is present in the free acid form; and
   wherein the composition is not administered at the same time as a statin.

2. The method of claim 1, wherein at least 95% by weight of the polyunsaturated fatty acid in the composition is present in the free acid form.

3. The method of claim 1, wherein DPA is present in the composition in a weight percent amount of at least 1.5%.

4. The method of claim 1, wherein DPA is present in the composition in a weight percent amount of at least 2%.

5. The method of claim 1, wherein DPA is present in the composition in a weight percent amount of at least 2.5%.

6. The method of claim 1, wherein DPA is present in the composition in a weight percent amount of at least 3%.

7. The method of claim 1, wherein DPA is present in the composition in a weight percent amount of at least 3.5%.

8. The method of claim 1, wherein DPA is present in the composition in a weight percent amount of at least 4%.

9. The method of claim 1, wherein DPA is present in the composition in a weight percent amount of at least 4.5%.

10. The method of claim 1, wherein the composition comprises a unit dose of at least 500 mg of the composition.

11. The method of claim 1, wherein the composition comprises a unit dose of about 1 gram of the composition.

12. The method of claim 1, comprising orally administering a dose of 2-4 grams per day of the composition.

13. The method of claim 12, wherein the dose is 2 grams per day.

14. The method of claim 1, further comprising orally administering to the patient a therapeutically effective amount of rosuvastatin, wherein the composition is not administered at the same time as the rosuvastatin.

15. The method of claim 1, wherein the patient is concurrently on statin therapy.

16. The method of claim 15, wherein the statin is selected from pravastatin, lovastatin, simvastatin, atorvastatin, fluvastatin, rosuvastatin, tenivastatin, and pitavastatin.

17. The method of claim 15, wherein the statin is rosuvastatin.

18. The method of claim 1, comprising administering the composition for a duration effective to reduce serum or plasma triglycerides by at least about 5% below pre-treatment levels.

19. The method of claim 1, comprising administering the composition for a duration effective to reduce serum or plasma triglycerides by at least about 10% below pre-treatment levels.

20. The method of claim 12, wherein the dose is 4 grams per day.

21. A method of treating hypertriglyceridemia, comprising orally administering to a patient having pre-treatment serum or plasma triglyceride levels of about 200 mg/dL to about 500 mg/dL a therapeutically effective amount of a pharmaceutical composition and a therapeutically effective amount of a statin; wherein
the pharmaceutical composition comprises:
eicosapentaenoic acid (EPA), in an amount of 50% to 60% by weight;
docosahexaenoic acid (DHA), in an amount of 17% to 23% by weight; and
docosapentaenoic acid (C22:5 n-3) (DPA), in an amount of 1% to 8% by weight;
wherein at least 90% by weight of the polyunsaturated fatty acid in the composition is present in the free acid form;
the statin is administered on a dosage schedule different from the pharmaceutical composition; and
the method comprises administering a single statin.

22. The method of claim 21, wherein the statin is selected from pravastatin, lovastatin, simvastatin, atorvastatin, fluvastatin, rosuvastatin, tenivastatin, and pitavastatin.

23. The method of claim 21, wherein the statin is rosuvastatin.

24. The method of claim 21, wherein the composition is not administered at the same time as a statin.

25. The method of claim 21, wherein at least 95% by weight of the polyunsaturated fatty acid in the composition is present in the free acid form.

26. The method of claim 21, wherein DPA is present in the composition in a weight percent amount of at least 1.5%.

27. The method of claim 21, wherein DPA is present in the composition in a weight percent amount of at least 2%.

28. The method of claim 21, wherein DPA is present in the composition in a weight percent amount of at least 2.5%.

29. The method of claim 21, wherein DPA is present in the composition in a weight percent amount of at least 3%.

30. The method of claim 21, wherein DPA is present in the composition in a weight percent amount of at least 3.5%.

31. The method of claim 21, wherein DPA is present in the composition in a weight percent amount of at least 4%.

32. The method of claim 21, wherein DPA is present in the composition in a weight percent amount of at least 4.5%.

33. The method of claim 21, wherein the composition comprises a unit dose of at least 500 mg of the composition.

34. The method of claim 21, wherein the composition comprises a unit dose of about 1 gram of the composition.

35. The method of claim 21, comprising orally administering a dose of 2-4 grams per day of the composition.

36. The method of claim 35, wherein the dose is 2 grams per day.

37. The method of claim 35, wherein the dose is 4 grams per day.

38. The method of claim 21, comprising administering the composition for a duration effective to reduce serum or plasma triglycerides by at least about 5% below pre-treatment levels.

39. The method of claim 21, comprising administering the composition for a duration effective to reduce serum or plasma triglycerides by at least about 10% below pre-treatment levels.

40. A method of treating hypertriglyceridemia, comprising orally administering to a patient having pre-treatment serum or plasma triglyceride levels of about 200 mg/dL to about 500 mg/dL a therapeutically effective amount of a pharmaceutical composition comprising polyunsaturated fatty acids as the sole active pharmaceutical ingredient; wherein
at least 90% by weight of the polyunsaturated fatty acid in the composition is present in the free acid form; and
the polyunsaturated fatty acids comprise:
eicosapentaenoic acid (EPA), in an amount of 50% to 60% by weight of the composition;
docosahexaenoic acid (DHA), in an amount of 17% to 23% by weight of the composition; and
docosapentaenoic acid (C22:5 n-3) (DPA), in an amount of 1% to 8% by weight of the composition.

41. The method of claim 40, wherein the polyunsaturated fatty acids further comprise:
heneicosapentaenoic acid (C21:5 n-3);
arachidonic acid (C20:4 n-6) (AA);
eicosatetraenoic acid (C20:4 n-3);
moroctic acid (C18:4 n-3);
docosapentaenoic acid (C22:5 n-6); and
linoleic acid (C18:2 n-6).

42. The method of claim 40, wherein the patient is concurrently on statin therapy with a statin selected from pravastatin, lovastatin, simvastatin, atorvastatin, fluvastatin, rosuvastatin, tenivastatin, and pitavastatin.

43. The method of claim 40, wherein the patient is concurrently on statin therapy with rosuvastatin.

* * * * *